United States Patent
Duchateau et al.

(10) Patent No.: US 10,472,613 B2
(45) Date of Patent: Nov. 12, 2019

(54) METHOD FOR MODULATING CAR-INDUCED IMMUNE CELLS ACTIVITY

(71) Applicant: CELLECTIS, Paris (FR)

(72) Inventors: Philippe Duchateau, Draveil (FR); Alexandre Juillerat, New York, NY (US); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 262 days.

(21) Appl. No.: 15/517,708

(22) PCT Filed: Oct. 7, 2015

(86) PCT No.: PCT/EP2015/073197
§ 371 (c)(1),
(2) Date: Apr. 7, 2017

(87) PCT Pub. No.: WO2016/055551
PCT Pub. Date: Apr. 14, 2016

(65) Prior Publication Data
US 2017/0292118 A1    Oct. 12, 2017

(30) Foreign Application Priority Data
Oct. 7, 2014 (DK) .................................. 2014 70623

(51) Int. Cl.
| | | |
|---|---|---|
| *C07K 14/705* | (2006.01) | |
| *C12N 5/16* | (2006.01) | |
| *C07K 14/725* | (2006.01) | |
| *C12N 5/078* | (2010.01) | |
| *C12N 5/0783* | (2010.01) | |
| *C12N 5/10* | (2006.01) | |
| *C12N 5/07* | (2010.01) | |
| *C12N 15/02* | (2006.01) | |
| *C12N 15/87* | (2006.01) | |

(52) U.S. Cl.
CPC ............ *C12N 5/163* (2013.01); *C07K 14/705* (2013.01); *C07K 14/7051* (2013.01); *C12N 5/06* (2013.01); *C12N 5/0634* (2013.01); *C12N 5/0636* (2013.01); *C12N 5/10* (2013.01); *C12N 15/02* (2013.01); *C12N 15/87* (2013.01); *C07K 2317/622* (2013.01); *C07K 2319/01* (2013.01); *C07K 2319/03* (2013.01); *C07K 2319/70* (2013.01); *C07K 2319/74* (2013.01)

(58) Field of Classification Search
CPC ....................................................... C07K 14/705
USPC ............................................................ 424/130.1
See application file for complete search history.

(56) References Cited

U.S. PATENT DOCUMENTS

2014/0271635 A1    9/2014  Brogdon et al.

FOREIGN PATENT DOCUMENTS

| WO | WO 2012/079000 A1 | 6/2012 |
| WO | WO 2014/127261 A1 * | 8/2014 |
| WO | WO 2014/138704 A1 | 9/2014 |
| WO | WO 2014/145252 A2 | 9/2014 |
| WO | WO 2014/152177 A1 | 9/2014 |

OTHER PUBLICATIONS

Haynes et al (J Immunol, 2001, 166: 182-187).*
Bridgeman et al (J Immunology, 2010, 184: 6938-3949).*
Torikai et al (Blood, 2012, 14: 5697-5705).*
Berdien et al (Gene Therapy, 2014, 21: 539-548).*
Fedorov et al, "Novel Approaches to Enhance the Specificity and Safety of Engineered T Cells," The Cancer Journal, USA, Jan. 1, 2014, pp. 160-165, vol. 20, No. 2.
Fedorov et al., "PD-1—and CTLA-4-Based Inhibitory Chimeric Antigen Receptors (iCARs) Divert Off-Target Immunotherapy Responses," Science Translational Medicine, US, Dec. 11, 2013, pp. 78-89, vol. 5, No. 215.
International Preliminary Report on Patentability issued in PCT/EP2015/073197 dated Feb. 3, 2017.
International Search Report and Written Opinion issued in PCT/EP2015/073197 dated Feb. 8, 2016.
Jensen et al., "Design and implementation of adoptive therapy with chimeric antigen receptor-modified T cells," Immunological Reviews, Dec. 13, 2013, pp. 127-144, vol. 257, No. 1.

* cited by examiner

*Primary Examiner* — Sean E Aeder
(74) *Attorney, Agent, or Firm* — Arrigo, Lee, Guttman & Mouta-Bellum LLP

(57) ABSTRACT

The present invention relates to a method to modulate the level of activation of an engineered immune cell (such as a Chimeric Antigen Receptor T-cell) for immunotherapy. The present invention also relates to cells obtained by the present method, preferably comprising said modulable/tunable chimeric antigen receptors for use in therapeutic or prophylactic treatment.

Figure 1A:
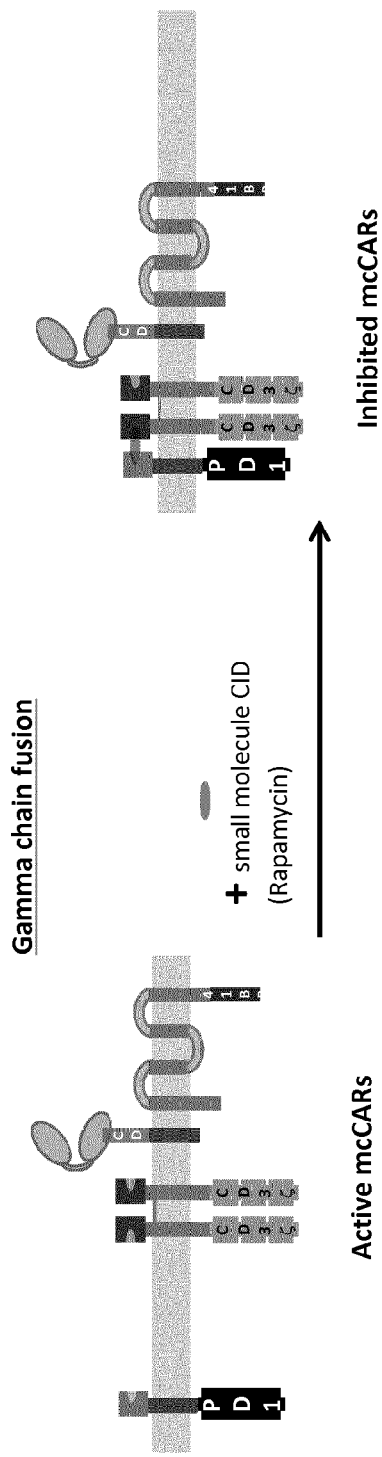

29 Claims, 5 Drawing Sheets
Specification includes a Sequence Listing.

METHOD FOR MODULATING CAR-INDUCED IMMUNE CELLS ACTIVITY

CROSS-REFERENCE TO RELATED APPLICATIONS

This application is a National Stage entry of International Application No.: PCT/EP2015/073197, filed Oct. 7, 2015, which claims priority to Danish Patent Application No. PA201470623, filed Oct. 7, 2014. The disclosure of the priority application is hereby incorporated in its entirety by reference.

FIELD OF THE DESCRIPTION

The present invention relates to a method to modulate the transduction signal of a CAR (chimeric antigen receptor) the level of this transduction signal determining the level of activation of an engineered immune cell, such as a Chimeric Antigen Receptor T-cell used in immunotherapy. In particular, the inventors have developed a molecular switch system and new CAR architectures allowing a tunable activation of said cells upon administration of a soluble compound that induces co-localization of inhibitory and activating signaling domains, especially via chemical induced dimerization (CID). Consequently, the activation of an engineered immune cell triggered by a Chimeric Antigen Receptor (CAR), can be monitored or shunted via inhibitory signaling domain(s) on demand. The invention opens the way to a prospect of a tunable and safer adoptive immunotherapy.

BACKGROUND OF THE INVENTION

Adoptive immunotherapy, which involves the transfer of autologous antigen-specific T-cells generated ex vivo, is a promising strategy to treat cancer. The T-cells used for adoptive immunotherapy can be generated either by expansion of antigen-specific T cells or redirection of T-cells through genetic engineering (Park, Rosenberg et al. 2011). Transfer of viral antigen specific T-cells is a well-established procedure used for the treatment of transplant associated viral infections and rare viral-related malignancies. Similarly, isolation and transfer of tumor specific T-cells has been shown to be successful in treating melanoma. Novel specificities in T-cells have been successfully generated through the genetic transfer of transgenic T cell receptors or chimeric antigen receptors (CARs). CARs are synthetic receptors consisting of a targeting moiety that is associated with one or more signaling domains in a single fusion molecule. CARs have successfully allowed T-cells to be redirected against antigens expressed at the surface of tumor cells from various malignancies including lymphomas and solid tumors (Jena, Dotti et al. 2010).

The first generation of CAR-modified T cell showed success in pre-clinical trials and has entered phase I clinical trials. Clinical trials have commenced in ovarian cancer, neuroblastoma and various types of leukemia and lymphoma (clinicaltrials.gov). The clinical trials showed little evidence of anti-tumor activity with insufficient activation, persistence and homing to cancer tissue. Diverse studies have reported partial first-generation CARs in the absence of costimulation leads to anergy and failure of in vivo expansion.

To overcome these limitations, second and the third generation CAR-modification T cells were designed in order to enhance the activation signal, proliferation, production of cytokines and effector function of CAR-modified T cell in preclinical trials. Second-generation CARs were developed to incorporate the intracellular domains of one or more costimulatory molecules such as CD28, OX40, and 4-1BB within the endodomain, and these improved antigen-specific T-cell activation and expansion. Third-generation CARs include a combination of costimulatory endodomains. Both the second and the third generation CAR-modified T cell have entered clinical trials now. The first clinical trial, which has involved T-cells expressing a CAR combining an anti-CD19 binding domain with a 4-1BB costimulatory domain and CD3zeta as an activating signaling domain has led some patients to a complete remission, which has been ongoing 10 months after treatment. The CAR-modified T cells were found to expand 3-logs in these patients, infiltrating and lysing cancer tissue. Interestingly, a fraction of these cells displayed a memory phenotype of T cell for preventive tumor relapses. Although these CAR-modified T cell produced significant therapeutic effect, their activity led to life-threatening tumor lysis 3 weeks after the first infusion of CAR-modified T cell.

Recently adverse events were reported which stress the requirement of special precautions while using second and third generation of CAR-modified T cells. One patient died 5 days after cyclophosphamide chemotherapy followed by infusion of CAR-modified T cells recognizing the antigen ERBB2 (HER-2/neu) (Morgan et al. 2010). The toxicity leads to a clinically significant release of pro-inflammatory cytokines, pulmonary toxicity, multi-organ failure and eventual death of the patient. This and other adverse events highlight the need for caution when employing CAR-modified T cells, as unlike antibodies against tumor-associated antigens, these cells are not cleared from the body within a short amount of time.

There are many on-going researches to develop a safer CAR-based immunotherapy. Several studies reports diverse systems which aim to improve the efficacy and safety of T immunotherapy. T-cell mediated immunity in healthy persons includes multiple sequential steps regulated by a balance between co-stimulatory and inhibitory signals that fine-tune the immunity response. The inhibitory signals referred to as immune checkpoints (such as CTLA-4- or PD-1) are crucial for the maintenance of self-tolerance and also to limit immune-mediated collateral tissue damage (Dolan et al, 2014).

Recently, inhibitory chimeric antigen receptors (iCARs) were designed having as objective to put the brakes on T cell function upon encountering off-target cells. The iCAR is made up of an antigen-specific single-chain variable fragment (scFv) fused to a T cell inhibitory signaling domain. Cells expressing a tumor-associated antigen but not a normal-tissue antigen would induce T cell activation, cytotoxicity and cytokine signaling to kill the on-target cells. In a study (Federov et al. 2013), CTLA-4- or PD-1-based iCARs were shown to selectively limit cytokine secretion, cytotoxicity, and proliferation induced through the endogenous T cell receptor or an activating chimeric receptor. Therefore, to function, the iCAR technology relies on a preliminary selection of 2 antigens: one tumor associated antigen and one normal-tissue antigen. Moreover, the inhibitory effect of PD-1 or CTLA-4 is operating only on off-target cells.

Another system is described in Budde et al. (2013) in which a CD20 Chimeric Antigen Receptor is combined with an inducible caspase 9 (iC9) suicide switch. In the application US 2014/0286987, the latter gene is made functional in the presence of the prodrug AP1903 (tacrolimus) by binding to the mutated FK506-binding protein (FKBP1). A clinical trial is ongoing sponsored by the company Bellicum in which the above capsase technology (CaspaCID™) is engineered into GD2 targeted third generation CAR T cells. Viral transduction transfers DNA from a vector into the target cell and the vector-derived DNA directs expression of chemical induction dimerization (CID) and accessory proteins. In presence of the AP1903 drug, there will be a dimerization of the CID proteins, thus turning on the signal cascade. In the event of a serious of life-threatening toxicity caused by the administered T cells, AP1903 will be infused to trigger rapid destruction and elimination of the CaspaCID™-enabled cells. One important characteristic is that this expression is restricted to the cytoplasm of the cell. Moreover, according to the Bellicum's system, there is no possibility to modulate the activity of the T-cells, since the expression of CaspaCID™ in contact with the drug leads to the death of the T-cells. A similar apoptosis-inducing system based on a multimerizing agent is described in the application WO 2014/152177.

There is a need of a CAR-based immunotherapy technology which is able to inhibit or modulate, by addition of a soluble compound, the activation of chimeric antigen receptor (CAR) immune cells without killing them; which is flexible as the effect of the soluble compound can be either intracellular or extracellular, and which is independent of on/off target cells selection.

The present invention here provides such immunotherapy by which activation can be specifically inhibited/modulated in case of their cytotoxicity (i.e. when needed) by administration of a particular soluble compound.

SUMMARY OF THE INVENTION

In one aspect, the present invention provides methods for modulating the level of activation of a Chimeric Antigen Receptor-engineered immune cell, such as a CAR-T cell by administration of a soluble compound.

The latter, which may be, in a preferred aspect, a small molecule (such as rapalogs), or a bispecific antibody, triggers a co-localization of at least one binding domain, and consequently enhances a modulation of CAR-engineered immune cell via the action of inhibitory signaling domain(s).

According to one aspect of the invention, an inhibitory membrane protein (IMP) comprising a binding (or dimerization) domain is co-expressed with a CAR into an immune cell. The CAR and the IMP are made both reactive to a soluble compound, especially through a second binding domain comprised within the CAR, thereby allowing the co-localization, by dimerization or ligand recognition, of the inhibitory signaling domain borne by the IMP and of the signal transducing domain borne by the CAR, having the effect of turning down the CAR activation. The inhibitory signaling domain is preferably the programmed death-1 (PD-1), which attenuates T-cell receptor (TCR)-mediated activation of IL-2 production and T-cell proliferation. In Sheppard et al. (2004), it is shown that PD-1 modulation of T-cell function involves inhibition of TCR-mediated phosphorylation through ZAP70 and association with CD3zeta.

The invention provides with several conformations that fall within the scope of the invention—for instance, depending of the type of soluble compound used, either the binding (or dimerization) domains can be extracellular or intracellular (FIGS. 1 and 2). On another hand, the Chimeric Antigen Receptor (CAR) expressed in the immune cell can be either a multi-chain CAR or a single-chain CAR.

Figure 3:
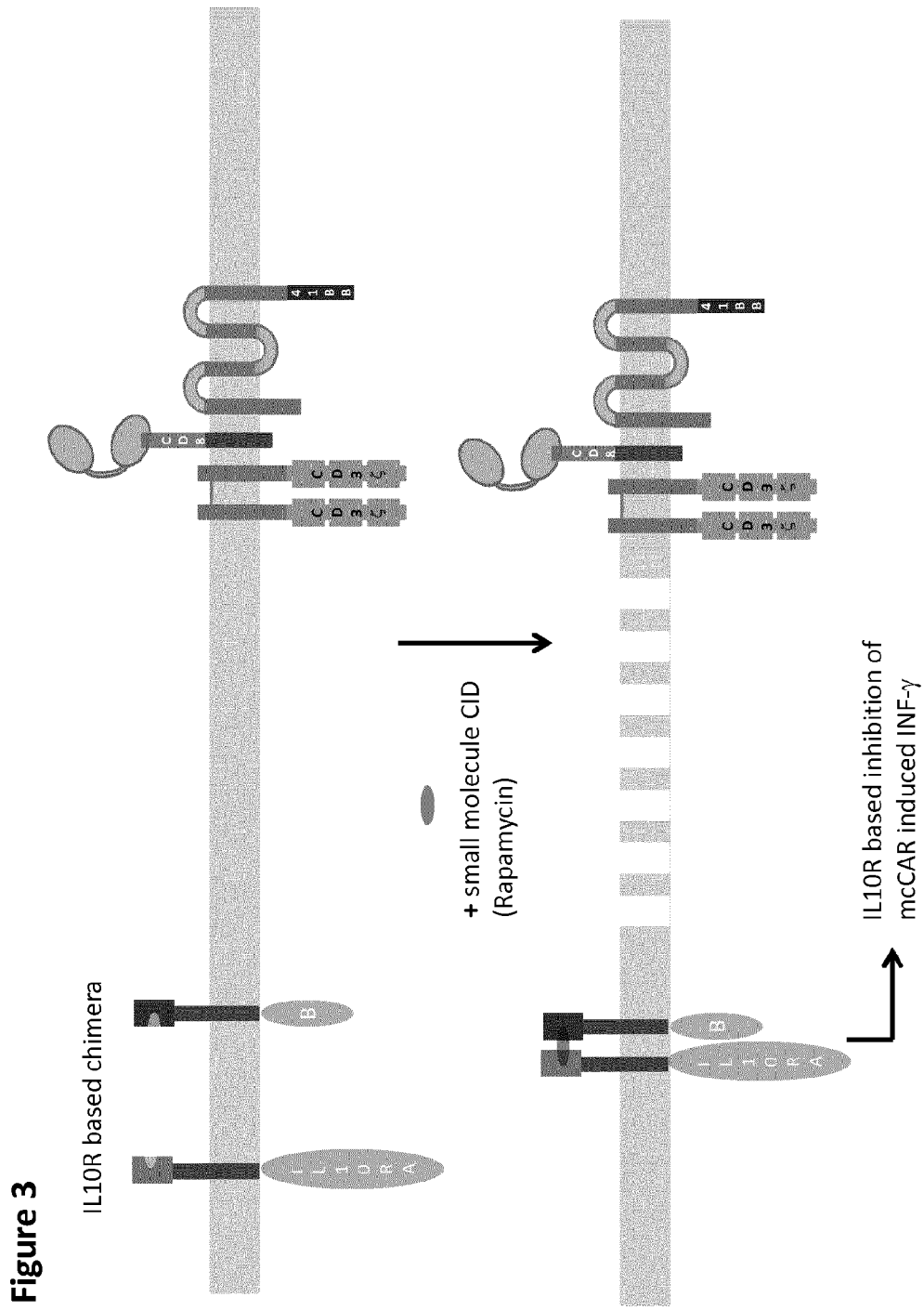

The invention also provides a switch system independent from the selected CAR architecture, which does not necessarily requires inclusion of a second binding or dimerization domain into the CAR. According to this later aspect, the first and second binding (or dimerizing) domains are part of at least two heterologous inhibition membrane proteins (IMPs) expressed at the surface of the immune cells, allowing the dimerization and the activation of an inhibitory signaling domain acting as a (indirect) molecular switch inhibiting CAR induced activation. An example of such switch involves the IL-10 pathway as shown in FIG. 3. The dimerization inducer such as rapamycin allows the co-localization of the two dimerization domains. Once dimerized, IL-10R inhibits synthesis of pro-inflammatory cytokines such as IFN-γ, IL-2, IL-3, TNFα and GM-CSF. It appears that this inhibition is mediated by a cascade of reactions involving several intermediates, such as receptor-associated Janus kinase 1 (Jak1) and tyrosine kinase 2 (Tyk2) kinases, leading to tyrosine phosphorylation of STAT proteins as described in Finbloom et al. (1995).

Also, the present invention encompasses the isolated cells or cell lines obtainable by the method of the invention, more particularly isolated immune cells comprising or expressing any of the proteins, polypeptides, allelic variants, altered or deleted genes or vectors described herein. According to previous developments carried out by the applicants and described in WO 2013176915, the immune cells of the present invention or cell lines can be further engineered for allogeneous implantation into patients, for instance by disrupting T-cell receptors.

Following from the above, a further aspect of the invention concerns methods for treating or preventing conditions, such as cancer, where CAR induced immune cells are useful for targeting pathological cells in a patient, and where there is a need to keep the immune cell proliferation under control using a soluble compound.

BRIEF DESCRIPTION OF THE FIGURES AND TABLES

FIG. 1: Schematic representation of an extracellular based chemical induced dimerization (CID) strategy using PD-1 as inhibitory signaling domain, when both binding domains of the inhibitory membrane protein (IMP) complex and the multi-chain Chimeric Antigen Receptor (CAR) are localized extracellularly.

The system is composed of 2 parts: a first one comprises a polypeptide called inhibitory membrane protein (IMP) and the second one corresponds to a Chimeric Antigen Receptor (CAR). The IMP is a transmembrane protein with an extracellular moiety which is a dimerization domain capable to bind to a chemical inducer dimerization (CID) agent, and with an intracellular moiety which contains an inhibitory signaling domain (PD1 here).

Figure 1B:
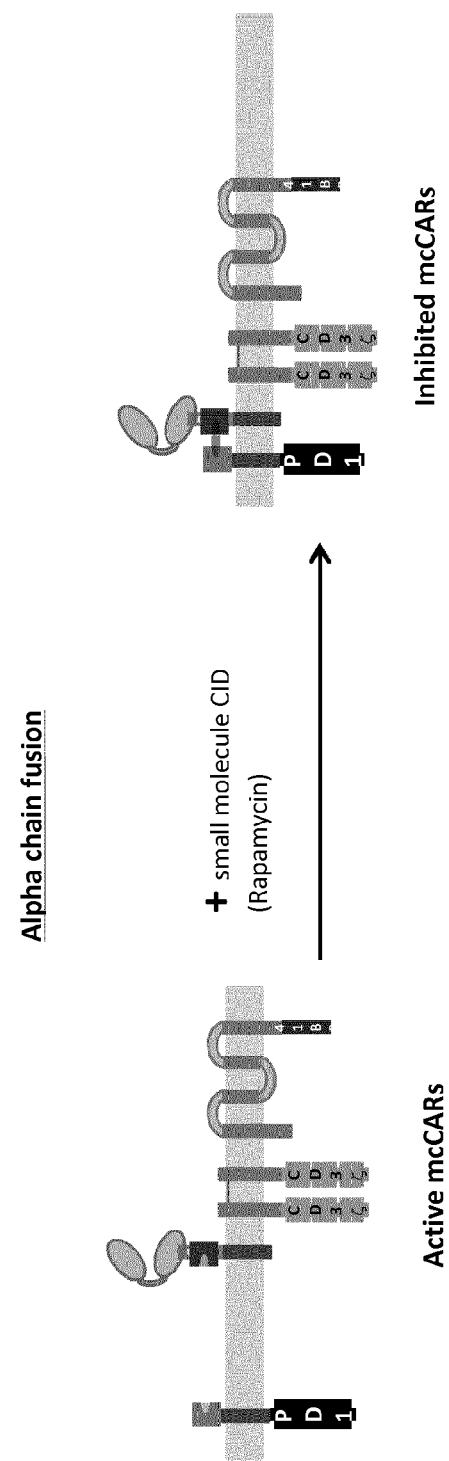

The CAR represented in the drawing is a multichain CAR (mcCAR here) having 3 chains (α, β and γ) derived from Fc Receptor as described in WO 2014039523. The α chain bears a scFv binding domain recognizing a surface marker ligand, the β chain bears a co-stimulatory domain (41-BB here) and the γ chain bears a intracellular transduction signaling domain (CD3ζ here). FIG. 1A shows dimerization domains borne on the extracellular part of the γ chain; FIG. 1B shows a dimerization domain borne on the extracellular part of the α chain.

When the immune cell expressing the IMP molecule and the mcCAR is not in contact with a CID agent, the mcCAR can function in a normal way, i.e. in fine destroy the target cells which are recognized by the scFv specific moiety. In case of an inappropriate or excessive action of the mcCAR, CID agent (rapamycin here) may be administered to the patient in order to trigger the modulable inhibition switch such as explained thereafter.

In both configurations (FIG. 1A and FIG. 1B), the presence of rapamycin allows a co-localization of the 2 dimerization domains (one on IMP molecule and the other on α- or γ-chain of mcCAR), i.e. these 2 dimerization domains come closer each other. By this action, the inhibitory signaling domain PD1 colocalizes with the transduction signaling domain CD3ζ of the mcCAR. A dephosphorylation of the latter enhances a reactions cascade starting from CD3ζ and ultimately leads to an inhibition of the mcCAR.

FIG. 2: Schematic representation of an intracellular based chemical induced dimerization (CID) strategy using PD-1 as inhibitory signaling domain, when both binding domains of the inhibitory membrane protein (IMP) complex and the multi-chain Chimeric Antigen Receptor (CAR) are localized intracellularly.

Figure 2A:
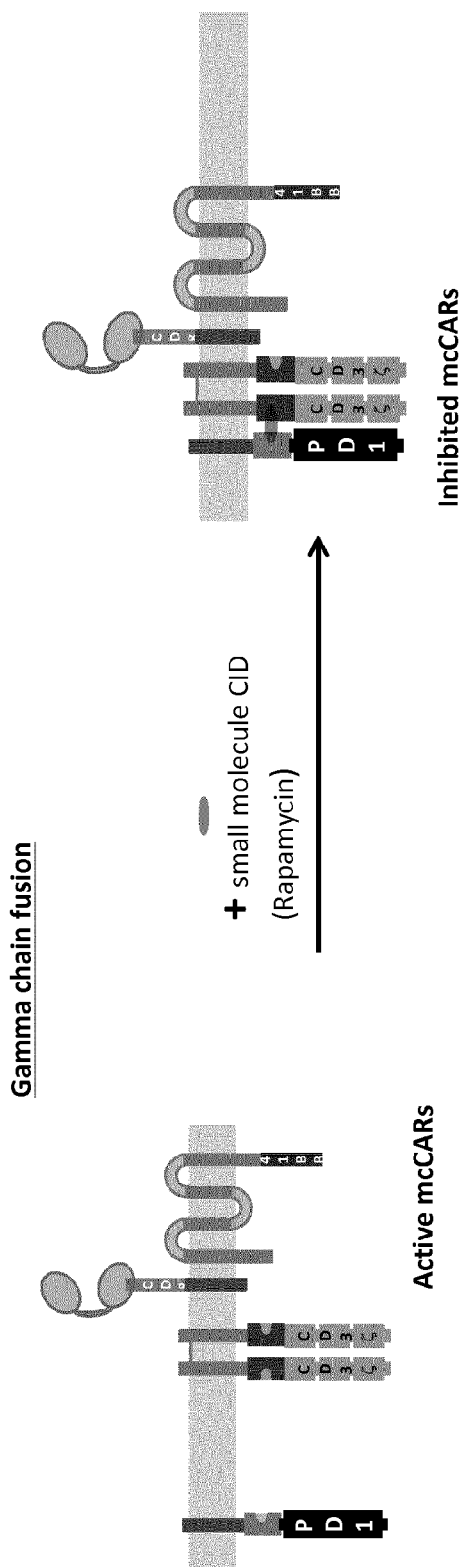
Figure 2B:
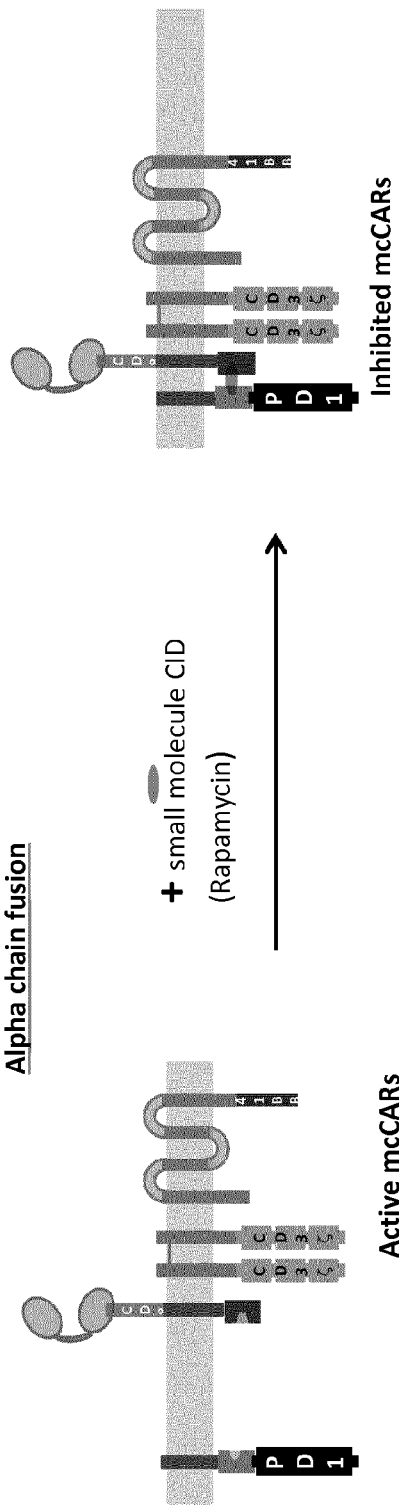

The system is composed of 2 parts such as presented in FIG. 1, FIG. 2A and FIG. 2B corresponding to the cases when the dimerization domains are borne on the α chain and on the γ chain of mcCAR respectively. A difference with FIG. 1 is that the dimerization domains of the IMP protein and mcCAR are located intracellularly. The functioning process is the same than that of FIG. 1, excepted that the rapamycin needs to traverse the membrane of the immune cell to be able to bind to the binding domains.

FIG. 3: Schematic representation of an extracellular based chemical induced dimerization (CID) strategy using IL-10R as inhibitory signaling domain, when both binding domains of the inhibitory membrane protein (IMP) P complex are localized extracellularly. The system presented here is a different of those presented in FIGS. 1 and 2 in the sense that the dimerization domain are borne on the IMP complex and not on the mcCAR. It is based on an IMP complex and a Chimeric Antigen Receptor (here a mcCAR). The IMP complex is composed of 2 independent proteins, each one transmembrane, having extracellularly a dimerization domain, and intracellularly one monomer of the IL-10R inhibitory signaling domain (monomer IL-10Rα and monomer IL-10Rβ). The mcCAR is the same that the one presented in FIGS. 1 and 2.

Figure 4:
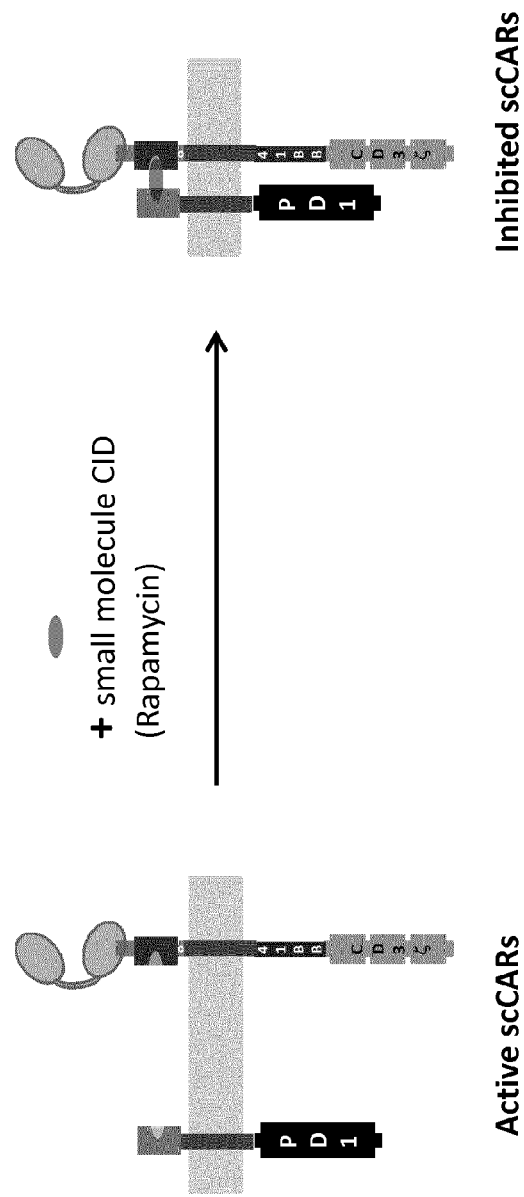

FIG. 4: Schematic representation of an extracellular based chemical induced dimerization (CID) strategy using PD-1 as inhibitory signaling domain in the IMP molecule, and a single-chain CAR; when both binding domains in the IMP molecule and scCAR are localized extracellularly. In the absence of small molecule, the scCAR can function when it meets the tumoral cell surface antigen. In the presence of the small molecule, there is a dimerization of the CID binding domains, allowing a "co-localization" of the 2 polypeptides chains, and then the PD-1 can play its inhibitory role on the scCAR. The latter stops to function.

Figure 5:
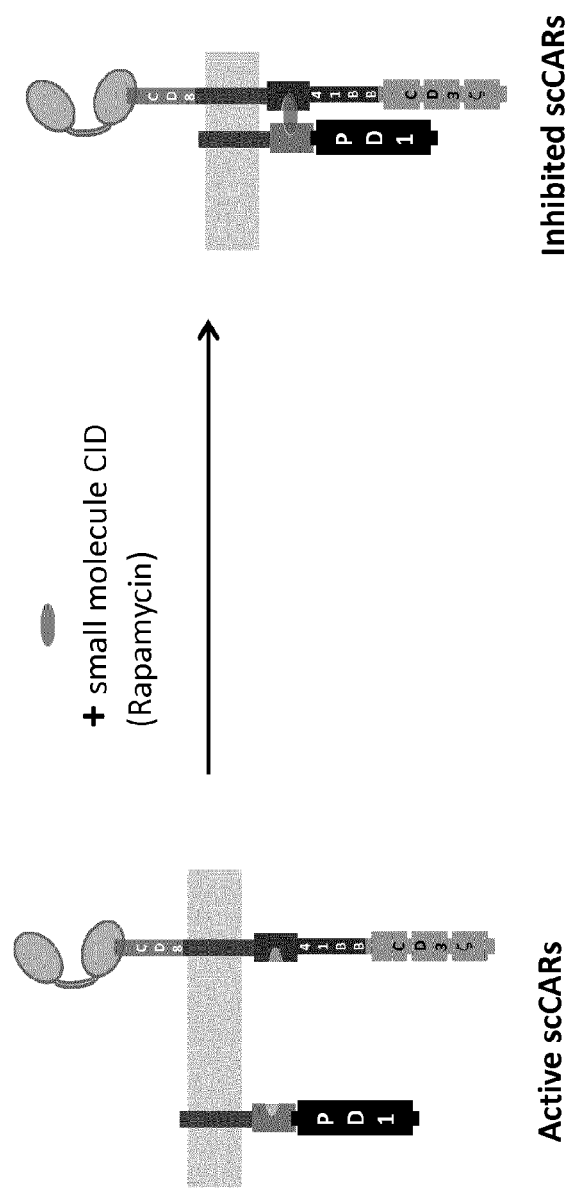

FIG. 5: Schematic representation Schematic representation of an intracellular based chemical induced dimerization (CID) strategy using PD-1 as inhibitory signaling domain in the IMP molecule, and a single-chain CAR; when both binding domains in the IMP molecule and scCAR are localized intracellularly. This is the same principle than that of the extracellular one depicted in FIG. 4, excepted that the small molecule must cross the membrane to be able to dimerize the 2 intracellular CID binding domains.

When needed, i.e. in case of an inappropriate or excessive effect of the CAR, the rapamycin is administered to the patient. The rapamycin allows the dimerization of the 2 dimerization domains borne on the IMP complex. This enhances the colocalization of the 2 monomers of IL-10R, and consequently its inhibitory activity on the CAR via a reaction cascade involving interferon IFN-γ and JAK-STAT signaling pathway. Therefore, the functional IL-10R dimer can indirectly monitor or shunt the activation of an immune cell by the Chimeric Antigen Receptor (CAR).

The following tables show the sequences for all components which are encompassed in the construction of the IMP complex and of the Chimeric Antigen Receptor (CAR).

TABLE 1

Exemplary sequences of modulable/tunable multi-chain CAR based on PD-1 inhibitory signaling domain presented in FIG. 1 Extracellular CID strategy-, when the CID protein is located on the gamma chain.

| Component | Functional domains | Description | SEQ ID # | Raw amino acid sequence |
|---|---|---|---|---|
| | | | | Multi-chain CAR |
| Alpha-chain | Signal sequence scFv | FcεRIα-SP CD123-scFv | SEQ ID NO. 1 SEQ ID NO. 2 | MAPAMESPTLLCVALLFFAPDGVLA MAPAMESPTLLCVALLFFAPDGVLAQIQLVQSGPELKKPGETVKISCKASGYIFTNYGMNWVKQAPGK SFKMMGWINTYTGESTYSADFKGRFAFSLETSASTAYLHINDLKNEDTATYFCARSGYDPMDYWGQ GTSVTVSSGGGGSGGGGSGGGGSDIVLTQSPASLAVSLGQRATISCRASESVDNYGNTFMHWYQQK PGQPPKLLIYRASNLESGIPARFSGSGSRTDFTLTINPVEADDVATYYCQQSNEDPTFGAGTKLELKRS DP |
| | | Klo43-3-scFv | SEQ ID NO. 3 | MAPAMESPTLLCVALLFFAPDGVLAEVKLVESGGGLVQPGGSLSLSCAASGFTFTDYYMSWVRQPPG KALEWLALIRSKADGYTTEYSASVKGRFTLSRDDSQSILYLQMNALRPEDSATYYCARDAAYYSYYSPEG AMDYWGQGTSVTVSSGGGGSGGGGSGGGGSMADYKDIVMTQSHKFMSTSVGDRVNITCKASQN VDSAVAWYQQKPGQSPKALIYSASYRYSGVPDRFTGRGSGTDFTLTISSVQAEDLAVYYCQQYYSTPW TPGGGTKLEIKRSDP |
| | | 5T4WT19-scFv | SEQ ID NO. 4 | MAPAMESPTLLCVALLFFAPDGVLAEVQLQQSGPDLVKPGASVKISCKASGYSFTGYYMHWVKQSHG KSLEWIGRINPNNGVTLYNQKFKDKAILTVDKSSTAYMELRSLTSEDSAVVYCARSTMITNYVMDYW GQVTSVTVSSGGGGSGGGGSGGGGSSIVMTQTPFLLVSAGDRVTITCKASQSVSNDVAWYQQKPG QSPTLLISYTSSRYAGVPDRFIGSGYGDFTFTISTLQAEDLAVYFCQQDYNSPPTFGGGTKLEIKRSDP |
| | | VH-4G7-scFv | SEQ ID NO. 5 | MAPAMESPTLLCVALLFFAPDGVLAEVQLQQSGPELIKPGASVKMSCKASGYTFTSYVMHWVKQKP GQGLEWIGYINPYNDGTKYNEKFKGKATLTSDKSSTAYMELSSLTSEDSAVVYCARGTYYYGSRVFDY WGQGTTLTVSSGGGGSGGGGSGGGGSDIVMTQAAPSIPVTPGESVSISCRSSKSLLNSNGNTYLYWF LQRPGQSPQLLIYRMSNLASGVPDRFSGSGSGTAFTLRISRVEAEDVGVYYCMQHLEYPFTFGAGTKL ELKRSDP |
| | Hinge | CD8a IgG1 | SEQ ID NO. 6 SEQ ID NO. 7 | TTTPAPRPPTPAPTIASQPLSLRPEACRPAAGGAVHTRGLDFACD EPKSPDKTHTCPPCPAPPVAGPSVFLPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | Transmembrane + intracellular domain-with hinge- | EpoR_D2 | SEQ ID NO. 8 | APVGLVARLADESGHVVLRWLPPEPETPMTSHIRYEVDVSAGNGAGSVQRVEILEGRTECVLSNLRGRT RYTFAVRARMAEPSFGGFWSAWSEPVSLLTPSD |
| | | Alpha-TI-A | SEQ ID NO. 9 | IFIPLLVVILFAVDTGLFISTQQQVTFLLKIRTRKGFRLLNPHPKPNPKNR |
| | Transmembrane + intracellular domain-without hinge- | Alpha-TI-B | SEQ ID NO. 10 | TTTPAPRPPTPAPTIASQPLSLRPEACRPAAGGAVHTRGLDFACDFFIPLLVVILFAVDTGLFISTQQQVT FLLKIRTRKGFRLLNPHPKPNPKNR |
| | CD19 alpha chain | | SEQ ID NO. 11 | MAPAMESPTLLCVALLFFAPDGVLAEVQLQQSGPELIKPGASVKMSCKASGYTFTSYVMHWVKQKP GQGLEWIGYINPYNDGTKYNEKFKGKATLTSDKSSTAYMELSSLTSEDSAVVYCARGTYYYGSRVFDY WGQGTTLTVSSGGGGSGGGGSGGGGSDIVMTQAAPSIPVTPGESVSISCRSSKSLLNSNGNTYLYWF LQRPGQSPQLLIYRMSNLASGVPDRFSGSGSGTAFTLRISRVEAEDVGVYYCMQHLEYPFTFGAGTKL ELKRADITTTPAPRPPTPAPTIASQPLSLRPEACRPAAGGAVHTRGLDFACDFFIPLLVVILFAVDTGLFIST QQQVTFLLKIRTRKGFRLLNPHPKPNPKNN |
| Beta-chain | beta-41BB chain | | SEQ ID NO. 12 | MDTESNRRANLALPQEPSSVPAPEVLEISPQEVSSGRLLKSASSPPLHTWLTVLKKEQEFLGVTQILTAM ICLCFGTVVCSVLDISHIEGDIFSSFKAGYPFWGAIFFSISGMLSIISERRNATYLVRGSLGANTASSIAGGT GITILINLKKSLAYIHIHSCQKFETKCFMASFSTEIVVMLFLTILGLGSAVSLTICGAGEELKGNKVPEKR GRKKLLYIFKQPFMRPVQTTQEEDGCCSCRFPEEEEGGCEL |

TABLE 1-continued

Exemplary sequences of modulable/tunable multi-chain CAR based on PD-1 inhibitory signaling domain presented in FIG. 1 Extracellular CID strategy-, when the CID protein is located on the gamma chain.

| Component | Functional domains | Description | SEQ ID # | Raw amino acid sequence |
|---|---|---|---|---|
| Gamma-chain | Signal sequence | Gamma-ss | SEQ ID NO. 13 | MAIPAVLLLLLLVEQAAAG |
| | CID_Protein | FKBP | SEQ ID NO. 14 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEGSGAP |
| | | FRB | SEQ ID NO. 15 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIGSGAP |
| | Hinge | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | | EpoR_D2 | SEQ ID NO. 8 | APVGLVARLADESGHVLRWLPPPETPMTSHIRYEVDVSAGNGAGSVQRVEILEGRTECVLSNLRGRT RYTFAVRARMAEPSFGGFWSAWSEPVSLLTPSD |
| | Transmembrane + intracellular domain- with hinge- | Gamma-TI-A | SEQ ID NO. 16 | IGEPQLCYILDAILFLYGIVLTLLYCRLKIQVRKAAITSYEKSRVKFSRSADAPAYQQGQNQLYNELNLGRRE EYDVLDKRRGRDPEMGGKPRRKNPQEGLYNELQKDKMAEAYSEIGMKGERRRGKGHDGLYQGLSTA TKDTYDALHMQALPPRE |
| | Transmembrane + intracellular domain- without hinge- | Gamma-TI-B | SEQ ID NO. 17 | LGEPQLCYILDAILFLYGIVLTLLYCRLKIQVRKAAITSYEKSRVKFSRSADAPAYQQGQNQLYNELNLGRR EEYDVLDKRRGRDPEMGGKPRRKNPQEGLYNELQKDKMAEAYSEIGMKGERRRGKGHDGLYQGLST ATKDTYDALHMQALPPRE |
| | | | | IMP complex |
| Sequence signal | | VH-4G7-ss | SEQ ID NO. 18 | MALPVTALLLPLALLLHAARPG |
| Dimerization CID_Protein part | | FKBP | SEQ ID NO. 14 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEGSGAP |
| | | FRB | SEQ ID NO. 15 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIGSGAP |
| Hinge | | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | | EpoR_D2 | SEQ ID NO. 8 | APVGLVARLADESGHVLRWLPPPETPMTSHIRYEVDVSAGNGAGSVQRVEILEGRTECVLSNLRGRT RYTFAVRARMAEPSFGGFWSAWSEPVSLLTPSD |
| Trans membrane domain | | CD8a | SEQ ID NO. 19 | IYIWAPLAGTCGVLLLSLVITLYCR |
| | | 4-1BB | SEQ ID NO. 20 | IISFFLAITSTALLFLLFFLTLRFSVVKRGR |
| | | DAP10 | SEQ ID NO. 21 | ILLAGLVAADAVASLLIVGAVFLCARR |
| | | CD28 | SEQ ID NO. 22 | FWVLVVVGGVLACYSLLVTVAPIIFWVRSKRR |
| Inhibitory signaling domain | | PD1 | SEQ ID NO. 23 | SRAARGTIGARRTGQPLKEDPSAVPVFSVDYGELDFQWREKTPEPPVPCVPEQTEYATIVFPSGMGTS SPARRGSADGPRSAQPLRPEDGHCSWPLE |

TABLE 2

Exemplary sequences of modulable/tunable multi-chain CAR based on PD-1 inhibitory signaling domain presented in FIG. 1. Extracellular CID strategy-, when the CID protein is located on the a chain.

| Component | Functional domains | Description | SEQ ID # | Raw amino acid sequence |
|---|---|---|---|---|
| | | | | Multi-chain CAR |
| Alpha-chain | Signal sequence | FcεRIα-SP | SEQ ID NO. 1 | MAPAMESPTLLCVALLFAPDGVLA |
| | scFv | CD123-scFv | SEQ ID NO. 2 | MAPAMESPTLLCVALLFAPDGVLAQIQLVQSGPELKKPGETVKISCKASGYIFTNYGMNWVKQAPGK SFKMMGWINTYTGESTYSADFKGRFAFSLETSASTAYLHINDLKNEDTATYFCARSGSYDPMDYWGQ GTSVTVSSGGGGSGGGGSGGGGSDIVLTQSPASLAVSLGQRATISCRASESVDNYGNTFMHWYQQK PGQPPKLLIYRASNLESGIPARFSGSGSRTDFTLTINPVEADDVATYYCQQSNEDPTFGAGTKLELKRS DPG |
| | | Klo43-3-scFv | SEQ ID NO. 3 | MAPAMESPTLLCVALLFAPDGVLAEVKLVESGGGLVQPGGSLSLSCAASGFTFTDYYMSWVRQPPG KALEWLALIRSKADGYTTEYSASVKGRFTLSRDDSQSILYLQMNALRPEDSATYYCARDAAYYSYYSPEG AMDYWGQGTSVTVSSGGGGSGGGGSGGGGSMADYKDIVMTQSHKFMSTSVGDRVNITCKASQN VDSAVAWYQQKPGQSPKALIYSASYRYSGVPDRFTGRGSGTDFTLTISSVQAEDLAVYYCQQYYSTPW TFGGGTKLEIKRSDPG |
| | | 5T4WT19-scFv | SEQ ID NO. 4 | MAPAMESPTLLCVALLFAPDGVLAEVQLQQSGPDLVKPGASVKISCKASGYSFTGYYMHWVKQSHG KSLEWIGRINPNNGVTLYNQKFKDKAILTVDKSSTAYMELRSLTSEDSAVVYCARSTMITNYVMDYW GQVTSVTVSSGGGGSGGGGSGGGGSSIVMTQTPTFLLVSAGDRVTITCKASQSVSNDVAWYQQKPG QSPTLLISYTSSRYAGVPDRFIGSGYGTDFTFTISTLQAEDLAVYFCQQDYNSPPTFGGGTKLEIKRSDPG |
| | | VH-4G7-scFv | SEQ ID NO. 5 | MAPAMESPTLLCVALLFAPDGVLAEVQLQQSGPELIKPGASVKMSCKASGYTFTSYVMHWVKQKP GQGLEWIGYINPYNDGTKYNEKFKGKATLTSDKSSSTAYMELSSLTSEDSAVYYCARGTYYYGSRVFDY WGQGTTLTVSSGGGGSGGGGSGGGGSDIVMTQAAPSIPVTPGESVSISCRSSKSLLNSNGNTYLYWF LQRPGQSPQLLIYRMSNLASGVPDRFSGSGSGTAFTLRISRVEAEDVGVYYCMQHLEYPFTFGAGTKL ELKRSDPG |
| | CID protein | FKBP | SEQ ID NO. 14 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEGSGAP |
| | | FRB | SEQ ID NO. 15 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIGSGAP |
| | Hinge | CD8α | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | Transmembrane + intracellular domain-with hinge- | EpoR_D2 | SEQ ID NO. 8 | APVGLVARLADESGHVVLRWLPPPETPMTSHIRYEVDVSAGNGAGSVQRVEILEGRTECVLSNLRGRT RYTFAVRARMAEPSFGGFWSAWSEPVSLLTPSD |
| | | Gamma-TI-A | SEQ ID NO. 9 | IGEPQLCYILDAILFLYGIVLTLLYCRLKIQVRKAAITSYEKSRVKFSRSADAPAYQQGQNQLYNELNLGRRE EYDVLDKRRGRDPEMGGKPRRKNPQEGLYNELQKDKMAEAYSEIGMKGERRRGKGHDGLYQGLSTA TKDTYDALHMQALPPRE |
| | Transmembrane + intracellular-without hinge- | Gamma-TI-B | SEQ ID NO. 10 | LGEPQLCYILDAILFLYGIVLTLLYCRLKIQVRKAAITSYEKSRVKFSRSADAPAYQQGQNQLYNELNLGRR EEYDVLDKRRGRDPEMGGKPRRKNPQEGLYNELQKDKMAEAYSEIGMKGERRRGKGHDGLYQGLST ATKDTYDALHMQALPPRE |
| Beta-chain | | beta-41BB chain | SEQ ID NO. 12 | MDTESNRRANLALPQEPSSVPAFEVLEISPQEVSSGRLLKSASSPPLHTWLTVLKKEQEFLGVTQILTAM ICLCFGTVVCSVLDISHIEGDIFSSFKAGYPFWGAIFFSISGMLSIISERRNATYLVRGSLGANTASSIAGGT GITILIINLKKSLAYIHIHSCQKFFETKCFMASFSTEIVVMLFLTILGLGSAVSLTICGAGEELKGNKVPEKR GRKKLLYIFKQPFMRPVQTTQEEDGCSCRFPEEEGGCEL |

TABLE 2-continued

Exemplary sequences of modulable/tunable multi-chain CAR based on PD-1 inhibitory signaling domain presented in FIG. 1. Extracellular CID strategy-, when the CID protein is located on the a chain.

| Component | Functional domains | Description | SEQ ID # | Raw amino acid sequence |
|---|---|---|---|---|
| Gamma-chain | Signal sequence CID_Protein | Gamma-ss | SEQ ID NO. 13 | MAIPAVLLLLLLVEQAAAG |
| | | FKBP | SEQ ID NO. 14 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEGSGAP |
| | | FRB | SEQ ID NO. 15 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIGSGAP |
| | Hinge | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | | EpoR_D2 | SEQ ID NO. 8 | APVGLVARLADESGHVVLRWLPPPETPMTSHIRYEVDVSAGNGAGSVQRVEILEGRTECVLSNLRGRT RYTFAVRARMAEPSFGGFWSAWSEPVSLLTPSD |
| | Transmembrane + intracellular domain-with hinge- | Gamma-TI-A | SEQ ID NO. 16 | IGEPQLCYILDAILFLYGIVLTILLYCRLKIQVRKAAITSYEKSRVKFSRSADAPAYQQGNQLYNELNLGRRE EYDVLDKRRGRDPEMGGKPRRKNPQEGLYNELQKDKMAEAYSEIGMKGERRRGKGHDGLYQGLSTA TKDTYDALHMQALPPRE |
| | Transmembrane + intracellular domain-without hinge-CD19 alpha chain | Gamma-TI-B | SEQ ID NO. 17 | LGEPQLCYILDAILFLYGIVLTILLYCRLKIQVRKAAITSYEKSRVKFSRSADAPAYQQGNQLYNELNLGRR EEYDVLDKRRGRDPEMGGKPRRKNPQEGLYNELQKDKMAEAYSEIGMKGERRRGKGHDGLYQSLST ATKDTYDALHMQALPPRE |
| | | | SEQ ID NO. 11 | MAPAMESPTLLCVALLFFAPDGVLAEVQLQQSGPELIKPGASVKMSCKASGYTFTSYVMHWVKQKP GQGLEWIGYINPYNDGTKYNEKFKGKATLTSDKSSSTAYMELSSLTSEDSAVYYCARGTYYYGSRVFDY WGQGTTLTVSSGGGGSGGGGSGGGGSDIVMTQAAPSIPVTPGESVSISCRSSKSLLNSNGNTYLYWF LQRPGQSPQLLIYRMSNLASGVPDRFSGSGSGTAFTLRISRVEAEDVGVYYCMQHLEYPFTFGAGTKL ELKRADTTTPAPRPPTPAPTIASQPLSLRPEACRPAAGGAVHTRGLDFACDFFIPLLVVILFAVDTGLFIST QQQVTFLLKIKRTRKGFRLLNPHPKPNPKNN |

IMP complex

| | | | | |
|---|---|---|---|---|
| Sequence signal | | VH-4G7-ss | SEQ ID NO. 18 | MALPVTALLLPLALLLHAARPG |
| Dimerization CID_Protein part | | FKBP | SEQ ID NO. 14 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEGSGAP |
| | | FRB | SEQ ID NO. 15 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIGSGAP |
| Hinge | | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | | EpoR_D2 | SEQ ID NO. 8 | APVGLVARLADESGHVVLRWLPPPETPMTSHIRYEVDVSAGNGAGSVQRVEILEGRTECVLSNLRGRT RYTFAVRARMAEPSFGGFWSAWSEPVSLLTPSD |
| Transmembrane domain | | CD8a | SEQ ID NO. 19 | IYIWAPLAGTCGVLLLSLVITLYCR |
| | | 4-1BB | SEQ ID NO. 20 | IISFFLALTSTALLFLLFFLTLRFSVVKRGR |
| | | DAP10 | SEQ ID NO. 21 | ILLAGLVAADAVASLLIVGAVFLCARR |
| | | CD28 | SEQ ID NO. 22 | IFWVLVVVGGVLACYSLLVTVAFIIFWVRSKRR |
| Inhibitory signaling domain | | PD1 | SEQ ID NO. 23 | SRAARGTIGARRTGQPLKEDPSAVPVFSVDYGELDFQWREKTPEPPVPCVPEQTEYATIVFPSGMGTS SPARRGSADGPRSAQPLRPEDGHCSWPLE |

TABLE 3

Exemplary sequences of modulable/tunable multi-chain CAR based on PD-1 inhibitory signaling domain presented in FIG. 1. Intracellular CID strategy-, when the CID protein is located on the alpha chain. Several IMP molecules are possible depending of the positioning of the CID protein (dimerization part) and of the PD1 protein.

| Component | Functional domains | Description | SEQ ID # | Raw amino acid sequence |
|---|---|---|---|---|
| | | | | Multi-chain CAR |
| Alpha-chain | Signal sequence | FcεRIα-SP | SEQ ID NO. 1 | MAPAMESPTLLCVALLFFAPDGVLA |
| | svFc | CD123-scFv | SEQ ID NO. 2 | MAPAMESPTLLCVALLFFAPDGVLAQIQLVQSGPELKKPGETVKISCKASGYIFTNYGMNWVKQAPGK SFKWMGWINTYTGESTYSADFKGRFAFSLETSASTAYLHINDLKNEDTATYFCARSGGYDPMDYWGQ GTSVIVSSGSGGSGGSGGSGGDIVLTQSPASLAVSLGQRATISCRASESVDNYGNTFMHWYQQK PGQPPKLLIYRASNLESGIPARFSGSGSRTDFTLTINPVEADDVATYYCQQSNEDPPTFGAGTKLELKRS DP |
| | | Klo43-3-scFv | SEQ ID NO. 3 | MAPAMESPTLLCVALLFFAPDGVLAEVKLVESGGGLVQPGGSLSLSCAASGFTFTDYYMSWVRQPPG KALEWLALIRSKADGYTTEYSASVKGRFTLSRDDSQSILYLQMNALRPEDSATYYCARDAAYYSYSPEG AMDYWGQGTSVTVSSGGGGSGGGGSGGGGSMADYKDIVMTQSHKFMSTSVGDRVNITCKASQN VDSAVAWYQQKPGQSPKALIYSASYRYSGVPDRFTGRGSGTDFTLTISSVQAEDLAVYYCQQYYSTPW TFGGGTKLEIKRSDP |
| | | 5T4WT19-scFv | SEQ ID NO. 4 | MAPAMESPTLLCVALLFFAPDGVLAEVQLQQSGPDLVKPGASVKISCKASGYSFTGYYMHWVKQSHG KSLEWIGRINPNNGVTLYNQKFKDKAILTVDKSSTTAYMELRSLTSEDSAVYYCARSTMITNVMDYW GQVTSVTVSSGGGGSGGGGSGGGGSSIVMTQTPTFLLVSAGDRVTITCKASQSVSNDVAWYQQKPG QSPTLLISYTSSRYAGVPDRFIGSGYGTDFTFTISTLQAEDLAVYFCQQDYNSPPTFGGGTKLEIKRSDP |
| | | VH-4G7-scFv | SEQ ID NO. 5 | MAPAMESPTLLCVALLFFAPDGVLAEVQLQQSGPELIKPGASVKMSCKASGYTFTSYVMHWVKQKP GQGLEWIGYINPYNDGTKYNEKFKGKATLTSDKSSTAYMELSSLTSEDSAVYYCARGTYYYGSRVFDY WGQGTTLTVSSGGGGSGGGGSGGGGSDIVMTQAAPSIPVTPGESVSISCRSSKSLLNSNGNTYLYWF LQRPGQSPQLLIYRMSNLASGVPDRFSGSGSGTAFTLRISRVEAEDVGVYYCMQHLEYPTFGAGTKL ELKRSDP |
| | Hinge | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEV HNAKTKPREEQYNSTYRVVSVLTVLHQDWLNGKEYKCKVSNKALPAPIEKTISKAKGQPREPQVYTLPP SRDELTKNQVSLTCLVKGFYPSDIAVEWESNGQPENNYKTTPPVLDSDGSFFLYSKLTVDKSRWQQGN VFSCSVMHEALHNHYTQKSLSLSPGKKD |
| | | EpoR_D2 | SEQ ID NO. 8 | APVGLVARLADESGHVVLRWLPPPETPMTSHIRYEVDVSAGNGAGSVQRVEILEGRTECVLSNLRGRT RYTPAVRARMAEPSFGGFWSAWSEPVSLLTPSD |
| | Transmembrane + intracellular domain-with hinge- | Alpha-TI-A | SEQ ID NO. 9 | IFIPLLVVILFAVDTGLFISTQQQVTFLLKIKRTRKGFRLLNPHPKPNPKNNR |
| | Transmembrane + intracellular domain-without hinge. | Alpha-TI-B | SEQ ID NO. 10 | TTTPAPRPPTPAPTIASQPLSLRPEACRPAAGGAVHTRGLDFACDFFIPLLVVILFAVDTGLFISTQQQVT FLLKIKRTRKGFRLLNPHPKPNPKNNR |

TABLE 3-continued

Exemplary sequences of modulable/tunable multi-chain CAR based on PD-1 inhibitory signaling domain presented in FIG. 1. Intracellular CID strategy-, when the CID protein is located on the alpha chain. Several IMP molecules are possible depending of the positioning of the CID protein (dimerization part) and of the PD1 protein.

| Component | Functional domains | Description | SEQ ID # | Raw amino acid sequence |
|---|---|---|---|---|
| | | | | Without linker |
| | Dimerization part | FKBP_pos4-ter-alpha | SEQ ID NO. 24 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEE |
| | | FRB_pos4-ter-alpha | SEQ ID NO. 25 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIE |
| | | | | With linker |
| | | CD28 | SEQ ID NO. 26 | SRLLHSDYMNMTPRRPGPTRKHYQPYAPPRDFAAYRSGSGSGS |
| | | 4-1BB | SEQ ID NO. 27 | GRKKLLYIFKQPFMRPVQTTQEEDGCSCRFPEEEEGGCELGSGSGSGS |
| | | OX40 | SEQ ID NO. 28 | ALYLLRRDQRLPPDAHKPPGGGSFRTPIQEEQADAHSTLAKIGSGSGSGS |
| | | DAP10 | SEQ ID NO. 29 | PRRSPAQEDGKVYINMPGRGGSGSGSGS |
| | | CD18 | SEQ ID NO. 30 | KALIHLSDLREYRRFPEKEKLKSQWNNDNPLFKSATTTVMNPKFAESGSGSGS |
| | | CD28 | SEQ ID NO. 31 | RSKRSRLLHSDYMNMTPRRPGPTRKHYQPYAPPRDFAAYRSGSGSGS |
| | | CD275 | SEQ ID NO. 32 | RDRCLQHSYAGAWAVSPETELTGHVGSGSGSGS |
| | | HVEM | SEQ ID NO. 33 | CVKRRKPRGDVKVIVSVQRKRQEAEGEATVIEALQAPPDVTTVAVEETIPSFTGRSPNHGSGSGSGS |
| | | LIGHT | SEQ ID NO. 34 | MEESVVRPSVFVVDGQTDIPFTRLGRSHRRQSCSVARGSGSGSGS |
| | | CD40L | SEQ ID NO. 35 | MIETYNQTSPRSAATGLPISMKGSGSGSGS |
| | | GITR | SEQ ID NO. 36 | QLGLHIWQLRSQCMWPRETQLLLEVPPSTEDARSCQFPEEERGERSAEEKGRLGDLWVGSGSGSGS |
| | | TIM1 | SEQ ID NO. 37 | KKYPFKKEVQQLSVSFSSLQIKALQNAVEKEVQAEDNIYIENSLYATDGSGSGSGS |
| | | SLAM | SEQ ID NO. 38 | QLRRRGKTNHYQTVEKKSLTIYAQVQKPGPLQKKLDSFPAQDPCTTIYVAATEPVPESVQETNSITV YASVTLPESGSGSGSGS |
| | | CD2 | SEQ ID NO. 39 | KRKKQRSRRNDEELETRAHRVATERGRKPHQIPASTPQNPATSQHPPPPPGHRSQAPSHRPPPGH RVQHQPQKPRPPAPSGTQVHQQKGPPLPRPRVQPKPPHGAAENSLSPSSNGSGSGSGS |
| | | TLT-2 | SEQ ID NO. 40 | KKRHMASYSMCSDPSTRDPPGREPEPYVEVYLIGSGSGSGS |
| | | LAG3 | SEQ ID NO. 41 | HLWRRQWRPRRFSALEQGIHPPQAQSKIEELEQPEPEPEPEPEPEPEQLGSGSGSGS |
| | | DAP12 | SEQ ID NO. 42 | YFLGRLVPRGRGAEEAATRKQRITETESPYQELQGQRSDVYSDLNTQRPYYKGSGSGSGS |
| | | CD84 | SEQ ID NO. 43 | RLFKRRQGRIFPEGSCLNTFTKNPYAASKKTIYTYIMASRNTQPAESRIYDEILQSKVLPSKEEPVNTVYS EVQFADKMGKASTQDSKPGTSSYEIVIGSGSGS |
| | | CD244 | SEQ ID NO. 44 | EFLTIYEDVKDLKTRRNHEQEQTFPGGGSTIYSMIQSQSSAPTSQEPAYTLYSLIQPSRKSGSRKRNHSP SFNSTIYEVIGKSQPKAQNPARLSRKELENFDVYSGSGSGSGS |
| | | CD229 | SEQ ID NO. 45 | LYSVLSOGYEKLDTPLRPARQQPTPTSDSSSDSNLTTEEDEDRPEVHKPISGRYEVFDQVTQEGAGHD PAPEGQADYDVTPYTVEVSVVGENTMYAQVFNLQGKTPVSQKEESSATIYCSIRKPQVVPPQQN DLEIPESPTYENFTGSGSGSGS |
| | | LTBR | SEQ ID NO. 46 | KAHPYFPDLVQPLLPISGDVSPVSTGLPAAPVLEAGVPQQQSPLDLTREPQLEPGEQSQVAHGTNGIH VTGGSMTITGNIYIYNGPVLGGPPGCPGDLPATPEPPYPIPEEGDPGPPGLSTPHQEDGKAWHLAETE HCGATPSNGSGSGSGS |
| | | FKBP_pos5-ter-alpha | SEQ ID NO. 47 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEE |
| | | FRB_pos5-ter-alpha | SEQ ID NO. 48 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIE |
| Beta-chain | beta-41BB chain | | SEQ ID NO. 12 | MDTESNRRANLALFQEPSSVPAFEVLEISPQEVSSGRLLKSASSPPLHTWLTVLKKEQEFLGVTQILTAM ICLCFGTVVCSVLDISHIREGDIFSSFKAGYPFWGAIFFSISGMLSIISERRNATYLVRGSLGANTASSIAGGT GITILIINLKKSLAYIHIHSCQKFFETKCFMASFSTEIVVMMLFTILGLGSAVSLTICGAGEELKGNKVPEKR GRKKLLYIFKQPFMRPVQTTQEEDGCSCRFPEEEEGGCEL |

TABLE 3-continued

Exemplary sequences of modulable/tunable multi-chain CAR based on PD-1 inhibitory signaling domain presented in FIG. 1. Intracellular CID strategy-, when the CID protein is located on the alpha chain.
Several IMP molecules are possible depending of the positioning of the CID protein (dimerization part) and of the PD1 protein.

| Component | Functional domains | Description | SEQ ID # | Raw amino acid sequence |
|---|---|---|---|---|
| Gamma-chain | gamma-CD3z chain | | SEQ ID NO. 49 | MIPAVVLLLLLVEQAAALGEPQLCYILDAILFLYGIVLTLLYCRLKIQVRKAAITSYEKSRVKFSRSADAPAY QQGQNQLYNELNLGREEYDVLDKRRGRDPEMGGKPRRKNPQEGLYNELQKDKMAEAYSEIGMKG ERRRGKGHDGLYQGLSTATKDTYDALHMQALPPR |
| | | | | IMP complex (IMP molecule #1) |
| Sequence signal | | VH-4G7-ss | SEQ ID NO. 18 | MALPVTALLLPLALLLHAARPGSD |
| Transmembrane domain | | CD8a | SEQ ID NO. 19 | IYIWAPLAGTCGVLLLSLVITLYCR |
| | | 4-1BB | SEQ ID NO. 20 | IISFFLALTSTALLELLFFLTLRFSVVKRGR |
| | | DAP10 | SEQ ID NO. 21 | ILLAGLVAADAVASLLIVGAVFLCARR |
| | | CD28 | SEQ ID NO. 22 | IFWVLVVVGGVLACYSLLVTVAFIIFWVRSKRR |
| Dimerization part CID_Protein | | FKBP_pos3-IMP | SEQ ID NO. 24 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVEDVELLKLEGSS |
| | | FRB_pos3-IMP | SEQ ID NO. 25 | SGGRVAILWHEMWHEGLEEASRLYFGERNVKGMPEVLEPLHAMMERGPQTLKETSFNQAYGRDLM EAQEWCRKYMKSGNVKDLTQAWDLYYHVRRIGSGSS |
| Inhibitory signaling domain | | PD1 | SEQ ID NO. 23 | SRAARGTIGARRTGQPLKEDPSAVPVFSVDYGELDFQWREKTPEPPVPCVPEQTEYATIVFPSGMGTS SPARRGSADGPRSAQLRPEDGHCSWPLE |
| | | | | IMP complex (IMP molecule #2) |
| Sequence signal | | VH-4G7-ss | SEQ ID NO. 18 | MALPVTALLLPLALLLHAARPGSD |
| Transmembrane domain | | CD8a | SEQ ID NO. 26 | IYIWAPLAGTCGVLLLSLVITLYCR |
| | | 4-1BB | SEQ ID NO. 27 | IISFFLALTSTALLELLFFLTLRFSVVKRGR |
| | | DAP10 | SEQ ID NO. 28 | ILLAGLVAADAVASLLIVGAVFLCARR |
| | | CD28 | SEQ ID NO. 29 | IFWVLVVVGGVLACYSLLVTVAFIIFWVRSKRR |
| Linker | | CD28 N | SEQ ID NO. 26 | SRLLHSDYMNMTPRRPGPTRKHYQPYAPPRDFAAYRSGSGSGSGS |
| | | 4-1BB | SEQ ID NO. 27 | GRKKLLYIFKQPFMRPVQTTQEEDGCSCREPEEEEGGCELGSGSGSGS |
| | | OX40 | SEQ ID NO. 28 | ALVLLRRDQRLPPDAHKPPGGGSFRTPIQEEQADAHSTLAKIGSGSGSGS |
| | | DAP10 | SEQ ID NO. 29 | PRRSPAQEDGKVYINMPGRGGSGSGSGS |
| | | CD18 | SEQ ID NO. 30 | KALIHLSDLREYRRPEKEKLKSQWNNDNPLFKSATTTVMNPKFAESGSGSGSGS |
| | | CD28 | SEQ ID NO. 31 | RSKRSRLLHSDYMNMTPRRPGPTRKHYQPYAPPRDFAAYRSGSGSGSGS |
| | | CD275 | SEQ ID NO. 32 | RDRCLQHSYAGAWAVSPETELTGHVGSGSGSGS |
| | | HVEM | SEQ ID NO. 33 | CVKRRKPRGDVVKVIVSVQRKRQEAEGEATVIEALQAPPDVTTVAVEETIPSFTGRSPNHGSGSGSGS |
| | | LIGHT | SEQ ID NO. 34 | MEESVVRPSVFVVDGQTDIPFTRLGRSHRRQSCSVARGSGSGSGS |
| | | CD40L | SEQ ID NO. 35 | MIETYNQTSPRSAATGLPISMKGSGSGS |
| | | GITR | SEQ ID NO. 36 | QLGLHIWQLRSQCMWPRETQLLLEVPPSTEDARSCQFPEEERGERSAEEKGRLGDLWVGSGSGSGS |
| | | TIM1 | SEQ ID NO. 37 | KKYPFKKEVQQLSVSFSSLQIKALQNAVEKEVQAEDNIYIENSLYATDSGSGSGS |
| | | SLAM | SEQ ID NO. 38 | QLRRRGKTNHYQTTVEKKSLTIYAQVQKPGPLQKKLDSFPAQDCTTIVAATEPVPESVQETNSITV YASVTLPESGSGSGSGS |
| | | CD2 | SEQ ID NO. 39 | KRKKQRSRRNDEELETRAHRVATERGRKPHQIPASTQNPATSQHPPPPPGHRSQAPSHRPPPPGH RVQHQPQKPPAPSGTQVHQQKGPPLPRPRVQPKPPHGAAENSLSPSSNGSGSGSGS |
| | | TLT-2 | SEQ ID NO. 40 | KKRHMASYSMCSDPSTRDPPGRPEPYVEVLIGSGSGSGS |
| | | LAG3 | SEQ ID NO. 41 | HLWRRQWRPRRFSALEQGIHPPQAQSKIEELEQEPEPEPEPEPEPEPEPEQLGSGSGSGS |
| | | DAP12 | SEQ ID NO. 42 | YFLGRLVPRGRGAEEAATRKQRITETESPYQELQGQRSDVYSDLNTQRPYYKGSGSGSGS |
| | | CD84 | SEQ ID NO. 43 | RLFKRRQGRIFPEGSCLNTFTKNPYAASKKTIYTYIMASRNTQPAESRIYDEILQSKVLPSKEEPVNTVYS EVQFADKMGKASTQDSKPPGTSSYEIVIGSGSGSGS |

TABLE 3-continued

Exemplary sequences of modulable/tunable multi-chain CAR based on PD-1 inhibitory signaling domain presented in FIG. 1. Intracellular CID strategy-, when the CID protein is located on the alpha chain. Several IMP molecules are possible depending of the positioning of the CID protein (dimerization part) and of the PD1 protein.

| Component | Functional domains | Description | SEQ ID # | Raw amino acid sequence |
|---|---|---|---|---|
| | | CD244 | SEQ ID NO. 44 | EFLTIYEDVKDLKTRRNHEQEQTFPGGGSTIYSMIQSQSSAPTSQEPAYTLYSLIQPSRKSGSRKRNHSP SFNSTIYEVIGKSQPKAQNPARLSRKELENFDVYSGSGSGSGS |
| | | CD229 | SEQ ID NO. 45 | LYSVLSOGYEKLDITPLRPARQQPTPTSDSSSDSNLTTEEDEDRPEVHKPISGRYEVFDQVTQEGAGHD PAPEGQADYPDVTPVTEVSVQGENTMYAQVFNLQGKTPVSQKEESSATIYCSIRKPQVVPPQQN DLEIPESPTYENFTGSGSGSGS |
| | | LTBR | SEQ ID NO. 46 | KAHPYFPDLVQPLLPISGDVSPVSTGLPAAPVLEAGVPQQQSPLDLTREPQLEPGEQQSOVAHGTNGIH VTGGSMTIITGNIIYIYNGPVLGGPPGPGDLPATPEPPYPIPEEGDPGPPGLSTPHQEDGKAWHLAETE HCGATPSNGSGSGSGS |
| Dimerization part CID_Protein | | FKBP_pos4-IMP | SEQ ID NO. 51 | SGGVOVETISPGDGRTFPKRGQTCVVHYTGMLEDGKKFDSSRDRNKPFKFMLGKQEVIRGWEEGVA QMSVGQRAKLTISPDYAYGATGHPGIIPPHATLVFDVELLKLEGSGSG |
| | | FRB_pos4-IMP | SEQ ID NO. 52 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVPRRIGSGSG |
| Inhibitory signaling domain | | PD1_pos5-ter | SEQ ID NO. 53 | SRAARGTIGARRTGQPLKEDPSAVPVFSVDYGELDFQWREKTPEPPVPCVPEQTEYATIVFPSGMGTS SPARRGSADGPRSAQPLRPEDGHCSWPLE |

IMP complex (IMP molecule #3)

| Component | Functional domains | Description | SEQ ID # | Raw amino acid sequence |
|---|---|---|---|---|
| Sequence signal | | | SEQ ID NO. 18 | MALPVTALLLPLALLLHAARPGSD |
| Transmembrane domain | | VH-4G7-ss | SEQ ID NO. 26 | IYIWAPLAGTCGVLLLLSLVITLYCR |
| | | CD8a | SEQ ID NO. 27 | IISFFLALTSTALLFLLFFLTLRRSVVKRGR |
| | | 4-1BB | SEQ ID NO. 28 | ILLAGLIVAADAVASLLIVGAVFLCARR |
| | | DAP10 | SEQ ID NO. 29 | IFWVLVVVGGVLACYSLLVTVAFIIFWVRSKRR |
| | | CD28 | SEQ ID NO. 30 | SRAARGTIGARRTGQPLKEDPSAVPVFSVDYGELDFQWREKTPEPPVPCVPEQTEYATIVFPSGMGTS SPARRGSADGPRSAQPLRPEDGHCSWPLGSGSGS |
| Inhibitory signaling domain | | PD1_pos3 | SEQ ID NO. 50 | SRLLHSDYMNMTPRRPGPTRKHYQPYAPPRDFAAYRSGSGSGSGS |
| Linker | | CD28 | SEQ ID NO. 26 | GRKKLLYIFKQPFMRPVQTTQEEDGCSCREPEEEEGGCELGSGSGSGS |
| | | 4-1BB | SEQ ID NO. 27 | ALYLLRRDQRLPPDAHKPPGGGSFRTPIQEEQADAHSTLAKIGSGSGSGS |
| | | OX40 | SEQ ID NO. 28 | PRRSPAQEDGKVYINMPGRGGSGSGSGS |
| | | DAP10 | SEQ ID NO. 29 | KALIHLSDLREYRRFPEKEKLKSQWNNDNPLFKSATTTVNNPKFAESGSGSGSGS |
| | | CD18 | SEQ ID NO. 30 | RSKRSRLLHSDYMNMTPRRPGPTRKHYQPYAPPRDFAAYRSGSGSGSGS |
| | | CD28 | SEQ ID NO. 31 | RDRCLQHSYAGAWAVSPETELTGHVGSGSGSGS |
| | | CD275 | SEQ ID NO. 32 | CVKRRKPRGDVVKVIVSVQRKRQEAEGEATVIEALQAPPDVTTVAVEETIPSFTGRSPNHGSGSGSGS |
| | | HVEM | SEQ ID NO. 33 | MEESVVRPSVFVVDGQTDIPFTRLGRSHRRQSCSVARGSGSGSGS |
| | | LIGHT | SEQ ID NO. 34 | MIETYNQTSPRSAATGLPISMKGSGSGSGS |
| | | CD40L | SEQ ID NO. 35 | QLGLHIWQLRSQCMWPRETQLLLEVPPSTEDARSCQFPEEERGERSAEEKGRLGDLWVGSGSGSGS |
| | | GITR | SEQ ID NO. 36 | KKYFFKKEVQQLSVSFSSLQIKALQNAVEKEVQAEDNIYIENSLYATDGSGSGSGS |
| | | TIM1 | SEQ ID NO. 37 | QLRRRGKTNHYQTTVEKKSLTIYAQVQKPGPLQKKLDSFPAQDPCTTIYVAATEPVPESVQETNSITV YASVTLPESGSGSGSGS |
| | | SLAM | SEQ ID NO. 38 | KRKKQRSRRNDEELETRAHRVATEERGRKPHQIPASTPQNPATSQHPPPPPGHRSQAPSHRPPPGH RVQHQPQKRPPAPSGTQVHQQKGPPLPRPVQPKPPHGAAENSLSPSSNGSGSGSGS |
| | | CD2 | SEQ ID NO. 39 | KKRHMASYSMCSDPSTRDPPGRPEPYVEVYLIGSGSGSGS |
| | | TLT-2 | SEQ ID NO. 40 | HLWMRQWRPRRESALEQGIHPPQAQSKIELEQEPEPEPEPEPEPEPEPEQLGSGSGSGS |
| | | LAG3 | SEQ ID NO. 41 | YFLGRLVPRGRGAEAATRKQRITETESPYQELQGQRSDVYSDLNTQRPYYKGSGSGSGS |
| | | DAP12 | SEQ ID NO. 42 | RLFKRRQGRIFPEGSCLNFTKNPYAASKKTIYTYIMASRNTQPAESRIYDEILQSKVLPSKEEPVNTVYS |
| | | CD84 | SEQ ID NO. 43 | EVQPADKMGKASTQDSKPPGTSSYEIVIGSGSGSGS |

TABLE 3-continued

Exemplary sequences of modulable/tunable multi-chain CAR based on PD-1 inhibitory signaling domain presented in FIG. 1. Intracellular CID strategy-, when the CID protein is located on the alpha chain. Several IMP molecules are possible depending of the positioning of the CID protein (dimerization part) and of the PD1 protein.

| Component | Functional domains | Description | SEQ ID # | Raw amino acid sequence |
|---|---|---|---|---|
| | | CD244 | SEQ ID NO. 44 | EFLTIYEDVKDLKTRRNHEQEQTFPGGGSTIYSMIQSQSSAPTSQEPAYTLYSLIQPSRKSGSRKRNHSP SFNSTIYEVIGKSQPKAQNPARLSRKELENFDVYSGSGSGSGS |
| | | CD229 | SEQ ID NO. 45 | LYSVLSQGYEKLDIPLRPARQQPTPTSDSSDSNLTTEEDEDRPEVHKPISGRYEVFDQVTQEGAGHD PAPEGQADYDPVTPVTEVESVVGENTMYAQVFNLQGKTPVSQKEESSATIYCSIRKPQVVPPPQQN DLEIPESPTYENFTGSGSGSGS |
| | | LTBR | SEQ ID NO. 46 | KAHPYFPDLVQPLLPISGDVSPVSTGLPAAPVLEAGVPQQQSPLDLTREPQLEPGEQQSQVAHGTNGIH VTGGSMTITGNIYIYNGPVLIGGPPGPGDLPATPEPPYPIPEEGDPGPPGLSTPHQEDGKAWHLAETE HCGATPSNGSGSGSGS |
| Dimerization part | CID_Protein | FKBP_pos4-ter-IMP | SEQ ID NO. 54 | SGGVQVETISPGDGRTFPKRGQTCVVHYTGMLEDGKKFDSSRDRNKPFKFMLGKQEVIRGWEEGVA QMSVGQRAKLTISPDYAYGATGHPGIIPHATLVFDVELLKLEE |
| | | FRB_pos4-ter-IMP MTOR_HUMAN | SEQ ID NO. 55 | SGGRVAILWHEMWHEGLEEASRLYFGERNVKGMFEVLEPLHAMMERGPQTLKETSFNQAYGRDLM EAQEWCRKYMKSGNVKDLTQAWDLYYHVFRRIE |

IMP complex (IMP molecule #4)

| Sequence signal | | MALPVTALLLPLALLLHAARPGSD | SEQ ID NO. 18 | MALPVTALLLPLALLLHAARPGSD |
|---|---|---|---|---|
| Transmembrane domain | | VH-4G7-ss | SEQ ID NO. 19 | IYIWAPLAGTCGVLLLSLVITLYCR |
| | | CD8a | SEQ ID NO. 20 | IISFFLALTSTALLFLLFFLTLRFSVVKRGR |
| | | 4-1BB | SEQ ID NO. 21 | ILLAGLVAADAVASLLIVGAVFLCARR |
| | | DAP10 | SEQ ID NO. 22 | IFWVLVVVGVLACYSLLVTVAFIIFWVRSKRR |
| | | CD28 | | |
| | | CD28_HUMAN | | |
| Linker | | CD28 | SEQ ID NO. 26 | SRLLHSDYMNMTPRRPGPTRKHYQPYAPPRDFAAYRSGSGSGSGS |
| | | 4-1BB | SEQ ID NO. 27 | GRKKLLYIFKQPFMRPVQTTQEEDGCSCRFPEEEEGGCELGSGSGSGS |
| | | OX40 | SEQ ID NO. 28 | ALYLLRRDQRLPPDAHKPPGGGSFRTPIQEEQADAHSTLAKIGSGSGSGS |
| | | DAP10 | SEQ ID NO. 29 | PRRSPAQEDGKVYINMPGRGGSGSGSGS |
| | | CD18 | SEQ ID NO. 30 | KALIHLSDLREYRRFEKEKLKSQWNNDNPLFKSATTTVNNPKFAESGSGSGSGS |
| | | CD28 | SEQ ID NO. 31 | RSKRSRLLHSDYMNMTPRRPGPTRKHYQPYAPPRDFAAYRSGSGSGSGS |
| | | CD275 | SEQ ID NO. 32 | RDRCLQHSYAGAWAVSPETELTGHVGSGSGSGS |
| | | HVEM | SEQ ID NO. 33 | CVKRRKPRGDVVKVIVSVQRKRQEAEGEATVIEALQAPPDVTTVAVEETIPSFTGRSPNHGSGSGSGS |
| | | LIGHT | SEQ ID NO. 34 | MEESVVRPSVFVVDGQTDIPFTRLGRSHRRQSCSVARGSGSGSGS |
| | | CD40L | SEQ ID NO. 35 | MIETYNQTSPRSAATGLPISMKGSGSGSGS |
| | | GITR | SEQ ID NO. 36 | QLGLHIWQLRSQCMWPRETQLLLEVPPSTEDARSCQFPEEERGERSAEEKGRLGDLWVGSGSGSGS |
| | | TIM1 | SEQ ID NO. 37 | KKYFFKKEVQQLSVSFSSLQIKALQNAVEKEVQAEDNIYIENSLYATDGSGSGSGS |
| | | SLAM | SEQ ID NO. 38 | QLRRRGKTNHYQTTVEKKSLTIYAQVQKPGPLQKKLDSFPAQDPCTTIYVAATEPVPESVQETNSITV YASVTLPESGSGSGSGS |
| | | CD2 | SEQ ID NO. 39 | KRKKQRSRNDEELETRAHRVATERGRKPHQIPASTPQNPATSQHPPPPPGHRSQAPSHRPPPPGH RVQHQPQKRPPAPSGTVHQKGPPLPRPVQKPPHGAAENSLSPSSNGSGSGSGS |
| | | TLT-2 | SEQ ID NO. 40 | KKRHMASYSMCSDPSTRDPPGRPEPYVEVYLIGSGSGSGS |
| | | LAG3 | SEQ ID NO. 41 | HLWRRQWRPRRFSALEQGIHPPQAQSKIEIELEQEPEPEPEPEPEPEPEPEQLGSGSGSGS |
| | | DAP12 | SEQ ID NO. 42 | YFLGRLVPRGRGAAEAATRKQRITETESPYQELQGQRSDVYSDLNTQRPYYKGSGSGSGS |
| | | CD84 | SEQ ID NO. 43 | RLFKRRQGRIFPEGSCLNTFTKNPVAASKKTIYTYIMASRNTQPAESRIYDEIIQSKVLPSKEEPVNTVYS EVQFADKMGKASTQDSKPPGTSSYEIVIGSGSGSGS |

TABLE 3-continued

Exemplary sequences of modulable/tunable multi-chain CAR based on PD-1 inhibitory signaling domain presented in FIG. 1. Intracellular CID strategy-, when the CID protein is located on the alpha chain. Several IMP molecules are possible depending of the positioning of the CID protein (dimerization part) and of the PD1 protein.

| Component | Functional domains | Description | SEQ ID # | Raw amino acid sequence |
|---|---|---|---|---|
| | | CD244 | SEQ ID NO. 44 | EFLTIYEDVKDLKTRRNHEQEQTFPGGGSTIYSMIQSQSSAPTSQEPAYTLYSLIQPSRKSGSRKRNHSP SFNSTIYEVIGKSQPKAQNPARLSRKELENFDVYSGSGSGS |
| | | CD229 | SEQ ID NO. 45 | LYSVLSQGYEKLDTPLRPARQQPTPTSDSSSDSNLTTEEDEDRPEVHKPISGRYEVFDQVTQEGAGHD PAPEGQADYDPVTPYVTEVESVVGENTMYAQVFNLQGKTPVSQKEESSATIYCSIRKPQVVPPPQQN DLEIPESPTYENFTGSGSGSGS |
| | | LTBR | SEQ ID NO. 46 | KAHPYFPDLVQPLLPISGDVSPVSTGLPAAPVLEAGVPQQQSPLDLTREPQLEPGEQSQVAHGTNGIH VTGGSMTITGNIYIYNGPVLGGPPGPGDLPATPEPPYPIPEEGDPGPPGLSTPHQEDGKAWHLAETE HCGATPSNGSGSGSGS |
| Inhibitory signaling domain | | PD1_pos4 | SEQ ID NO. 56 | SRAARGTIGARRTGQPLKEDPSAVPVFSVDYGELDFQWREKTPEPPVPCVPEQTEYATIVFPSGMGTS SPARRGSADGPRSAQPLRPEDGHCSWPLGSGSG |
| Dimerization part | CID_Protein | FKBP_pos5-ter-IMP | SEQ ID NO. 57 | GVQVETISPGDGRTFPKRGQTCVVHYTGMLEDGKKFDSSRDRNKPFKFMLGKQEVIRGWEEGVAQ MSVGQRAKLTISPDYAYGATGHPGIIPPHATLVFDVELLKLEE |
| | | FRB_pos5-ter-IMP | SEQ ID NO. 58 | GRVAILWHEMWHEGLEEASRLYFGERNVKGMFEVLEPLHAMMERGPQTLKETSFNQAYGRDLMEA QEWCRKYMKSGNVKDLTQAWDLYYHVFRRIE |

TABLE 4

Exemplary sequences of modulable/tunable multi-chain CAR based on IL-10R inhibitory signaling domain presented in FIG. 3

| Component | Functional domains | Description | SEQ ID # | Raw amino acid sequence |
|---|---|---|---|---|
| Multi-chain CAR | | | | |
| Alpha-chain | signal sequence | FcεR1α-SP | SEQ ID NO. 1 | MAPAMESPTLLCVALLFFAPDGVLA |
| | | CD123-scFv | SEQ ID NO. 2 | MAPAMESPTLLCVALLFFAPDGVLAQIQLVQSGPELKKPGETVKISCKASGYIFTNYGMNWVKQAPGKSFKWMGWINTYTGESTYSADFKGRFAFSLETSASTAYLHINDLKNEDTATYFCARSGYDPMDYWGQGTSVTVSSGGGGSGGGGSGGGGSDIVLTQSPASLAVSLGQRATISCRASESVDNYGNTFMHWYQQKPGQPPKLLIYRASNLESGIPARPSGSGRTDFTLTINPVEADDVATYYCQQSNEDPPTFGAGTKLELKRSDP |
| | | Klo43-3-scFv | SEQ ID NO. 3 | MAPAMESPTLLCVALLFFAPDGVLAEVKLVESGGGLVQPGGSLSLSCAASGFTFTDYYMSWRQPPGKALEWLALIRSKADGTTEYSASVKGRFTLSRDDSQSILVLQMNALRPEDSATYYCARDAAYYSYYSPEGAMDYWGQGTSVTVSSGGGGSGGGGSGGGGSMADYKDIVMTQSHKFMSTSVGDRVNITCKASQNVDSAVAWYQQKPGQSPKALLYSASYRYSGVPDRFTGRGSGTDFTLTISSVQAEDLAVYYCQQYYSTPWTFGGGTKLEIKRSDP |
| | | 5T4WT19-scFv | SEQ ID NO. 4 | MAPAMESPTLLCVALLFFAPDGVLAEVQLQQSGPDLVKPGASVKISCKASGYSFTGYMHWKQSHGKSLEWIGRINPNNGVILYNQKFKDKAILTVDKSSTTAYMELRSLTSEDSAVYYCARSTMITNYVMDYWGQVTSVTVSSGGGGSGGGGSSIVMTQTPTFLLVSAGDRVTITCKASQSVSNDVAWYQQKPGQSPTLLISYTSSRYAGVPDRFIGSGYGTDFTFTISTLQAEDLAVFCQQDYNSPPTFGGGTKLEIKRSDP |
| | | VH-4G7-scFv | SEQ ID NO. 5 | MAPAMESPTLLCVALLFFAPDGVLAEVQLQQSGPELIKPGASVKMSCKASGYTFTSVMHWVKQKPGQGLEWIGYINPYNDGTKYNEKFKGKATLTSDKSSTAYMELSSLTSEDSAVYYCARGTYYYGSRVFDYWGQGTTLTVSSGGGGSGGGGSGGGGSDIVMTQAAPSIPVTPGESVSISCRSSKSLLNSNGNTYLYWFLQRPGQSPQLLIYRMSNLASGVPDRFSGSGSGTAFTLRISRVEAEDVGVYYCMQHLEYPPTFGAGTKLELKRSDP |
| | Hinge | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGKKD |
| | | EpoR_D2 | SEQ ID NO. 8 | APVGLVARLADESGHVVLRWLPPPETPMTSHIRYEVEVDVSAGNGAGSVQRVEILEGRTECVLSNLRGRTRYTFAVRARMAEPSFGGFWSAWSEPVSLLTPSD |
| | Transmembrane + intracellular domain-with hinge- | Alpha-TI-A | SEQ ID NO. 9 | IFIPLLVVILFAVDTGLFISTQQQVTFLLKIKRTRKGFRLLNPHPKPNPKNR |
| | Transmembrane + intracellular domain-without hinge- | Alpha-TI-B | SEQ ID NO. 10 | TTTPAPRPPTPAPTIASQPLSLRPEACRPAAGGAVHTRGLDFACDFFIPLLVVILFAVDTGLFISTQQQVTFLLKIKRTRKGFRLLNPHPKPNPKNR |
| | CD19 alpha chain | | SEQ ID NO. 11 | MAPAMESPTLLCVALLFFAPDGVLAEVQLQQSGPELIKPGASVKMSCKASGYTFTSVMHWKQKPGQGLEWIGYINPYNDGTKYNEKFKGKATLTSDKSSTAYMELSSLTSEDSAVYYCARGTYYYGSRVFDYWGQGTTLTVSSGGGGSGGGGSGGGGSDIVMTQAAPSIPVTPGESVSISCRSSKSLLNSNGNTYLYWFLQRPGQSPQLLIYRMSNLASGVPDRFSGSGSGTAFTLRISRVEAEDVGVYYCMQHLEYPPTFGAGTKLELKRADTTTPAPRPPTPAPTIASQPLSLRPEACRPAAGGAVHTRGLDFACDFFIPLLVVILFAVDTGLFISTQQQVTFLLKIKRTRKGFRLLNPHPKPNPKNN |

TABLE 4-continued

Exemplary sequences of modulable/tunable multi-chain CAR based on IL-10R inhibitory signaling domain presented in FIG. 3

| Component | Functional domains | Description | SEQ ID # | Raw amino acid sequence |
|---|---|---|---|---|
| Gamma-chain | | gamma-CD3z chain | SEQ ID NO. 49 | MIPAVLLLLLVEQAAALGEPQLCYILDAILFLYGIVLTLLYCRLKIQVRKAAITSYEKSRVKFSRSADAPA YQGQNQLYNELNLGRREYDVLDKRRGRDPEMGGKPRRKNPQEGLYNELQKDKMAEAYSEIGM KGERRRGKGHDGLYQGLSTATKDTYDALHMQALPPR |
| Beta-chain | | beta-41BB chain | SEQ ID NO. 12 | MDTESNRRANLALPQEPSSVPAFEVLEISPQEVSSGRLLKSASSPPLHTWLTVLKKEQEFLGVTQILTA MICLCFGTVVCSVLDISHIEGDIFSSFKAGYPWGAIPFSISGMLSIISERRNATYLVRGSLGANTASSIA GGTGITLIINLKKSLAYIHIHSCQKFFETKCFMASFSTEIVVMMLFLTILGLGSAVSLTICGAGEELKGNK VPEKRGRKKLLYIFKQPFMRPVQTTQEEDGCSCRFPEEEGGCEL |

IL-10A- and IL-10B based IMP molecules

| | | | | |
|---|---|---|---|---|
| Signal sequence | | VH-4G7-ss | SEQ ID NO. 18 | MALPVTALLLPLALLLHAARPG |
| | | FKBP | SEQ ID NO. 14 | SGGVQVETISPGDGRTFPKRGQTCVVHYTGMLEDGKKFDSSRDRNKPFKFMLGKQEVIRGWEEGV AQMSVGQRAKLTISPDYAYGATGHPGIIPPHATLVFDVELLKLEGSGAP |
| Dimerization part | | FRB | SEQ ID NO. 15 | SGGRVAILWHEMWHEGLEEASRLYFGERNVKGMFEVLEPLHAMMERGPQTLKETSFNQAYGRDL MEAQEWCRKYMKSGNVKDLTQAWDLYYHVFRRIGSGAP |
| Hinge | | CD8a | SEQ ID NO. 6 | TTTPAPRPPTPAPTIASQPLSLRPEACRPAAGGAVHTRGLDFACD |
| | | IgG1 | SEQ ID NO. 7 | EPKSPDKTHTCPPCPAPPVAGPSVFLFPPKPKDTLMIARTPEVTCVVVDVSHEDPEVKFNWYVDGV EVHNAKTKPREEQYNSTYRVVSVLTVLHQDWLNGKEYKCKVSNKALPAPIEKTISKAKGQPREPQVY TLPPSRDELTKNQVSLTCLVKGFYPSDIAVEWESNGQPENNYKTTPPVLDSDGSFFLYSKLTVDKSRW QQGNVFSCSVMHEALHNHYTQKSLSLSPGKKD |
| | | EpoR_D2 | SEQ ID NO. 8 | APVGLVARLADESGHVVLRWLPPPETPMTSHIRYEVDVSAGNGAGSVQRVEILEGRTECVLSNLRG RTRYTFAVRARMAEPSFGGFWSAWSEPVSLLTPSD |
| Transmembrane domain + inhibitory signaling domain | IR-10RA inhibitory domain | Il10R1_HUMAN | SEQ ID NO. 59 | IVIFFAVFLLLSGALAYCLALQLYVRRKKLPSVLLFKKPSPFIFISQRPSPETQDTIHPLDEEAFLKVSPEL KNLDLHGSTDSGFGSTKPSLQTEEPQFLLPDPHPQADRTLGNREPPVLGDSCSSGSSNSTDSGICLQE PSLSPSTGPTWEQQVGSNSRGQDDSGIDLVQNSEGRAGDTQGGSALGHHSPPEVPGEEDPAAV APQGYLRQTRCAEEKATKTGCLEEESPLIDGLGPKFGRCLVDEAGLHPPALAKGYLKQDPLEMTLASS GAPTGQWNQPTEEWSLLALSSCCDLGISDWSFAHDLAPLGCVAAPGGLLGSNSDLVTLPLISSLQS SE |
| | IR-10B inhibitory domain | Il10R2_HUMAN | SEQ ID NO. 60 | IWWVAVILMASVFMVCLALLGCFALLWCVYKKTKYAFSPRNSLPQHLKEFLGHPHHNTLLFFSFPLS DENDVFDKLSVIAEDSESGKQNPGDSCSLGTPPGQGPQSE |

DETAILED DESCRIPTION OF THE INVENTION

The ability to control functional responses in adoptive T cell therapy is a key issue. In such therapeutic strategies, T cells are engineered by expressing surface-exposed chimeric antigen receptor (CAR) that achieves high tumor specific target cell recognition. However, to control and minimize potential toxic effects, design of modulable switch systems is highly desirable.

The inventors developed methods of engineering such immune cells based on the design of a chimeric multi-protein complex which is able to inactivate the Chimeric Antigen Receptor (CAR) through the addition of a soluble compound, such as rapalogs.

In particular, the present invention provides a method for modulating the level of activation of an engineered immune cell, said method comprising the following steps of:

(a) transfecting an immune cell with at least a first polynucleotide encoding a Chimeric Antigen Receptor (CAR), which can be activated in-vivo and/or in vitro by an external ligand; said CAR comprising a first binding domain and;

(b) further transfecting said immune cell with at least a second polynucleotide encoding an engineered inhibitory membrane protein (IMP) complex, comprising at least one intracellular inhibitory signaling domain and one second binding domain, such that said immune cell co-expresses, said CAR, and said inhibitory membrane protein (IMP) complex, and;

(c) contacting said engineered immune cell with said external ligand, so that a signal is transduced by the CAR, and then;

(d) reducing the level of said signal transduction of said CAR by adding a soluble compound that binds the binding domain of said IMP and the binding domain of the CAR molecule to co-localize said IMP and said CAR, thereby modulating the level of activation of the engineered immune cell.

By "modulating" the level of activation, it is intended that an inhibition response is obtained on the CAR-engineered immune cells by the administration of a soluble compound, and preferably not a destructive response in contrast to other systems from the prior art. This is particularly useful to adjust the CAR induced activation to patient's needs and more critically, when a severe case of adverse event occurs in a patient.

According to a preferred embodiment, said signal of transduction of the CAR is an activation of the immune cell and said immune cell is activated.

According to another preferred embodiment, the co-localization of the IMP and CAR molecules has the effect of switching off the CAR signal transduction.

One interesting feature of the system of the invention is its flexibility based on the co-localization of proteins i.e no-covalent binding. Thus, after a short while following the discontinuation of administration of the soluble compound (such as a rapalog), one can expect the soluble compound will not bind anymore the binding domains, the "switch off" will cease to be operational, and the CAR engineered immune cells will be able to retrieve their potential.

According to a preferred embodiment, first and second binding domains are CID binding domains.

In the present invention, it is also contemplated the possibility to perform a «fine tuning» of a CAR transduction signal: a dose of soluble can be adjusted; depending of the severity of the adverse event following an inadequate/excessive activity of the CAR engineered immune cells administrated to the patient.

The signal transduced by a CAR in an engineered immune cell may be an activation signal or an inactivation signal on the engineered immune cell, depending of the nature of the signal. This depends on the transduction signaling domain included in the CAR (activating or inhibiting signaling domain, which is expressed by the immune cell When the immune cell expresses a "positive CAR" which usually comprise an activation domain comprising ITAM component(s), with the effect of activating said cell (i.e. its immune function) upon recognition of a tumoral surface specific-antigen, then the IMP will act as a brake on the cell activation, and further as a "switch-off" system. Conversely, in the event the transduction signal is generated by a "negative CAR" that comprises, for instance, an inhibitory signaling domain, such as immunoreceptor tyrosine-based inhibition motif (ITIM), then the inhibition will be partially or totally lifted, acting as a "switch-on" system.

Inhibitory Membrane Protein (IMP) Complex

According to another aspect, the present invention discloses an inhibitory dual CAR/IMP complex, comprising at least two transmembrane chimeric polypeptides:
- a first one encoding a Chimeric Antigen Receptor which comprises one dimerization binding domain;
- the second one encoding an engineered inhibitory membrane protein (IMP) complex, said IMP complex comprising at least one intracellular inhibitory signaling domain and one dimerization binding domain.

According to a preferred embodiment, said inhibitory dual CAR/IMP complex comprises dimerization binding domains which are located extracellularly.

According to an embodiment, the CAR which is part of said inhibitory dual CAR/IMP complex is a multi-chain CAR.

According to an embodiment, the CAR which is part of said inhibitory dual CAR/IMP complex is a single-chain CAR.

In one embodiment, the intra inhibitory domain which is part of the engineered inhibitory membrane protein (IMP) complex is the PD-1 protein (also called "Programmed cell death protein 1" or CD279).

According to a preferred embodiment, the dimerization binding domains are FKBP or FRB. According to a more preferred embodiment, said first and second binding domains have at least 80% identity with SEQ ID NO 14 and SEQ ID NO 15.

According to the invention, the inhibitory membrane (IMP) complex corresponds to at least one transmembrane chimeric protein; the latter containing at least one intracellular inhibitory signaling domain and one binding domain.

In one embodiment, the IMP complex involves one transmembrane chimeric protein, comprising at least one inhibitory signaling domain and a first binding domain that can bind to a second binding domain borne on the Chimeric Antigen Receptor (CAR) through the presence of a soluble compound (FIGS. 1 and 2).

These inhibitory signaling domains may belong to the "immune checkpoints" molecules effectively serve as "brakes" to down-modulate or inhibit an immune response.

Amongst these inhibitory signaling domains, some can be "functional" inhibitors because they can interact by (reversible) post-translational modification, such as by dephosphorylation mechanism (i.e. for PD-1), some can be "structural" inhibitors, such as antibodies (preferably an humanized intrabodies) which can physically block the protein.

According to the invention, these inhibitory signaling domains can be from, but are not limited to, Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as VSTM3, accession number: NM_173799), LAIR1 (also known as CD305, GenBank accession number: CR542051.1, (Meyaard, Adema et al. 1997)), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7 (Nicoll, Ni et al. 1999), SIGLEC9 (Zhang, Nicoll et al. 2000; Ikehara, Ikehara et al. 2004), TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF (Quigley, Pereyra et al. 2010), GUCY1A2, GUCY1A3, GUCY1B2, GUCY1B3, which proteins have been described as having ability to inhibit immune cells activation.

A particular preferred inhibitory signaling domain is from PD-1 and preferably comprises the amino acid sequence that has at least 80% sequence identity with SEQ ID NO.23.

Beside these immune checkpoints (such as PD-1), other inhibitors towards the immune response are encompassed within the invention: for instance, some cytokines.

According to an alternative embodiment, the IMP complex of the invention involves two transmembrane chimeric proteins, each comprising a binding domain that may be bound by a soluble compound (FIG. 3).

In accordance with one preferred embodiment, inhibitory signaling domains are the interleukin IL-10Rα and IL-10Rβ monomers, and preferably comprise the amino acid sequences that have at least 80% sequence identity with SEQ ID NO.59 and SEQ ID NO.60 respectively.

In general, IL-10R is composed of two subunits to be active: IL-10Rα (Ref. Uniprot: Q13651; RefSeq: NP_001549); and IL-10R13 (Ref. Uniprot: Q08334, RefSeq: NM_000628 for the human species). According to Satoshi et al. 1999), the inhibitory action of IL-10 on immune cells—such as the CAR-lymphocytes T of the invention—is obtained via the inhibition of expression of both interferon α- and interferon γ-induced genes.

Typically, IL10RA/IL10B polypeptides of the invention respectively comprise the amino acid sequence has at least 80% sequence identity with SEQ ID NO: 59 and SEQ ID NO: 60 respectively.

The inhibitory action of the IL-10R occurs after the dimerization of the IL10RA/IL10B polypeptides and leads to the inhibition of cytokines such as interferon IFN-γ, IL-2, IL-3 or TNF-α involving the JAK-STAT signaling pathway (Finbloom et al. 1995). Therefore, the functional IL-10R dimer can indirectly monitor or shunt the activation of an immune cell by the Chimeric Antigen Receptor (CAR).

In addition to IL-10R interleukin, other examples of switches can be used according to the system presented in FIG. 3, as long as they are negative regulators on immune cells and they are multimeric. Amongst them, one can find TGF-β (transforming growth factor beta), VEGF (Vascular endothelial growth factor), or the apoptosis inducing-multimeric receptors such as TNFR (tumor necrosis factor receptor) or DR3 (Death-receptor-3).

In view of the preceding, one of the particularities of an IMP according to the invention comprising an inhibitory signaling domain such as IL-10R is that this inhibitory system does not require any component from the CAR to initiate its action. Consequently, it can be used in combination with any CAR regardless its specificity and architecture, to down regulate activated CAR T-cell, acting as a "universal" switch. Subsequently, the invention contemplates the combined use of a CAR and a molecular switch as previously described whatever be the antigen targeted by the CAR.

The transmembrane part of the IMP complex is chosen amongst not only those used for the Chimeric Antigen Receptor (CAR) as presented in the following section "Chimeric Antigen Receptor" but also by many others which appear suitable for the skilled person in the construction of such multipart polypeptide.

The binding domain of the IMP complex according to the invention is a protein which can bind to a soluble compound which, via the signaling domain, mediates a modulation on the activation of the CAR. Preferably, the system of the invention is composed of two binding domains which can co-localized or dimerized by the intervention of soluble compound.

The binding domain of the present invention is preferably a dimerization domain.

According to one or the other above embodiments, either these two binding domains are borne on two different IMPs, or one binding domain is part of one IMP and the other on the CAR, depending of the type and action of the inhibitory signaling domain used.

According to a preferred embodiment, both binding domains interact with the same soluble compound.

By "co-localization" or "dimerization" (also called "chemically induced dimerization" or CID) of the two binding domains is meant that the two proteins come close together to make is a macromolecular complex, non-covalently bound, in the presence of a certain small molecule, enzyme or other dimerizing agent. This CID system allows the manipulation of signaling pathways in the case of the present invention.

According to one embodiment, the binding or dimerization domains are extracellular. This configuration is favored/ more favorable when the small molecule acting as dimerizing agent is not immunogenic and/or cannot come easily across the membrane of the immune cell. The first and second binding or dimerization domains can be borne respectively on the IMP protein and on the CAR structure (FIG. 1), or both on two separate 2 polypeptides from the IMP complex (FIG. 3) depending of the inhibiting signaling domain used (by instance, IL10R versus PD-1). In the first situation, where one binding domain is present on the CAR structure, the action of the inhibitory signaling domain will be directly on the CAR, in contrast to the second situation, where the IMP complex has an inhibitory function on the immune cell activation that is deemed independent from the activation by the CAR.

According to the alternative embodiment, the binding or dimerization domains are intracellular. This conformation applies when one binding or dimerization domain is part of one IMP (having an inhibitory signaling domain) and a second one is part of the CAR (FIG. 2). This chemical induction dimerization (CID) strategy will be preferred, for instance, when potential immunogenic small molecules are used.

The localization of the binding/dimerization domain on the alpha chain may be advantageous for a structural or conformational reason.

Still within the scope of the invention, dimerization domains are the preferred binding domains, therefore one binding domain binds to another domain, when they are put in presence of a dimerizing agent.

Amongst binding domains which may be contemplated, one can find number of couples such as FKBP/FKBP with the dimerizing agent FK1012 (Spencer et al, 1993); FKBP/CAN with the dimerizing agent FK506 (Ho et al, 1996); FKBP/CyP-Fas with the dimerizing agent FKCsA (Belshaw et al, 1996); FKBP/FRB with the dimerizing agent rapamycin (Rivera et al, 1996); GyrB/GyrB with the dimerizing agent coumermycin (Farrar et al, 1996); GAI/GID1 with the dimerizing agent gibberellin (Miyamoto et al, 2012). In the last publication, the system has been shown functioning not only in higher plant but in mammalian cells.

According to a preferred embodiment, the binding domains are FKBP/FRB, and the dimerizing agent is a rapalog, and according to a more preferred embodiment, the rapalog is rapamycin.

In accordance with particular embodiments, the binding domains FKBP/FRB are polypeptides comprising the amino acid sequence that has at least 80% sequence identity with SEQ ID NO:14 and SEQ ID NO: 15 respectively.

According to one embodiment, the present invention relates to a retroviral vector comprising the polynucleotide as described previously.

Soluble Compounds

By «soluble compound» is meant compounds that will be soluble in the serum of a patient, so that it will not precipitate and will act on the various engineered immune cells present in patient's blood circulation. A soluble compound according to the invention is preferably a small molecules", but may also be bi-specific antibodies. A "small molecule", as used herein, is a low molecular weight (<2000 daltons) organic compound. Non-limiting examples of small molecules which find application in the present invention include the macrolide rapamycin and its analogs, also known as "rapalogs", such as AP21967, Deforolimus (AP23573), everolimus (RAD001), and temsirolimus (CCI-779). Other non-limiting examples of small molecules which find application in the present invention include tacrolimus (FK506), FK506 derivatives, such as FK1012, FK506 analogs, such as AP1903. Yet other non-limiting examples of small molecules which find application in the present invention include coumermycin, gibberellin, HaXs, AP1510, AP20187 and AP21967. These "small molecules" can rapidly diffuse across cell membranes so that they can reach intracellular sites of action and to bind to a specific protein; they act as an effector, modifying the activity of function of the protein. Libraries of such compounds can be found, for instance, in the Small Molecule Libraries at nlm.nih.gov.

Amongst preferred small molecules, the ones which are particularly suited to the invention are the agents able to dimerize binding domains, called also dimerizing agents, such as rapalogs.

Rapalogs correspond to rapamycin analogs, including rapamycin (sirolimus), CCI779 (temsirolimus) and RAD001 (everolimus). Rapamycin is a macrocyclic antibiotic produced by the bacterium *Streptomyces hygroscopicus* found in the soil of Easter Island. Rapamycin was discovered as a potent antifungal agent, but it also exhibited what was at first considered to be an undesirable immunosuppressive effect, which subsequently led to its development as a clinically useful drug. Amongst the "soluble compounds" envisioned by the invention, one may also contemplate the use of antibodies, and more particularly bispecific and monoclonal antibodies. Like the small molecules and dimerizing agents, bispecific monoclonal antibodies are designed in such a way that their epitopes can bind simultaneously both binding domains borne on IMP complex and/or the CAR structure. Their bindings generally allow co-localization of the inhibitory signaling domains of the IMP complex and/or the CAR, and consequently a modulated action on the CAR.

As few examples, preferred bispecific monoclonal antibodies can be directed to an epitope of the FRB protein and one of the FKBP protein; or to two different epitopes of the FKBP protein; or to an epitope on the KBP protein and one on the CAN protein; or to an epitope on the FKBP protein and one on the CyP-Fas protein; or to two different epitopes of the GyrB protein; or to one epitope on the GAI and one of the GID1 protein. Methods for obtaining bi-specific monoclonal antibodies are well known in the art (Springer T. A, 1985).

Chimeric Antigen Receptors

The present invention aims to produce engineered immune cells in which the level of activation can be modulated through the IMP/CAR system. In order to allow this modulation, the present invention provides with specific design for the production of Chimeric Antigen Receptors (CAR) which are more prompt to interact with the IMP complex, either directly (FIGS. 1-2) or indirectly (FIG. 3).

In general, CAR consists of an extracellular single chain antibody (scFv) fused to the intracellular signaling domain of the T-cell antigen receptor complex zeta chain (scFv:ζ) and have the ability, when expressed in T-cells, to redirect antigen recognition based on the monoclonal antibody's specificity as described elsewhere (WO2010025177A, WO 2012079000A WO2013126712A, EP2126054A) Several examples of CAR which may be used in the present invention is a CAR directing against CD123 (clones #43 and #32716 from Cellectis), CS1 and TPBG (5T4) and can comprise as non-limiting example the amino acid sequences: SEQ ID NO:2, SEQ ID NO.3, SEQ ID NO.4 and SEQ ID NO.5.

Recent advances in the immunophenotyping of AML cells have revealed several AML associated cell surface antigens that may act as targets for future therapies. The interleukin 3 receptor alpha chain (IL-3Rα; CD123—NCBI reference: NP_001254642) has been identified as a potential immunotherapeutic target since it is over-expressed on AML tumor cells compared to normal hematopoietic stem cells. Additionally, two phase I trials for CD123-specific therapeutics have been completed with both drugs displaying good safety profiles (ClinicalTrials.gov ID: NCT00401739 and NCT00397579).

One candidate antigen of immunotherapies for solid tumors, including the colorectal, ovarian and gastric and also for non-solid tumors such as childhood acute lymphoblastic leukemia (ALL) is the trophoblast glycoprotein, also known as TPBG or 5T4 (UniProt: Q13641). 5T4 is often referred to as an oncofetal antigen due to its expression in foetal trophoblast (where it was first discovered) or trophoblast glycoprotein (TPBG). 5T4 protein is an N-glycosylated transmembrane 72 kDa glycoprotein containing seven leucine-rich repeat regions (Hole et al, 1988). The 5T4 antigen was found to be expressed in number of carcinoma including gastric (Starzynska et al. 1995), ovarian and carcinoma (Wrigley et al. 1995). Also, 5T4 oncofetal antigen is expressed in high risk of relapse childhood pre-B acute lymphoblastic leukemia (Castro et al. 2012). It has very limited expression in normal tissue but is widespread in malignant tumors throughout their development (Carsberg et al. 1995).

CS1 (Gene ref: CS1 UNQ576/PRO1138, Uniprot ref: Q9NQ25) is a cell surface glycoprotein belonging to the CD2 subset of the immunoglobulin superfamily (IgSF) and is highly expressed by multiple myeloma cells, but minimally expressed by normal cells (Chu et al. 2013). The new Chimeric Antigen Receptor architectures according to the invention include an additional binding domain, distinct from that antigen recognition domain directed against a component present on the target cell, and that will be reactive with the same soluble component that acts on the IMP protein.

Single chain CAR according to the invention is basically a conventional single chain generation CAR which contains in supplement a binding (or dimerization) domain to the soluble molecule.

Depending of the CID strategy used, the binding (or dimerization) domain may be located extracellularly or intracellularly.

Both $2^{nd}$ generation CAR (no combination of co-stimulatory molecules) and $3^{rd}$ generation CARs (combination of co-stimulatory molecules) are contemplated in the scope of the present invention.

In one configuration of the present invention where the binding (or dimerization) domain is extracellular, a CAR according to the invention can contain one or several of the following components:

(a) a signal sequence and one of the 2 antigen-specific targeting regions (either the heavy chain or the light chain of scFV);
(b) optionally a linker;
(c) a binding (or dimerizing) domain
(d) the remaining antigen-specific targeting region (either the heavy chain or the light chain of scFV);
(e) optionally a hinge (or interspacer);
(f) a transmembrane domain;
(g) an intracellular domain containing at least one co-stimulatory molecule.

From the above structure, the position of the binding (or dimerization) domain relative to that the other extracellular components may change.

The invention may also involve a multi chain CAR as previously described by the applicant in WO 2014039523A or in PCT/EP2014/059662.

Both multichain Chimeric Antigen Receptor (mcCAR) and single chain Chimeric Antigen Receptor (scCAR) configurations are encompassed in the scope of the invention. Multi chain CAR structure according to the invention can be adapted from previous multi chain CAR, by introducing a binding (or dimerization) domain, which is sensitive to a soluble compound.

Depending of the CID strategy used, the binding domain may be located extracellularly or intracellularly as shown in FIGS. 1-2.

In the situation where the multi chain CAR is derived from a Fc receptor as described in WO 2014039523A, the binding (or dimerization) domain may be positioned either on the alpha chain (FCεRα), beta chain FCεRβ) or gamma chain (FCεRγ).

According to a particular embodiment, the engineered immune cells are transfected by a multi-chain based chimeric antigen receptor (CAR) wherein one of the dimerization domains is part of the α-chain.

Such mcCAR can comprise one or a subset of the following components:

an alpha chain (FCεRα) containing:
(a) a signal sequence and an antigen-specific targeting region;
(b) a binding (or dimerization) domain;
(c) an extracellular spacer domain (hinge);
(d) a transmembrane domain;
a beta chain (FCεRβ) containing:
(a) a signal sequence;
(b) an extracellular spacer domain (hinge);
(c) a transmembrane domain;
(d) a co-stimulatory ligand;
a gamma chain (FCεRγ) containing:
(a) a signal sequence;
(b) an extracellular spacer domain (hinge);
(c) a transmembrane domain;
(d) a signal transducing domain.

According to a another particular embodiment, the engineered immune cells are transfected by a multi-chain based chimeric antigen receptor (mcCAR) wherein one of the dimerization domains is part of the γ-chain; such mcCAR can comprise one or a subset of the following components:

an alpha chain (FCεRα) containing:
(a) a signal sequence and an antigen-specific targeting region;
(b) an extracellular spacer domain (hinge);
(c) a transmembrane domain;
(d) optionally, one or more intracellular domain;
a beta chain (FCεRβ) containing:
(a) a signal sequence;
(b) an extracellular spacer domain (hinge);
(c) a transmembrane domain;
(d) a co-stimulatory ligand;
a gamma chain (FCεRγ) containing at least:
(a) a signal sequence;
(b) a binding (or dimerization) domain;
(c) an extracellular spacer domain (hinge);
(d) a transmembrane domain;
(e) a signal transducing domain.

The term "extracellular ligand-binding domain" as used herein is defined as an oligo- or polypeptide that is capable of binding a ligand. Preferably, the domain will be capable of interacting with a cell surface molecule.

Said extracellular ligand-binding domain is a single chain antibody fragment (scFv) comprising the light ($V_L$) and the heavy ($V_H$) variable fragment of a target antigen specific monoclonal antibody specific to a particular target antigen joined by a flexible linker. Binding domain specific to a specific antigen other than scFv can also be used for pre-defined targeting of lymphocytes, such as camelid or shark (VNAR) single-domain antibody fragments or receptor ligands like a vascular endothelial growth factor polypeptide, an integrin-binding peptide, heregulin or an IL-13 mutein, antibody binding domains, antibody hypervariable loops or CDRs as non-limiting examples.

Said first transmembrane polypeptide may further comprise a stalk region between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence. In a preferred embodiment said stalk region is a part of human CD8 alpha chain (e.g. NP_001139345.1).

Thus, the expression of multi-chain CAR in immune cells results in modified cells that selectively and eliminate defined targets, including but not limited to malignant cells carrying a respective tumor-associated surface antigen or virus infected cells carrying a virus-specific surface antigen, or target cells carrying a lineage-specific or tissue-specific surface antigen.

A multi-chain CAR according to the invention can comprise several extracellular ligand-binding domains, to simultaneously bind different elements in target thereby augmenting immune cell activation and function. The extracellular ligand-binding domains may be placed in tandem on the same transmembrane polypeptide, and optionally can be separated by a linker. In another embodiment, said different extracellular ligand-binding domains can be placed on different transmembrane polypeptides composing the multi-chain CAR. The present invention may relate to a population of multi-chain CARs comprising each one different extracellular ligand binding domains.

Also, the invention may encompass engineered immune cells which express at the surface of said cell a population of multi-chain CAR each one comprising different extracellular ligand binding domains. The present invention may relate to engineered immune cell in which are introduced polynucleotides encoding polypeptides composing a population of multi-chain CAR each one comprising different extracellular ligand binding domains. By population of multi-chain CARs, it is meant at least two, three, four, five, six or more multi-chain CARs each one comprising different extracellular ligand binding domains. The different extracellular ligand binding domains according to the present invention may simultaneously bind different elements in target thereby augmenting immune cell activation and function.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines. Thus, the term "signal transducing domain" refers to the portion of a protein which transduces the effector signal function signal and directs the cell to perform a specialized function. Examples of signal transducing domain for use in multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

The signal transduction domain of the multi-chain CAR of the present invention may comprise a co-stimulatory signal molecule. A co-stimulatory molecule is a cell surface molecule other than an antigen receptor or their ligands that is required for an efficient immune response.

"Co-stimulatory ligand" refers to a molecule on an antigen presenting cell that specifically binds a cognate co-stimulatory molecule on a T-cell, thereby providing a signal which, in addition to the primary signal provided by, for instance, binding of a TCR/CD3 complex with an MHC molecule loaded with peptide, mediates a T cell response, including, but not limited to, proliferation activation, differentiation and the like. A co-stimulatory ligand can include but is not limited to CD7, B7-1 (CD80), B7-2 (CD86), PD-L1, PD-L2, 4-1BBL, OX40L, inducible costimulatory ligand (ICOS-L), intercellular adhesion molecule (ICAM, CD30L, CD40, CD70, CD83, HLA-G, MICA, M1CB, HVEM, lymphotoxin beta receptor, 3/TR6, ILT3, ILT4, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as but not limited to, CD27, CD28, 4-IBB, OX40, CD30, CD40, PD-1, ICOS, lymphocyte function-associated antigen-1 (LFA-1), CD2, CD7, LTGHT, NKG2C, B7-H3, a ligand that specifically binds with CD83.

A "co-stimulatory molecule" refers to the cognate binding partner on a T-cell that specifically binds with a co-stimulatory ligand, thereby mediating a co-stimulatory response by the cell, such as, but not limited to proliferation. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

Said signal transducing domain may be a TNFR-associated Factor 2 (TRAF2) binding motifs, intracytoplasmic tail of costimulatory TNFR member family. Cytoplasmic tail of costimulatory TNFR family member contains TRAF2 binding motifs consisting of the major conserved motif (P/S/A)X(Q/E)E) or the minor motif (PXQXXD), wherein X is any amino acid. TRAF proteins are recruited to the intracellular tails of many TNFRs in response to receptor trimerization.

The signal transduction domain of the multi-chain CAR of the present invention may comprise a part of co-stimulatory signal molecule which is 4-1BB (GenBank: AAA53133).

The distinguishing features of appropriate transmembrane polypeptides comprise the ability to be expressed at the surface of an immune cell, in particular lymphocyte cells or Natural killer (NK) cells, and to interact together for directing cellular response of immune cell against a predefined target cell. The different transmembrane polypeptides of the multi-chain CAR of the present invention comprising an extracellular ligand-biding domain and/or a signal transducing domain interact together to take part in signal transduction following the binding with a target ligand and induce an immune response. The transmembrane domain can be derived either from a natural or from a synthetic source. The transmembrane domain can be derived from any membrane-bound or transmembrane protein. As non-limiting examples, the transmembrane polypeptide can be a subunit of the T cell receptor such as α, β, γ or, polypeptide constituting CD3 complex, IL2 receptor p55 (α chain), p75 (β chain) or γ chain, subunit chain of Fc receptors, in particular Fcγ receptor III or CD proteins. Alternatively the transmembrane domain can be synthetic and can comprise predominantly hydrophobic residues such as leucine and valine.

The multi-chain CAR may comprise a transmembrane polypeptide derived from a FcεRI chain, such as a FcεRI α chain, in which the extracellular domain is replaced by an extracellular ligand-binding domain.

Said multi-chain CAR may comprise a part of FcεRI alpha chain and a part of FcεRI beta chain or variant thereof such that said FcεRI chains spontaneously dimerize together to form a dimeric Chimeric Antigen Receptor. The multi-chain Chimeric Antigen may comprise a part of FcεRI alpha chain and a part of a FcεRI gamma chain or variant thereof such that said FcεRI chains spontaneously trimerize together to form a trimeric Chimeric Antigen Receptor. Another alternative is a multi-chain Chimeric Antigen Receptor which may comprise a part of FcεRI alpha chain, a part of FcεRI beta chain and a part of FcεRI gamma chain or variants thereof such that said FcεRI chains spontaneously tetramerize together to form a tetrameric Chimeric Antigen Receptor.

Polynucleotides, Vectors:

The present invention also relates to polynucleotides, vectors encoding the above described modulable/tunable IMP complex and CAR polypeptide structures according to the invention. The present invention provides polynucleotides, including DNA and RNA molecules that encode the transmembrane polypeptides disclosed herein that can be included in the multi-chain or mono-chain CAR. In particular, the invention relates to a polynucleotide comprising a nucleic acid sequence encoding at least one transmembrane polypeptide composing the multi-chain/mono-chain CAR as described above. More particularly the invention relates to a polynucleotide comprising two or more nucleic acid sequences encoding transmembrane polypeptides composing the multi-chain/mono-chain CAR as described above.

The polynucleotide may consist in an expression cassette or expression vector (e.g. a plasmid for introduction into a bacterial host cell, or a viral vector such as a baculovirus vector for transfection of an insect host cell, or a plasmid or viral vector such as a lentivirus for transfection of a mammalian host cell).

According to one embodiment, the transfection realized during the method of the invention for producing an engineered immune is performed using of a lentiviral or a retroviral vector for a stable integration of the CAR and/or IMP into the immune cells genome According to another embodiment, said transfection is performed by the use of CAR/IMP encoding polycistronic mRNA for a transitory expression.

The different nucleic acid sequences can be included in one polynucleotide or vector which comprises a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

To direct, transmembrane polypeptide such as FcεR into the secretory pathway of a host cell, a secretory signal sequence (also known as a leader sequence, prepro sequence or pre sequence) is provided in polynucleotide sequence or vector sequence. The secretory signal sequence may be that of FcεR, or may be derived from another secreted protein (e.g., t-PA) or synthesized de novo. The secretory signal sequence is operably linked to the transmembrane nucleic acid sequence, i.e., the two sequences are joined in the correct reading frame and positioned to direct the newly synthesized polypeptide into the secretory pathway of the host cell. Secretory signal sequences are commonly positioned 5' to the nucleic acid sequence encoding the polypeptide of interest, although certain secretory signal sequences may be positioned elsewhere in the nucleic acid sequence of interest (see, e.g., Welch et al., U.S. Pat. No. 5,037,743; Holland et al., U.S. Pat. No. 5,143,830). In a preferred embodiment the signal peptide comprises the residues 1 to 25 of the FcεRI alpha chain (NP_001992.1).

Those skilled in the art will recognize that, in view of the degeneracy of the genetic code, considerable sequence variation is possible among these polynucleotide molecules. Preferably, the nucleic acid sequences of the present invention are codon-optimized for expression in mammalian cells, preferably for expression in human cells. Codon-optimization refers to the exchange in a sequence of interest of codons that are generally rare in highly expressed genes of a given species by codons that are generally frequent in highly expressed genes of such species, such codons encoding the amino acids as the codons that are being exchanged.

Engineered Immune Cells

The present invention also relates to an isolated immune cell which is a Chimeric Antigen Receptor (CAR) having at least an engineered (IMP) inhibitory membrane protein.

The immune cell to be used in accordance of the present invention may, for instance, be a T-cell, a cytotoxic T cell, a regulatory T cell or a NK cell.

According to a particular embodiment, the immune cell is a T-cell.

Said engineered immune cells may be infused into a patient upon the step of IMP complex transfection and before the step of incubation with the external ligand (such as a surface antigen).

According to certain embodiment, the present invention provides a modulable/tunable CAR immune cell which is also engineered to be allogeneic. This non-autologous characteristic is particularly useful for the development of a standardized therapy in which allogeneic therapeutic cells could be pre-manufactured and available for immediate administration to patients.

Such methods comprise the step of inactivating at least one gene encoding a T-Cell Receptor (TCR) component, in particular TCRα, TCRβ genes.

The step of inactivation of, for instance the TCR component may be performed at any time during the manufacturing of the modulable/tunable CAR-engineered immune cell of the invention. However, it is preferable to perform it before the transfection steps in order to not interact too much on the growth/expansion of the cells.

Is also encompassed in the scope of the present invention, the possibility to engineer further the immune cells (i.e T-cells) to make them resistant to chemotherapy drugs, such as purine nucleotide analogs (clofarabine, flubarabine . . . ).

One way particularly suitable according to the invention to realize these gene inactivations is the use of exonucleases such as TALE nucleases. This can be performed such as described elsewhere (WO2012138927 and prior art cited in the next section "DEFINITIONS").

Methods of Engineering Immune Cells

The present invention also relates to a method for producing an modulable/tunable CAR-engineered immune cell comprising two steps of transfection, the first one being of at least a first polynucleotide encoding a Chimeric Antigen Receptor (CAR); and the second one of a second polynucleotide having the inhibitory membrane protein (IMP) complex, and finally a step of selection of immune cells having co-expressed the said polynucleotides.

In another embodiment, the present invention relates to a method of producing engineered immune cells for immunotherapy comprising introducing into said cells the different polypeptides composing said CAR/IMP and expanding said cells. In a preferred embodiment, said polynucleotides are included in lentiviral vectors in view of being stably expressed in the cells. Such lentivirus vectors may comprise a marker gene such as GFP and/or firefly luciferase.

In still another embodiment, said transfection step a) in the method of producing engineered immune cells is performed by insertion of the CAR and IMP polynucleotides via recombination process, preferably homologous. This embodiment has the advantage to a more specific integration, and less ectopic insertions. In a preferred embodiment, such site-specific insertion is made by expressing an exogenous specific-endonuclease and the addition of at least one polynucleotide template encoding said CAR/IMP peptides. As an example, the site-specific insertion may be done in the TCR gene, which allows reducing or disabling TCR (T cell receptor) function, with the effect of rendering the immune cells, in particular T-cells less alloreactive. This later aspect is particular sought to reduce the risk of GVHD in a context of immunotherapy where the immune cells are allogeneic.

Specific nucleases usually create double-stranded break (DSBs) at desired locations in the genome, and harness the cell's endogenous mechanisms to repair the induced break by natural processes of homologous recombination (HR) and non-homologous end-joining (NHEJ). Engineered nucleases such as zinc finger nucleases (ZFNs), Transcription Activator-Like Effector Nucleases (TALENs), engineered homing endonucleases and RNA or DNA guided endonucleases, such as CRISPR/Cas, CPF1 or Argonaute systems, are particularly appropriate to carry out gene insertion or inactivation according to the present invention.

Among other references, TALEN and Cas9 systems are respectively described in WO 2013/176915 and WO 2014/191128. The Zinc-finger nucleases (ZFNs) have been initially described in Kim, Y G; Cha, J.; Chandrasegaran, S. (1996). "Hybrid restriction enzymes: zinc finger fusions to Fok I cleavage domain". Proc Natl Acad Sci USA 93 (3): 1156-60.

Delivery Methods

The different methods described above involve expressing a protein of interest such as IMP complex, Chimeric Antigen Receptor (CAR) into a cell. Polypeptides may be expressed in the cell as a result of the introduction of polynucleotides encoding said polypeptides into the cell. Alternatively, said polypeptides could be produced outside the cell and then introduced thereto. Methods for introducing a polynucleotide construct into cells are known in the art and include as non limiting examples stable transformation methods wherein the polynucleotide construct is integrated into the genome of the cell, transient transformation methods wherein the polynucleotide construct is not integrated into the genome of the cell and virus mediated methods. Said polynucleotides may be introduced into a cell by for example, recombinant viral vectors (e.g. retroviruses, adenoviruses), liposome and the like. For example, transient transformation methods include for example microinjection, electroporation or particle bombardment. Said polynucleotides may be included in vectors, more particularly plasmids or virus, in view of being expressed in cells. Said plasmid vector can comprise a selection marker which provides for identification and/or selection of cells which received said vector. Different transgenes can be included in one vector. Said vector can comprise a nucleic acid sequence encoding ribosomal skip sequence such as a sequence encoding a 2A peptide. 2A peptides, which were identified in the Aphthovirus subgroup of picornaviruses, causes a ribosomal "skip" from one codon to the next without the formation of a peptide bond between the two amino acids encoded by the codons (see Donnelly et al., J. of General Virology 82: 1013-1025 (2001); Donnelly et al., J. of Gen. Virology 78: 13-21 (1997); Doronina et al., Mol. And. Cell. Biology 28(13): 4227-4239 (2008); Atkins et al., RNA 13: 803-810 (2007)). By "codon" is meant three nucleotides on an mRNA (or on the sense strand of a DNA molecule) that are translated by a ribosome into one amino acid residue. Thus, two polypeptides can be synthesized from a single, contiguous open reading frame within an mRNA when the polypeptides are separated by a 2A oligopeptide sequence that is in frame. Such ribosomal skip mechanisms are well known in the art and are known to be used by several vectors for the expression of several proteins encoded by a single messenger RNA.

Polynucleotides encoding polypeptides according to the present invention can be mRNA which is introduced directly into the cells, for example by electroporation. The inventors determined the optimal condition for mRNA electroporation in T-cell. The inventor used the cytoPulse technology which allows, by the use of pulsed electric fields, to transiently permeabilize living cells for delivery of material into the cells. The technology, based on the use of PulseAgile (BTX Havard Apparatus, 84 October Hill Road, Holliston, Mass. 01746, USA) electroporation waveforms grants the precise control of pulse duration, intensity as well as the interval between pulses (U.S. Pat. No. 6,010,613 and International PCT application WO2004083379). All these parameters can be modified in order to reach the best conditions for high transfection efficiency with minimal mortality. Basically, the first high electric field pulses allow pore formation, while subsequent lower electric field pulses allow to move the polynucleotide into the cell.

Activation and Expansion of T-Cells

Whether prior to or after genetic modification of the T-cells, the T-cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. T-cells can be expanded in vitro or in vivo. Generally, the T cells of the invention are expanded by contact with an agent that stimulates a CD3 TCR complex and a co-stimulatory molecule on the surface of the T-cells to create an activation signal for the T-cell. For example, chemicals such as calcium ionophore A23187, phorbol 12-myristate 13-acetate (PMA), or mitogenic lectins like phytohemagglutinin (PHA) can be used to create an activation signal for the T-cell. As non limiting examples, T-cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T-cells, a ligand that binds the accessory molecule is used. For example, a population of T-cells can be contacted with an anti-CD3 antibody and an anti-CD28 antibody, under conditions appropriate for stimulating proliferation of the T-cells. To stimulate proliferation of either CD4+ T-cells or CD8+ T-cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell.

Conditions appropriate for T-cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, IL-21 and TNF—or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T-cells. Antibiotics, e.g., penicillin and streptomycin, are included only in experimental cultures, not in cultures of cells that are to be infused into a subject. The target cells are maintained under conditions necessary to support growth; for example, an appropriate temperature (e.g., 37° C.) and atmosphere (e.g., air plus 5% CO2). T cells that have been exposed to varied stimulation times may exhibit different characteristics.

Therapeutic Applications

In another embodiment, isolated immune cells obtained as previously described can be used in adoptive cell immunotherapy.

According to an alternative embodiment, said immunes cells are recovered from the patient himself. According to one embodiment, said immune cells are recovered from donors.

According to another embodiment, said immune cells are rendered allogeneic in order to prepare batch of cells which can be administered to a panel of patients and not only the donor himself. This feature, which represents a real advantage in economic terms, is compulsory to drop the risk of graft rejection.

To achieve this goal, the immune cells such as T-cells undergo a knock-out (KO) in the T-cell receptor (TCR) gene that is responsible for recognizing antigens bound to major histocompatibility complex (MHC) molecules. By inactivating the TCR gene, the latter cannot engage with antigenic peptide and MHC (peptide/MHC), and therefore there is not activation of the T lymphocyte According to an embodiment, the inactivation of the TCR gene by knock-out (KO) is performed by endonucleases, preferably by TALE-nucleases.

In particular, said T-cells according to the present invention can be used for treating cancer, infections or auto-immune disease in a patient in need thereof.

In another aspect, the present invention relies on methods for treating patients in need thereof, said method comprising at least one of the following steps:

(a) providing an isolated T-cell obtainable by any one of the methods previously described;

(b) Administrating said cells to said patient.

Said T-cells of the invention can undergo robust in vivo expansion and can persist for an extended amount of time.

Said treatment can be ameliorating, curative or prophylactic. This may be done under standard protocols and reproduced as many times as needed. The resulting modified T-cells may be administrated to the patient or to one or several patients depending of its availability as an "off the shelf" therapeutic product.

Cells that can be used with the disclosed methods are described in the previous section. Said treatment can be used to treat patients diagnosed with cancer, viral infection and autoimmune disorders. Cancers that may be treated include tumors that are not vascularized, or not yet substantially vascularized, as well as vascularized tumors. The cancers may comprise nonsolid tumors (such as hematological tumors, for example, leukemias and lymphomas) or may comprise solid tumors. Types of cancers to be treated with the allogeneic T-cell resistant to drugs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included. In an embodiment of the present invention, childhood acute lymphoblastic leukemia (ALL) and amyotrophic myeloma leukemia (AML) diseases are typically treated by allogeneic drug resistant T-cells according to the invention. This can be achieved by using drug resistant KO TRAC CD19+ CAR T-cells and drug resistant KO TRAC CD123+ T-cells respectively. "TRAC" refers to "T cell receptor α constant"» and corresponds to TCRα subunit constant gene.

It can be a treatment in combination with one or more therapies against cancer selected from the group of antibodies therapy, chemotherapy, cytokines therapy, dendritic cell therapy, gene therapy, hormone therapy, laser light therapy and radiation therapy.

Said treatment may be administrated into patients undergoing an immunosuppressive treatment, such as cells or population of cells, which have been made resistant to at least one drug agent due to either expression of a drug resistance gene or the inactivation of a drug sensitizing gene. In this aspect, the drug treatment should help the selection and expansion of the T-cells according to the invention within the patient.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, intracranially, by intravenous or intralymphatic injection, or intraperitoneally. In one embodiment, the cell compositions of the present invention are preferably administered by intravenous injection.

The administration of the cells or population of cells can consist of the administration of $10^3$-$10^{10}$ cells per kg body weight, preferably $10^5$ to $10^6$ cells/kg body weight including all integer values of cell numbers within those ranges. The cells or population of cells can be administered in one or more doses. In another embodiment, said effective amount of cells are administered as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

Said effective amount of cells or pharmaceutical composition may be preferably administrated parenterally. Said administration can be an intravenous administration. Said administration can be directly done by injection within a tumor.

Cells may be administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. The T-cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). The cell compositions of the present invention may be administered to a patient in conjunction with (e.g., before, simultaneously or following) bone marrow transplantation, T-cell ablative therapy using either chemotherapy agents such as, fludarabine, external-beam radiation therapy (XRT), cyclophosphamide, or antibodies such as OKT3 or CAMPATH. The cell compositions of the present invention may be administered following 8-cell ablative therapy such as agents that react with CD20, e.g., Rituxan. For example, subjects may undergo standard treatment with high dose chemotherapy followed by peripheral blood stem cell transplantation. Following the transplant, subjects may receive an infusion of the expanded immune cells of the present invention. Expanded cells may be administered before or following surgery.

Pharmaceutical Composition

The isolated T-cells of the present invention may be administered either alone, or as a pharmaceutical composition in combination with diluents and/or with other components. Briefly, pharmaceutical compositions of the present invention may comprise T-cells as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g. aluminum hydroxide); and preservatives. Compositions of the present invention are preferably formulated for intravenous administration. Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials Kit and Vector The present invention encompasses a kit or a vector for engineering immune cells with modulable level of activation, which comprises:
- a first polynucleotide encoding a Chimeric Antigen Receptor (CAR); and
- a second polynucleotide encoding an engineered inhibitory membrane protein (IMP) complex as described above in the "Inhibitory membrane complex" paragraph.

Definitions

In the description above, a number of terms are used extensively. The following definitions are provided to facilitate understanding of the present embodiments.

Amino acid residues in a polypeptide sequence are designated herein according to the one-letter code, in which, for example, Q means Gln or Glutamine residue, R means Arg or Arginine residue and D means Asp or Aspartic acid residue.

Nucleotides are designated as follows: one-letter code is used for designating the base of a nucleoside: a is adenine, t is thymine, c is cytosine, and g is guanine. For the degenerated nucleotides, r represents g or a (purine nucleotides), k represents g or t, s represents g or c, w represents a or t, m represents a or c, y represents t or c (pyrimidine nucleotides), d represents g, a or t, v represents g, a or c, b represents g, t or c, h represents a, t or c, and n represents g, a, t or c.

As used herein, "nucleic acid" or "nucleic acid molecule" refers to nucleotides and/or polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., enantiomeric forms of naturally-occurring nucleotides), or a combination of both. Nucleic acids can be either single stranded or double stranded.

By "gene" is meant the basic unit of heredity, consisting of a segment of DNA arranged in a linear manner along a chromosome, which codes for a specific protein or segment of protein, small RNA and the like. A gene typically includes a promoter, a 5' untranslated region, one or more coding sequences (exons), optionally introns, a 3' untranslated region. The gene may further comprise a terminator, enhancers and/or silencers.

By "genome" it is meant the entire genetic material contained in a cell such as nuclear genome, chloroplastic genome, mitochondrial genome.

By "mutation" is intended the substitution, deletion, insertion of one or more nucleotides/amino acids in a polynucleotide (cDNA, gene) or a polypeptide sequence. Said mutation can affect the coding sequence of a gene or its regulatory sequence. It may also affect the structure of the genomic sequence or the structure/stability of the encoded mRNA.

"TALE-nuclease" refers to engineered proteins resulting from the fusion of a DNA binding domain typically derived from Transcription Activator like Effector proteins (TALE), with an endonuclease catalytic domain. Such catalytic domain is preferably a nuclease domain and more preferably a domain having endonuclease activity, like for instance I-TevI, ColE7, NucA and Fok-I. In a particular embodiment, said nuclease is a monomeric TALE-Nuclease. A monomeric Nuclease is a nuclease that does not require dimerization for specific recognition and cleavage, such as the fusions of engineered DNA binding domain with the catalytic domain of I-TevI described in WO2012138927. In another particular embodiment, said rare-cutting endonuclease is a dimeric TALE-nuclease, preferably comprising a DNA binding domain fused to FokI. TALE-nuclease have been already described and used to stimulate gene targeting and gene modifications (Boch, Scholze et al. 2009; Moscou and Bogdanove 2009; Christian, Cermak et al. 2010). Such engineered TALE-nucleases are commercially available under the trade name TALEN™ (Cellectis, 8 rue de la Croix Jarry, 75013 Paris, France).

The term "cleavage" refers to the breakage of the covalent backbone of a polynucleotide. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. Double stranded DNA, RNA, or DNA/RNA hybrid cleavage can result in the production of either blunt ends or staggered ends.

By "chimeric antigen receptor" (CAR) it is meant a chimeric receptor which comprises an extracellular ligand-binding domain, a transmembrane domain and a signaling transducing domain.

The term "extracellular ligand-binding domain" as used herein is defined as an oligo- or polypeptide that is capable of binding a ligand. Preferably, the domain will be capable of interacting with a cell surface molecule. For example, the extracellular ligand-binding domain may be chosen to recognize a ligand that acts as a cell surface marker on target cells associated with a particular disease state.

In a preferred embodiment, said extracellular ligand-binding domain comprises a single chain antibody fragment (scFv) comprising the light ($V_L$) and the heavy ($V_H$) variable fragment of a target antigen specific monoclonal antibody joined by a flexible linker. In a preferred embodiment, said scFV is derived from a CD123, 5T4 or CS1 antibody.

The signal transducing domain or intracellular signaling domain of the CAR according to the present invention is responsible for intracellular signaling following the binding of extracellular ligand binding domain to the target resulting in the activation of the immune cell and immune response. Preferred examples of signal transducing domain for use in a CAR can be the cytoplasmic sequences of the T-cell receptor and co-receptors that act in concert to initiate signal transduction following antigen receptor engagement. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. In particular embodiment the signal transduction domain of the CAR of the present invention comprises a co-stimulatory signal molecule. A co-stimulatory molecule is a cell surface molecule other than an antigen receptor or their ligands that is required for an efficient immune response. Co-stimulatory molecules include, but are not limited to an MHC class I molecule, BTLA and Toll ligand receptor. Examples of costimulatory molecules include CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83 and the like.

The CAR according to the present invention is expressed on the surface membrane of the cell. Thus, the CAR can comprise a transmembrane domain. The distinguishing features of appropriate transmembrane domains comprise the ability to be expressed at the surface of a cell, preferably in the present invention an immune cell, in particular lymphocyte cells or Natural killer (NK) cells, and to interact together for directing cellular response of immune cell against a predefined target cell. The transmembrane domain can further comprise a stalk region_between said extracellular ligand-binding domain and said transmembrane domain. The term "stalk region" used herein generally means any oligo- or polypeptide that functions to link the transmembrane domain to the extracellular ligand-binding domain. In particular, stalk region are used to provide more flexibility and accessibility for the extracellular ligand-binding domain. A stalk region may comprise up to 300 amino acids, preferably 10 to 100 amino acids and most preferably 25 to 50 amino acids. Stalk region may be derived from all or part of naturally occurring molecules, such as from all or part of the extracellular region of CD8, CD4 or CD28, or from all or part of an antibody constant region. Alternatively the stalk region may be a synthetic sequence that corresponds to a naturally occurring stalk sequence, or may be an entirely synthetic stalk sequence.

Downregulation or mutation of target antigens is commonly observed in cancer cells, creating antigen-loss escape variants. Thus, to offset tumor escape and render immune cells more specific to target, the CD19 specific CAR can comprise another extracellular ligand-binding domains, to simultaneously bind different elements in target thereby augmenting immune cell activation and function. Examples of CD19 specific CAR are ScFv FMC63 (Kochenderfer J N, Wilson W H, Janik J E, et al. *Eradication of B-lineage cells and regression of lymphoma in a patient treated with autolo-* gous T cells genetically engineered to recognize CD19. Blood 2010; 116(20):4099-410) or ScFv 4G7 CAR (described in the application filed under the number PCT/EP2014/059662). In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the CAR. In another embodiment, the present invention relates to a population of CARs comprising each one different extracellular ligand binding domains. In a particular, the present invention relates to a method of engineering immune cells comprising providing an immune cell and expressing at the surface of said cell a population of CAR each one comprising different extracellular ligand binding domains. In another particular embodiment, the present invention relates to a method of engineering an immune cell comprising providing an immune cell and introducing into said cell polynucleotides encoding polypeptides composing a population of CAR each one comprising different extracellular ligand binding domains. By population of CARs, it is meant at least two, three, four, five, six or more CARs each one comprising different extracellular ligand binding domains. The different extracellular ligand binding domains according to the present invention can preferably simultaneously bind different elements in target thereby augmenting immune cell activation and function. The present invention also relates to an isolated immune cell which comprises a population of CARs each one comprising different extracellular ligand binding domains.

The terms "vector" refer to a nucleic acid molecule capable of transporting another nucleic acid to which it has been linked. A "vector" in the present invention includes, but is not limited to, a viral vector, a plasmid, a RNA vector or a linear or circular DNA or RNA molecule which may consists of a chromosomal, non chromosomal, semi-synthetic or synthetic nucleic acids. Preferred vectors are those capable of autonomous replication (episomal vector) and/or expression of nucleic acids to which they are linked (expression vectors). Large numbers of suitable vectors are known to those of skill in the art and commercially available.

By "delivery vector" is intended any delivery vector which can be used in the present invention to put into cell contact (i.e "contacting") or deliver inside cells or subcellular compartments (i.e "introducing") agents/chemicals and molecules (proteins or nucleic acids) needed in the present invention. It includes, but is not limited to liposomal delivery vectors, viral delivery vectors, drug delivery vectors, chemical carriers, polymeric carriers, lipoplexes, polyplexes, dendrimers, microbubbles (ultrasound contrast agents), nanoparticles, emulsions or other appropriate transfer vectors.

Viral vectors include retrovirus, adenovirus, parvovirus (e. g. adenoassociated viruses), coronavirus, negative strand RNA viruses such as orthomyxovirus (e. g., influenza virus), rhabdovirus (e. g., rabies and vesicular stomatitis virus), paramyxovirus (e. g. measles and Sendai), positive strand RNA viruses such as picornavirus and alphavirus, and double-stranded DNA viruses including adenovirus, herpesvirus (e. g., Herpes Simplex virus types 1 and 2, Epstein-Barr virus, cytomegalovirus), and poxvirus (e. g. vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996).

By "lentiviral vector" is meant HIV-Based lentiviral vectors that are very promising for gene delivery because of their relatively large packaging capacity, reduced immunogenicity and their ability to stably transduce with high efficiency a large range of different cell types. Lentiviral vectors are usually generated following transient transfection of three (packaging, envelope and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration in the DNA of infected cells. By "integrative lentiviral vectors (or LV)", is meant such vectors as non limiting example, that are able to integrate the genome of a target cell. At the opposite by "non-integrative lentiviral vectors (or NILV)" is meant efficient gene delivery vectors that do not integrate the genome of a target cell through the action of the virus integrase.

By cell or cells is intended any eukaryotic living cells, primary cells and cell lines derived from these organisms for in vitro cultures.

By "primary cell" or "primary cells" are intended cells taken directly from living tissue (i.e. biopsy material) and established for growth in vitro, that have undergone very few population doublings and are therefore more representative of the main functional components and characteristics of tissues from which they are derived from, in comparison to continuous tumorigenic or artificially immortalized cell lines. As non limiting examples cell lines can be selected from the group consisting of CHO-K1 cells; HEK293 cells; Caco2 cells; U2-OS cells; NIH 3T3 cells; NSO cells; SP2 cells; CHO-S cells; DG44 cells; K-562 cells, U-937 cells; MRC5 cells; IMR90 cells; Jurkat cells; HepG2 cells; HeLa cells; HT-1080 cells; HCT-116 cells; Hu-h7 cells; Huvec cells; Molt 4 cells.

Because some variability may arise from the genomic data from which these polypeptides derive, and also to take into account the possibility to substitute some of the amino acids present in these polypeptides without significant loss of activity (functional variants), the invention encompasses polypeptides variants of the above polypeptides that share at least 70%, preferably at least 80%, more preferably at least 90% and even more preferably at least 95% identity with the sequences provided in this patent application.

The present invention is thus drawn to polypeptides comprising a polypeptide sequence that has at least 70%, preferably at least 80%, more preferably at least 90%, 95% 97% or 99% sequence identity with amino acid sequence selected from the group consisting of SEQ ID NO: 1 to SEQ ID NO: 60.

"identity" refers to sequence identity between two nucleic acid molecules or polypeptides. Identity can be determined by comparing a position in each sequence which may be aligned for purposes of comparison. When a position in the compared sequence is occupied by the same base, then the molecules are identical at that position. A degree of similarity or identity between nucleic acid or amino acid sequences is a function of the number of identical or matching nucleotides at positions shared by the nucleic acid sequences. Various alignment algorithms and/or programs may be used to calculate the identity between two sequences, including FASTA, or BLAST which are available as a part of the GCG sequence analysis package (University of Wisconsin, Madison, Wis.), and can be used with, e.g., default setting. For example, polypeptides having at least 70%, 85%, 90%, 95%, 98% or 99% identity to specific polypeptides described herein and preferably exhibiting substantially the same functions, as well as polynucleotide encoding such polypeptides, are contemplated.

In addition to a general method for engineering T-cells resistant to purine nucleotide analogs (PNA) drugs, in particular clofarabine and fludarabine, by endonuclease inactivation of dcK gene(s).

General Methods

Primary Cells

Peripheral blood mononuclear cells are isolated by density gradient centrifugation from buffy coats from healthy volunteer donors (Etablissement Francais du Sang). T lymphocytes are then purified using the EasySep human T cell enrichment kit (Stemcell Technologies), and activated with Dynabeads Human T-Activator CD3/CD28 (Life Technologies) in X-vivo 15 medium (Lonza) supplemented with 20 ng/ml IL-2 (Miltenyi) and 5% human AB serum (Seralab).

Cell Lines

The CD123-positive cell lines such as KG1a or MOLM13 and CD123-negative cell line such as RPMI-8226 for multiple myeloma (MM) are obtained from the American Type Culture Collection. Typically, the cells are cultured in RPMI 1640 supplemented with 10-20% heat-inactivated FCS, 2 mmol/L L-glutamine and 100 units/ml penicillin, and 100 µg/mL streptomycin.

Synthesis of IMP/CAR Encoding mRNAs

All individual chains of the CAR architecture were amplified by PCR to introduce a T7 promoter and a stop codon sequence prior to mRNA synthesis. mRNA encoding the proteins of interest were in vitro transcribed from the PCR product and polyadenylated using the mMessage mMachine T7 Ultra kit (Life technologies) following the manufacturer's instructions. RNAs were purified with RNeasy columns (Qiagen), eluted in cytoporation medium T and quantified by measuring absorbance at 260 nm using a Nanodrop ND-1000 spectrophotometer. Quality of the RNA was verified on a denaturing formaldehyde/MOPS agarose gel.

Transiently Expression in T Cells

The switch system of the present invention constituted of a CAR and a second polynucleotide encoding an engineered inhibitory membrane protein (IMP) complex are expressed in human T cells after electroporation of polycistronic mRNA. T cells were electroporated with capped and polyadenylated polycistronic mRNA that were produced using the mMESSAGE mMACHINE kit and linearized plasmids as template. The plasmids used as template contained the T7 RNA polymerase promoter followed by a polycistronic DNA sequence encoding the different CAR/IMP variants.

The electroporation of the polycistronic mRNAs into the human T cells is proceeded using the CytoLVT-S device (Cellectis), according to the following protocol: $5 \times 10^6$ T cells preactivated several days (3-5) with anti CD3/CD28 coated beads and IL2 are resuspended in cytoporation buffer T, and electroporated with 45 µg of mRNA. Twenty-four hours after electroporation, human T cells engineered using polycistronic mRNAs encoding the multi-chain CARs are labeled with a fixable viability dye eFluor-780 and a PE-conjugated goat anti mouse IgG F(ab')2 fragment specific, and analysed by flow cytometry.

The live T cells engineered using polycistronic mRNAs express the multi-chain CARs on their surface.

Lenviral Expression in T Cells

In Vitro Screening of CAR-Specific IMP/CAR

The polycistronic genes encoding a CAR and a second polynucleotide encoding an engineered inhibitory membrane protein (IMP) complex are vectorized in human T cells using lentiviral vectors as reported previously. Firstly the cell surface expression profile is assessed over time of the 2 above polynucleotide-encoded peptides in transduced T cells. For that purpose, the anti-CD123 scFv/Fc fusion protein may be used. Typically, it is observed that both peptides are highly expressed on the cell surface 3 days post transduction and remained relatively highly expressed over a 2 weeks period. The capacity of both peptides is then assessed to mediate antigen-dependent T cells activation. To address this issue, activity assays is performed using a CD123-positive cell line (as KG1 or MOLM13), and a CD123-negative cell line (RPMI-8226). It is generally observed that both peptides are able to activate T cells in the presence of CD123-positive cell line but not in the presence of CD123-negative cell line as shown with the results of the degranulation assay, the cytotoxicity assay and the IFNγ secretion assay.

EXAMPLES

Example 1. Assembly of IMPs (Switch-Off Receptors) and Engineered Multi Chain CARs (mcCARs)

Assembly of constructs are done using Golden Gate assembly strategies according to published protocols [such as Engler C, Kandzia R, Marillonnet 5; (2008) "*A one pot, one step, precision cloning method with high throughput capability*", PLoS One. 3(11)]. Switch-off receptors and engineered CARs are thus cloned in separated shuttle cloning plasmid. Non exhaustive examples for assembled constructs are given in the following Table 5; all of the systems presented here are "switch OFF".

Sequences of modules to assemble IMPs (switch-off receptors) are obtained from the SEQ ID NO. 61-64 (extracellular CID binding domain) or 83-98 (intracellular CID binding domain) and from engineered mcCAR with SEQ ID NO.65-76 (extracellular CID binding domain) or 99-106 (intracellular CID binding domain). Their configuration is depicted in the FIGS. 2A and 2B.

TABLE 5

Switch OFF receptors and engineered CARs

| Component | Architecture: Signal sequence Interacting partner Hinge transmembrane intracellular | SEQ ID NO. | Aminoacid sequence |
|---|---|---|---|
| | EXTRA CELLULAR CID BINDING DOMAINS | | |
| IMP complex (switch OFF receptor) | CD8a-ss FKBP CD8a CD8a PD1 | 61 | MALPVTALLLPLALLLHAARPGSGGVQVETISPGDGRTFPKRGQTCVVHYTGMLEDGKKFDSSRDRNKPFKFMLGKQEVIRG WEEGVAQMSVGQRAKLTISPDYAYGATGHPGIIPPHATLVDVELLKLEGSGAPTTTPAPRPPTPAPTIASQPLSLRPEACR PAAGGAVHTRGLDFACDIYIWAPLAGTGVLLLSLVITLYCRSRAARGTIGARRTGQPLKEDPSAVPVFSVDYGELDFQWRE KTPEPPVPCVPEQTEYATIVFPSGMGTSSPARRGSADGPRSAQPLRPEDGHCSWPLE |
| | CD8a-ss FRB IgG1 4-1BB PD1 | 62 | MALPVTALLLPLALLLHAARPGSGGRVAILWHEMWHEGLEEASRLYFGERNVKGMFEVLEPLHAMMERGPQTLKETSFNQAY GRDLMEAQEWCRKYMKSGNVKDLTQAWDLYYHVFRRIGSGAPEPKSPDKTHTCPPCPAPPVAGPSVFLFPPKPKDTLMIART PEVTCVVVDVSHEDPEVKFNWYVDGVEVHNAKTKPREEQYNSTYRVVSVLTVLHQDWLNGKEYKCKVSNKALPAPIEKTISK AKGQPREPQVYTLPPSRDELTKNQVSLTCLVKGFYPSDIAVEWESNGQPENNYKTTPPVLDSGSFFLYSKLTVDKSRWQQG NVFSCSVMHEALHNHYTQKSLSLSPGKKDIISFFLALTSTALLLFLLFFLTLRFSVVKRGRSAARGTIGARRTGQPLKEDPS AVPVFSVDYGELDFQWREKTPEPPVPCVPEQTEYATIVFPSGMGTSSPARRGSADGPRSAQPLRPEDGHCSWPLE |
| | CD8a-ss FKBP EpoR_D2 DAP10 PD1 | 63 | MALPVTALLLPLALLLHAARPGSGGVQVETISPGDGRTFPKRGQTCVVHYTGMLEDGKKFDSSRDRNKPFKFMLGKQEVIRG WEEGVAQMSVGQRAKLTISPDYAYGATGHPGIIPPHATLVFDVELLKLEGSGAPAPVGLVARLADESGHVVLRWLPPPETPM TSHIRYEVDVSAGNGAGSVQRREILEGRTECVLSNLRGRTRYTFAVRARMAEPSFGGFWSAWSEPVSLLTPSDILLAGLVAA DAVASLLIVGAVFLCARRSRAARGTIGARRTGQPLKEDPSAVPVFSVDYGELDFQWREKTPEPPVPCVPEQTEYATIVFPSG MGTSSPARRGSADGPRSAQPLRPEDGHCSWPLE |
| | CD8a-ss FRB CD8a CD28 PD1 | 64 | MALPVTALLLPLALLLHAARPGSGGRVAILWHEMWHEGLEEASRLYFGERNVKGMFEVLEPLHAMMERGPQTLKETSFNQAY GRDLMEAQEWCRKYMKSGNVKDLTQAWDLYYHVFRRIGSGAPTTTPAPRPPTPAPTIASQPLSLRPEACRPAAGGAVHTRGL DFACDIFWLVVVGGVLACYSLLVTVAFIIFWVRSKRRSRAARGTIGARRTGQPLKEDPSAVPVFSVDYGELDFQWREKTPE PPVPCVPEQTEYATIVFPSGMGTSSPARRGSADGPRSAQPLRPEDGHCSWPLE |
| CID binding domain on γ chain of multi chain CAR | Gamma-ss FKBP CD8a Gamma-CD3z | 65 | MAIPAVVLLLLLLVEQAAAGSGGVQVETISPGDGRTFPKRGQTCVVHYTGMLEDGKKFDSSRDRNKPFKFMLGKQEVIRGWE EGVAQMSVGQRAKLTISPDYAYGATGHPGIIPPHATLVFDVELLKLEGSGAPTTTPAPRPPTPAPTIASQPLSLRPEACRPA ACGAVHTRGLDFACDIGEPQLCYILDAILFLYGIVLTLLYCRLKIQVRKAAITSYEKSRVKFSRSADAPAYQQGQNLYNEL NLGRREEYDVLDKRRGRDPEMGGKPRRKNPQEGLYNELQKDKMAEAYSEIGMKGERRRGKGHDGLYQGLSTATKDTYDALHM QALPPRE |
| | Gamma-ss FRB IgG1 Gamma-CD3z | 66 | MAIPAVVLLLLLLVEQAAAGSGGRVAILWHEMWHEGLEEASRLYFGERNVKGMFEVLEPLHAMMERGPQTLKETSFNQAYGR DLMEAQEWCRKYMKSGNVKDLTQAWDLYYHVFRRIGSGAPEPKSPDKTHTCPPCPAPPVAGPSVFLFPPKPKDTLMIARTPE VTCVVVDVSHEDPEVKFNWYVDGVEVHNAKTKPREEQYNSTYRVVSVLTVLHQDWLNGKEYKCKVSNKALPAPIEKTISKAK GQPREPQVYTLPPSRDELTKNQVSLTCLVKGFYPSDIAVEWESNGQPENNYKTTPPVLDSGSFFLYSKLTVDKSRWQQGNV FSCSVMHEALHNHYTQKSLSLSPGKKDIGEPQLCYILDAILFLYGIVLTLLYCRLKIQVRKAAITSYEKSRVKFSRSADAPA YQQGQNLYNELNLGRREEYDVLDKRRGRDPEMGGKPRRKNPQEGLYNELQKDKMAEAYSEIGMKGERRRGKGHDGLYQGLS TATKDTYDALHMQALPPRE |

TABLE 5-continued

Switch OFF receptors and engineered CARs

| Component | Architecture: signal sequence Interacting partner Hinge transmembrane intracellular | SEQ ID NO. | Aminoacid sequence |
|---|---|---|---|
| | Gamma-ss FKBP EpoR_D2 Gamma-CD3z | 67 | MAIPAVVLLLLLLVEQAAAGSGGVQVETISPGDGRTFPKRGQTCVVHYTGMLEDGKKFDSSRDRNKPFKFMLGKQEVIRGWE EGVAQMSVGQRAKLTISPDYAYGATGHPGIIPHATLVFDVELLKLEGSGAPAPGVLARLADESGHVVLRMLPPPETPMTS HIRYEVDVSAGNGAGSVQRVEILEGRIECVLSNLRGRTRYTFAVRARMAEPSFGGFWSAWSEPVSLLTPSDIGEPQLCYILD AILFLYGIVLTLLYCRLKIQVRKAAIISYEKSRVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDTYDALHMQALPPRE |
| | Gamma-ss FKBP FRB CD8a Gamma-CD3z | 68 | MAIPAVVLLLLLLVEQAAAGSGGRVAILWHEMWHEGLEEASRLYFGERNVKGMFEVLEPLHAMMERGPQTLKETSFNQAYGR DLMEAQEWCRKYMKSGNVEDLTQAWDLYYHVFRRIGSGAPTTTPAPRPPTPAPTIASQPLSLRPEACRPAAGGAVHTRGLDF ACDIGEPQLCYILDAILFLYGIVLTLLYCRLKIQVRKAATTSYEKSRVKFSRSADAPAYQQGQNQLYNELNLGRREEYDVLD KRRGRDPEMGGKPRRKNPQEGLYNELQKDKMAEAYSEIGMKGERRRGKGHDGLYQGLSTATKDTYDALHMQALPPRE |
| | Gamma-ss FKBP Gamma-CD3z | 69 | MAIPAVVLLLLLLVEQAAAGSGGVQVETISPGDGRTFPKRGQTCVVHYTGMLEDGKKFDSSRDRNKPFKFMLGKQEVIRGWE EGVAQMSVGQRAKLTISPDYAYGATGHPGIIPHATLVFDVELLKLEGSGAPLGEPQLCYILDAILFLYGIVLTLLYCRLKI QVRKAAITSYEKSRVKFSRSADAPAYQQGQNQLYNELNLGRREEYDVLDKRRGRDPEMGGKPRRKNPQEGLYNELQKDKMAE AYSEIGMKGERRRGKGHDGLYQGLSTATKDTYDALHMQALPPRE |
| | Gamma-ss FRB FKBP Gamma-CD3z | 70 | MAIPAVVLLLLLLVEQAAAGSGGRVAILWHEMWHEGLEEASRLYFGERNVKGMFEVLEPLHAMMERGPQTLKETSFNQAYGR DLMEAQEWCRKYMKSGNVKDLTQAWDLYYHVFRRIGSGAPLGEPQLCYILDAILFLYGIVLTLLYCRLKIQVRKAAITSYEK SRVKFSRSADAPAYQQGQNQLYNELNLGRREEYDVLDKRRGRDPEMGGKPRRKNPQEGLYNELQKDKMAEAYSEIGMKGERR RGKGHDGLYQGLSTATKDTYDALHMQALPPRE |
| CID binding domain on α chain of multi chain CAR | VH-4G7-scFv FKBP EpoR_D2 Alpha | 71 | MAPAMESPTLLCVALLFFAPDGVLAEVQLQQSGPELIKPGASVKMSCKASGYTFTSYVMHWVKQPGQGLEWIGYINPYNDG TKYNEKFKGKATLTSDKSSSTAYMELSSLTSEDSAVYYCARGTYYYGSRVFDYWGQGTTLTVSSGGGGSGGGGSGGGGSDIV MTQAAPSIPVTPGESVSISCRSSKSLLNSNGNTYLYWFLQRPGQSPQLLIYRMSNLASGVPDRFSGSGSGTAFTLRISRVEA EDVGVYYCMQHLEYPPTFGAGTKLELKRSDPGSSGGVQVETISPGDGRTFPKRGQTCVVHYTGMLEDGKKFDSSRDRNKPFKF MLGKQEVIRGWEEGVAQMSVGQRAKLTISPDYAYGATGHPGIIPPHATLVFDVELLKLEGSGAPAPGVLVARLADESGHVVL RWLPPPETPMTSHIRYEVDVSAGNGAGSVQRVEILEGRTECVLSNLRGRTRYTFAVRARMAEPSFGGFWSAWSEPVSLLTPS DIFIPLLVVILFAVDTGLFISTQQQVTFLLKIKRTRKGFRLLNPHPKPNPKNNE |
| | VH-4G7-scFv FRB EpoR_D2 Alpha | 72 | MAPAMESPTLLCVALLFFAPDGVLAEVQLQQSGPELIKPGASVKMSCKASGYTFTSYVMHWVKQPGQGLEWIGYINPYNDG TKYNEKFKGKATLTSDKSSSTAYMELSSLTSEDSAVYYCARGTYYYGSRVFDYWGQGTTLTVSSGGGGSGGGGSGGGGSDIV MTQAAPSIPVTPGESVSISCRSSKSLLNSNGNTYLYWFLQRPGQSPQLLIYRMSNLASGVPDRFSGSGSGTAFTLRISRVEA EDVGVYYCMQHLEYPPTFGAGTKLELKRSDPGSGGRVAILWHEMWHEGLEEASRLYFGERNVKGMFEVLEPLHAMMERGPQT LKETSFNQAYGRDLMEAQEWCRKYMKSGNVKDLTQAWDLYYHVERRIGSGAPAPGVLVARLADESGHVVLRWLPPPETPMTS HIRYEVDVSAGNGAGSVQRVEILEGRTECVLSNLRGRTRYTFAVRARMAEPSFGGFWSAWSEPVSLLTPSDIFIPLLVVILF AVDTGLFISTQQQVTFLLKIKRTRKGFRLLNPHPKPNPKNNE |
| | VH-4G7-scFv FKBP IgG1 Alpha | 73 | MAPAMESPTLLCVALLFFAPDGVLAEVQLQQSGPELIKPGASVKMSCKASGYTFTSYVMHWVKQPGQGLEWIGYINPYNDG TKYNEKFKGKATLTSDKSSSTAYMELSSLTSEDSAVYYCARGTYYYGSRVFDYWGQGTTLTVSSGGGGSGGGGSGGGGSDIV MTQAAPSIPVTPGESVSISCRSSKSLLNSNGNTYLYWFLQRPGQSPQLLIYRMSNLASGVPDRFSGSGSGTAFTLRISRVEA EDVGVYYCMQHLEYPPTFGAGTKLELKRSDPGSGGVQVETISPGDGRTFPKRGQTCVVHYTGMLEDGKKFDSSRDRNKPFKF MLGKQEVIRGWEEGVAQMSVGQRAKLTISPDYAYGATGHPGIIPPHATLVFDVELLKLEGSGAPEPKSPDKTHTCPPCAPP VAGPSVFLFPPKPKDTLMIARTPEVTCVVVDVSHEDPEVKFNWYVDGVEVHNAKTKPREEQYNSTYRVVSVLTVLHQDWLNG |

TABLE 5-continued

Switch OFF receptors and engineered CARs

| Component | Architecture: Signal sequence Interacting partner Hinge transmembrane intracellular | SEQ ID NO. | Aminoacid sequence |
|---|---|---|---|
| | VH-4G7-scFv FRB IgG1 Alpha | 74 | KEYKCKVSNKALPAPIEKTISKAKGQPREPQVYTLPPSRDELTKNQVSLTCLVKGFYPSDIAVEWESNGQPENNYKTTPPVL DSDGSFFLYSKLTVDKSRWQQGNVFSCSVMHEALHNHYTQKSLSLSPGKKDIFIPLLVILFAVDTGLFISTQQVTFLLKI KRTRKGFRLLNPHPKPNPKNNE |
| | VH-4G7-scFv FRB CD8a Alpha | 75 | MAPAMESPTLLCVALLFFAPDGVLAEVQLQQSGPELIKPGASVKMSCKASGYTFTSYVMHWVKQPGQGLEMIGYINPYNDG TKYNEKFKGKATLTSDKSSSTAYMELSSLTSEDSAVYYCARGTYYYGSRVFDYWGQGTTLTVSSGGGGSGGGGSGGGGSDIV MTQAAPSIPVTPGESVSISCRSSKSLLNSGNTYLYWFLQRPGQSPQLLIYRMSNLASGVPDRFSGSGSGTAFTLRISRVEA EDVGVYYCMQHLEYPTFGAGTKLELKRSDPGSGGRVAILWHEMWHEGLEEASRLYFGERNVKGMPEVLEPLHAMMERGPQT LKETSFNQAYGRDLMEAQEWCRKYMKSGNVKDLTQAWDLYYHVFRRIGSGAPEPKSPDKHTCPPCPAPVAGPSVFLFPPK PKDILMIARTPEVTCVVVDVSHEDPEVKFNWYVDGVEVHNAKTKPREEQYNSTYRVVSVLTVLHQDWLNGKEYKCKVSNKAL PAPIEKTISKAKGQPREPQVYTLPPSRDELTKNQVSLTCLVKGFYPSDIAVEWESNGQPENNYKTTPPVLDSDGSFFLYSKL TVDKSRWQQGNVFSCSVMHEALHNHYTQKSLSLSPGKKDIFIPLLVILFAVDTGLFISTQQVTFLLKIKRTRKGFRLLNP HPKPNPKNNE |
| | VH-4G7-scFv FRB CD8a Alpha | 76 | MAPAMESPTLLCVALLFFAPDGVLAEVQLQQSGPELIKPGASVKMSCKASGYTFTSYVMHWVKQPGQGLEMIGYINPYNDG TKYNEKFKGKATLTSDKSSSTAYMELSSLTSEDSAVYYCARGTYYYGSRVFDYWGQGTTLTVSSGGGGSGGGGSGGGGSDIV MTQAAPSIPVTPGESVSISCRSSKSLLNSGNTYLYWFLQRPGQSPQLLIYRMSNLASGVPDRFSGSGSGTAFTLRISRVEA EDVGVYYCMQHLEYPTFGAGTKLELKRSDPGSGGQVETISPDGRTFPKRGQTCVVHYTGMLEDGKKFDSSRDRNKPFKF MLGKQEVIRGWEEGVAQMSVGQRAKLTISPDYAYGATGHPGIIPPHATLVFDVELLKLEGSGAPTTTPAPRPPTPAPTIASQ PLSLRPEACRPAAGGAVHTRGLDFACDFFIPLLVVILFAVDTGLFISTQQQVTFLLKIKTRKGFRLLNPHPKPNPKNNE |
| | sc_scFv CD12 FKBP CD8a 4-1BB-CD3z | 77 | MALPVTALLLPLALLLHAARPQIQLVQSGPELKKPGETVKISCKASGYIFTNYGMNWVKQAPGKSFKWMGWINTYTGESTYS ADFKGRFAFSLETSASTAYLHINDLKNEDTATYFCARSGGYDMDYWGQGTSVTVSSGGGGSGGGGSGGGGSDIVLTQSPAS LAVSLGQRATISCRASESVDNYGNTFMHWYQQKPGQPPKLLIYRASNLESGIPARSGSGSRTDFTLTINPVEADDVATYYC QQSNEDPPTFGAGTKLELKRSDPGSGGQVETISPDGRTFPKRGQTCVVHYTGMLEDGKKFDSSRDRNKPFKFMLGKQEVI RGWEEGVAQMSVGQAVHTRGLDFACDIYIWAPLAGTCGVLLLSLVITLYCRRGRKKLLYIFKQPFMRPVQTTQEEDGCSCRFPEEEEGG CRPAAGGAVHTRGLDFACDPAYQQGONQLYNELNLGRREEYDVLDKRRGRDPEMGGKPRRKNPQEGLYNELQKDKMAEAYSEIGMKGE RRRGKGHDGLYQGLSTATKDTYDALHMQALPPRE |
| | sc_scFv CD12 FRB CD8a 4-1BB-CD3z | 78 | MALPVTALLLPLALLLHAARPQIQLVQSGPELKKPGETVKISCKASGYIFTNYGMNWVKQAPGKSFKWMGWINTYTGESTYS ADFKGRFAFSLETSASTAYLHINDLKNEDTATYFCARSGGYDMDYWGQGTSVTVSSGGGGSGGGGSGGGGSDIVLTQSPAS LAVSLGQRATISCRASESVDNYGNTFMHWYQQKPGQPPKLLIYRASNLESGIPARSGSGSRTDFTLTINPVEADDVATYYC QQSNEDPPTFGAGTKLELKRSDPGSGGRVAILMHEMWHEGLEEASRLYFGERNVKGMFEVLEPLHAMMERGPQTLKETSFNQ AYGRDLMEAQEWCRKYMKSGNVKDLTQAWDLYYHVFRRIGSGAPTTTPAPRPPTPAPTIASQPLSLRPEACRPAAGGAVHTR GLDFACDIYIWAPLAGTCGVLLLSLVITLYCRRGRKKLLYIFKQPFMRPVQTTQEEDGCSCRFPEEEEGGCELRVKFSRSAD APAYQQGQNQLYNELNLGRREEYDVLDKRRGRDPEMGGKPRRKNPQEGLYNELQKDKMAEAYSEIGMKGERRRGKGHDGLYQ GLSTATKDTYDALHMQALPPRE |
| | sc_scFv CD12 FKBP IgG1 | 79 | MALPVTALLLPLALLLHAARPQIQLVQSGPELKKPGETVKISCKASGYIFTNYGMNWVKQAPGKSFKWMGWINTYTGESTYS ADFKGRFAFSLETSASTAYLHINDLKNEDTATYFCARSGGYDMDYWGQGTSVTVSSGGGGSGGGGSGGGGSDIVLTQSPAS LAVSLGQRATISCRASESVDNYGNTFMHWYQQKPGQPPKLLIYRASNLESGIPARFSGSGSRTDFTLTINPVEADDVATYYC QQSNEDPPTFGAGTKLELKRSDPGSGGQVETISPDGRTFPKRGQTCVVHYTGMLEDGKKFDSSRDRNKPFKFMLGKQEVI |

TABLE 5-continued

Switch OFF receptors and engineered CARs

| Component | Architecture: signal sequence Interacting partner Hinge transmembrane intracellular | SEQ ID NO. | Aminoacid sequence |
|---|---|---|---|
| | CD8a 4-1BB-CD3z | | RGWEEGVAQMSVGQRAKLTISPDYAYGATGHPGIIPPHATLVFDVELLKLEGSGAPEPKSPDKTHTCPPCPAPPVAGPSVFL FPPKPKDTLMIARTPEVTCVVVDVSHEDPEVKFNWYVDGVEVHNAKTKPREEQYNSTYRVVSVLTVLHQDWLNGKEYKCKVS NKALPAPIEKTISKAKGQPREPQVYTLPPSRDELTKNQVSLTCLVKGFYPSDIAVEWESNGQPENNYKTTPPVLDSDGSFFL YSKLTVDKSRWQQGNVFSCSVMHEALHNHYTQKSLSLSPGKKDIYIWAPLAGTCGVLLLSLVITLYCRRGRKKLLYIFKQPF MRPVQTTQEEDGCSCREPEEEEGGCELRVKFSRSADAPAYQQGQNQLYNELNLGRREEYDVLDKRRGRDPEMGGKPRRKNPQ EGLYNELQKDKMAEAYSEIGMKGERRRGKGHDGLYQGLSTATKDTYDALHMQALPPRE |
| | sc_scFV_CD12 FRB IgG1 CD8a 4-1BB-CD3z | 80 | MALPVTALLLPLALLLHAARPQIQLVQSGPELKKPGETVKISCKASGYIFTNYGMNWVKQAPGKSFKWMGWINTYTGESTYS ADFKGRFAFSLETSASTAYLHINDLKNEDTATYFCARSGGYDPMDYWGQGTSVTVSSGGGGSGGGGSGGGGSDIVLTQSPAS LAVSLGQRATISCRASESVDNYGNTFMHWYQQKPGQPPKLLIYRASNLESGIPARFSGSGSRTDFTLTINPVEADDVATYYC QQSNEDPPTFGAGTKLELKRSDPGSGSGRVAILWHEMWHEGLEEEASRLYFGERNVKGMFEVLEPLHAMMERGPQTLKETSFNQ AYGRDLMEAQEWCRKTYMKSGNVKDLTQAWDLYYHYPRRIGSGAPEPKSPDKTHTCPPCPAPPVAGPSVFLFPPKPKDTLMIA RTPEVTCVVVDVSHEDPEVKFNWYVDGVEVHNAKTKPREEQYNSTYRVVSVLTVLHQDWLNGKEYKCKVSNKALPAPIEKTI SKAKGQPREPQVYTLPPSRDELTKNQVSLTCLVKGFYPSDIYIWAPLAGTCGVLLLSLVITLYCRRGRKKLLYIFKQFMRPVQTTQEEDG QGNVFSCSVMHEALHNHYTQKSLSLSPGKKDIYIWAPLAGTCGVLLLSLVITLYCRRGRKKLLYIFKQFMRPVQTTQEEDG CSCRFPEEEEGGCELRVKFSRSADAPAYQQGQNQLYNELNLGRREEYDVLDKRRGRDPEMGGKPRRKNPQEGLYNELQKDKM AEAYSEIGMKGERRRGKGEDGLYQGLSTATKDTYDALHMQALPPRE |
| | sc_scFV_CD12 FRB FKBP EpoR_D2 CD8a 4-1BB-CD3z | 81 | MALPVTALLLPLALLLHAARPQIQLVQSGPELKKPGETVKISCKASGYIFTNYGMNWVKQAPGKSFKWMGWINTYTGESTYS ADFKGRFAFSLETSASTAYLHINDLKNEDTATYFCARSGGYDPMDYWGQGTSVTVSSGGGGSGGGGSGGGGSDIVLTQSPAS LAVSLGQRATISCRASESDPGSGVQETISPGDGRTFPKRGQTCVVHYTGMLEDGKKFPDSSRDRNKPFKFMLGKQEVI QQSNEDPPTFGAGTKLELKRSDPGSGVQVQRVEILEGRTECVLSNLRGRTRYTFAVRARMAEPSEGGFWSAWSEPVSLLTPSDIYIWAPL PMTSHIRYEVDVSAGNGAGSVQRVEILEGRTECVLSNLRGRTRYTFAVRARMAEPSEGGFWSAWSEPVSLLTPSDIYIWAPL AGTCGVLLLSLVITLYCRRGRKKLLYIFKQPFMRPVQTTQEEDGCSCRFPEEEEGCELRVKFSRSADAPAYQQGQNQLYNE LNLGRREEYDVLDKRRGRDPEMGGKPRRKNPQEGLYNELQKDKMAEAYSEIGMKGERRRGKGHDGLYQGLSTATKDTYDALH MQALPPRE |
| | sc_scFV_CD12 FRB EpoR_D2 CD8a 4-1BB-CD3z | 82 | MALPVTALLLPLALLLHAARPQIQLVQSGPELKKPGETVKISCKASGYIFTNYGMNWVKQAPGKSFKWMGWINTYTGESTYS ADFKGRFAFSLETSASTAYLHINDLKNEDTATYFCARSGGYDPMDYWGQGTSVTVSSGGGGSGGGGSGGGGSDIVLTQSPAS LAVSLGQRATISCRASESVDNYGNTFMHWYQQKPGQPPKLLIYRASNLESGIPARFSGSGSRTDFTLTINPVEADDVATYYC QQSNEDPPTFGAGTKLELKRSDPGSGSGRVAILWHEMWHEGLEEEASRLYFGERNVKGMFEVLEPLHAMMERGPQTLKETSFNQ AYGRDLMEAQEWCRKTYMKSGNVKDLTQAWDLYYHYPRRIGSGAPAPVGLVARLADESGHVVLRWLPPPETPMTSHIRYEVDV SAGNGAGSVQRVEILEGRTECVLSNLRGRTRYTFAVRARMAEPSEGGFWSAWSEPVSLLTPSDIYIWAPLAGTCGVLLLSLV ITLYCRRGRKKLLYIFKQPFMRPVQTTQEEDGCSCRFPEEEEGCELRVKFSRSADAPAYQQGQNQLYNELNLGRREEYDVL DKRRGRDPEMGGKPRRKNPQEGLYNELQKDKMAEAYSEIGMKGERRRGKGHDGLYQGLSTATKDTYDALHMQALPPRE |

INTRA CELLULAR CID BINDING DOMAINS

| IMP complex (switch OFF receptor) | VH-4G7-ss CD8a FKBP PD1 | 83 | MALPVTALLLPLALLLHAARPGSDIYIWAPLAGTCVLLLSLVITLYGRSGGVQVETISPGDGRTFPKRGQTCVVHYTGMLE DGKKFDSSRDRNKPFKFMLGKQEVIRGWEEGVAQMSVGQRAKLTISPDYAYGATGHPGIIPPHATLVFDVELLKLEGSGSSS RAARGTIGAARRTGQPLKEDPSAVPVFSVDYGELDFQWREKTPEPPVPCVPEQTEYATIVFPSGMGTSSPARRGSADGPRSAQ PLRPEDGHCSWPLE |

TABLE 5-continued

Switch OFF receptors and engineered CARs

| Component | Architecture: signal sequence Interacting partner Hinge transmembrane intracellular | SEQ ID NO. | Aminoacid sequence |
|---|---|---|---|
| | VH-<br>4G7-ss<br>CD8a<br>FRB<br>PD1 | 84 | MALPVTALLLPLALLLHAARPGSDIYIWAPLAGTCGVLLLSLVITLYCRSGGRVAILWHEMWHEGLEEASRLYFGERNVKGM<br>FEVLEPLHAMMERGPQTLKETSFNQAYGRDLMEAQEWCRKYMKSGNVKDLTQAWDLYYHVFRRIGSGSSSRAARGTIGARRT<br>GQPLKEDPSAVPVFSVDYGELDFQWREKTPEPPVPCVPEQTEYATIVFPSGMGTSSPARRGSADGPRSAQPLRPEDGHCSWP<br>LE |
| | VH-<br>4G7-ss<br>CD8a<br>OX40<br>FKBP<br>PD1 | 85 | MALPVTALLLPLALLLHAARPGSDIYIWAPLAGTCGVLLLSLVITLYCRALYLLRRDQRLPPDAHKPPGGGSFRTPIQEEQA<br>DAHSTLAKIGSGSGSSGGVQVETISPGDGRTFPKRGQTCVVHYTGMLEDGKKFDSSRDRNKPFKFMLGKQEVIRGWEEGV<br>AQMSVGQRAKLTISPDYAYGATGHPGIIPPHATLVFDVELLKLEGSGSGSRAARGTIGARRTGQPLKEDPSAVPVFSVDYGE<br>LDFQWREKTPEPPVPCVPEQTEYATIVFPSGMGTSSPARRGSADGPRSAQPLRPEDGHCSWPLE |
| | VH-<br>4G7-ss<br>CD8a<br>DAP10<br>FKBP<br>PD1 | 86 | MALPVTALLLPLALLLHAARPGSDIYIWAPLAGTCGVLLLSLVITLYGRPRRSPAQEDGKVYINMPGRGGSGSGSSGGVQ<br>VETISPGDGRTFPKRGQTCVVHYTCMLEDGKKFDSSRDRNKPFKFMLCKQEVIRGWEEGVAQMSVGQRAKLTISPDYAYGAT<br>GHPGIIPPHATLVFDVELLKLEGSGSGSRAARGTIGARRTGQPLKEDPSAVPVFSVDYGELDFQWREKTPEPPVPCVPEQTE<br>YATIVFPSGMGTSSPARRGSADGPRSAQPLRPEDGHCSWPLE |
| | VH-<br>4G7-ss<br>CD8a<br>HVEM<br>FKBP<br>PD1 | 87 | MALPVTALLLPLALLLHAARPGSDIYIWAPLAGTCGVLLLSLVITLYCRCVKRRKPRGDVVKVIVSVQRKRQEAEGEATVIE<br>ALQAPPDVTTVAVEETIPSFTGRSPNHGSGSGSSGGVQVETISPGDRTFPKRGQTCVVHYTGMLEDGKKFDSSRDRNKP<br>FKFMLGKQEVIRGWEEGVAQMSVGQRAKLTISPDYAYGATGHPGIIPPHATLVFDVELLKLEGSGSGSRAARGTIGARRTGQ<br>PLKEDPSAVPVFSVDYGELDFQWREKTPEPPVPCVPEQTEYATIVFPSGMGTSSPARRGSADGPRSAQPLRPEDGHCSWPLE |
| | VH-<br>4G7-ss<br>CD8a<br>OX40<br>FRB<br>PD1 | 88 | MALPVTALLLPLALLLHAARPGSDIYIWAPLAGTCGVLLLSLVITLYCRALYLLRRDQRLPPDAHKPPGGGSFRTPIQEEQA<br>DAHSTLAKIGSGSGSSGGRVAILWHEMWHEGLEEASRLYFGERNVKGMFEVLEPLHAMMERGPQTLKETSFNQAYGRDLM<br>EAQEWCRKYMKSGNVKDLTQAWDLYYHVFRRIGSGSGSRAARGTIGARRTGQPLKEDPSAVPVFSVDYGELDFQWREKTPEP<br>PVPCVPEQTEYATIVFPSGMGTSSPARRGSADGPRSAQPLRPEDGHCSWPLE |
| | VH-<br>4G7-ss<br>CD8a<br>DAP10<br>FRB<br>PD1 | 89 | MALPVTALLLPLALLLHAARPGSDIYIWAPLAGTCGVLLLSLVITLYCRPPRRSPAQEDGKVYINMPGRGGSGSGSSGGRV<br>AILWHEMWHEGLEEASRLYFGERNVKGMFEVLEPLHAMMERGPQTLKETSFNQAYGRDLMEAQEWCRKYMKSGNVKDLTQAW<br>DLYYHVFRRIGSGSGSRAARGTIGARRTGQPLKEDPSAVPVFSVDYGELDFQWREKTPEPPVPCVPEQTEYATIVFPSGMGT<br>SSPARRGSADGPRSAQPLRPEDGHCSWPLE |
| | VH-<br>4G7-ss<br>CD8a<br>HVEM<br>FRB<br>PD1 | 90 | MALPVTALLLPLALLLHAARPGSDIYIWAPLAGTCGVLLLSLVITLYCRCVKRRKPRGDVVKVIVSVQRKRQEAEGEATVIE<br>ALQAPPDVTTVAVEETIPSFTGRSPNHGSGSGSSGGRVAILWHEMWHEGLEEASRLYFGERNVKGMFEVLEPLHAMMERG<br>PQTLKETSFNQAYGRDLMEAQEWCRKYMKSGNVKDLTQAWDLYYHVFRRIGSGSGSRAARGTIGARRTCQPLKEDPSAVPVF<br>SVDYGELDFQWREKTPEPPVPCVPEQTEYATIVFPSGMGTSSPARRGSADGPRSAQPLRPEDGHCSWPLE |

TABLE 5-continued

Switch OFF receptors and engineered CARs

| Component | Architecture: signal sequence Interacting partner Hinge transmembrane intracellular | SEQ ID NO. | Aminoacid sequence |
|---|---|---|---|
| | VH-4G7-ss CD8a PD1 FKBP | 91 | MALPVTALLLPLALLLHAARPGSDIYIWAPLAGTCGVLLLSLVITLYCRSRAARGTIGARRTGQPLKEDPSAVPVFSVDYGE LDFQWREKTPEPPVPCVPEQTEYATIVFPSGMTSSPARRGSADGPRSAQPLRPEDGHCSWPLGSGSSGGVQVETISPDG RTFPKRGQTCVVHYTGMLEDGKKFDSSRDRNKPFKFMLGKQEVIRGWEEGVAQMSVGQRAKLTISPDYAYGATGHPGIIPPH ATLVFDVELLKLEE |
| | VH-4G7-ss CD8a PD1 FRB | 92 | MALPVTALLLPLALLLHAARPGSDIYIWAPLAGTCGVLLLSLVITLYCRSRAARGTIGARRTGQPLKEDPSAVPVFSVDYGE LDFQWREKTPEPPVPCVPEQTEYATIVFPSGMTSSPARRGSADGPRSAQPLRPEDGHCSWPLGSGSSGGRVAILWHEMWH EGLEEASRLYFGERNVKGMFEVLEPLHAMMERGPQTLKETSFNQAYGRDLMEAQEWCRKYMKSGNVKDLTQAWDLYYHVFRR IE |
| | VH-4G7-ss CD8a OX40 PD1 FKBPr | 93 | MALPVTALLLPLALLLHAARPGSDIYIWAPLAGTCGVLLLSLVITLYCRALYLLRRDQRLPPDAHKPPGGGSFRTPIQEEQA DAHSTLAKIGSGSGSGSSSRAARGTIGARRTGQPLKEDPSAVPVFSVDYGELDFQWREKTPEPPVPCVPEQTEYATIVFPSGM GTSSPARRGSADGPRSAQPLRPEDGHCSWPLGSGSGGVQVETISPDGRTFPKRGQTCVVHYTGMLEDGKKFDSSRDRNKPF KFMLGKQEVIRGWEEGVAQMSVGQRAKLTISPDYAYGATGHPGIIPPHATLVFDVELLKLEE |
| | VH-4G7-ss CD8a DAP10 PD1 FKBP | 94 | MALPVTALLLPLALLLHAARPGSDIYIWAPLAGTCGVLLLSLVITLYCRPRRSPAQEDGKVYINMPGRGGSGSGSSRAAR GTIGARRTGQPLKEDPSAVPVFSVDYGELDFQWREKTPEPPVPCVPEQTEYATIVFPSGMTSSPARRGSADGPRSAQPLRP EDGHCSWPLGSGSGGVQVETISPDGRTFPKRGQTCVVHYTGMLEDGKKFDSSRDRNKPFKFMLGKQEVIRGWEEGVAQMSV GQRAKLTISPDYAYGATGHPGIIPPHATLVFDVELLKLEE |
| | VH-4G7-ss CD8a HVEM PD1 FKBP | 95 | MALPVTALLLPLALLLHAARPGSDIYIWAPLAGTCGVLLLSLVITLYCRCVKRRKPRGDVVKVIVSVQRKRQEAEGEATVIE ALQAPPDVTTVAVEETIPSFTGRSPNHGSGSGSGSSRAARGTIGARRTGQPLKEDPSAVPVFSVDYGELDFQWREKTPEPPV PCVPEQTEYATIVFPSGMTSSPARRGSADGPRSAQPLRPEDGHCSWPLGSGSGGVQVETISPDGRTFPKRGQTCVVHYTG MLEDGKKFDSSRDRNKPFKFMLGKQEVIRGWEEGVAQMSVGQRAKLTISPDYAYGATGHPGIIPPHATLVFDVELLKLEE |
| | VH-4G7-ss CD8a OX40 PD1 FRB | 96 | MALPVTALLLPLALLLHAARPGSDIYIWAPLAGTCGVLLLSLVITLYCRALYLLRRDQRLPPDAHKPPGGGSFRTPIQEEQA DAHSTLAKIGSGSGSGSSSRAARGTIGARRTGQPLKEDPSAVPVFSVDYGELDFQWREKTPEPPVPCVPEQTEYATIVFPSGM GTSSPARRGSADGPRSAQPLRPEDGHCSWPLGSGSGGRVAILWHEMWHEGLEEASRLYFGERNVKGMFEVLEPLHAMMERGP QTLKETSFNQAYGRDLMEAQEWCRKYMKSGNVKDLTQAWDLYYHVFRRIE |
| | VH-4G7-ss CD8a DAP10 PD1 FRB | 97 | MALPVTALLLPLALLLHAARPGSDIYIWAPLAGTCGVLLLSLVITLYCRPRRSPAQEDGKVYINMPGRGGSGSGSSRAAR GTIGARRTGQPLKEDPSAVPVFSVDYGELDFQWREKTPEPPVPCVPEQTEYATIVFPSGMTSSPARRGSADGPRSAQPLRP EDGHCSWPLGSGSGGRVAILWHEMWHEGLEEASRLYFGERNVKEPLHAMMERGPQTLKETSFNQAYGRDLMEAQEW CRKYMKSGNVKDLTQAWDLYYHVFRRIE |

TABLE 5-continued

Switch OFF receptors and engineered CARs

| Component | Architecture: Signal sequence Interacting partner Hinge transmembrane intracellular | SEQ ID NO. | Aminoacid sequence |
|---|---|---|---|
| | VH-4G7-ss CD8a HVEM PD1 FRB | 98 | MALPVTALLLPLALLLHAARPGSDIYIWAPLAGTCGVLLLSLVITLYCRCVKRRKPRGDVVKIVSVQRKRQEAGEATVIE ALQAPPDVTTVAVEETIPSFTGRSPNHGSGSGSSSRAARGTIGAARTGQPLKEDSAVPFSVDYGELDFQWREKTPEPPV PCVPEQTEYATIVFPSGMGTSSPARRGSADQPRSAQPLRPEDGHCSWPLGSGSGGRVAILWHEMWHEGLEEASRLYFGERNV KGMFEVLEPLHAMMERGPQTLKETSFNQAYGRDLMEAQEWCRKYMKSGNVKDLTQAWDLYYHVFRRIE |
| CID binding domain on single-chain CAR | CD123-scFv CD8a HVEM FKBP | 99 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSRTDFTLTINPVEADDVA SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGGAVHTRGLDFACDFFIPLLVVIL FAVDTGLFISTQQQVTFLLKIKRTKGFRLLNPHPKPNPKNNRSGGVQVETISPGDGRTFPKRGQTCVVHYTGMLEDGKKFD SSRDRNKPFKMLGKQEVIRGWEEGVAQMSVGQRAKLTISPDYAYGATGHPGIIPPHATLVFDVELLKLEE |
| | CD123-scFv CD8a OX40 FKBP | 100 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSDIVLTQ SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGGRVAILWHEMWHEGLEEASRLYFGERNVKGMFEVLEP LHAMMERGPQTLKETSFNQAYGRDLMEAQEWCRKYMKSGNVKDLTQAWDLYYHVFRRIE |
| | CD123-scFv CD8a DAP10 FKBP | 101 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSRTDFTLTINPVEADDVA SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGAVHTRGLDFACDFFIPLLVVIL FAVDTGLFISTQQQVTFLLKIKRTKGFRLLNPHPKPNPKNNRALYLLRRDQRLPPDAHKPGGGSFRTPIQEEQADAHSTL AKIGSGSGSGSGSGGVQVETISPGDGRTFPKRGQTCVVHYTGMLEDGKKFDSSRDRNKPFKFMLGKQEVIRGWEEGVAQMSVG QRAKLTISPDYAYGATGHPGIIPPHATLVFDVELLKLEE |
| | CD123-scFv CD8a OX40 FKBP | 102 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSDIVLTQ SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAQEDGKVIINMPGRGSGSGSGGVQVETISP FAVDTGLFISTQQQVTFLLKIKRTKGFRLLNPHPKPNPKNPRPRSPAQEDGKVINNMPGRGSGSGSGGVQVETISP GDGRTFPKRGQTCVVHYTGMLEDGKKFDSSRDRNKPFKFMLGKQEVIRGWEEGVAQMSVGQRAKLTISPDYAYGATGHPGI PPHATLVFDVELLKLEE |
| | CD123-scFv CD8a HVEM FKBP | 103 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSDIVLTQ SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGGAVHTRGLDFACDFFIPLLVVIL FAVDTGLFISTQQQVTFLLKIKRTKGFRLLNPHPKPNPKNNRCVKRKPRGDVVKIVSVQRKRQEAEGEATVIEALQAPP DVTTVAVEETIPSFTGRSPNHGSGSGSGGVQVETISPGDGRTFPKRGQTCVVHYTGMLEDGKKFDSSRDRNKPFKFMLG KQEVIRGWEEGVAQMSVGQRAKLTISPDYAYGATGHPGIIPPHATLVFDVELLKLEE |
| | CD123-scFv CD8a OX40 FRB | 104 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSDIVLTQ SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGAVHTRGLDFACDFFIPLLVVIL FAVDTGLFISTQQQVTFLLKIKRTKGFRLLNPHPKPNPKNNRALYLLRRDQRLPPDAHKPGGGSFRTPIQEEQADAHSTL |

TABLE 5-continued

Switch OFF receptors and engineered CARs

| Component | Architecture: Signal sequence Interacting partner Hinge transmembrane intracellular | SEQ ID NO. | Aminoacid sequence |
|---|---|---|---|
| | CD123-scFv CD8a CD8a DAP10 FRB | 105 | AKIGSGSGSGSGSGGRVAILWHEMWHEGLEEASRLYFGERNVKGMFEVLEPLHAMMERGPQTLKETSFNQAYGRDLMEAQEWC RKYMKSGNVKDLTQAWDLYYHVFRRIE |
| | CD123-scFv CD8a CD8a 41BB-CD3z FRB | 106 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSDIVLTQ SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGGAVHTRGLDFACDFFIPLLVVIL FAVDTGLFISTQQQVTFLLKIKRTRKGFRLLNPHPKPNPKNNRPRRSPAQEDGKVVINMPGRGGSGSGSGSGGRVAILWHE MWHEGLEEASRLYFGERNVKGMFEVLEPLHAMMERGPQTLKETSFNQAYGRDLMEAQEWCRKYMKSGNVKDLTQAWDLYYHV FRRIE |
| | CD123-scFv CD8a CD8a HVEM FRB | 107 | MAPAMESPTLLCVALLFFAPDGVLAQIQLVQSGPELKKPGETVKISCKASGYIFTNYGMNWVKQAPGKSFKWMGWINTYTGE STYSADFKGRFAFSLETSASTAYLHINDLKNEDTATYFCARSGGYDPMDYWGQGTSVTVSSGGGGSGGGGSGGGGSDIVLTQ SPASLAVSLGQRATISCRASESVDNYGNTFMHWYQQKPGQPPKLLIYRASNLESGIPARFSGSGSRTDFTLTINPVEADDVA TYYCQQSNEDPPTFGAGTKLELKRSDPTTTPAPRPPTPAPTIASQPLSLRPEACRPAAGGAVHTRGLDFACDFFIPLLVVIL FAVDTGLFISTQQQVTFLLKIKRTRKGFRLLNPHPKPNPKNNRCVKRKRPGDVVKIVSVQRKRQEAEGEATVIEALQAPP DVTTVAVEETIPSFTGRSPNHGSGSGSGSGGRVAILWHEMWHEGLEEASRLYFGERNVKGMFEVLEPLHAMMERGPQTLKE TSFNQAYGRDLMEAQEWCRKYMKSGNVKDLTQAWDLYYHVFRRIE |
| | klo43_scFv CD8a CD8a 41BB-CD3z FKBP | 108 | MALPVTALLLPLALLLHAARPEVKLVESGGGLVQPGGSLSLSCAASGFTFTDYYMSWVRQPPGKALEWLALIRSKADGYTTE YSASVKGRFTLSRDDSQSILYLQMNALRPEDSATYYCARDAAYYSYYSPEGAMDYWGQGTSVTVSSGGGGSGGGGSGGGGSM ADYKDIVMTQSHKFMSTSVGDRVNITCKASQNVDSAVAWYQQKPGQSPKALIYSASYRYSGVPDRFTGRGSGTDFTLTISSV QAEDLAVYYCQQYYSTPWTFGGGTKLEIKRSDPTTTPAPRPPTPAPTIASQPLSLRPEACRPAAGGAVHTRGLDFACDIYIW APLAGTCGVLLLSLVITLYCRRGRKKLLYIFKQPFMRPVQTTQEEDGCSCRFPEEEEGGCELRVKFSRSADAPAYQQGQNQL YNELNLGRREEYDVLDKRRGRDPEMGGKPRRKNPQEGLYNELQKDKMAEAYSEIGMKGERRRGKGHDGLYQGLSTATKDTYD ALHMQALPPRSSGGVQVETISPGDGRTFPKRGQTCVVHYTGMLEDGKKFDSSRDRNKPFKFMLGKQEVIRGWEEGVAQMSVG QRAKLTISPDYAYGATGHPGIIPPHATLVFDVELLKLEE |
| | klo43_scFv CD8a CD8a 41BB-CD3z FRB | 109 | MALPVTALLLPLALLLHAARPEVKLVESGGGLVQPGGSLSLSCAASGFTFTDYYMSWVRQPPGKALEWLALIRSKADGYTTE YSASVKGRFTLSRDDSQSILYLQMNALRPEDSATYYCARDAAYYSYYSPEGAMDYWGQGTSVTVSSGGGGSGGGGSGGGGSM ADYKDIVMTQSHKFMSTSVGDRVNITCKASQNVDSAVAWYQQKPGQSPKALIYSASYRYSGVPDRFTGRGSGTDFTLTISSV QAEDLAVYYCQQYYSTPWTFGGGTKLEIKRSDPTTTPAPRPPTPAPTIASQPLSLRPEACRPAAGGAVHTRGLDFACDIYIW APLAGTCGVLLLSLVITLYCRRGRKKLLYIFKQPFMRPVQTTQEEDGCSCRFPEEEEGGCELGSGSGSGGVQVETISPGD GRTFPKRGQTCVVHYTGMLEDGKKEDSSRDRNKPFKFMLGKQEVIRGWEEGVAQMSVGQRAKLTISPDYAYGATGHPGIIPP HATLVFDVELLKLEGSSGRVKFSRSADAPAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPRE |
| | klo43_scFv CD8a CD8a | 110 | MALPVTALLLPLALLLHAARPEVKLVESGGGLVQPGGSLSLSCAASGFTFTDYYMSWVRQPPGKALEWLALIRSKADGYTTE YSASVKGRFTLSRDDSQSILYLQMNALRPEDSATYYCARDAAYYSYYSPEGAMDYWGQGTSVTVSSGGGGSGGGGSGGGGSM ADYKDIVMTQSHKFMSTSVGDRVNITCKASQNVDSAVAWYQQKPGQSPKALIYSASYRYSGVPDRFTGRGSGTDFTLTISSV QAEDLAVYYCQQYYSTPWTFGGGTKLEIKRSDPTTTPAPRPPTPAPTIASQPLSLRPEACRPAAGGAVHTRGLDFACDIYIW |

TABLE 5-continued

Switch OFF receptors and engineered CARs

| Component | Architecture: Signal sequence Interacting partner Hinge transmembrane intracellular | SEQ ID NO. | Aminoacid sequence |
|---|---|---|---|
| | 41BB FRB CD3z | | APLAGTCGVLLLSLVITLYCRGRKKLLYIFKQPFMRPVQTTQEEDGCSCRFPEEEEGGCELGSGSGSGSGGRVAILWHEMW HEGLEEASRLYFGERNVKGMFEVLEPLHAMMERGPQTLKETSFNQAYGRDLMEAQEWCRKYMKSGNVKDLTQAWDLYYHVFR RIGSGSGRVKFSRSADAPAYQQGQNQLYNELNLGRREEYDVLDKRRGRDPEMGGKPRRKNPQEGLYNELQKDKMAEAYSEIG MKGERRRGKGHDGLYQGLSTATKDTYDALHMQALPPRE |
| | klo43_ scFV CD8a CD8a FKBP 41BB-CD3z | 111 | MALPVTALLLPLAILLHAARPEVKLVESGGGLVQPGGSLSLSCAASGFTFTDYYMSWVRQPPGKALEWLALIRSKADGYTTE YSASVKGRFTLSRDDSQSILYLQMNALRPEDSATYYCARDAAYYSYYSPEGAMDYWGQGTSVTVSSGGGGSGGGGSGGGGSM ADYKDIVMTQSHKFMSTSVGDRVNITCKASQNVDSAVAWYQQKPGQSPKALIYSASYRYSGVPDRFTGRGSGTDFTLTISSV QAEDLAVYYCQQYYSTPWTFGGGTKLEIKRSDPTTTPAPRPPTPAPTIASQPLSLRPEACRPAAGGAVHTRGLDFACDIYIW APLAGTCGVLLLSLVITLYCRSGGVQVETISPGDGRTFPKRGQTCVVHYTGMLEDGKKFDSSRDNKPFKFMLGKQEVIRGW EEGVAQMSVGQRAKLTISPDYAYGATGHPGIIPPHATLVFDVELLKLEGSSSRGRKKLLYIFKQPFMRPVQTTQEEDGCSC RFPEEEEGGCELRVKFSRSADAPAYQQGQNQLYNELNLGRREEYDVLDKRRGRDPEMGGKPRRKNPQEGLYNELQKDKMAEA YSEIGMKGERRRGKHDGLYQGLSTATKDTYDALHMQALPPRE |
| | klo43_ scFV CD8a CD8a FRB 41BB-CD3z | 112 | MALPVTALLLPLAILLHAARPEVKLVESGGGLVQPGGSLSLSCAASGFTFTDYYMSWVRQPPGKALEWLALIRSKADGYTTE YSASVKGRFTLSRDDSQSILYLQMNALRPEDSATYYCARDAAYYSYYSPEGAMDYWGQGTSVTVSSGGGGSGGGGSGGGGSM ADYKDIVMTQSHKFMSTSVGDRVNITCKASQNVDSAVAWYQQKPGQSPKALIYSASYRYSGVPDRFTGRGSGTDFTLTISSV QAEDLAVYYCQQYYSTPWTFGGGTKLEIKRSDPTTTPAPRPPTPAPTIASQPLSLRPEACRPAAGGAVHTRGLDFACDIYIW APLAGTCGVLLLSLVITLYCRSGGRVAILWHEMWHEGLEEASRLYFGERNVKGMFEVLEPLHAMMERGPQTLKETSFNQAYG RDLMEAQEWCRKYMKSGNVKDLTQAWDLYYHVFRRIGSGSSRGRKKLLYIFKQPFMRPVQTTQEEDGCSCRFPEEEEGGCEL RVKFSRSADAPAYQQGQNQLYNELNLGRREEYDVLDKRRGRDPEMGGKPRRKNPQEGLYNELQKDKMAEAYSEIGMKGERRR GKGHDGLYQGLSTATKDTYDALHMQALPPRE |

Switch-off receptors and engineered CARs, including additional adequate chains of the mcCAR (beta and gamma or alpha), are further subcloned in a lentiviral production plasmid, possibly upstream a 2A cis-acting hydrolase element (GSG-P2A and GSG-T2A ribosomal skip peptides) followed by a reporter marker (e.g. fluorescent proteins), or membranar protein (such as RQR8) either separately or together separated by 2A cis-acting hydrolase elements. Standard molecular biology technics such as PCR, enzymatic restriction digestion and ligation are applied to create all constructions.

Example 2. Lentiviral Delivery of Switch-Off Receptors and Engineered mcCARs in Primary T-Cells Viral vectors are either produced according to standard protocols or by an external contractor. Primary T-cells are transduced simultaneously or sequentially using switch-off receptor and engineered mcCAR lentiviral particles. The transduced T-cells are purified for positive engineered mcCAR and switch-off receptor expression using bulk FACS sorting or magnetic separation. The whole bulk engineered mcCAR/switch-off receptor positive population is then assessed for engineered mcCAR driven activation (degranulation/cytotoxicity), proliferation, and cytokine release using a model cell line expressing the engineered CAR target antigens in absence of small molecule (Rapamycin, rapalogs or synthetic rapalogs). The same experiment is then reproduced in presence of the small molecule to assess the inhibition properties of the system.

Example 3. Assembly of Switch-Off Receptors and Engineered scCARs (Single Chain CARs)

Sequences of modules to assemble IMPs (switch-off receptors) are obtained from the SEQ ID NO. 61-64 (extracellular CID binding domain) or 83-98 (intracellular CID binding domain) and from engineered scCAR with SEQ ID NO.77-82 (extracellular CID binding domain) or 107-112 (intracellular CID binding domain) such as depicted in the above Table 5. Their configuration is depicted in the FIGS. 4 (extracellular CID binding domain) and FIG. 5 (intracellular CID binding domain).

Assembly of constructs are done using Golden Gate assembly strategies according to published protocols. Switch-off receptors and engineered CARs are thus cloned in separated shuttle cloning plasmid. Switch-off receptors and engineered scCARs are further subcloned in a lentiviral production plasmid, possibly upstream a 2A cis-acting hydrolase element followed by a reporter marker (e.g. fluorescent proteins) either separately or together separated by 2A cis-acting hydrolase elements. Standard molecular biology technics such as PCR, enzymatic restriction digestion and ligation are applied to create all constructions.

Example 4. Lentiviral Delivery of Switch-Off Receptors and Engineered scCARs in Primary T-Cells Viral vectors were either produced according to standard protocols or by an external contractor. Primary T-cells are transduced simultaneously or sequentially using switch-off receptor and engineered scCAR lentiviral particles. The transduced T-cells are purified for positive engineered scCAR and switch-off receptor expression using bulk FACS sorting or magnetic separation. The whole bulk engineered scCAR/switch-off receptor positive population is then assessed for engineered scCAR driven activation (degranulation/cytotoxicity), proliferation, and cytokine release using a model cell line expressing the engineered CAR target antigens in absence of small molecule (Rapamycin, rapalogs or synthetic rapalogs). The same experiment is then reproduced in presence of the small molecule to assess the inhibition properties of the system.

REFERENCES

Belshaw, P J; Ho, S N; Crabtree, G R; Schreiber, S L (1996). "Controlling protein association and subcellular localization with a synthetic ligand that induces heterodimerization of proteins.". *Proceedings of the National Academy of Sciences of the United States of America* 93 (10): 4604-7

Bierer, B. E., G. Hollander, et al. (1993). "Cyclosporin A and FK506: molecular mechanisms of immunosuppression and probes for transplantation biology." Curr Opin Immunol 5(5): 763-73.

Boch, J., H. Scholze, et al. (2009). "Breaking the code of DNA binding specificity of TAL-type III effectors." Science 326(5959): 1509-12.

Carsberg, C. J., Myers, K. A., Evans, G. S., Allen, T. D., Stern, P. L (1995) "Metastasis-associated 5T4 oncofoetal antigen is concentrated at microvillus projections of the plasma membrane"*J. Cell. Sci.* 108 (8):2905-16

Castro, F. V., McGinn, O. J., Krishnan, S., Marinov, G., Rutkowski, A. J., Elkord, E., Burt, D. J., Holland, M., Vaghjiani, R., Gallego, A., Saha, V. and Stern, P. L. (2012). "5T4 oncofetal antigen is expressed in high risk of relapse childhood pre-B acute lymphoblastic leukemia and is associated with a more invasive and chemotactic phenotype." Leukemia 26(7):1487-98

Chu J., Deng, Y. Benson, D. M., Hughes T., Zhang, J., Peng, Y., Mao, H., Yi, L, Ghoshal, K., He, X., Devine, S. M., Zhang, X., Caligiuri, M. A., Hofmeister, C. C. and Yu, J. (2013). "CS1-specific chimeric antigen receptor (CAR)-engineered natural killer cells enhance in vitro and in vivo antitumor activity against human multiple myeloma". Leukemia Deaglio S, Mehta K, Malavasi F (2001). "Human CD38: a (r)evolutionary story of enzymes and receptors". Leuk. Res. 25 (1): 1-12.)

Dolan, D. E., and Gupta S. (2014). "PD-1 Pathway Inhibitors: Changing the Landscape of Cancer Immunotherapy", Cancer Control, Vol. 21 (3):231-237

Doronina, V. A., C. Wu, et al. (2008). "Site-specific release of nascent chains from ribosomes at a sense codon." Mol Cell Biol 28(13): 4227-39.

Farrar, M A; Alberol-Ila, J; Perlmutter, R M (Sep. 12, 1996). "Activation of the Raf-1 kinase cascade by coumermycin-induced dimerization.". *Nature* 383 (6596): 178-81.

Fedorov, V. D., Themeli, M., Sadelain, M. (2013). "PD-1- and CTLA-4-Based Inhibitory Chimeric Antigen Receptors (iCARs) Divert Off-Target Immunotherapy Responses". *Sci Transl Med* 5 (215).

Finbloom, D. S., and Winestock, K. D. (1995). "IL-10 induces the tyrosine phosphorylation of tyk2 and Jak1 and the differential assembly of STAT1 alpha and STAT3 complexes in human T cells and monocytes." The Journal of Immunology 155(3): 1079-1090

Henderson, D. J., I. Naya, et al. (1991). "Comparison of the effects of FK-506, cyclosporin A and rapamycin on IL-2 production." Immunology 73(3): 316-21.

Ho, S N; Biggar, S R; Spencer, D M; Schreiber, S L; Crabtree, G R (Aug. 29, 1996). "Dimeric ligands define a role for transcriptional activation domains in reinitiation.". *Nature* 382 (6594): 822-6.

Hole, N., and Stern, P. L., (1988). "A 72 kD trophoblast glycoprotein defined by a monoclonal antibody." Br. J. Cancer 54: 239-246.

Jena, B., G. Dotti, et al. (2010). "Redirecting T-cell specificity by introducing a tumor-specific chimeric antigen receptor." Blood 116(7):1035-44

Ito, S., Ansari, P., Sakatsume, M., Dickensheets, H., Vazquez, N., Donnelly, R. P., Larner, A. C., and Finbloom D. S. (1999). "Interleukin-10 Inhibits Expression of Both Interferon—and Interferon γ-Induced Genes by Suppressing Tyrosine Phosphorylation of STAT1". Blood: 93 (5).

Jena, B., G. Dotti, et al. (2010). "Redirecting T-cell specificity by introducing a tumor-specific chimeric antigen receptor." Blood 116(7): 1035-44.

Liu, J., M. W. Albers, et al. (1992). "Inhibition of T cell signaling by immunophilin-ligand complexes correlates with loss of calcineurin phosphatase activity." Biochemistry 31(16): 3896-901.

Miyamoto, T; DeRose, R; Suarez, A; Ueno, T; Chen, M; Sun, T P; Wolfgang, M J; Mukherjee, C; Meyers, D J; Inoue, T (2012). "Rapid and orthogonal logic gating with a gibberellin-induced dimerization system.". *Nature chemical biology* 8 (5): 465-70.

Moscou, M. J. and A. J. Bogdanove (2009). "A simple cipher governs DNA recognition by TAL effectors." Science 326(5959): 1501.

Park, T. S., S. A. Rosenberg, et al. (2011). "Treating cancer with genetically engineered T cells." Trends Biotechnol 29(11): 550-7.

Rivera, V M; Clackson, T; Natesan, S; Pollock, R; Amara, J F; Keenan, T; Magari, S R; Phillips, T; Courage, N L; Cerasoli F, Jr; Holt, D A; Gilman, M (September 1996). "A humanized system for pharmacologic control of gene expression." *Nature Medicine* 2 (9): 1028-32.

Sheppard, K. A., Fitz, L. J., Lee, J. M., Benander, C., George, J. A., Wooters, J., Qiu, Y., Jussif. J. M., Carter, L. L., Wood, C. R., Chaudhary, D. (2004) "PD-1 inhibits T-cell receptor induced phosphorylation of the ZAP70/CD3zeta signalosome and downstream signaling to PKCtheta". FEBS Lett. 10, 574(1-3):37-41.

Spencer, D. M., Wandless, T. J., Schreiber, S. L., Crabtree, G. R. (1993). "Controlling signal transduction with synthetic ligands". *Science* 262 (5136): 1019-24.

Springer, T. A. (1985) "Hybridoma technology in biosciences and medecine", Plenum Press.

Starzynska, T., Wiechowska-Kozlowska, A., Marlicz, K., et al. (1998). "5T4 oncofetal antigen in gastric carcinoma and its clinical significance". Eur J Gastroenterol Hepatol 10 (6): 479-84.

Wrigley, E. McGown A T., Rennison J., Swindell R. Crowther, D. Starzynska T. and (1995). "Stern P. L. 5T4 oncofetal antigen expression in ovarian carcinoma". International Journal of Gynecological Cancer. 5 (4):269-274.

---

The invention claimed is:

1. A method comprising:
   contacting an engineered immune cell with an external ligand,
   wherein the engineered immune cell co-expresses a Chimeric Antigen Receptor (CAR) comprising a first dimerization domain comprising FKBP or FRB, the CAR being activated in vivo and/or in vitro by the external ligand, and an engineered inhibitory membrane protein (IMP) complex, the IMP comprising at least one intracellular inhibitory signaling domain from PD1 and one second dimerization domain comprising FKBP or FRB, and
   wherein the external ligand binds to the CAR, which results in a signal transduction through the CAR; and
   adding rapamycin or a rapalog that binds to the first dimerization domain comprising FKBP or FRB of the CAR and to the second dimerization domain comprising FKBP or FRB of the IMP to form a non-covalently bonded macromolecular complex between said CAR and IMP.

2. The method according to claim 1, wherein said signal transduction of the CAR is an activation of the engineered immune cell.

3. The method according to claim 1, wherein the formation of the non-covalently bonded macromolecular complex between the CAR and the IMP switches off the CAR signal transduction.

4. The method according to claim 1, wherein said engineered immune cell is a T-cell.

5. The method according to claim 1, wherein said CAR is a single chain CAR.

6. The method according to claim 1, wherein said CAR is a multi-chain CAR (mcCAR).

7. The method according to claim 1, wherein said dimerization domains are extracellular domains.

8. The method according to claim 1, wherein the dimerization domains are intracellular domains.

9. The method according to claim 1, wherein said first and second dimerization domains have at least 80% identity with SEQ ID No. 14 and SEQ ID No. 15, respectively.

10. A method for producing an engineered immune cell expressing a CAR non-covalently bound to an IMP complex, comprising
    transfecting into an immune cell at least a first polynucleotide encoding a CAR comprising a first dimerization domain comprising FKBP or FRB, and at least a second polynucleotide encoding an engineered IMP complex comprising at least one inhibitory signaling domain from PD1 and a second dimerization domain comprising FKBP or FRB that when contacted with rapamycin or a rapalog are capable of non-covalently binding to each other through the presence of the rapamycin or a rapalog, and
    wherein the IMP complex binds to the CAR through the rapamycin or a rapalog.

11. The method according to claim 10, wherein the immune cell is transfected by a retroviral vector.

12. The method according to claim 10, wherein the immune cell is transfected by a polycistronic CAR/IMP-encoding mRNA.

13. The method according to claim 10, further comprising inactivating at least one gene encoding a T-cell receptor (TCR) component.

14. The method according to claim 13, wherein the at least one TCR component is inactivated by a TALE nuclease.

15. A CAR/IMP complex comprising at least two transmembrane chimeric polypeptides, wherein
    a first transmembrane polypeptide is a CAR comprising a first dimerization domain comprising FKBP or FRB; and
    a second transmembrane polypeptide is an engineered IMP complex, said IMP complex comprising at least one intracellular inhibitory signaling domain from PD1 and a second dimerization domain comprising FKBP or FRB;
    wherein the dimerization domains are capable of non-covalently binding to each other through the presence of rapamycin or a rapalog.

16. The CAR/IMP complex according to claim 15, wherein both dimerization domains are located extracellularly.

17. The CAR/IMP complex according to claim 15, wherein the CAR is a mcCAR.

18. The CAR/IMP complex according to claim 15, wherein the CAR is a single-chain CAR.

19. The CAR/IMP complex according to claim 15, wherein said first and second dimerization domains have at least 80% identity with SEQ ID NO 14 and SEQ ID NO 15, respectively.

20. An engineered immune cell comprising a surface expressed CAR and an IMP, said IMP comprising at least one intracellular inhibitory signaling domain from PD1, wherein said CAR and IMP each comprises a dimerization domain comprising FKBP or FRB, both dimerization domains interacting with rapamycin or a rapalog to form a non-covalently bonded macromolecular complex between said CAR and IMP.

21. The engineered immune cell according to claim 20, wherein both dimerization domains are extracellular.

22. The engineered immune cell according to claim 20, wherein both dimerization domains are intracellular.

23. The engineered immune cell according to claim 20, wherein the CAR is a mcCAR.

24. The engineered immune cell according to claim 23, wherein the mcCAR comprises at least an alpha chain (FCεRα), a beta chain (FCεRβ) and a gamma chain (FCεRγ).

25. The engineered immune cell according to claim 24, wherein the dimerization domain of the CAR is part of the alpha chain (FCεRα).

26. The engineered immune cell according to claim 24, wherein mcCAR comprises:
    an alpha chain (FCεRα) comprising at least:
        (a) a signal sequence and an antigen-specific targeting region;
        (b) a dimerization domain;
        (c) an extracellular spacer domain (hinge); and
        (d) a transmembrane domain;
    a beta chain (FCεRβ) comprising at least:
        (a) a signal sequence;
        (b) an extracellular spacer domain (hinge);
        (c) a transmembrane domain; and
        (d) a co-stimulatory ligand;
    a gamma chain (FCεRγ) comprising at least:
        (a) a signal sequence;
        (b) an extracellular spacer domain (hinge);
        (c) a transmembrane domain; and
        (d) a signal transducing domain.

27. The engineered immune cell according to claim 20, wherein said engineered immune cell is recovered from a donor.

28. The engineered immune cell according to claim 20, wherein said engineered immune cell is recovered from a patient.

29. A method comprising administering the engineered immune cell according to claim 20 to a patient, and rapamycin or a rapalog to modulate the formation of a non-covalently bonded macromolecular complex between said CAR and IMP said immune cell in the patient.

* * * * *

SEQUENCE LISTING

```
<160> NUMBER OF SEQ ID NOS: 112

<210> SEQ ID NO 1
<211> LENGTH: 25
<212> TYPE: PRT
<213> ORGANISM: homo sapiens
<220> FEATURE:
<223> OTHER INFORMATION: Signal sequence FcER1-SP

<400> SEQUENCE: 1

Met Ala Pro Ala Met Glu Ser Pro Thr Leu Leu Cys Val Ala Leu Leu
1               5                   10                  15

Phe Phe Ala Pro Asp Gly Val Leu Ala
            20                  25

<210> SEQ ID NO 2
<211> LENGTH: 273
<212> TYPE: PRT
<213> ORGANISM: artificial sequence
<220> FEATURE:
<223> OTHER INFORMATION: CD123-scFv

<400> SEQUENCE: 2

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
            20                  25                  30

Gly Pro Glu Leu Lys Lys Pro Gly Glu Thr Val Lys Ile Ser Cys Lys
        35                  40                  45

Ala Ser Gly Tyr Ile Phe Thr Asn Tyr Gly Met Asn Trp Val Lys Gln
    50                  55                  60

Ala Pro Gly Lys Ser Phe Lys Trp Met Gly Trp Ile Asn Thr Tyr Thr
65                  70                  75                  80
```

Gly Glu Ser Thr Tyr Ser Ala Asp Phe Lys Gly Arg Phe Ala Phe Ser
            85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
            115                 120                 125

Pro Met Asp Tyr Trp Gly Gln Gly Thr Ser Val Thr Val Ser Ser Gly
    130                 135                 140

Gly Gly Gly Ser Gly Gly Gly Ser Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Asn Tyr Gly Asn
            180                 185                 190

Thr Phe Met His Trp Tyr Gln Gln Lys Pro Gly Gln Pro Pro Lys Leu
        195                 200                 205

Leu Ile Tyr Arg Ala Ser Asn Leu Glu Ser Gly Ile Pro Ala Arg Phe
    210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
                245                 250                 255

Pro Pro Thr Phe Gly Ala Gly Thr Lys Leu Glu Leu Lys Arg Ser Asp
            260                 265                 270

Pro

<210> SEQ ID NO 3
<211> LENGTH: 283
<212> TYPE: PRT
<213> ORGANISM: artificial sequence
<220> FEATURE:
<223> OTHER INFORMATION: Klo43-3-scFv

<400> SEQUENCE: 3

Met Ala Pro Ala Met Glu Ser Pro Thr Leu Leu Cys Val Ala Leu Leu
1               5                   10                  15

Phe Phe Ala Pro Asp Gly Val Leu Ala Glu Val Lys Leu Val Glu Ser
            20                  25                  30

Gly Gly Gly Leu Val Gln Pro Gly Gly Ser Leu Ser Leu Ser Cys Ala
        35                  40                  45

Ala Ser Gly Phe Thr Phe Thr Asp Tyr Tyr Met Ser Trp Val Arg Gln
    50                  55                  60

Pro Pro Gly Lys Ala Leu Glu Trp Leu Ala Leu Ile Arg Ser Lys Ala
65                  70                  75                  80

Asp Gly Tyr Thr Thr Glu Tyr Ser Ala Ser Val Lys Gly Arg Phe Thr
            85                  90                  95

Leu Ser Arg Asp Asp Ser Gln Ser Ile Leu Tyr Leu Gln Met Asn Ala
            100                 105                 110

Leu Arg Pro Glu Asp Ser Ala Thr Tyr Tyr Cys Ala Arg Asp Ala Ala
            115                 120                 125

Tyr Tyr Ser Tyr Tyr Ser Pro Glu Gly Ala Met Asp Tyr Trp Gly Gln
    130                 135                 140

Gly Thr Ser Val Thr Val Ser Ser Gly Gly Gly Gly Ser Gly Gly Gly
145                 150                 155                 160

```
Gly Ser Gly Gly Gly Gly Ser Met Ala Asp Tyr Lys Asp Ile Val Met
                165                 170                 175

Thr Gln Ser His Lys Phe Met Ser Thr Ser Val Gly Asp Arg Val Asn
            180                 185                 190

Ile Thr Cys Lys Ala Ser Gln Asn Val Asp Ser Ala Val Ala Trp Tyr
        195                 200                 205

Gln Gln Lys Pro Gly Gln Ser Pro Lys Ala Leu Ile Tyr Ser Ala Ser
    210                 215                 220

Tyr Arg Tyr Ser Gly Val Pro Asp Arg Phe Thr Gly Arg Gly Ser Gly
225                 230                 235                 240

Thr Asp Phe Thr Leu Thr Ile Ser Ser Val Gln Ala Glu Asp Leu Ala
                245                 250                 255

Val Tyr Tyr Cys Gln Gln Tyr Tyr Ser Thr Pro Trp Thr Phe Gly Gly
            260                 265                 270

Gly Thr Lys Leu Glu Ile Lys Arg Ser Asp Pro
        275                 280

<210> SEQ ID NO 4
<211> LENGTH: 271
<212> TYPE: PRT
<213> ORGANISM: artificial sequence
<220> FEATURE:
<223> OTHER INFORMATION: 5T4WT19-scFv

<400> SEQUENCE: 4

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Asp Leu Val Lys Pro Gly Ala Ser Val Lys Ile Ser Cys Lys
        35                  40                  45

Ala Ser Gly Tyr Ser Phe Thr Gly Tyr Tyr Met His Trp Val Lys Gln
    50                  55                  60

Ser His Gly Lys Ser Leu Glu Trp Ile Gly Arg Ile Asn Pro Asn Asn
65                  70                  75                  80

Gly Val Thr Leu Tyr Asn Gln Lys Phe Lys Asp Lys Ala Ile Leu Thr
                85                  90                  95

Val Asp Lys Ser Ser Thr Thr Ala Tyr Met Glu Leu Arg Ser Leu Thr
            100                 105                 110

Ser Glu Asp Ser Ala Val Tyr Tyr Cys Ala Arg Ser Thr Met Ile Thr
        115                 120                 125

Asn Tyr Val Met Asp Tyr Trp Gly Gln Val Thr Ser Val Thr Val Ser
    130                 135                 140

Ser Gly Gly Gly Gly Ser Gly Gly Gly Ser Gly Gly Gly Gly Ser
145                 150                 155                 160

Ser Ile Val Met Thr Gln Thr Pro Thr Phe Leu Leu Val Ser Ala Gly
                165                 170                 175

Asp Arg Val Thr Ile Thr Cys Lys Ala Ser Gln Ser Val Ser Asn Asp
            180                 185                 190

Val Ala Trp Tyr Gln Gln Lys Pro Gly Gln Ser Pro Thr Leu Leu Ile
        195                 200                 205

Ser Tyr Thr Ser Ser Arg Tyr Ala Gly Val Pro Asp Arg Phe Ile Gly
    210                 215                 220

Ser Gly Tyr Gly Thr Asp Phe Thr Phe Thr Ile Ser Thr Leu Gln Ala
225                 230                 235                 240
```

-continued

Glu Asp Leu Ala Val Tyr Phe Cys Gln Gln Asp Tyr Asn Ser Pro Pro
                245                 250                 255

Thr Phe Gly Gly Gly Thr Lys Leu Glu Ile Lys Arg Ser Asp Pro
            260                 265                 270

<210> SEQ ID NO 5
<211> LENGTH: 277
<212> TYPE: PRT
<213> ORGANISM: artificial sequence
<220> FEATURE:
<223> OTHER INFORMATION: VH-4G7-scFv

<400> SEQUENCE: 5

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

Gly Pro Glu Leu Ile Lys Pro Gly Ala Ser Val Lys Met Ser Cys Lys
            35                  40                  45

Ala Ser Gly Tyr Thr Phe Thr Ser Tyr Val Met His Trp Val Lys Gln
        50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro
        275

<210> SEQ ID NO 6
<211> LENGTH: 45
<212> TYPE: PRT
<213> ORGANISM: homo sapiens
<220> FEATURE:
<223> OTHER INFORMATION: CD8A hinge

<400> SEQUENCE: 6

```
Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
                35                  40                  45
```

<210> SEQ ID NO 7
<211> LENGTH: 233
<212> TYPE: PRT
<213> ORGANISM: homo sapiens
<220> FEATURE:
<223> OTHER INFORMATION: IGHG1 hinge

<400> SEQUENCE: 7

```
Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
                35                  40                  45

Asp Val Ser His Glu Asp Pro Glu Val Lys Phe Asn Trp Tyr Val Asp
50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
                100                 105                 110

Pro Ala Pro Ile Glu Lys Thr Ile Ser Lys Ala Lys Gly Gln Pro Arg
                115                 120                 125

Glu Pro Gln Val Tyr Thr Leu Pro Pro Ser Arg Asp Glu Leu Thr Lys
                130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
                180                 185                 190

Lys Leu Thr Val Asp Lys Ser Arg Trp Gln Gln Gly Asn Val Phe Ser
                195                 200                 205

Cys Ser Val Met His Glu Ala Leu His Asn His Tyr Thr Gln Lys Ser
                210                 215                 220

Leu Ser Leu Ser Pro Gly Lys Lys Asp
225                 230
```

<210> SEQ ID NO 8
<211> LENGTH: 101
<212> TYPE: PRT
<213> ORGANISM: homo sapiens
<220> FEATURE:
<223> OTHER INFORMATION: EpoR_D2 hinge

<400> SEQUENCE: 8

```
Ala Pro Val Gly Leu Val Ala Arg Leu Ala Asp Glu Ser Gly His Val
1               5                   10                  15

Val Leu Arg Trp Leu Pro Pro Pro Glu Thr Pro Met Thr Ser His Ile
```

```
                    20                  25                  30

Arg Tyr Glu Val Asp Val Ser Ala Gly Asn Gly Ala Gly Ser Val Gln
                35                  40                  45

Arg Val Glu Ile Leu Glu Gly Arg Thr Glu Cys Val Leu Ser Asn Leu
        50                  55                  60

Arg Gly Arg Thr Arg Tyr Thr Phe Ala Val Arg Ala Arg Met Ala Glu
65                  70                  75                  80

Pro Ser Phe Gly Gly Phe Trp Ser Ala Trp Ser Glu Pro Val Ser Leu
                    85                  90                  95

Leu Thr Pro Ser Asp
            100

<210> SEQ ID NO 9
<211> LENGTH: 53
<212> TYPE: PRT
<213> ORGANISM: artificial sequence
<220> FEATURE:
<223> OTHER INFORMATION: Alpha-TI-A TM domain

<400> SEQUENCE: 9

Ile Phe Ile Pro Leu Leu Val Val Ile Leu Phe Ala Val Asp Thr Gly
1               5                   10                  15

Leu Phe Ile Ser Thr Gln Gln Val Thr Phe Leu Leu Lys Ile Lys
                20                  25                  30

Arg Thr Arg Lys Gly Phe Arg Leu Leu Asn Pro His Pro Lys Pro Asn
                35                  40                  45

Pro Lys Asn Asn Arg
    50

<210> SEQ ID NO 10
<211> LENGTH: 98
<212> TYPE: PRT
<213> ORGANISM: artificial sequence
<220> FEATURE:
<223> OTHER INFORMATION: Alpha-TI-B TM domain

<400> SEQUENCE: 10

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Phe Phe Ile
                35                  40                  45

Pro Leu Leu Val Val Ile Leu Phe Ala Val Asp Thr Gly Leu Phe Ile
        50                  55                  60

Ser Thr Gln Gln Val Thr Phe Leu Leu Lys Ile Lys Arg Thr Arg
65                  70                  75                  80

Lys Gly Phe Arg Leu Leu Asn Pro His Pro Lys Pro Asn Pro Lys Asn
                85                  90                  95

Asn Arg

<210> SEQ ID NO 11
<211> LENGTH: 373
<212> TYPE: PRT
<213> ORGANISM: artificial sequence
<220> FEATURE:
<223> OTHER INFORMATION: CD19 alpha chain

<400> SEQUENCE: 11
```

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ala Asp Thr Thr Thr Pro Ala Pro Arg Pro Pro Thr Pro Ala
        275                 280                 285

Pro Thr Ile Ala Ser Gln Pro Leu Ser Leu Arg Pro Glu Ala Cys Arg
    290                 295                 300

Pro Ala Ala Gly Gly Ala Val His Thr Arg Gly Leu Asp Phe Ala Cys
305                 310                 315                 320

Asp Phe Phe Ile Pro Leu Leu Val Val Ile Leu Phe Ala Val Asp Thr
                325                 330                 335

Gly Leu Phe Ile Ser Thr Gln Gln Gln Val Thr Phe Leu Leu Lys Ile
            340                 345                 350

Lys Arg Thr Arg Lys Gly Phe Arg Leu Leu Asn Pro His Pro Lys Pro
        355                 360                 365

Asn Pro Lys Asn Asn
    370

<210> SEQ ID NO 12
<211> LENGTH: 257
<212> TYPE: PRT
<213> ORGANISM: artificial sequence
<220> FEATURE:
<223> OTHER INFORMATION: beta-41BB chain
```

<400> SEQUENCE: 12

Met Asp Thr Glu Ser Asn Arg Arg Ala Asn Leu Ala Leu Pro Gln Glu
1               5                   10                  15

Pro Ser Ser Val Pro Ala Phe Glu Val Leu Glu Ile Ser Pro Gln Glu
            20                  25                  30

Val Ser Ser Gly Arg Leu Leu Lys Ser Ala Ser Ser Pro Pro Leu His
        35                  40                  45

Thr Trp Leu Thr Val Leu Lys Lys Glu Gln Glu Phe Leu Gly Val Thr
    50                  55                  60

Gln Ile Leu Thr Ala Met Ile Cys Leu Cys Phe Gly Thr Val Val Cys
65                  70                  75                  80

Ser Val Leu Asp Ile Ser His Ile Glu Gly Asp Ile Phe Ser Ser Phe
                85                  90                  95

Lys Ala Gly Tyr Pro Phe Trp Gly Ala Ile Phe Ser Ile Ser Gly
            100                 105                 110

Met Leu Ser Ile Ile Ser Glu Arg Arg Asn Ala Thr Tyr Leu Val Arg
            115                 120                 125

Gly Ser Leu Gly Ala Asn Thr Ala Ser Ser Ile Ala Gly Gly Thr Gly
    130                 135                 140

Ile Thr Ile Leu Ile Ile Asn Leu Lys Lys Ser Leu Ala Tyr Ile His
145                 150                 155                 160

Ile His Ser Cys Gln Lys Phe Phe Glu Thr Lys Cys Phe Met Ala Ser
            165                 170                 175

Phe Ser Thr Glu Ile Val Val Met Met Leu Phe Leu Thr Ile Leu Gly
            180                 185                 190

Leu Gly Ser Ala Val Ser Leu Thr Ile Cys Gly Ala Gly Glu Glu Leu
    195                 200                 205

Lys Gly Asn Lys Val Pro Glu Lys Arg Gly Arg Lys Lys Leu Leu Tyr
210                 215                 220

Ile Phe Lys Gln Pro Phe Met Arg Pro Val Gln Thr Thr Gln Glu Glu
225                 230                 235                 240

Asp Gly Cys Ser Cys Arg Phe Pro Glu Glu Glu Glu Gly Gly Cys Glu
            245                 250                 255

Leu

<210> SEQ ID NO 13
<211> LENGTH: 20
<212> TYPE: PRT
<213> ORGANISM: artificial sequence
<220> FEATURE:
<223> OTHER INFORMATION: Sequence signal Gamma

<400> SEQUENCE: 13

Met Ala Ile Pro Ala Val Val Leu Leu Leu Leu Leu Val Glu Gln
1               5                   10                  15

Ala Ala Ala Gly
            20

<210> SEQ ID NO 14
<211> LENGTH: 114
<212> TYPE: PRT
<213> ORGANISM: homo sapiens
<220> FEATURE:
<223> OTHER INFORMATION: FKBP

<400> SEQUENCE: 14

```
Ser Gly Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
            20                  25                  30

Glu Asp Gly Lys Lys Phe Asp Ser Ser Arg Asp Arg Asn Lys Pro Phe
                35                  40                  45

Lys Phe Met Leu Gly Lys Gln Glu Val Ile Arg Gly Trp Glu Glu Gly
            50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu Gly Ser Gly
                100                 105                 110

Ala Pro
```

<210> SEQ ID NO 15
<211> LENGTH: 102
<212> TYPE: PRT
<213> ORGANISM: homo sapiens
<220> FEATURE:
<223> OTHER INFORMATION: FRB

<400> SEQUENCE: 15

```
Ser Gly Gly Arg Val Ala Ile Leu Trp His Glu Met Trp His Glu Gly
1               5                   10                  15

Leu Glu Glu Ala Ser Arg Leu Tyr Phe Gly Glu Arg Asn Val Lys Gly
            20                  25                  30

Met Phe Glu Val Leu Glu Pro Leu His Ala Met Met Glu Arg Gly Pro
            35                  40                  45

Gln Thr Leu Lys Glu Thr Ser Phe Asn Gln Ala Tyr Gly Arg Asp Leu
        50                  55                  60

Met Glu Ala Gln Glu Trp Cys Arg Lys Tyr Met Lys Ser Gly Asn Val
65                  70                  75                  80

Lys Asp Leu Thr Gln Ala Trp Asp Leu Tyr Tyr His Val Phe Arg Arg
                85                  90                  95

Ile Gly Ser Gly Ala Pro
                100
```

<210> SEQ ID NO 16
<211> LENGTH: 156
<212> TYPE: PRT
<213> ORGANISM: artificial sequence
<220> FEATURE:
<223> OTHER INFORMATION: Gamma-TI-A

<400> SEQUENCE: 16

```
Ile Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser Arg Val Lys Phe Ser
            35                  40                  45

Arg Ser Ala Asp Ala Pro Ala Tyr Gln Gln Gly Gln Asn Gln Leu Tyr
        50                  55                  60

Asn Glu Leu Asn Leu Gly Arg Arg Glu Glu Tyr Asp Val Leu Asp Lys
65                  70                  75                  80
```

```
Arg Arg Gly Arg Asp Pro Glu Met Gly Gly Lys Pro Arg Arg Lys Asn
                85                  90                  95

Pro Gln Glu Gly Leu Tyr Asn Glu Leu Gln Lys Asp Lys Met Ala Glu
            100                 105                 110

Ala Tyr Ser Glu Ile Gly Met Lys Gly Glu Arg Arg Arg Gly Lys Gly
        115                 120                 125

His Asp Gly Leu Tyr Gln Gly Leu Ser Thr Ala Thr Lys Asp Thr Tyr
    130                 135                 140

Asp Ala Leu His Met Gln Ala Leu Pro Pro Arg Glu
145                 150                 155

<210> SEQ ID NO 17
<211> LENGTH: 156
<212> TYPE: PRT
<213> ORGANISM: artificial sequence
<220> FEATURE:
<223> OTHER INFORMATION: Gamma-TI-B

<400> SEQUENCE: 17

Leu Gly Glu Pro Gln Leu Cys Tyr Ile Leu Asp Ala Ile Leu Phe Leu
1               5                   10                  15

Tyr Gly Ile Val Leu Thr Leu Leu Tyr Cys Arg Leu Lys Ile Gln Val
            20                  25                  30

Arg Lys Ala Ala Ile Thr Ser Tyr Glu Lys Ser Arg Val Lys Phe Ser
        35                  40                  45

Arg Ser Ala Asp Ala Pro Ala Tyr Gln Gln Gly Gln Asn Gln Leu Tyr
    50                  55                  60

Asn Glu Leu Asn Leu Gly Arg Arg Glu Glu Tyr Asp Val Leu Asp Lys
65                  70                  75                  80

Arg Arg Gly Arg Asp Pro Glu Met Gly Gly Lys Pro Arg Arg Lys Asn
                85                  90                  95

Pro Gln Glu Gly Leu Tyr Asn Glu Leu Gln Lys Asp Lys Met Ala Glu
            100                 105                 110

Ala Tyr Ser Glu Ile Gly Met Lys Gly Glu Arg Arg Arg Gly Lys Gly
        115                 120                 125

His Asp Gly Leu Tyr Gln Gly Leu Ser Thr Ala Thr Lys Asp Thr Tyr
    130                 135                 140

Asp Ala Leu His Met Gln Ala Leu Pro Pro Arg Glu
145                 150                 155

<210> SEQ ID NO 18
<211> LENGTH: 22
<212> TYPE: PRT
<213> ORGANISM: artificial sequence
<220> FEATURE:
<223> OTHER INFORMATION: VH-4G7-ss

<400> SEQUENCE: 18

Met Ala Leu Pro Val Thr Ala Leu Leu Leu Pro Leu Ala Leu Leu Leu
1               5                   10                  15

His Ala Ala Arg Pro Gly
            20

<210> SEQ ID NO 19
<211> LENGTH: 25
<212> TYPE: PRT
<213> ORGANISM: homo sapiens
<220> FEATURE:
<223> OTHER INFORMATION: CD8a TM
```

```
<400> SEQUENCE: 19

Ile Tyr Ile Trp Ala Pro Leu Ala Gly Thr Cys Gly Val Leu Leu Leu
1               5                   10                  15

Ser Leu Val Ile Thr Leu Tyr Cys Arg
            20                  25

<210> SEQ ID NO 20
<211> LENGTH: 31
<212> TYPE: PRT
<213> ORGANISM: homo sapiens
<220> FEATURE:
<223> OTHER INFORMATION: 4-1BB TM

<400> SEQUENCE: 20

Ile Ile Ser Phe Phe Leu Ala Leu Thr Ser Thr Ala Leu Leu Phe Leu
1               5                   10                  15

Leu Phe Phe Leu Thr Leu Arg Phe Ser Val Val Lys Arg Gly Arg
            20                  25                  30

<210> SEQ ID NO 21
<211> LENGTH: 27
<212> TYPE: PRT
<213> ORGANISM: homo sapiens
<220> FEATURE:
<223> OTHER INFORMATION: DAP10 TM

<400> SEQUENCE: 21

Ile Leu Leu Ala Gly Leu Val Ala Ala Asp Ala Val Ala Ser Leu Leu
1               5                   10                  15

Ile Val Gly Ala Val Phe Leu Cys Ala Arg Arg
            20                  25

<210> SEQ ID NO 22
<211> LENGTH: 33
<212> TYPE: PRT
<213> ORGANISM: homo sapiens
<220> FEATURE:
<223> OTHER INFORMATION: CD28 TM

<400> SEQUENCE: 22

Ile Phe Trp Val Leu Val Val Gly Gly Val Leu Ala Cys Tyr Ser
1               5                   10                  15

Leu Leu Val Thr Val Ala Phe Ile Ile Phe Trp Val Arg Ser Lys Arg
            20                  25                  30

Arg

<210> SEQ ID NO 23
<211> LENGTH: 97
<212> TYPE: PRT
<213> ORGANISM: homo sapiens
<220> FEATURE:
<223> OTHER INFORMATION: PD1 inhibitory signaling domain

<400> SEQUENCE: 23

Ser Arg Ala Ala Arg Gly Thr Ile Gly Ala Arg Arg Thr Gly Gln Pro
1               5                   10                  15

Leu Lys Glu Asp Pro Ser Ala Val Pro Val Phe Ser Val Asp Tyr Gly
            20                  25                  30

Glu Leu Asp Phe Gln Trp Arg Glu Lys Thr Pro Glu Pro Pro Val Pro
                35                  40                  45

Cys Val Pro Glu Gln Thr Glu Tyr Ala Thr Ile Val Phe Pro Ser Gly
        50                  55                  60
```

```
Met Gly Thr Ser Ser Pro Ala Arg Arg Gly Ser Ala Asp Gly Pro Arg
 65                  70                  75                  80

Ser Ala Gln Pro Leu Arg Pro Glu Asp Gly His Cys Ser Trp Pro Leu
                 85                  90                  95

Glu

<210> SEQ ID NO 24
<211> LENGTH: 110
<212> TYPE: PRT
<213> ORGANISM: homo sapiens
<220> FEATURE:
<223> OTHER INFORMATION: FKBP_pos3_IMP

<400> SEQUENCE: 24

Ser Gly Gly Val Gln Val Glu Thr Ile Ser Pro Gly Asp Gly Arg Thr
  1               5                  10                  15

Phe Pro Lys Arg Gly Gln Thr Cys Val Val His Tyr Thr Gly Met Leu
                 20                  25                  30

Glu Asp Gly Lys Lys Phe Asp Ser Ser Arg Asp Arg Asn Lys Pro Phe
             35                  40                  45

Lys Phe Met Leu Gly Lys Gln Glu Val Ile Arg Gly Trp Glu Glu Gly
 50                  55                  60

Val Ala Gln Met Ser Val Gly Gln Arg Ala Lys Leu Thr Ile Ser Pro
 65                  70                  75                  80

Asp Tyr Ala Tyr Gly Ala Thr Gly His Pro Gly Ile Ile Pro Pro His
                 85                  90                  95

Ala Thr Leu Val Phe Asp Val Glu Leu Leu Lys Leu Glu Glu
                100                 105                 110

<210> SEQ ID NO 25
<211> LENGTH: 98
<212> TYPE: PRT
<213> ORGANISM: homo sapiens
<220> FEATURE:
<223> OTHER INFORMATION: FRB_pos3_IMP

<400> SEQUENCE: 25

Ser Gly Gly Arg Val Ala Ile Leu Trp His Glu Met Trp His Glu Gly
  1               5                  10                  15

Leu Glu Glu Ala Ser Arg Leu Tyr Phe Gly Glu Arg Asn Val Lys Gly
                 20                  25                  30

Met Phe Glu Val Leu Glu Pro Leu His Ala Met Met Glu Arg Gly Pro
             35                  40                  45

Gln Thr Leu Lys Glu Thr Ser Phe Asn Gln Ala Tyr Gly Arg Asp Leu
 50                  55                  60

Met Glu Ala Gln Glu Trp Cys Arg Lys Tyr Met Lys Ser Gly Asn Val
 65                  70                  75                  80

Lys Asp Leu Thr Gln Ala Trp Asp Leu Tyr Tyr His Val Phe Arg Arg
                 85                  90                  95

Ile Glu

<210> SEQ ID NO 26
<211> LENGTH: 45
<212> TYPE: PRT
<213> ORGANISM: homo sapiens
<220> FEATURE:
<223> OTHER INFORMATION: CD28 linker

<400> SEQUENCE: 26
```

Ser Arg Leu Leu His Ser Asp Tyr Met Asn Met Thr Pro Arg Arg Pro
1               5                   10                  15

Gly Pro Thr Arg Lys His Tyr Gln Pro Tyr Ala Pro Pro Arg Asp Phe
                20                  25                  30

Ala Ala Tyr Arg Ser Gly Ser Gly Ser Gly Ser
        35                  40              45

<210> SEQ ID NO 27
<211> LENGTH: 48
<212> TYPE: PRT
<213> ORGANISM: homo sapiens
<220> FEATURE:
<223> OTHER INFORMATION: 4-1BB linker

<400> SEQUENCE: 27

Gly Arg Lys Lys Leu Leu Tyr Ile Phe Lys Gln Pro Phe Met Arg Pro
1               5                   10                  15

Val Gln Thr Thr Gln Glu Glu Asp Gly Cys Ser Cys Arg Phe Pro Glu
                20                  25                  30

Glu Glu Glu Gly Gly Cys Glu Leu Gly Ser Gly Ser Gly Ser Gly Ser
        35                  40                  45

<210> SEQ ID NO 28
<211> LENGTH: 50
<212> TYPE: PRT
<213> ORGANISM: homo sapiens
<220> FEATURE:
<223> OTHER INFORMATION: OX40 linker

<400> SEQUENCE: 28

Ala Leu Tyr Leu Leu Arg Arg Asp Gln Arg Leu Pro Pro Asp Ala His
1               5                   10                  15

Lys Pro Pro Gly Gly Gly Ser Phe Arg Thr Pro Ile Gln Glu Glu Gln
                20                  25                  30

Ala Asp Ala His Ser Thr Leu Ala Lys Ile Gly Ser Gly Ser Gly Ser
        35                  40                  45

Gly Ser
    50

<210> SEQ ID NO 29
<211> LENGTH: 28
<212> TYPE: PRT
<213> ORGANISM: homo sapiens
<220> FEATURE:
<223> OTHER INFORMATION: DAP10 linker

<400> SEQUENCE: 29

Pro Arg Arg Ser Pro Ala Gln Glu Asp Gly Lys Val Tyr Ile Asn Met
1               5                   10                  15

Pro Gly Arg Gly Gly Ser Gly Ser Gly Ser Gly Ser
                20                  25

<210> SEQ ID NO 30
<211> LENGTH: 54
<212> TYPE: PRT
<213> ORGANISM: homo sapiens
<220> FEATURE:
<223> OTHER INFORMATION: CD18 linker

<400> SEQUENCE: 30

Lys Ala Leu Ile His Leu Ser Asp Leu Arg Glu Tyr Arg Arg Phe Glu
1               5                   10                  15

-continued

```
Lys Glu Lys Leu Lys Ser Gln Trp Asn Asn Asp Asn Pro Leu Phe Lys
             20                  25                  30

Ser Ala Thr Thr Thr Val Met Asn Pro Lys Phe Ala Glu Ser Gly Ser
             35                  40                  45

Gly Ser Gly Ser Gly Ser
     50
```

<210> SEQ ID NO 31
<211> LENGTH: 49
<212> TYPE: PRT
<213> ORGANISM: homo sapiens
<220> FEATURE:
<223> OTHER INFORMATION: CD28 linker

<400> SEQUENCE: 31

```
Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
             20                  25                  30

Pro Arg Asp Phe Ala Ala Tyr Arg Ser Gly Ser Gly Ser Gly Ser Gly
             35                  40                  45

Ser
```

<210> SEQ ID NO 32
<211> LENGTH: 33
<212> TYPE: PRT
<213> ORGANISM: homo sapiens
<220> FEATURE:
<223> OTHER INFORMATION: CD275 linker

<400> SEQUENCE: 32

```
Arg Asp Arg Cys Leu Gln His Ser Tyr Ala Gly Ala Trp Ala Val Ser
1               5                   10                  15

Pro Glu Thr Glu Leu Thr Gly His Val Gly Ser Gly Ser Gly Ser Gly
             20                  25                  30

Ser
```

<210> SEQ ID NO 33
<211> LENGTH: 68
<212> TYPE: PRT
<213> ORGANISM: homo sapiens
<220> FEATURE:
<223> OTHER INFORMATION: HVEM linker

<400> SEQUENCE: 33

```
Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
             20                  25                  30

Glu Ala Leu Gln Ala Pro Pro Asp Val Thr Thr Val Ala Val Glu Glu
             35                  40                  45

Thr Ile Pro Ser Phe Thr Gly Arg Ser Pro Asn His Gly Ser Gly Ser
     50                  55                  60

Gly Ser Gly Ser
65
```

<210> SEQ ID NO 34
<211> LENGTH: 45
<212> TYPE: PRT
<213> ORGANISM: homo sapiens
<220> FEATURE:
<223> OTHER INFORMATION: LIGHT linker

<400> SEQUENCE: 34

Met Glu Glu Ser Val Val Arg Pro Ser Val Phe Val Val Asp Gly Gln
1               5                   10                  15

Thr Asp Ile Pro Phe Thr Arg Leu Gly Arg Ser His Arg Arg Gln Ser
            20                  25                  30

Cys Ser Val Ala Arg Gly Ser Gly Ser Gly Ser
        35                  40                  45

<210> SEQ ID NO 35
<211> LENGTH: 30
<212> TYPE: PRT
<213> ORGANISM: homo sapiens
<220> FEATURE:
<223> OTHER INFORMATION: CD40L linker

<400> SEQUENCE: 35

Met Ile Glu Thr Tyr Asn Gln Thr Ser Pro Arg Ser Ala Ala Thr Gly
1               5                   10                  15

Leu Pro Ile Ser Met Lys Gly Ser Gly Ser Gly Ser
            20                  25                  30

<210> SEQ ID NO 36
<211> LENGTH: 66
<212> TYPE: PRT
<213> ORGANISM: homo sapiens
<220> FEATURE:
<223> OTHER INFORMATION: GITR linker

<400> SEQUENCE: 36

Gln Leu Gly Leu His Ile Trp Gln Leu Arg Ser Gln Cys Met Trp Pro
1               5                   10                  15

Arg Glu Thr Gln Leu Leu Leu Glu Val Pro Pro Ser Thr Glu Asp Ala
            20                  25                  30

Arg Ser Cys Gln Phe Pro Glu Glu Glu Arg Gly Glu Arg Ser Ala Glu
        35                  40                  45

Glu Lys Gly Arg Leu Gly Asp Leu Trp Val Gly Ser Gly Ser Gly Ser
    50                  55                  60

Gly Ser
65

<210> SEQ ID NO 37
<211> LENGTH: 56
<212> TYPE: PRT
<213> ORGANISM: homo sapiens
<220> FEATURE:
<223> OTHER INFORMATION: TIM1 linker

<400> SEQUENCE: 37

Lys Lys Tyr Phe Phe Lys Lys Glu Val Gln Gln Leu Ser Val Ser Phe
1               5                   10                  15

Ser Ser Leu Gln Ile Lys Ala Leu Gln Asn Ala Val Glu Lys Glu Val
            20                  25                  30

Gln Ala Glu Asp Asn Ile Tyr Ile Glu Asn Ser Leu Tyr Ala Thr Asp
        35                  40                  45

Gly Ser Gly Ser Gly Ser Gly Ser
    50                  55

<210> SEQ ID NO 38

<211> LENGTH: 85
<212> TYPE: PRT
<213> ORGANISM: homo sapiens
<220> FEATURE:
<223> OTHER INFORMATION: SLAM linker

<400> SEQUENCE: 38

Gln Leu Arg Arg Arg Gly Lys Thr Asn His Tyr Gln Thr Thr Val Glu
1               5                   10                  15

Lys Lys Ser Leu Thr Ile Tyr Ala Gln Val Gln Lys Pro Gly Pro Leu
            20                  25                  30

Gln Lys Lys Leu Asp Ser Phe Pro Ala Gln Asp Pro Cys Thr Thr Ile
        35                  40                  45

Tyr Val Ala Ala Thr Glu Pro Val Pro Glu Ser Val Gln Glu Thr Asn
    50                  55                  60

Ser Ile Thr Val Tyr Ala Ser Val Thr Leu Pro Glu Ser Gly Ser Gly
65                  70                  75                  80

Ser Gly Ser Gly Ser
            85

<210> SEQ ID NO 39
<211> LENGTH: 124
<212> TYPE: PRT
<213> ORGANISM: homo sapiens
<220> FEATURE:
<223> OTHER INFORMATION: CD2 linker

<400> SEQUENCE: 39

Lys Arg Lys Lys Gln Arg Ser Arg Arg Asn Asp Glu Glu Leu Glu Thr
1               5                   10                  15

Arg Ala His Arg Val Ala Thr Glu Glu Arg Gly Arg Lys Pro His Gln
            20                  25                  30

Ile Pro Ala Ser Thr Pro Gln Asn Pro Ala Thr Ser Gln His Pro Pro
        35                  40                  45

Pro Pro Pro Gly His Arg Ser Gln Ala Pro Ser His Arg Pro Pro Pro
    50                  55                  60

Pro Gly His Arg Val Gln His Gln Pro Gln Lys Arg Pro Pro Ala Pro
65                  70                  75                  80

Ser Gly Thr Gln Val His Gln Gln Lys Gly Pro Pro Leu Pro Arg Pro
            85                  90                  95

Arg Val Gln Pro Lys Pro Pro His Gly Ala Ala Glu Asn Ser Leu Ser
        100                 105                 110

Pro Ser Ser Asn Gly Ser Gly Ser Gly Ser Gly Ser
    115                 120

<210> SEQ ID NO 40
<211> LENGTH: 40
<212> TYPE: PRT
<213> ORGANISM: homo sapiens
<220> FEATURE:
<223> OTHER INFORMATION: TLT-2 linker

<400> SEQUENCE: 40

Lys Lys Arg His Met Ala Ser Tyr Ser Met Cys Ser Asp Pro Ser Thr
1               5                   10                  15

Arg Asp Pro Pro Gly Arg Pro Glu Pro Tyr Val Glu Val Tyr Leu Ile
            20                  25                  30

Gly Ser Gly Ser Gly Ser Gly Ser
        35                  40

```
<210> SEQ ID NO 41
<211> LENGTH: 62
<212> TYPE: PRT
<213> ORGANISM: homo sapiens
<220> FEATURE:
<223> OTHER INFORMATION: LAG3 linker

<400> SEQUENCE: 41

His Leu Trp Arg Arg Gln Trp Arg Pro Arg Arg Phe Ser Ala Leu Glu
1               5                   10                  15

Gln Gly Ile His Pro Pro Gln Ala Gln Ser Lys Ile Glu Glu Leu Glu
            20                  25                  30

Gln Glu Pro Glu Pro Glu Pro Glu Pro Glu Pro Glu Pro Glu Pro Glu
        35                  40                  45

Pro Glu Pro Glu Gln Leu Gly Ser Gly Ser Gly Ser
    50                  55                  60

<210> SEQ ID NO 42
<211> LENGTH: 60
<212> TYPE: PRT
<213> ORGANISM: homo sapiens
<220> FEATURE:
<223> OTHER INFORMATION: DAP12 linker

<400> SEQUENCE: 42

Tyr Phe Leu Gly Arg Leu Val Pro Arg Gly Arg Gly Ala Ala Glu Ala
1               5                   10                  15

Ala Thr Arg Lys Gln Arg Ile Thr Glu Thr Glu Ser Pro Tyr Gln Glu
            20                  25                  30

Leu Gln Gly Gln Arg Ser Asp Val Tyr Ser Asp Leu Asn Thr Gln Arg
        35                  40                  45

Pro Tyr Tyr Lys Gly Ser Gly Ser Gly Ser Gly Ser
    50                  55                  60

<210> SEQ ID NO 43
<211> LENGTH: 107
<212> TYPE: PRT
<213> ORGANISM: homo sapiens
<220> FEATURE:
<223> OTHER INFORMATION: CD84 linker

<400> SEQUENCE: 43

Arg Leu Phe Lys Arg Arg Gln Gly Arg Ile Phe Pro Glu Gly Ser Cys
1               5                   10                  15

Leu Asn Thr Phe Thr Lys Asn Pro Tyr Ala Ala Ser Lys Lys Thr Ile
            20                  25                  30

Tyr Thr Tyr Ile Met Ala Ser Arg Asn Thr Gln Pro Ala Glu Ser Arg
        35                  40                  45

Ile Tyr Asp Glu Ile Leu Gln Ser Lys Val Leu Pro Ser Lys Glu Glu
    50                  55                  60

Pro Val Asn Thr Val Tyr Ser Glu Val Gln Phe Ala Asp Lys Met Gly
65                  70                  75                  80

Lys Ala Ser Thr Gln Asp Ser Lys Pro Pro Gly Thr Ser Ser Tyr Glu
                85                  90                  95

Ile Val Ile Gly Ser Gly Ser Gly Ser Gly Ser
            100                 105

<210> SEQ ID NO 44
<211> LENGTH: 113
<212> TYPE: PRT
```

<213> ORGANISM: homo sapiens
<220> FEATURE:
<223> OTHER INFORMATION: CD244 linker

<400> SEQUENCE: 44

```
Glu Phe Leu Thr Ile Tyr Glu Asp Val Lys Asp Leu Lys Thr Arg Arg
1               5                   10                  15

Asn His Glu Gln Glu Gln Thr Phe Pro Gly Gly Ser Thr Ile Tyr
                20                  25                  30

Ser Met Ile Gln Ser Gln Ser Ser Ala Pro Thr Ser Gln Glu Pro Ala
                35                  40                  45

Tyr Thr Leu Tyr Ser Leu Ile Gln Pro Ser Arg Lys Ser Gly Ser Arg
    50                  55                  60

Lys Arg Asn His Ser Pro Ser Phe Asn Ser Thr Ile Tyr Glu Val Ile
65                  70                  75                  80

Gly Lys Ser Gln Pro Lys Ala Gln Asn Pro Ala Arg Leu Ser Arg Lys
                85                  90                  95

Glu Leu Glu Asn Phe Asp Val Tyr Ser Gly Ser Gly Gly Ser Gly
                100                 105                 110

Ser
```

<210> SEQ ID NO 45
<211> LENGTH: 157
<212> TYPE: PRT
<213> ORGANISM: homo sapiens
<220> FEATURE:
<223> OTHER INFORMATION: CD229 linker

<400> SEQUENCE: 45

```
Leu Tyr Ser Val Leu Ser Gln Gly Tyr Glu Lys Leu Asp Thr Pro Leu
1               5                   10                  15

Arg Pro Ala Arg Gln Gln Pro Thr Pro Thr Ser Asp Ser Ser Ser Asp
                20                  25                  30

Ser Asn Leu Thr Thr Glu Glu Asp Glu Asp Arg Pro Glu Val His Lys
                35                  40                  45

Pro Ile Ser Gly Arg Tyr Glu Val Phe Asp Gln Val Thr Gln Glu Gly
    50                  55                  60

Ala Gly His Asp Pro Ala Pro Glu Gly Gln Ala Asp Tyr Asp Pro Val
65                  70                  75                  80

Thr Pro Tyr Val Thr Glu Val Glu Ser Val Val Gly Glu Asn Thr Met
                85                  90                  95

Tyr Ala Gln Val Phe Asn Leu Gly Lys Thr Pro Val Ser Gln Lys
                100                 105                 110

Glu Glu Ser Ser Ala Thr Ile Tyr Cys Ser Ile Arg Lys Pro Gln Val
                115                 120                 125

Val Pro Pro Pro Gln Gln Asn Asp Leu Glu Ile Pro Glu Ser Pro Thr
    130                 135                 140

Tyr Glu Asn Phe Thr Gly Ser Gly Ser Gly Ser Gly Ser
145                 150                 155
```

<210> SEQ ID NO 46
<211> LENGTH: 151
<212> TYPE: PRT
<213> ORGANISM: homo sapiens
<220> FEATURE:
<223> OTHER INFORMATION: LTBR linker

<400> SEQUENCE: 46

```
Lys Ala His Pro Tyr Phe Pro Asp Leu Val Gln Pro Leu Leu Pro Ile
  1               5                  10                 15

Ser Gly Asp Val Ser Pro Val Ser Thr Gly Leu Pro Ala Ala Pro Val
             20                  25                  30

Leu Glu Ala Gly Val Pro Gln Gln Gln Ser Pro Leu Asp Leu Thr Arg
         35                  40                  45

Glu Pro Gln Leu Glu Pro Gly Glu Gln Ser Val Ala His Gly Thr
 50                  55                  60

Asn Gly Ile His Val Thr Gly Gly Ser Met Thr Ile Thr Gly Asn Ile
 65                  70                  75                  80

Tyr Ile Tyr Asn Gly Pro Val Leu Gly Gly Pro Pro Gly Pro Gly Asp
                 85                  90                  95

Leu Pro Ala Thr Pro Glu Pro Tyr Pro Ile Pro Glu Glu Gly Asp
             100                 105                 110

Pro Gly Pro Pro Gly Leu Ser Thr Pro His Gln Glu Asp Gly Lys Ala
             115                 120                 125

Trp His Leu Ala Glu Thr Glu His Cys Gly Ala Thr Pro Ser Asn Gly
             130                 135                 140

Ser Gly Ser Gly Ser Gly Ser
145                 150
```

<210> SEQ ID NO 47
<211> LENGTH: 110
<212> TYPE: PRT
<213> ORGANISM: homo sapiens
<220> FEATURE:
<223> OTHER INFORMATION: FKBP_pos5-ter-alpha

<400> SEQUENCE: 47

```
Ser Gly Gly Val Gln Val Glu Thr Ile Ser Pro Gly Asp Gly Arg Thr
  1               5                  10                 15

Phe Pro Lys Arg Gly Gln Thr Cys Val Val His Tyr Thr Gly Met Leu
             20                  25                  30

Glu Asp Gly Lys Lys Phe Asp Ser Ser Arg Asp Arg Asn Lys Pro Phe
         35                  40                  45

Lys Phe Met Leu Gly Lys Gln Glu Val Ile Arg Gly Trp Glu Glu Gly
 50                  55                  60

Val Ala Gln Met Ser Val Gly Gln Arg Ala Lys Leu Thr Ile Ser Pro
 65                  70                  75                  80

Asp Tyr Ala Tyr Gly Ala Thr Gly His Pro Gly Ile Ile Pro Pro His
                 85                  90                  95

Ala Thr Leu Val Phe Asp Val Glu Leu Leu Lys Leu Glu Glu
             100                 105                 110
```

<210> SEQ ID NO 48
<211> LENGTH: 98
<212> TYPE: PRT
<213> ORGANISM: homo sapiens
<220> FEATURE:
<223> OTHER INFORMATION: FRB_pos5-ter-alpha

<400> SEQUENCE: 48

```
Ser Gly Gly Arg Val Ala Ile Leu Trp His Glu Met Trp His Glu Gly
  1               5                  10                 15

Leu Glu Glu Ala Ser Arg Leu Tyr Phe Gly Glu Arg Asn Val Lys Gly
             20                  25                  30

Met Phe Glu Val Leu Glu Pro Leu His Ala Met Met Glu Arg Gly Pro
             35                  40                  45
```

```
Gln Thr Leu Lys Glu Thr Ser Phe Asn Gln Ala Tyr Gly Arg Asp Leu
    50                  55                  60

Met Glu Ala Gln Glu Trp Cys Arg Lys Tyr Met Lys Ser Gly Asn Val
 65                  70                  75                  80

Lys Asp Leu Thr Gln Ala Trp Asp Leu Tyr Tyr His Val Phe Arg Arg
                85                  90                  95

Ile Glu

<210> SEQ ID NO 49
<211> LENGTH: 173
<212> TYPE: PRT
<213> ORGANISM: artificial sequence
<220> FEATURE:
<223> OTHER INFORMATION: gamma-CD3z chain

<400> SEQUENCE: 49

Met Ile Pro Ala Val Val Leu Leu Leu Leu Leu Val Glu Gln Ala
  1               5                  10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
                35                  40                  45

Gln Val Arg Lys Ala Ala Ile Thr Ser Tyr Glu Lys Ser Arg Val Lys
 50                  55                  60

Phe Ser Arg Ser Ala Asp Ala Pro Ala Tyr Gln Gln Gly Gln Asn Gln
 65                  70                  75                  80

Leu Tyr Asn Glu Leu Asn Leu Gly Arg Arg Glu Glu Tyr Asp Val Leu
                85                  90                  95

Asp Lys Arg Arg Gly Arg Asp Pro Glu Met Gly Gly Lys Pro Arg Arg
               100                 105                 110

Lys Asn Pro Gln Glu Gly Leu Tyr Asn Glu Leu Gln Lys Asp Lys Met
               115                 120                 125

Ala Glu Ala Tyr Ser Glu Ile Gly Met Lys Gly Glu Arg Arg Arg Gly
130                 135                 140

Lys Gly His Asp Gly Leu Tyr Gln Gly Leu Ser Thr Ala Thr Lys Asp
145                 150                 155                 160

Thr Tyr Asp Ala Leu His Met Gln Ala Leu Pro Pro Arg
                165                 170

<210> SEQ ID NO 50
<211> LENGTH: 101
<212> TYPE: PRT
<213> ORGANISM: homo sapiens
<220> FEATURE:
<223> OTHER INFORMATION: PD1_pos3

<400> SEQUENCE: 50

Ser Arg Ala Ala Arg Gly Thr Ile Gly Ala Arg Arg Thr Gly Gln Pro
  1               5                  10                  15

Leu Lys Glu Asp Pro Ser Ala Val Pro Val Phe Ser Val Asp Tyr Gly
                20                  25                  30

Glu Leu Asp Phe Gln Trp Arg Glu Lys Thr Pro Glu Pro Pro Val Pro
                35                  40                  45

Cys Val Pro Glu Gln Thr Glu Tyr Ala Thr Ile Val Phe Pro Ser Gly
 50                  55                  60

Met Gly Thr Ser Ser Pro Ala Arg Arg Gly Ser Ala Asp Gly Pro Arg
 65                  70                  75                  80
```

Ser Ala Gln Pro Leu Arg Pro Glu Asp Gly His Cys Ser Trp Pro Leu
                85                  90                  95

Gly Ser Gly Ser Ser
            100

<210> SEQ ID NO 51
<211> LENGTH: 114
<212> TYPE: PRT
<213> ORGANISM: homo sapiens
<220> FEATURE:
<223> OTHER INFORMATION: FKBP_pos4-IMP

<400> SEQUENCE: 51

Ser Gly Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
            20                  25                  30

Glu Asp Gly Lys Lys Phe Asp Ser Ser Arg Asp Arg Asn Lys Pro Phe
        35                  40                  45

Lys Phe Met Leu Gly Lys Gln Glu Val Ile Arg Gly Trp Glu Glu Gly
    50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu Gly Ser Gly
            100                 105                 110

Ser Gly

<210> SEQ ID NO 52
<211> LENGTH: 102
<212> TYPE: PRT
<213> ORGANISM: homo sapiens
<220> FEATURE:
<223> OTHER INFORMATION: FRB_pos4-IMP

<400> SEQUENCE: 52

Ser Gly Gly Arg Val Ala Ile Leu Trp His Glu Met Trp His Glu Gly
1               5                   10                  15

Leu Glu Glu Ala Ser Arg Leu Tyr Phe Gly Glu Arg Asn Val Lys Gly
            20                  25                  30

Met Phe Glu Val Leu Glu Pro Leu His Ala Met Met Glu Arg Gly Pro
        35                  40                  45

Gln Thr Leu Lys Glu Thr Ser Phe Asn Gln Ala Tyr Gly Arg Asp Leu
    50                  55                  60

Met Glu Ala Gln Glu Trp Cys Arg Lys Tyr Met Lys Ser Gly Asn Val
65                  70                  75                  80

Lys Asp Leu Thr Gln Ala Trp Asp Leu Tyr Tyr His Val Phe Arg Arg
                85                  90                  95

Ile Gly Ser Gly Ser Gly
            100

<210> SEQ ID NO 53
<211> LENGTH: 97
<212> TYPE: PRT
<213> ORGANISM: homo sapiens
<220> FEATURE:
<223> OTHER INFORMATION: PD1_pos5-ter

```
<400> SEQUENCE: 53

Ser Arg Ala Ala Arg Gly Thr Ile Gly Ala Arg Thr Gly Gln Pro
1               5                   10                  15

Leu Lys Glu Asp Pro Ser Ala Val Pro Val Phe Ser Val Asp Tyr Gly
            20                  25                  30

Glu Leu Asp Phe Gln Trp Arg Glu Lys Thr Pro Glu Pro Val Pro
        35                  40                  45

Cys Val Pro Glu Gln Thr Glu Tyr Ala Thr Ile Val Phe Pro Ser Gly
        50                  55                  60

Met Gly Thr Ser Ser Pro Ala Arg Arg Gly Ser Ala Asp Gly Pro Arg
65                  70                  75                  80

Ser Ala Gln Pro Leu Arg Pro Glu Asp Gly His Cys Ser Trp Pro Leu
                85                  90                  95

Glu

<210> SEQ ID NO 54
<211> LENGTH: 110
<212> TYPE: PRT
<213> ORGANISM: homo sapiens
<220> FEATURE:
<223> OTHER INFORMATION: FKBP_pos4-ter-IMP

<400> SEQUENCE: 54

Ser Gly Gly Val Gln Val Glu Thr Ile Ser Pro Gly Asp Gly Arg Thr
1               5                   10                  15

Phe Pro Lys Arg Gly Gln Thr Cys Val Val His Tyr Thr Gly Met Leu
            20                  25                  30

Glu Asp Gly Lys Lys Phe Asp Ser Ser Arg Asp Arg Asn Lys Pro Phe
        35                  40                  45

Lys Phe Met Leu Gly Lys Gln Glu Val Ile Arg Gly Trp Glu Glu Gly
        50                  55                  60

Val Ala Gln Met Ser Val Gly Gln Arg Ala Lys Leu Thr Ile Ser Pro
65                  70                  75                  80

Asp Tyr Ala Tyr Gly Ala Thr Gly His Pro Gly Ile Ile Pro Pro His
                85                  90                  95

Ala Thr Leu Val Phe Asp Val Glu Leu Leu Lys Leu Glu Glu
            100                 105                 110

<210> SEQ ID NO 55
<211> LENGTH: 98
<212> TYPE: PRT
<213> ORGANISM: homo sapiens
<220> FEATURE:
<223> OTHER INFORMATION: FRB_pos4-ter-IMP

<400> SEQUENCE: 55

Ser Gly Gly Arg Val Ala Ile Leu Trp His Glu Met Trp His Glu Gly
1               5                   10                  15

Leu Glu Glu Ala Ser Arg Leu Tyr Phe Gly Glu Arg Asn Val Lys Gly
            20                  25                  30

Met Phe Glu Val Leu Glu Pro Leu His Ala Met Met Glu Arg Gly Pro
        35                  40                  45

Gln Thr Leu Lys Glu Thr Ser Phe Asn Gln Ala Tyr Gly Arg Asp Leu
        50                  55                  60

Met Glu Ala Gln Glu Trp Cys Arg Lys Tyr Met Lys Ser Gly Asn Val
65                  70                  75                  80

Lys Asp Leu Thr Gln Ala Trp Asp Leu Tyr Tyr His Val Phe Arg Arg
```

Ile Glu

<210> SEQ ID NO 56
<211> LENGTH: 101
<212> TYPE: PRT
<213> ORGANISM: homo sapiens
<220> FEATURE:
<223> OTHER INFORMATION: PD1_pos4

<400> SEQUENCE: 56

Ser Arg Ala Ala Arg Gly Thr Ile Gly Ala Arg Arg Thr Gly Gln Pro
1               5                   10                  15

Leu Lys Glu Asp Pro Ser Ala Val Pro Val Phe Ser Val Asp Tyr Gly
            20                  25                  30

Glu Leu Asp Phe Gln Trp Arg Glu Lys Thr Pro Glu Pro Pro Val Pro
        35                  40                  45

Cys Val Pro Glu Gln Thr Glu Tyr Ala Thr Ile Val Phe Pro Ser Gly
    50                  55                  60

Met Gly Thr Ser Ser Pro Ala Arg Arg Gly Ser Ala Asp Gly Pro Arg
65                  70                  75                  80

Ser Ala Gln Pro Leu Arg Pro Glu Asp Gly His Cys Ser Trp Pro Leu
                85                  90                  95

Gly Ser Gly Ser Gly
            100

<210> SEQ ID NO 57
<211> LENGTH: 108
<212> TYPE: PRT
<213> ORGANISM: homo sapiens
<220> FEATURE:
<223> OTHER INFORMATION: FKBP_pos5-ter-IMP

<400> SEQUENCE: 57

Gly Val Gln Val Glu Thr Ile Ser Pro Gly Asp Gly Arg Thr Phe Pro
1               5                   10                  15

Lys Arg Gly Gln Thr Cys Val Val His Tyr Thr Gly Met Leu Glu Asp
            20                  25                  30

Gly Lys Lys Phe Asp Ser Ser Arg Asp Arg Asn Lys Pro Phe Lys Phe
        35                  40                  45

Met Leu Gly Lys Gln Glu Val Ile Arg Gly Trp Glu Glu Gly Val Ala
    50                  55                  60

Gln Met Ser Val Gly Gln Arg Ala Lys Leu Thr Ile Ser Pro Asp Tyr
65                  70                  75                  80

Ala Tyr Gly Ala Thr Gly His Pro Gly Ile Ile Pro Pro His Ala Thr
                85                  90                  95

Leu Val Phe Asp Val Glu Leu Leu Lys Leu Glu Glu
            100                 105

<210> SEQ ID NO 58
<211> LENGTH: 96
<212> TYPE: PRT
<213> ORGANISM: homo sapiens
<220> FEATURE:
<223> OTHER INFORMATION: FRB_pos5-ter-IMP

<400> SEQUENCE: 58

Gly Arg Val Ala Ile Leu Trp His Glu Met Trp His Glu Gly Leu Glu
1               5                   10                  15

```
Glu Ala Ser Arg Leu Tyr Phe Gly Glu Arg Asn Val Lys Gly Met Phe
            20                  25                  30

Glu Val Leu Glu Pro Leu His Ala Met Met Glu Arg Gly Pro Gln Thr
        35                  40                  45

Leu Lys Glu Thr Ser Phe Asn Gln Ala Tyr Gly Arg Asp Leu Met Glu
    50                  55                  60

Ala Gln Glu Trp Cys Arg Lys Tyr Met Lys Ser Gly Asn Val Lys Asp
65                  70                  75                  80

Leu Thr Gln Ala Trp Asp Leu Tyr Tyr His Val Phe Arg Arg Ile Glu
                85                  90                  95

<210> SEQ ID NO 59
<211> LENGTH: 344
<212> TYPE: PRT
<213> ORGANISM: homo sapiens
<220> FEATURE:
<223> OTHER INFORMATION: IR-10RA inhibitory domain

<400> SEQUENCE: 59

Ile Val Ile Ile Phe Phe Ala Phe Val Leu Leu Leu Ser Gly Ala Leu
1               5                   10                  15

Ala Tyr Cys Leu Ala Leu Gln Leu Tyr Val Arg Arg Arg Lys Lys Leu
            20                  25                  30

Pro Ser Val Leu Leu Phe Lys Lys Pro Ser Pro Phe Ile Phe Ile Ser
        35                  40                  45

Gln Arg Pro Ser Pro Glu Thr Gln Asp Thr Ile His Pro Leu Asp Glu
    50                  55                  60

Glu Ala Phe Leu Lys Val Ser Pro Glu Leu Lys Asn Leu Asp Leu His
65                  70                  75                  80

Gly Ser Thr Asp Ser Gly Phe Gly Ser Thr Lys Pro Ser Leu Gln Thr
                85                  90                  95

Glu Glu Pro Gln Phe Leu Leu Pro Asp Pro His Pro Gln Ala Asp Arg
            100                 105                 110

Thr Leu Gly Asn Arg Glu Pro Pro Val Leu Gly Asp Ser Cys Ser Ser
        115                 120                 125

Gly Ser Ser Asn Ser Thr Asp Ser Gly Ile Cys Leu Gln Glu Pro Ser
    130                 135                 140

Leu Ser Pro Ser Thr Gly Pro Thr Trp Glu Gln Gln Val Gly Ser Asn
145                 150                 155                 160

Ser Arg Gly Gln Asp Asp Ser Gly Ile Asp Leu Val Gln Asn Ser Glu
                165                 170                 175

Gly Arg Ala Gly Asp Thr Gln Gly Gly Ser Ala Leu Gly His His Ser
            180                 185                 190

Pro Pro Glu Pro Glu Val Pro Gly Glu Glu Asp Pro Ala Ala Val Ala
        195                 200                 205

Phe Gln Gly Tyr Leu Arg Gln Thr Arg Cys Ala Glu Glu Lys Ala Thr
    210                 215                 220

Lys Thr Gly Cys Leu Glu Glu Glu Ser Pro Leu Thr Asp Gly Leu Gly
225                 230                 235                 240

Pro Lys Phe Gly Arg Cys Leu Val Asp Glu Ala Gly Leu His Pro Pro
                245                 250                 255

Ala Leu Ala Lys Gly Tyr Leu Lys Gln Asp Pro Leu Glu Met Thr Leu
            260                 265                 270

Ala Ser Ser Gly Ala Pro Thr Gly Gln Trp Asn Gln Pro Thr Glu Glu
        275                 280                 285
```

```
Trp Ser Leu Leu Ala Leu Ser Ser Cys Ser Asp Leu Gly Ile Ser Asp
        290                 295                 300

Trp Ser Phe Ala His Asp Leu Ala Pro Leu Gly Cys Val Ala Ala Pro
305                 310                 315                 320

Gly Gly Leu Leu Gly Ser Phe Asn Ser Asp Leu Val Thr Leu Pro Leu
                325                 330                 335

Ile Ser Ser Leu Gln Ser Ser Glu
            340

<210> SEQ ID NO 60
<211> LENGTH: 107
<212> TYPE: PRT
<213> ORGANISM: homo sapiens
<220> FEATURE:
<223> OTHER INFORMATION: IR-10B inhibitory domain

<400> SEQUENCE: 60

Ile Trp Met Val Ala Val Ile Leu Met Ala Ser Val Phe Met Val Cys
1               5                   10                  15

Leu Ala Leu Leu Gly Cys Phe Ala Leu Leu Trp Cys Val Tyr Lys Lys
                20                  25                  30

Thr Lys Tyr Ala Phe Ser Pro Arg Asn Ser Leu Pro Gln His Leu Lys
            35                  40                  45

Glu Phe Leu Gly His Pro His His Asn Thr Leu Leu Phe Phe Ser Phe
        50                  55                  60

Pro Leu Ser Asp Glu Asn Asp Val Phe Asp Lys Leu Ser Val Ile Ala
65                  70                  75                  80

Glu Asp Ser Glu Ser Gly Lys Gln Asn Pro Gly Asp Ser Cys Ser Leu
                85                  90                  95

Gly Thr Pro Pro Gly Gln Gly Pro Gln Ser Glu
            100                 105

<210> SEQ ID NO 61
<211> LENGTH: 303
<212> TYPE: PRT
<213> ORGANISM: artificial sequence
<220> FEATURE:
<223> OTHER INFORMATION: IMP-exCID-n?1

<400> SEQUENCE: 61

Met Ala Leu Pro Val Thr Ala Leu Leu Leu Pro Leu Ala Leu Leu Leu
1               5                   10                  15

His Ala Ala Arg Pro Gly Ser Gly Gly Val Gln Val Glu Thr Ile Ser
                20                  25                  30

Pro Gly Asp Gly Arg Thr Phe Pro Lys Arg Gly Gln Thr Cys Val Val
            35                  40                  45

His Tyr Thr Gly Met Leu Glu Asp Gly Lys Lys Phe Asp Ser Ser Arg
        50                  55                  60

Asp Arg Asn Lys Pro Phe Lys Phe Met Leu Gly Lys Gln Glu Val Ile
65                  70                  75                  80

Arg Gly Trp Glu Glu Gly Val Ala Gln Met Ser Val Gly Gln Arg Ala
                85                  90                  95

Lys Leu Thr Ile Ser Pro Asp Tyr Ala Tyr Gly Ala Thr Gly His Pro
            100                 105                 110

Gly Ile Ile Pro Pro His Ala Thr Leu Val Phe Asp Val Glu Leu Leu
        115                 120                 125

Lys Leu Glu Gly Ser Gly Ala Pro Thr Thr Thr Pro Ala Pro Arg Pro
    130                 135                 140
```

```
Pro Thr Pro Ala Pro Thr Ile Ala Ser Gln Pro Leu Ser Leu Arg Pro
145                 150                 155                 160

Glu Ala Cys Arg Pro Ala Gly Gly Ala Val His Thr Arg Gly Leu
            165                 170                 175

Asp Phe Ala Cys Asp Ile Tyr Ile Trp Ala Pro Leu Ala Gly Thr Cys
            180                 185                 190

Gly Val Leu Leu Leu Ser Leu Val Ile Thr Leu Tyr Cys Arg Ser Arg
            195                 200                 205

Ala Ala Arg Gly Thr Ile Gly Ala Arg Arg Thr Gly Gln Pro Leu Lys
            210                 215                 220

Glu Asp Pro Ser Ala Val Pro Val Phe Ser Val Asp Tyr Gly Glu Leu
225                 230                 235                 240

Asp Phe Gln Trp Arg Glu Lys Thr Pro Glu Pro Pro Val Pro Cys Val
            245                 250                 255

Pro Glu Gln Thr Glu Tyr Ala Thr Ile Val Phe Pro Ser Gly Met Gly
            260                 265                 270

Thr Ser Ser Pro Ala Arg Arg Gly Ser Ala Asp Gly Pro Arg Ser Ala
            275                 280                 285

Gln Pro Leu Arg Pro Glu Asp Gly His Cys Ser Trp Pro Leu Glu
            290                 295                 300

<210> SEQ ID NO 62
<211> LENGTH: 485
<212> TYPE: PRT
<213> ORGANISM: artificial sequence
<220> FEATURE:
<223> OTHER INFORMATION: IMP-exCID-n?2

<400> SEQUENCE: 62

Met Ala Leu Pro Val Thr Ala Leu Leu Leu Pro Leu Ala Leu Leu Leu
1               5                   10                  15

His Ala Ala Arg Pro Gly Ser Gly Gly Arg Val Ala Ile Leu Trp His
            20                  25                  30

Glu Met Trp His Glu Gly Leu Glu Ala Ser Arg Leu Tyr Phe Gly
        35                  40                  45

Glu Arg Asn Val Lys Gly Met Phe Glu Val Leu Glu Pro Leu His Ala
50                  55                  60

Met Met Glu Arg Gly Pro Gln Thr Leu Lys Glu Thr Ser Phe Asn Gln
65                  70                  75                  80

Ala Tyr Gly Arg Asp Leu Met Glu Ala Gln Glu Trp Cys Arg Lys Tyr
            85                  90                  95

Met Lys Ser Gly Asn Val Lys Asp Leu Thr Gln Ala Trp Asp Leu Tyr
            100                 105                 110

Tyr His Val Phe Arg Arg Ile Gly Ser Gly Ala Pro Glu Pro Lys Ser
            115                 120                 125

Pro Asp Lys Thr His Thr Cys Pro Pro Cys Pro Ala Pro Pro Val Ala
            130                 135                 140

Gly Pro Ser Val Phe Leu Phe Pro Pro Lys Pro Lys Asp Thr Leu Met
145                 150                 155                 160

Ile Ala Arg Thr Pro Glu Val Thr Cys Val Val Val Asp Val Ser His
            165                 170                 175

Glu Asp Pro Glu Val Lys Phe Asn Trp Tyr Val Asp Gly Val Glu Val
            180                 185                 190

His Asn Ala Lys Thr Lys Pro Arg Glu Glu Gln Tyr Asn Ser Thr Tyr
            195                 200                 205
```

Arg Val Val Ser Val Leu Thr Val Leu His Gln Asp Trp Leu Asn Gly
    210                 215                 220

Lys Glu Tyr Lys Cys Lys Val Ser Asn Lys Ala Leu Pro Ala Pro Ile
225                 230                 235                 240

Glu Lys Thr Ile Ser Lys Ala Lys Gly Gln Pro Arg Glu Pro Gln Val
                245                 250                 255

Tyr Thr Leu Pro Pro Ser Arg Asp Glu Leu Thr Lys Asn Gln Val Ser
                260                 265                 270

Leu Thr Cys Leu Val Lys Gly Phe Tyr Pro Ser Asp Ile Ala Val Glu
            275                 280                 285

Trp Glu Ser Asn Gly Gln Pro Glu Asn Asn Tyr Lys Thr Thr Pro Pro
        290                 295                 300

Val Leu Asp Ser Asp Gly Ser Phe Phe Leu Tyr Ser Lys Leu Thr Val
305                 310                 315                 320

Asp Lys Ser Arg Trp Gln Gln Gly Asn Val Phe Ser Cys Ser Val Met
                325                 330                 335

His Glu Ala Leu His Asn His Tyr Thr Gln Lys Ser Leu Ser Leu Ser
                340                 345                 350

Pro Gly Lys Lys Asp Ile Ile Ser Phe Leu Ala Leu Thr Ser Thr
            355                 360                 365

Ala Leu Leu Phe Leu Leu Phe Phe Leu Thr Leu Arg Phe Ser Val Val
370                 375                 380

Lys Arg Gly Arg Ser Arg Ala Ala Arg Gly Thr Ile Gly Ala Arg Arg
385                 390                 395                 400

Thr Gly Gln Pro Leu Lys Glu Asp Pro Ser Ala Val Pro Val Phe Ser
                405                 410                 415

Val Asp Tyr Gly Glu Leu Asp Phe Gln Trp Arg Glu Lys Thr Pro Glu
            420                 425                 430

Pro Pro Val Pro Cys Val Pro Glu Gln Thr Glu Tyr Ala Thr Ile Val
            435                 440                 445

Phe Pro Ser Gly Met Gly Thr Ser Ser Pro Ala Arg Arg Gly Ser Ala
    450                 455                 460

Asp Gly Pro Arg Ser Ala Gln Pro Leu Arg Pro Glu Asp Gly His Cys
465                 470                 475                 480

Ser Trp Pro Leu Glu
            485

<210> SEQ ID NO 63
<211> LENGTH: 361
<212> TYPE: PRT
<213> ORGANISM: artificial sequence
<220> FEATURE:
<223> OTHER INFORMATION: IMP-exCID-n?3

<400> SEQUENCE: 63

Met Ala Leu Pro Val Thr Ala Leu Leu Leu Pro Leu Ala Leu Leu Leu
1               5                   10                  15

His Ala Ala Arg Pro Gly Ser Gly Gly Val Gln Val Glu Thr Ile Ser
                20                  25                  30

Pro Gly Asp Gly Arg Thr Phe Pro Lys Arg Gly Gln Thr Cys Val Val
            35                  40                  45

His Tyr Thr Gly Met Leu Glu Asp Gly Lys Lys Phe Asp Ser Ser Arg
        50                  55                  60

Asp Arg Asn Lys Pro Phe Lys Phe Met Leu Gly Lys Gln Glu Val Ile
65                  70                  75                  80

```
Arg Gly Trp Glu Glu Gly Val Ala Gln Met Ser Val Gly Gln Arg Ala
                85                  90                  95

Lys Leu Thr Ile Ser Pro Asp Tyr Ala Tyr Gly Ala Thr Gly His Pro
            100                 105                 110

Gly Ile Ile Pro Pro His Ala Thr Leu Val Phe Asp Val Glu Leu Leu
        115                 120                 125

Lys Leu Glu Gly Ser Gly Ala Pro Ala Pro Val Gly Leu Val Ala Arg
130                 135                 140

Leu Ala Asp Glu Ser Gly His Val Val Leu Arg Trp Leu Pro Pro Pro
145                 150                 155                 160

Glu Thr Pro Met Thr Ser His Ile Arg Tyr Glu Val Asp Val Ser Ala
                165                 170                 175

Gly Asn Gly Ala Gly Ser Val Gln Arg Val Glu Ile Leu Gly Arg
            180                 185                 190

Thr Glu Cys Val Leu Ser Asn Leu Arg Gly Arg Thr Arg Tyr Thr Phe
            195                 200                 205

Ala Val Arg Ala Arg Met Ala Glu Pro Ser Phe Gly Gly Phe Trp Ser
        210                 215                 220

Ala Trp Ser Glu Pro Val Ser Leu Leu Thr Pro Ser Asp Ile Leu Leu
225                 230                 235                 240

Ala Gly Leu Val Ala Ala Asp Ala Val Ala Ser Leu Leu Ile Val Gly
                245                 250                 255

Ala Val Phe Leu Cys Ala Arg Arg Ser Arg Ala Ala Arg Gly Thr Ile
                260                 265                 270

Gly Ala Arg Arg Thr Gly Gln Pro Leu Lys Glu Asp Pro Ser Ala Val
            275                 280                 285

Pro Val Phe Ser Val Asp Tyr Gly Glu Leu Asp Phe Gln Trp Arg Glu
        290                 295                 300

Lys Thr Pro Glu Pro Pro Val Pro Cys Val Pro Glu Gln Thr Glu Tyr
305                 310                 315                 320

Ala Thr Ile Val Phe Pro Ser Gly Met Gly Thr Ser Ser Pro Ala Arg
                325                 330                 335

Arg Gly Ser Ala Asp Gly Pro Arg Ser Ala Gln Pro Leu Arg Pro Glu
            340                 345                 350

Asp Gly His Cys Ser Trp Pro Leu Glu
        355                 360

<210> SEQ ID NO 64
<211> LENGTH: 299
<212> TYPE: PRT
<213> ORGANISM: artificial sequence
<220> FEATURE:
<223> OTHER INFORMATION: IMP-exCID-n?4

<400> SEQUENCE: 64

Met Ala Leu Pro Val Thr Ala Leu Leu Leu Pro Leu Ala Leu Leu Leu
1               5                   10                  15

His Ala Ala Arg Pro Gly Ser Gly Gly Arg Val Ala Ile Leu Trp His
            20                  25                  30

Glu Met Trp His Glu Gly Leu Glu Glu Ala Ser Arg Leu Tyr Phe Gly
        35                  40                  45

Glu Arg Asn Val Lys Gly Met Phe Glu Val Leu Glu Pro Leu His Ala
    50                  55                  60

Met Met Glu Arg Gly Pro Gln Thr Leu Lys Glu Thr Ser Phe Asn Gln
65                  70                  75                  80
```

Ala Tyr Gly Arg Asp Leu Met Glu Ala Gln Glu Trp Cys Arg Lys Tyr
                85                  90                  95

Met Lys Ser Gly Asn Val Lys Asp Leu Thr Gln Ala Trp Asp Leu Tyr
            100                 105                 110

Tyr His Val Phe Arg Arg Ile Gly Ser Gly Ala Pro Thr Thr Thr Pro
        115                 120                 125

Ala Pro Arg Pro Pro Thr Pro Ala Pro Thr Ile Ala Ser Gln Pro Leu
130                 135                 140

Ser Leu Arg Pro Glu Ala Cys Arg Pro Ala Ala Gly Gly Ala Val His
145                 150                 155                 160

Thr Arg Gly Leu Asp Phe Ala Cys Asp Ile Phe Trp Val Leu Val Val
                165                 170                 175

Val Gly Gly Val Leu Ala Cys Tyr Ser Leu Leu Val Thr Val Ala Phe
            180                 185                 190

Ile Ile Phe Trp Val Arg Ser Lys Arg Ser Arg Ala Ala Arg Gly
        195                 200                 205

Thr Ile Gly Ala Arg Arg Thr Gly Gln Pro Leu Lys Glu Asp Pro Ser
210                 215                 220

Ala Val Pro Val Phe Ser Val Asp Tyr Gly Glu Leu Asp Phe Gln Trp
225                 230                 235                 240

Arg Glu Lys Thr Pro Glu Pro Val Pro Cys Val Pro Gln Gln Thr
                245                 250                 255

Glu Tyr Ala Thr Ile Val Phe Pro Ser Gly Met Gly Thr Ser Ser Pro
            260                 265                 270

Ala Arg Arg Gly Ser Ala Asp Gly Pro Arg Ser Ala Gln Pro Leu Arg
                275                 280                 285

Pro Glu Asp Gly His Cys Ser Trp Pro Leu Glu
290                 295

<210> SEQ ID NO 65
<211> LENGTH: 335
<212> TYPE: PRT
<213> ORGANISM: artificial sequence
<220> FEATURE:
<223> OTHER INFORMATION: γ-mcCAR-exCID-n?1

<400> SEQUENCE: 65

Met Ala Ile Pro Ala Val Val Leu Leu Leu Leu Leu Val Glu Gln
1               5                   10                  15

Ala Ala Ala Gly Ser Gly Gly Val Gln Val Glu Thr Ile Ser Pro Gly
            20                  25                  30

Asp Gly Arg Thr Phe Pro Lys Arg Gly Gln Thr Cys Val Val His Tyr
        35                  40                  45

Thr Gly Met Leu Glu Asp Gly Lys Lys Phe Asp Ser Ser Arg Asp Arg
    50                  55                  60

Asn Lys Pro Phe Lys Phe Met Leu Gly Lys Gln Glu Val Ile Arg Gly
65                  70                  75                  80

Trp Glu Glu Gly Val Ala Gln Met Ser Val Gly Gln Arg Ala Lys Leu
                85                  90                  95

Thr Ile Ser Pro Asp Tyr Ala Tyr Gly Ala Thr Gly His Pro Gly Ile
            100                 105                 110

Ile Pro Pro His Ala Thr Leu Val Phe Asp Val Glu Leu Leu Lys Leu
        115                 120                 125

Glu Gly Ser Gly Ala Pro Thr Thr Thr Pro Ala Pro Arg Pro Pro Thr
130                 135                 140

```
Pro Ala Pro Thr Ile Ala Ser Gln Pro Leu Ser Leu Arg Pro Glu Ala
145                 150                 155                 160

Cys Arg Pro Ala Ala Gly Gly Ala Val His Thr Arg Gly Leu Asp Phe
            165                 170                 175

Ala Cys Asp Ile Gly Glu Pro Gln Leu Cys Tyr Ile Leu Asp Ala Ile
        180                 185                 190

Leu Phe Leu Tyr Gly Ile Val Leu Thr Leu Leu Tyr Cys Arg Leu Lys
            195                 200                 205

Ile Gln Val Arg Lys Ala Ala Ile Thr Ser Tyr Glu Lys Ser Arg Val
        210                 215                 220

Lys Phe Ser Arg Ser Ala Asp Ala Pro Ala Tyr Gln Gln Gly Gln Asn
225                 230                 235                 240

Gln Leu Tyr Asn Glu Leu Asn Leu Gly Arg Arg Glu Glu Tyr Asp Val
            245                 250                 255

Leu Asp Lys Arg Arg Gly Arg Asp Pro Glu Met Gly Gly Lys Pro Arg
            260                 265                 270

Arg Lys Asn Pro Gln Glu Gly Leu Tyr Asn Glu Leu Gln Lys Asp Lys
            275                 280                 285

Met Ala Glu Ala Tyr Ser Glu Ile Gly Met Lys Gly Glu Arg Arg Arg
            290                 295                 300

Gly Lys Gly His Asp Gly Leu Tyr Gln Gly Leu Ser Thr Ala Thr Lys
305                 310                 315                 320

Asp Thr Tyr Asp Ala Leu His Met Gln Ala Leu Pro Pro Arg Glu
                325                 330                 335

<210> SEQ ID NO 66
<211> LENGTH: 511
<212> TYPE: PRT
<213> ORGANISM: artificial sequence
<220> FEATURE:
<223> OTHER INFORMATION: γ-mcCAR-exCID-n?2

<400> SEQUENCE: 66

Met Ala Ile Pro Ala Val Val Leu Leu Leu Leu Leu Val Glu Gln
1               5                   10                  15

Ala Ala Ala Gly Ser Gly Gly Arg Val Ala Ile Leu Trp His Glu Met
                20                  25                  30

Trp His Glu Gly Leu Glu Glu Ala Ser Arg Leu Tyr Phe Gly Glu Arg
            35                  40                  45

Asn Val Lys Gly Met Phe Glu Val Leu Glu Pro Leu His Ala Met Met
        50                  55                  60

Glu Arg Gly Pro Gln Thr Leu Lys Glu Thr Ser Phe Asn Gln Ala Tyr
65                  70                  75                  80

Gly Arg Asp Leu Met Glu Ala Gln Glu Trp Cys Arg Lys Tyr Met Lys
            85                  90                  95

Ser Gly Asn Val Lys Asp Leu Thr Gln Ala Trp Asp Leu Tyr Tyr His
            100                 105                 110

Val Phe Arg Arg Ile Gly Ser Gly Ala Pro Glu Pro Lys Ser Pro Asp
        115                 120                 125

Lys Thr His Thr Cys Pro Pro Cys Pro Ala Pro Val Ala Gly Pro
        130                 135                 140

Ser Val Phe Leu Phe Pro Pro Lys Pro Lys Asp Thr Leu Met Ile Ala
145                 150                 155                 160

Arg Thr Pro Glu Val Thr Cys Val Val Val Asp Val Ser His Glu Asp
                165                 170                 175
```

```
Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly
            340                 345                 350

Lys Lys Asp Ile Gly Glu Pro Gln Leu Cys Tyr Ile Leu Asp Ala Ile
        355                 360                 365

Leu Phe Leu Tyr Gly Ile Val Leu Thr Leu Leu Tyr Cys Arg Leu Lys
    370                 375                 380

Ile Gln Val Arg Lys Ala Ala Ile Thr Ser Tyr Glu Lys Ser Arg Val
385                 390                 395                 400

Lys Phe Ser Arg Ser Ala Asp Ala Pro Ala Tyr Gln Gln Gly Gln Asn
                405                 410                 415

Gln Leu Tyr Asn Glu Leu Asn Leu Gly Arg Arg Glu Glu Tyr Asp Val
            420                 425                 430

Leu Asp Lys Arg Arg Gly Arg Asp Pro Glu Met Gly Gly Lys Pro Arg
        435                 440                 445

Arg Lys Asn Pro Gln Glu Gly Leu Tyr Asn Glu Leu Gln Lys Asp Lys
    450                 455                 460

Met Ala Glu Ala Tyr Ser Glu Ile Gly Met Lys Gly Glu Arg Arg Arg
465                 470                 475                 480

Gly Lys Gly His Asp Gly Leu Tyr Gln Gly Leu Ser Thr Ala Thr Lys
                485                 490                 495

Asp Thr Tyr Asp Ala Leu His Met Gln Ala Leu Pro Pro Arg Glu
            500                 505                 510

<210> SEQ ID NO 67
<211> LENGTH: 391
<212> TYPE: PRT
<213> ORGANISM: artificial sequence
<220> FEATURE:
<223> OTHER INFORMATION: γ-mcCAR-exCID-n?3

<400> SEQUENCE: 67

Met Ala Ile Pro Ala Val Val Leu Leu Leu Leu Leu Val Glu Gln
1               5                   10                  15

Ala Ala Ala Gly Ser Gly Gly Val Gln Val Glu Thr Ile Ser Pro Gly
            20                  25                  30
```

Asp Gly Arg Thr Phe Pro Lys Arg Gly Gln Thr Cys Val Val His Tyr
            35                  40                  45

Thr Gly Met Leu Glu Asp Gly Lys Lys Phe Asp Ser Ser Arg Asp Arg
 50                  55                  60

Asn Lys Pro Phe Lys Phe Met Leu Gly Lys Gln Glu Val Ile Arg Gly
 65                  70                  75                  80

Trp Glu Glu Gly Val Ala Gln Met Ser Val Gly Gln Arg Ala Lys Leu
                    85                  90                  95

Thr Ile Ser Pro Asp Tyr Ala Tyr Gly Ala Thr Gly His Pro Gly Ile
                100                 105                 110

Ile Pro Pro His Ala Thr Leu Val Phe Asp Val Glu Leu Leu Lys Leu
            115                 120                 125

Glu Gly Ser Gly Ala Pro Ala Pro Val Gly Leu Val Ala Arg Leu Ala
130                 135                 140

Asp Glu Ser Gly His Val Val Leu Arg Trp Leu Pro Pro Glu Thr
145                 150                 155                 160

Pro Met Thr Ser His Ile Arg Tyr Glu Val Asp Val Ser Ala Gly Asn
                    165                 170                 175

Gly Ala Gly Ser Val Gln Arg Val Glu Ile Leu Glu Gly Arg Thr Glu
                180                 185                 190

Cys Val Leu Ser Asn Leu Arg Gly Arg Thr Arg Tyr Thr Phe Ala Val
            195                 200                 205

Arg Ala Arg Met Ala Glu Pro Ser Phe Gly Gly Phe Trp Ser Ala Trp
210                 215                 220

Ser Glu Pro Val Ser Leu Leu Thr Pro Ser Asp Ile Gly Glu Pro Gln
225                 230                 235                 240

Leu Cys Tyr Ile Leu Asp Ala Ile Leu Phe Leu Tyr Gly Ile Val Leu
                245                 250                 255

Thr Leu Leu Tyr Cys Arg Leu Lys Ile Gln Val Arg Lys Ala Ala Ile
                260                 265                 270

Thr Ser Tyr Glu Lys Ser Arg Val Lys Phe Ser Arg Ser Ala Asp Ala
            275                 280                 285

Pro Ala Tyr Gln Gln Gly Gln Asn Gln Leu Tyr Asn Glu Leu Asn Leu
            290                 295                 300

Gly Arg Arg Glu Glu Tyr Asp Val Leu Asp Lys Arg Arg Gly Arg Asp
305                 310                 315                 320

Pro Glu Met Gly Gly Lys Pro Arg Arg Lys Asn Pro Gln Glu Gly Leu
                    325                 330                 335

Tyr Asn Glu Leu Gln Lys Asp Lys Met Ala Glu Ala Tyr Ser Glu Ile
                340                 345                 350

Gly Met Lys Gly Glu Arg Arg Arg Gly Lys Gly His Asp Gly Leu Tyr
                355                 360                 365

Gln Gly Leu Ser Thr Ala Thr Lys Asp Thr Tyr Asp Ala Leu His Met
370                 375                 380

Gln Ala Leu Pro Pro Arg Glu
385                 390

<210> SEQ ID NO 68
<211> LENGTH: 323
<212> TYPE: PRT
<213> ORGANISM: artificial sequence
<220> FEATURE:
<223> OTHER INFORMATION: γ-mcCAR-exCID-n?4

<400> SEQUENCE: 68

Met Ala Ile Pro Ala Val Val Leu Leu Leu Leu Leu Val Glu Gln
1               5                   10                  15

Ala Ala Ala Gly Ser Gly Gly Arg Val Ala Ile Leu Trp His Glu Met
            20                  25                  30

Trp His Glu Gly Leu Glu Glu Ala Ser Arg Leu Tyr Phe Gly Glu Arg
        35                  40                  45

Asn Val Lys Gly Met Phe Glu Val Leu Glu Pro Leu His Ala Met Met
    50                  55                  60

Glu Arg Gly Pro Gln Thr Leu Lys Glu Thr Ser Phe Asn Gln Ala Tyr
65                  70                  75                  80

Gly Arg Asp Leu Met Glu Ala Gln Glu Trp Cys Arg Lys Tyr Met Lys
                85                  90                  95

Ser Gly Asn Val Lys Asp Leu Thr Gln Ala Trp Asp Leu Tyr Tyr His
            100                 105                 110

Val Phe Arg Arg Ile Gly Ser Gly Ala Pro Thr Thr Pro Ala Pro
        115                 120                 125

Arg Pro Pro Thr Pro Ala Pro Thr Ile Ala Ser Gln Pro Leu Ser Leu
130                 135                 140

Arg Pro Glu Ala Cys Arg Pro Ala Ala Gly Gly Ala Val His Thr Arg
145                 150                 155                 160

Gly Leu Asp Phe Ala Cys Asp Ile Gly Glu Pro Gln Leu Cys Tyr Ile
                165                 170                 175

Leu Asp Ala Ile Leu Phe Leu Tyr Gly Ile Val Leu Thr Leu Leu Tyr
            180                 185                 190

Cys Arg Leu Lys Ile Gln Val Arg Lys Ala Ala Ile Thr Ser Tyr Glu
        195                 200                 205

Lys Ser Arg Val Lys Phe Ser Arg Ser Ala Asp Ala Pro Ala Tyr Gln
210                 215                 220

Gln Gly Gln Asn Gln Leu Tyr Asn Glu Leu Asn Leu Gly Arg Arg Glu
225                 230                 235                 240

Glu Tyr Asp Val Leu Asp Lys Arg Arg Gly Arg Asp Pro Glu Met Gly
                245                 250                 255

Gly Lys Pro Arg Arg Lys Asn Pro Gln Glu Gly Leu Tyr Asn Glu Leu
            260                 265                 270

Gln Lys Asp Lys Met Ala Glu Ala Tyr Ser Glu Ile Gly Met Lys Gly
        275                 280                 285

Glu Arg Arg Arg Gly Lys Gly His Asp Gly Leu Tyr Gln Gly Leu Ser
290                 295                 300

Thr Ala Thr Lys Asp Thr Tyr Asp Ala Leu His Met Gln Ala Leu Pro
305                 310                 315                 320

Pro Arg Glu

<210> SEQ ID NO 69
<211> LENGTH: 290
<212> TYPE: PRT
<213> ORGANISM: artificial sequence
<220> FEATURE:
<223> OTHER INFORMATION: γ-mcCAR-exCID-n?5

<400> SEQUENCE: 69

Met Ala Ile Pro Ala Val Val Leu Leu Leu Leu Leu Val Glu Gln
1               5                   10                  15

Ala Ala Ala Gly Ser Gly Gly Val Gln Val Glu Thr Ile Ser Pro Gly
            20                  25                  30

```
Asp Gly Arg Thr Phe Pro Lys Arg Gly Gln Thr Cys Val His Tyr
         35                  40                  45

Thr Gly Met Leu Glu Asp Gly Lys Lys Phe Asp Ser Ser Arg Asp Arg
 50                  55                  60

Asn Lys Pro Phe Lys Phe Met Leu Gly Lys Gln Glu Val Ile Arg Gly
 65                  70                  75                  80

Trp Glu Glu Gly Val Ala Gln Met Ser Val Gly Gln Arg Ala Lys Leu
                 85                  90                  95

Thr Ile Ser Pro Asp Tyr Ala Tyr Gly Ala Thr Gly His Pro Gly Ile
                100                 105                 110

Ile Pro Pro His Ala Thr Leu Val Phe Asp Val Glu Leu Leu Lys Leu
            115                 120                 125

Glu Gly Ser Gly Ala Pro Leu Gly Glu Pro Gln Leu Cys Tyr Ile Leu
130                 135                 140

Asp Ala Ile Leu Phe Leu Tyr Gly Ile Val Leu Thr Leu Leu Tyr Cys
145                 150                 155                 160

Arg Leu Lys Ile Gln Val Arg Lys Ala Ala Ile Thr Ser Tyr Glu Lys
                165                 170                 175

Ser Arg Val Lys Phe Ser Arg Ser Ala Asp Ala Pro Ala Tyr Gln Gln
                180                 185                 190

Gly Gln Asn Gln Leu Tyr Asn Glu Leu Asn Leu Gly Arg Arg Glu Glu
            195                 200                 205

Tyr Asp Val Leu Asp Lys Arg Gly Arg Asp Pro Glu Met Gly Gly
210                 215                 220

Lys Pro Arg Arg Lys Asn Pro Gln Glu Gly Leu Tyr Asn Glu Leu Gln
225                 230                 235                 240

Lys Asp Lys Met Ala Glu Ala Tyr Ser Glu Ile Gly Met Lys Gly Glu
                245                 250                 255

Arg Arg Arg Gly Lys Gly His Asp Gly Leu Tyr Gln Gly Leu Ser Thr
                260                 265                 270

Ala Thr Lys Asp Thr Tyr Asp Ala Leu His Met Gln Ala Leu Pro Pro
            275                 280                 285

Arg Glu
    290

<210> SEQ ID NO 70
<211> LENGTH: 278
<212> TYPE: PRT
<213> ORGANISM: artificial sequence
<220> FEATURE:
<223> OTHER INFORMATION: γ-mcCAR-exCID-n?6

<400> SEQUENCE: 70

Met Ala Ile Pro Ala Val Val Leu Leu Leu Leu Leu Val Glu Gln
 1               5                  10                  15

Ala Ala Ala Gly Ser Gly Gly Arg Val Ala Ile Leu Trp His Glu Met
                 20                  25                  30

Trp His Glu Gly Leu Glu Glu Ala Ser Arg Leu Tyr Phe Gly Glu Arg
             35                  40                  45

Asn Val Lys Gly Met Phe Glu Val Leu Glu Pro Leu His Ala Met Met
 50                  55                  60

Glu Arg Gly Pro Gln Thr Leu Lys Glu Thr Ser Phe Asn Gln Ala Tyr
 65                  70                  75                  80

Gly Arg Asp Leu Met Glu Ala Gln Glu Trp Cys Arg Lys Tyr Met Lys
                 85                  90                  95
```

```
Ser Gly Asn Val Lys Asp Leu Thr Gln Ala Trp Asp Leu Tyr Tyr His
            100                 105                 110

Val Phe Arg Arg Ile Gly Ser Gly Ala Pro Leu Gly Glu Pro Gln Leu
        115                 120                 125

Cys Tyr Ile Leu Asp Ala Ile Leu Phe Leu Tyr Gly Ile Val Leu Thr
    130                 135                 140

Leu Leu Tyr Cys Arg Leu Lys Ile Gln Val Arg Lys Ala Ala Ile Thr
145                 150                 155                 160

Ser Tyr Glu Lys Ser Arg Val Lys Phe Ser Arg Ser Ala Asp Ala Pro
                165                 170                 175

Ala Tyr Gln Gln Gly Gln Asn Gln Leu Tyr Asn Glu Leu Asn Leu Gly
            180                 185                 190

Arg Arg Glu Glu Tyr Asp Val Leu Asp Lys Arg Gly Arg Asp Pro
        195                 200                 205

Glu Met Gly Gly Lys Pro Arg Arg Lys Asn Pro Gln Glu Gly Leu Tyr
    210                 215                 220

Asn Glu Leu Gln Lys Asp Lys Met Ala Glu Ala Tyr Ser Glu Ile Gly
225                 230                 235                 240

Met Lys Gly Glu Arg Arg Arg Gly Lys Gly His Asp Gly Leu Tyr Gln
                245                 250                 255

Gly Leu Ser Thr Ala Thr Lys Asp Thr Tyr Asp Ala Leu His Met Gln
            260                 265                 270

Ala Leu Pro Pro Arg Glu
        275

<210> SEQ ID NO 71
<211> LENGTH: 546
<212> TYPE: PRT
<213> ORGANISM: artificial sequence
<220> FEATURE:
<223> OTHER INFORMATION: alpha-mcCAR-exCID-n?1

<400> SEQUENCE: 71

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175
```

```
Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Val Gln Val Glu Thr Ile Ser
        275                 280                 285

Pro Gly Asp Gly Arg Thr Phe Pro Lys Arg Gly Gln Thr Cys Val Val
    290                 295                 300

His Tyr Thr Gly Met Leu Glu Asp Gly Lys Lys Phe Asp Ser Ser Arg
305                 310                 315                 320

Asp Arg Asn Lys Pro Phe Lys Phe Met Leu Gly Lys Gln Glu Val Ile
                325                 330                 335

Arg Gly Trp Glu Glu Gly Val Ala Gln Met Ser Val Gly Gln Arg Ala
            340                 345                 350

Lys Leu Thr Ile Ser Pro Asp Tyr Ala Tyr Gly Ala Thr Gly His Pro
        355                 360                 365

Gly Ile Ile Pro Pro His Ala Thr Leu Val Phe Asp Val Glu Leu Leu
    370                 375                 380

Lys Leu Glu Gly Ser Gly Ala Pro Ala Pro Val Gly Leu Val Ala Arg
385                 390                 395                 400

Leu Ala Asp Glu Ser Gly His Val Val Leu Arg Trp Leu Pro Pro Pro
                405                 410                 415

Glu Thr Pro Met Thr Ser His Ile Arg Tyr Glu Val Asp Val Ser Ala
            420                 425                 430

Gly Asn Gly Ala Gly Ser Val Gln Arg Val Glu Ile Leu Glu Gly Arg
        435                 440                 445

Thr Glu Cys Val Leu Ser Asn Leu Arg Gly Arg Thr Arg Tyr Thr Phe
    450                 455                 460

Ala Val Arg Ala Arg Met Ala Glu Pro Ser Phe Gly Gly Phe Trp Ser
465                 470                 475                 480

Ala Trp Ser Glu Pro Val Ser Leu Leu Thr Pro Ser Asp Ile Phe Ile
                485                 490                 495

Pro Leu Leu Val Val Ile Leu Phe Ala Val Asp Thr Gly Leu Phe Ile
            500                 505                 510

Ser Thr Gln Gln Gln Val Thr Phe Leu Leu Lys Ile Lys Arg Thr Arg
        515                 520                 525

Lys Gly Phe Arg Leu Leu Asn Pro His Pro Lys Pro Asn Pro Lys Asn
    530                 535                 540

Asn Glu
545

<210> SEQ ID NO 72
<211> LENGTH: 534
<212> TYPE: PRT
<213> ORGANISM: artificial sequence
<220> FEATURE:
<223> OTHER INFORMATION: alpha-mcCAR-exCID-n?2
```

<400> SEQUENCE: 72

```
Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Gly Arg Val Ala Ile Leu Trp His
        275                 280                 285

Glu Met Trp His Glu Gly Leu Glu Glu Ala Ser Arg Leu Tyr Phe Gly
    290                 295                 300

Glu Arg Asn Val Lys Gly Met Phe Glu Val Leu Glu Pro Leu His Ala
305                 310                 315                 320

Met Met Glu Arg Gly Pro Gln Thr Leu Lys Glu Thr Ser Phe Asn Gln
                325                 330                 335

Ala Tyr Gly Arg Asp Leu Met Glu Ala Gln Glu Trp Cys Arg Lys Tyr
            340                 345                 350

Met Lys Ser Gly Asn Val Lys Asp Leu Thr Gln Ala Trp Asp Leu Tyr
        355                 360                 365

Tyr His Val Phe Arg Arg Ile Gly Ser Gly Ala Pro Ala Pro Val Gly
    370                 375                 380

Leu Val Ala Arg Leu Ala Asp Glu Ser Gly His Val Val Leu Arg Trp
385                 390                 395                 400

Leu Pro Pro Pro Glu Thr Pro Met Thr Ser His Ile Arg Tyr Glu Val
```

```
                    405                 410                 415
Asp Val Ser Ala Gly Asn Gly Ala Gly Ser Val Gln Arg Val Glu Ile
                420                 425                 430

Leu Glu Gly Arg Thr Glu Cys Val Leu Ser Asn Leu Arg Gly Arg Thr
            435                 440                 445

Arg Tyr Thr Phe Ala Val Arg Ala Arg Met Ala Glu Pro Ser Phe Gly
        450                 455                 460

Gly Phe Trp Ser Ala Trp Ser Glu Pro Val Ser Leu Thr Pro Ser
465                 470                 475                 480

Asp Ile Phe Ile Pro Leu Leu Val Val Ile Leu Phe Ala Val Asp Thr
                485                 490                 495

Gly Leu Phe Ile Ser Thr Gln Gln Gln Val Thr Phe Leu Leu Lys Ile
                500                 505                 510

Lys Arg Thr Arg Lys Gly Phe Arg Leu Leu Asn Pro His Pro Lys Pro
            515                 520                 525

Asn Pro Lys Asn Asn Glu
        530

<210> SEQ ID NO 73
<211> LENGTH: 678
<212> TYPE: PRT
<213> ORGANISM: artificial sequence
<220> FEATURE:
<223> OTHER INFORMATION: alpha-mcCAR-exCID-n?3

<400> SEQUENCE: 73

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
                20                  25                  30

Gly Pro Glu Leu Ile Lys Pro Gly Ala Ser Val Lys Met Ser Cys Lys
            35                  40                  45

Ala Ser Gly Tyr Thr Phe Thr Ser Tyr Val Met His Trp Val Lys Gln
        50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
```

-continued

```
            225                 230                 235                 240

Ile Ser Arg Val Glu Ala Glu Asp Val Gly Val Tyr Tyr Cys Met Gln
                        245                 250                 255

His Leu Glu Tyr Pro Phe Thr Phe Gly Ala Gly Thr Lys Leu Glu Leu
                        260                 265                 270

Lys Arg Ser Asp Pro Gly Ser Gly Val Gln Val Glu Thr Ile Ser
                        275                 280                 285

Pro Gly Asp Gly Arg Thr Phe Pro Lys Arg Gly Gln Thr Cys Val Val
            290                 295                 300

His Tyr Thr Gly Met Leu Glu Asp Gly Lys Lys Phe Asp Ser Ser Arg
        305                 310                 315                 320

Asp Arg Asn Lys Pro Phe Lys Phe Met Leu Gly Lys Gln Glu Val Ile
                        325                 330                 335

Arg Gly Trp Glu Glu Gly Val Ala Gln Met Ser Val Gly Gln Arg Ala
                        340                 345                 350

Lys Leu Thr Ile Ser Pro Asp Tyr Ala Tyr Gly Ala Thr Gly His Pro
                        355                 360                 365

Gly Ile Ile Pro Pro His Ala Thr Leu Val Phe Asp Val Glu Leu Leu
            370                 375                 380

Lys Leu Glu Gly Ser Gly Ala Pro Glu Pro Lys Ser Pro Asp Lys Thr
        385                 390                 395                 400

His Thr Cys Pro Pro Cys Pro Ala Pro Val Ala Gly Pro Ser Val
                        405                 410                 415

Phe Leu Phe Pro Pro Lys Pro Lys Asp Thr Leu Met Ile Ala Arg Thr
                        420                 425                 430

Pro Glu Val Thr Cys Val Val Asp Val Ser His Glu Asp Pro Glu
                        435                 440                 445

Val Lys Phe Asn Trp Tyr Val Asp Gly Val Glu Val His Asn Ala Lys
                        450                 455                 460

Thr Lys Pro Arg Glu Glu Gln Tyr Asn Ser Thr Tyr Arg Val Val Ser
        465                 470                 475                 480

Val Leu Thr Val Leu His Gln Asp Trp Leu Asn Gly Lys Glu Tyr Lys
                        485                 490                 495

Cys Lys Val Ser Asn Lys Ala Leu Pro Ala Pro Ile Glu Lys Thr Ile
                        500                 505                 510

Ser Lys Ala Lys Gly Gln Pro Arg Glu Pro Gln Val Tyr Thr Leu Pro
                        515                 520                 525

Pro Ser Arg Asp Glu Leu Thr Lys Asn Gln Val Ser Leu Thr Cys Leu
            530                 535                 540

Val Lys Gly Phe Tyr Pro Ser Asp Ile Ala Val Glu Trp Glu Ser Asn
        545                 550                 555                 560

Gly Gln Pro Glu Asn Asn Tyr Lys Thr Thr Pro Pro Val Leu Asp Ser
                        565                 570                 575

Asp Gly Ser Phe Phe Leu Tyr Ser Lys Leu Thr Val Asp Lys Ser Arg
                        580                 585                 590

Trp Gln Gln Gly Asn Val Phe Ser Cys Ser Val Met His Glu Ala Leu
                        595                 600                 605

His Asn His Tyr Thr Gln Lys Ser Leu Ser Leu Ser Pro Gly Lys Lys
                        610                 615                 620

Asp Ile Phe Ile Pro Leu Leu Val Val Ile Leu Phe Ala Val Asp Thr
        625                 630                 635                 640

Gly Leu Phe Ile Ser Thr Gln Gln Val Thr Phe Leu Leu Lys Ile
                        645                 650                 655
```

```
Lys Arg Thr Arg Lys Gly Phe Arg Leu Leu Asn Pro His Pro Lys Pro
            660                 665                 670

Asn Pro Lys Asn Asn Glu
        675

<210> SEQ ID NO 74
<211> LENGTH: 666
<212> TYPE: PRT
<213> ORGANISM: artificial sequence
<220> FEATURE:
<223> OTHER INFORMATION: alpha-mcCAR-exCID-n?4

<400> SEQUENCE: 74

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Gly Arg Val Ala Ile Leu Trp His
        275                 280                 285

Glu Met Trp His Glu Gly Leu Glu Glu Ala Ser Arg Leu Tyr Phe Gly
    290                 295                 300

Glu Arg Asn Val Lys Gly Met Phe Glu Val Leu Glu Pro Leu His Ala
305                 310                 315                 320

Met Met Glu Arg Gly Pro Gln Thr Leu Lys Glu Thr Ser Phe Asn Gln
                325                 330                 335
```

Ala Tyr Gly Arg Asp Leu Met Glu Ala Gln Glu Trp Cys Arg Lys Tyr
            340                 345                 350

Met Lys Ser Gly Asn Val Lys Asp Leu Thr Gln Ala Trp Asp Leu Tyr
            355                 360                 365

Tyr His Val Phe Arg Arg Ile Gly Ser Gly Ala Pro Glu Pro Lys Ser
            370                 375                 380

Pro Asp Lys Thr His Thr Cys Pro Pro Cys Pro Ala Pro Pro Val Ala
385                 390                 395                 400

Gly Pro Ser Val Phe Leu Phe Pro Pro Lys Pro Lys Asp Thr Leu Met
                405                 410                 415

Ile Ala Arg Thr Pro Glu Val Thr Cys Val Val Val Asp Val Ser His
            420                 425                 430

Glu Asp Pro Glu Val Lys Phe Asn Trp Tyr Val Asp Gly Val Glu Val
            435                 440                 445

His Asn Ala Lys Thr Lys Pro Arg Glu Glu Gln Tyr Asn Ser Thr Tyr
        450                 455                 460

Arg Val Val Ser Val Leu Thr Val Leu His Gln Asp Trp Leu Asn Gly
465                 470                 475                 480

Lys Glu Tyr Lys Cys Lys Val Ser Asn Lys Ala Leu Pro Ala Pro Ile
                485                 490                 495

Glu Lys Thr Ile Ser Lys Ala Lys Gly Gln Pro Arg Glu Pro Gln Val
            500                 505                 510

Tyr Thr Leu Pro Pro Ser Arg Asp Glu Leu Thr Lys Asn Gln Val Ser
            515                 520                 525

Leu Thr Cys Leu Val Lys Gly Phe Tyr Pro Ser Asp Ile Ala Val Glu
        530                 535                 540

Trp Glu Ser Asn Gly Gln Pro Glu Asn Asn Tyr Lys Thr Thr Pro Pro
545                 550                 555                 560

Val Leu Asp Ser Asp Gly Ser Phe Phe Leu Tyr Ser Lys Leu Thr Val
                565                 570                 575

Asp Lys Ser Arg Trp Gln Gln Gly Asn Val Phe Ser Cys Ser Val Met
            580                 585                 590

His Glu Ala Leu His Asn His Tyr Thr Gln Lys Ser Leu Ser Leu Ser
            595                 600                 605

Pro Gly Lys Lys Asp Ile Phe Ile Pro Leu Leu Val Val Ile Leu Phe
        610                 615                 620

Ala Val Asp Thr Gly Leu Phe Ile Ser Thr Gln Gln Gln Val Thr Phe
625                 630                 635                 640

Leu Leu Lys Ile Lys Arg Thr Arg Lys Gly Phe Arg Leu Leu Asn Pro
                645                 650                 655

His Pro Lys Pro Asn Pro Lys Asn Asn Glu
            660                 665

<210> SEQ ID NO 75
<211> LENGTH: 490
<212> TYPE: PRT
<213> ORGANISM: artificial sequence
<220> FEATURE:
<223> OTHER INFORMATION: alpha-mcCAR-exCID-n?5

<400> SEQUENCE: 75

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
                35                  40                  45

Ala Ser Gly Tyr Thr Phe Thr Ser Tyr Val Met His Trp Val Lys Gln
 50                  55                  60

Lys Pro Gly Gln Gly Leu Glu Trp Ile Gly Tyr Ile Asn Pro Tyr Asn
 65                  70                  75                  80

Asp Gly Thr Lys Tyr Asn Glu Lys Phe Lys Gly Lys Ala Thr Leu Thr
                 85                  90                  95

Ser Asp Lys Ser Ser Ser Thr Ala Tyr Met Glu Leu Ser Ser Leu Thr
                100                 105                 110

Ser Glu Asp Ser Ala Val Tyr Tyr Cys Ala Arg Gly Thr Tyr Tyr
                115                 120                 125

Gly Ser Arg Val Phe Asp Tyr Trp Gly Gln Gly Thr Thr Leu Thr Val
130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
                180                 185                 190

Ser Asn Gly Asn Thr Tyr Leu Tyr Trp Phe Leu Gln Arg Pro Gly Gln
                195                 200                 205

Ser Pro Gln Leu Leu Ile Tyr Arg Met Ser Asn Leu Ala Ser Gly Val
                210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
                260                 265                 270

Lys Arg Ser Asp Pro Gly Ser Gly Gly Val Gln Val Glu Thr Ile Ser
                275                 280                 285

Pro Gly Asp Gly Arg Thr Phe Pro Lys Arg Gly Gln Thr Cys Val Val
                290                 295                 300

His Tyr Thr Gly Met Leu Glu Asp Gly Lys Lys Phe Asp Ser Ser Arg
305                 310                 315                 320

Asp Arg Asn Lys Pro Phe Lys Phe Met Leu Gly Lys Gln Glu Val Ile
                325                 330                 335

Arg Gly Trp Glu Glu Gly Val Ala Gln Met Ser Val Gly Gln Arg Ala
                340                 345                 350

Lys Leu Thr Ile Ser Pro Asp Tyr Ala Tyr Gly Ala Thr Gly His Pro
                355                 360                 365

Gly Ile Ile Pro Pro His Ala Thr Leu Val Phe Asp Val Glu Leu Leu
370                 375                 380

Lys Leu Glu Gly Ser Gly Ala Pro Thr Thr Thr Pro Ala Pro Arg Pro
385                 390                 395                 400

Pro Thr Pro Ala Pro Thr Ile Ala Ser Gln Pro Leu Ser Leu Arg Pro
                405                 410                 415

Glu Ala Cys Arg Pro Ala Ala Gly Gly Ala Val His Thr Arg Gly Leu
                420                 425                 430

Asp Phe Ala Cys Asp Phe Ile Pro Leu Leu Val Val Ile Leu Phe
                435                 440                 445

```
Ala Val Asp Thr Gly Leu Phe Ile Ser Thr Gln Gln Gln Val Thr Phe
    450                 455                 460

Leu Leu Lys Ile Lys Arg Thr Lys Gly Phe Arg Leu Leu Asn Pro
465                 470                 475                 480

His Pro Lys Pro Asn Pro Lys Asn Asn Glu
                485                 490

<210> SEQ ID NO 76
<211> LENGTH: 478
<212> TYPE: PRT
<213> ORGANISM: artificial sequence
<220> FEATURE:
<223> OTHER INFORMATION: alpha-mcCAR-exCID-n?6

<400> SEQUENCE: 76

Met Ala Pro Ala Met Glu Ser Pro Thr Leu Leu Cys Val Ala Leu Leu
1               5                   10                  15

Phe Phe Ala Pro Asp Gly Val Leu Ala Glu Val Gln Leu Gln Gln Ser
            20                  25                  30

Gly Pro Glu Leu Ile Lys Pro Gly Ala Ser Val Lys Met Ser Cys Lys
        35                  40                  45

Ala Ser Gly Tyr Thr Phe Thr Ser Tyr Val Met His Trp Val Lys Gln
    50                  55                  60

Lys Pro Gly Gln Gly Leu Glu Trp Ile Gly Tyr Ile Asn Pro Tyr Asn
65                  70                  75                  80

Asp Gly Thr Lys Tyr Asn Glu Lys Phe Lys Gly Lys Ala Thr Leu Thr
                85                  90                  95

Ser Asp Lys Ser Ser Ser Thr Ala Tyr Met Glu Leu Ser Ser Leu Thr
            100                 105                 110

Ser Glu Asp Ser Ala Val Tyr Tyr Cys Ala Arg Gly Thr Tyr Tyr Tyr
        115                 120                 125

Gly Ser Arg Val Phe Asp Tyr Trp Gly Gln Gly Thr Thr Leu Thr Val
    130                 135                 140

Ser Ser Gly Gly Gly Gly Ser Gly Gly Gly Gly Ser Gly Gly Gly Gly
145                 150                 155                 160

Ser Asp Ile Val Met Thr Gln Ala Ala Pro Ser Ile Pro Val Thr Pro
                165                 170                 175

Gly Glu Ser Val Ser Ile Ser Cys Arg Ser Ser Lys Ser Leu Leu Asn
            180                 185                 190

Ser Asn Gly Asn Thr Tyr Leu Tyr Trp Phe Leu Gln Arg Pro Gly Gln
        195                 200                 205

Ser Pro Gln Leu Leu Ile Tyr Arg Met Ser Asn Leu Ala Ser Gly Val
    210                 215                 220

Pro Asp Arg Phe Ser Gly Ser Gly Ser Gly Thr Ala Phe Thr Leu Arg
225                 230                 235                 240

Ile Ser Arg Val Glu Ala Glu Asp Val Gly Val Tyr Tyr Cys Met Gln
                245                 250                 255

His Leu Glu Tyr Pro Phe Thr Phe Gly Ala Gly Thr Lys Leu Glu Leu
            260                 265                 270

Lys Arg Ser Asp Pro Gly Ser Gly Gly Arg Val Ala Ile Leu Trp His
        275                 280                 285

Glu Met Trp His Glu Gly Leu Glu Ala Ser Arg Leu Tyr Phe Gly
    290                 295                 300

Glu Arg Asn Val Lys Gly Met Phe Glu Val Leu Glu Pro Leu His Ala
305                 310                 315                 320
```

Met Met Glu Arg Gly Pro Gln Thr Leu Lys Glu Thr Ser Phe Asn Gln
            325                 330                 335

Ala Tyr Gly Arg Asp Leu Met Glu Ala Gln Glu Trp Cys Arg Lys Tyr
        340                 345                 350

Met Lys Ser Gly Asn Val Lys Asp Leu Thr Gln Ala Trp Asp Leu Tyr
            355                 360                 365

Tyr His Val Phe Arg Arg Ile Gly Ser Gly Ala Pro Thr Thr Thr Pro
        370                 375                 380

Ala Pro Arg Pro Pro Thr Pro Ala Pro Thr Ile Ala Ser Gln Pro Leu
385                 390                 395                 400

Ser Leu Arg Pro Glu Ala Cys Arg Pro Ala Ala Gly Gly Ala Val His
            405                 410                 415

Thr Arg Gly Leu Asp Phe Ala Cys Asp Phe Phe Ile Pro Leu Leu Val
        420                 425                 430

Val Ile Leu Phe Ala Val Asp Thr Gly Leu Phe Ile Ser Thr Gln Gln
            435                 440                 445

Gln Val Thr Phe Leu Leu Lys Ile Lys Arg Thr Arg Lys Gly Phe Arg
        450                 455                 460

Leu Leu Asn Pro His Pro Lys Pro Asn Pro Lys Asn Asn Glu
465                 470                 475

<210> SEQ ID NO 77
<211> LENGTH: 608
<212> TYPE: PRT
<213> ORGANISM: artificial sequence
<220> FEATURE:
<223> OTHER INFORMATION: CD123-scCAR extra CID n?1

<400> SEQUENCE: 77

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
    50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

```
Ala Ser Asn Leu Glu Ser Gly Ile Pro Ala Arg Phe Ser Gly Ser Gly
210                 215                 220
Ser Arg Thr Asp Phe Thr Leu Thr Ile Asn Pro Val Glu Ala Asp Asp
225                 230                 235                 240
Val Ala Thr Tyr Tyr Cys Gln Gln Ser Asn Glu Asp Pro Pro Thr Phe
            245                 250                 255
Gly Ala Gly Thr Lys Leu Glu Leu Lys Arg Ser Asp Pro Gly Ser Gly
            260                 265                 270
Gly Val Gln Val Glu Thr Ile Ser Pro Gly Asp Gly Arg Thr Phe Pro
        275                 280                 285
Lys Arg Gly Gln Thr Cys Val Val His Tyr Thr Gly Met Leu Glu Asp
290                 295                 300
Gly Lys Lys Phe Asp Ser Ser Arg Asp Arg Asn Lys Pro Phe Lys Phe
305                 310                 315                 320
Met Leu Gly Lys Gln Glu Val Ile Arg Gly Trp Glu Glu Gly Val Ala
            325                 330                 335
Gln Met Ser Val Gly Gln Arg Ala Lys Leu Thr Ile Ser Pro Asp Tyr
            340                 345                 350
Ala Tyr Gly Ala Thr Gly His Pro Gly Ile Ile Pro Pro His Ala Thr
        355                 360                 365
Leu Val Phe Asp Val Glu Leu Leu Lys Leu Glu Gly Ser Gly Ala Pro
370                 375                 380
Thr Thr Thr Pro Ala Pro Arg Pro Pro Thr Pro Ala Pro Thr Ile Ala
385                 390                 395                 400
Ser Gln Pro Leu Ser Leu Arg Pro Glu Ala Cys Arg Pro Ala Ala Gly
            405                 410                 415
Gly Ala Val His Thr Arg Gly Leu Asp Phe Ala Cys Asp Ile Tyr Ile
            420                 425                 430
Trp Ala Pro Leu Ala Gly Thr Cys Gly Val Leu Leu Leu Ser Leu Val
        435                 440                 445
Ile Thr Leu Tyr Cys Arg Arg Gly Arg Lys Lys Leu Leu Tyr Ile Phe
450                 455                 460
Lys Gln Pro Phe Met Arg Pro Val Gln Thr Thr Gln Glu Glu Asp Gly
465                 470                 475                 480
Cys Ser Cys Arg Phe Pro Glu Glu Glu Glu Gly Gly Cys Glu Leu Arg
            485                 490                 495
Val Lys Phe Ser Arg Ser Ala Asp Ala Pro Ala Tyr Gln Gln Gly Gln
            500                 505                 510
Asn Gln Leu Tyr Asn Glu Leu Asn Leu Gly Arg Arg Glu Glu Tyr Asp
        515                 520                 525
Val Leu Asp Lys Arg Arg Gly Arg Asp Pro Glu Met Gly Gly Lys Pro
530                 535                 540
Arg Arg Lys Asn Pro Gln Glu Gly Leu Tyr Asn Glu Leu Gln Lys Asp
545                 550                 555                 560
Lys Met Ala Glu Ala Tyr Ser Glu Ile Gly Met Lys Gly Glu Arg Arg
            565                 570                 575
Arg Gly Lys Gly His Asp Gly Leu Tyr Gln Gly Leu Ser Thr Ala Thr
            580                 585                 590
Lys Asp Thr Tyr Asp Ala Leu His Met Gln Ala Leu Pro Pro Arg Glu
        595                 600                 605
```

<210> SEQ ID NO 78
<211> LENGTH: 596
<212> TYPE: PRT

<213> ORGANISM: artificial sequence
<220> FEATURE:
<223> OTHER INFORMATION: CD123-scCAR extra CID n?2

<400> SEQUENCE: 78

```
Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
130                 135                 140

Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

Ala Ser Asn Leu Glu Ser Gly Ile Pro Ala Arg Phe Ser Gly Ser Gly
        210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Arg Ser Asp Pro Gly Ser Gly
            260                 265                 270

Gly Arg Val Ala Ile Leu Trp His Glu Met Trp His Glu Gly Leu Glu
        275                 280                 285

Glu Ala Ser Arg Leu Tyr Phe Gly Glu Arg Asn Val Lys Gly Met Phe
290                 295                 300

Glu Val Leu Glu Pro Leu His Ala Met Met Glu Arg Gly Pro Gln Thr
305                 310                 315                 320

Leu Lys Glu Thr Ser Phe Asn Gln Ala Tyr Gly Arg Asp Leu Met Glu
                325                 330                 335

Ala Gln Glu Trp Cys Arg Lys Tyr Met Lys Ser Gly Asn Val Lys Asp
            340                 345                 350

Leu Thr Gln Ala Trp Asp Leu Tyr Tyr His Val Phe Arg Arg Ile Gly
        355                 360                 365

Ser Gly Ala Pro Thr Thr Thr Pro Ala Pro Arg Pro Pro Thr Pro Ala
370                 375                 380

Pro Thr Ile Ala Ser Gln Pro Leu Ser Leu Arg Pro Glu Ala Cys Arg
```

```
                385                 390                 395                 400
        Pro Ala Ala Gly Gly Ala Val His Thr Arg Gly Leu Asp Phe Ala Cys
                        405                 410                 415

Asp Ile Tyr Ile Trp Ala Pro Leu Ala Gly Thr Cys Gly Val Leu Leu
                        420                 425                 430

Leu Ser Leu Val Ile Thr Leu Tyr Cys Arg Arg Gly Arg Lys Lys Leu
                        435                 440                 445

Leu Tyr Ile Phe Lys Gln Pro Phe Met Arg Pro Val Gln Thr Thr Gln
                450                 455                 460

Glu Glu Asp Gly Cys Ser Cys Arg Phe Pro Glu Glu Glu Glu Gly Gly
        465                 470                 475                 480

Cys Glu Leu Arg Val Lys Phe Ser Arg Ser Ala Asp Ala Pro Ala Tyr
                        485                 490                 495

Gln Gln Gly Gln Asn Gln Leu Tyr Asn Glu Leu Asn Leu Gly Arg Arg
                        500                 505                 510

Glu Glu Tyr Asp Val Leu Asp Lys Arg Arg Gly Arg Asp Pro Glu Met
                        515                 520                 525

Gly Gly Lys Pro Arg Arg Lys Asn Pro Gln Glu Gly Leu Tyr Asn Glu
                530                 535                 540

Leu Gln Lys Asp Lys Met Ala Glu Ala Tyr Ser Glu Ile Gly Met Lys
        545                 550                 555                 560

Gly Glu Arg Arg Arg Gly Lys Gly His Asp Gly Leu Tyr Gln Gly Leu
                        565                 570                 575

Ser Thr Ala Thr Lys Asp Thr Tyr Asp Ala Leu His Met Gln Ala Leu
                        580                 585                 590

Pro Pro Arg Glu
                595

<210> SEQ ID NO 79
<211> LENGTH: 796
<212> TYPE: PRT
<213> ORGANISM: artificial sequence
<220> FEATURE:
<223> OTHER INFORMATION: CD123-scCAR extra CID n?3

<400> SEQUENCE: 79

Met Ala Leu Pro Val Thr Ala Leu Leu Leu Pro Leu Ala Leu Leu Leu
        1               5                   10                  15

His Ala Ala Arg Pro Gln Ile Gln Leu Val Gln Ser Gly Pro Glu Leu
                        20                  25                  30

Lys Lys Pro Gly Glu Thr Val Lys Ile Ser Cys Lys Ala Ser Gly Tyr
                    35                  40                  45

Ile Phe Thr Asn Tyr Gly Met Asn Trp Val Lys Gln Ala Pro Gly Lys
                50                  55                  60

Ser Phe Lys Trp Met Gly Trp Ile Asn Thr Tyr Thr Gly Glu Ser Thr
        65                  70                  75                  80

Tyr Ser Ala Asp Phe Lys Gly Arg Phe Ala Phe Ser Leu Glu Thr Ser
                        85                  90                  95

Ala Ser Thr Ala Tyr Leu His Ile Asn Asp Leu Lys Asn Glu Asp Thr
                    100                 105                 110

Ala Thr Tyr Phe Cys Ala Arg Ser Gly Gly Tyr Asp Pro Met Asp Tyr
                    115                 120                 125

Trp Gly Gln Gly Thr Ser Val Thr Val Ser Ser Gly Gly Gly Gly Ser
                130                 135                 140

Gly Gly Gly Gly Ser Gly Gly Gly Gly Ser Asp Ile Val Leu Thr Gln
```

```
            145                 150                 155                 160
        Ser Pro Ala Ser Leu Ala Val Ser Leu Gly Gln Arg Ala Thr Ile Ser
                        165                 170                 175
        Cys Arg Ala Ser Glu Ser Val Asp Asn Tyr Gly Asn Thr Phe Met His
                        180                 185                 190
        Trp Tyr Gln Gln Lys Pro Gly Gln Pro Pro Lys Leu Leu Ile Tyr Arg
                        195                 200                 205
        Ala Ser Asn Leu Glu Ser Gly Ile Pro Ala Arg Phe Ser Gly Ser Gly
                        210                 215                 220
        Ser Arg Thr Asp Phe Thr Leu Thr Ile Asn Pro Val Glu Ala Asp Asp
        225                 230                 235                 240
        Val Ala Thr Tyr Tyr Cys Gln Gln Ser Asn Glu Asp Pro Pro Thr Phe
                        245                 250                 255
        Gly Ala Gly Thr Lys Leu Glu Leu Lys Arg Ser Asp Pro Gly Ser Gly
                        260                 265                 270
        Gly Val Gln Val Glu Thr Ile Ser Pro Gly Asp Gly Arg Thr Phe Pro
                        275                 280                 285
        Lys Arg Gly Gln Thr Cys Val Val His Tyr Thr Gly Met Leu Glu Asp
                        290                 295                 300
        Gly Lys Lys Phe Asp Ser Ser Arg Asp Arg Asn Lys Pro Phe Lys Phe
        305                 310                 315                 320
        Met Leu Gly Lys Gln Glu Val Ile Arg Gly Trp Glu Glu Gly Val Ala
                        325                 330                 335
        Gln Met Ser Val Gly Gln Arg Ala Lys Leu Thr Ile Ser Pro Asp Tyr
                        340                 345                 350
        Ala Tyr Gly Ala Thr Gly His Pro Gly Ile Ile Pro Pro His Ala Thr
                        355                 360                 365
        Leu Val Phe Asp Val Glu Leu Leu Lys Leu Glu Gly Ser Gly Ala Pro
                        370                 375                 380
        Glu Pro Lys Ser Pro Asp Lys Thr His Thr Cys Pro Pro Cys Pro Ala
        385                 390                 395                 400
        Pro Pro Val Ala Gly Pro Ser Val Phe Leu Phe Pro Pro Lys Pro Lys
                        405                 410                 415
        Asp Thr Leu Met Ile Ala Arg Thr Pro Glu Val Thr Cys Val Val Val
                        420                 425                 430
        Asp Val Ser His Glu Asp Pro Glu Val Lys Phe Asn Trp Tyr Val Asp
                        435                 440                 445
        Gly Val Glu Val His Asn Ala Lys Thr Lys Pro Arg Glu Glu Gln Tyr
                        450                 455                 460
        Asn Ser Thr Tyr Arg Val Val Ser Val Leu Thr Val Leu His Gln Asp
        465                 470                 475                 480
        Trp Leu Asn Gly Lys Glu Tyr Lys Cys Lys Val Ser Asn Lys Ala Leu
                        485                 490                 495
        Pro Ala Pro Ile Glu Lys Thr Ile Ser Lys Ala Lys Gly Gln Pro Arg
                        500                 505                 510
        Glu Pro Gln Val Tyr Thr Leu Pro Pro Ser Arg Asp Glu Leu Thr Lys
                        515                 520                 525
        Asn Gln Val Ser Leu Thr Cys Leu Val Lys Gly Phe Tyr Pro Ser Asp
                        530                 535                 540
        Ile Ala Val Glu Trp Glu Ser Asn Gly Gln Pro Glu Asn Asn Tyr Lys
        545                 550                 555                 560
        Thr Thr Pro Pro Val Leu Asp Ser Asp Gly Ser Phe Phe Leu Tyr Ser
                        565                 570                 575
```

-continued

```
Lys Leu Thr Val Asp Lys Ser Arg Trp Gln Gln Gly Asn Val Phe Ser
                580                 585                 590

Cys Ser Val Met His Glu Ala Leu His Asn His Tyr Thr Gln Lys Ser
            595                 600                 605

Leu Ser Leu Ser Pro Gly Lys Lys Asp Ile Tyr Ile Trp Ala Pro Leu
        610                 615                 620

Ala Gly Thr Cys Gly Val Leu Leu Leu Ser Leu Val Ile Thr Leu Tyr
625                 630                 635                 640

Cys Arg Arg Gly Arg Lys Lys Leu Leu Tyr Ile Phe Lys Gln Pro Phe
                645                 650                 655

Met Arg Pro Val Gln Thr Thr Gln Glu Glu Asp Gly Cys Ser Cys Arg
            660                 665                 670

Phe Pro Glu Glu Glu Glu Gly Gly Cys Glu Leu Arg Val Lys Phe Ser
        675                 680                 685

Arg Ser Ala Asp Ala Pro Ala Tyr Gln Gln Gly Gln Asn Gln Leu Tyr
690                 695                 700

Asn Glu Leu Asn Leu Gly Arg Arg Glu Glu Tyr Asp Val Leu Asp Lys
705                 710                 715                 720

Arg Arg Gly Arg Asp Pro Glu Met Gly Gly Lys Pro Arg Arg Lys Asn
                725                 730                 735

Pro Gln Glu Gly Leu Tyr Asn Glu Leu Gln Lys Asp Lys Met Ala Glu
            740                 745                 750

Ala Tyr Ser Glu Ile Gly Met Lys Gly Glu Arg Arg Arg Gly Lys Gly
        755                 760                 765

His Asp Gly Leu Tyr Gln Gly Leu Ser Thr Ala Thr Lys Asp Thr Tyr
770                 775                 780

Asp Ala Leu His Met Gln Ala Leu Pro Pro Arg Glu
785                 790                 795

<210> SEQ ID NO 80
<211> LENGTH: 784
<212> TYPE: PRT
<213> ORGANISM: artificial sequence
<220> FEATURE:
<223> OTHER INFORMATION: CD123-scCAR extra CID n?4

<400> SEQUENCE: 80

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
                20                  25                  30

Lys Lys Pro Gly Glu Thr Val Lys Ile Ser Cys Lys Ala Ser Gly Tyr
            35                  40                  45

Ile Phe Thr Asn Tyr Gly Met Asn Trp Val Lys Gln Ala Pro Gly Lys
        50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
130                 135                 140
```

```
Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
            165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

Ala Ser Asn Leu Glu Ser Gly Ile Pro Ala Arg Phe Ser Gly Ser Gly
    210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
            245                 250                 255

Gly Ala Gly Thr Lys Leu Glu Leu Lys Arg Ser Asp Pro Gly Ser Gly
            260                 265                 270

Gly Arg Val Ala Ile Leu Trp His Glu Met Trp His Glu Gly Leu Glu
        275                 280                 285

Glu Ala Ser Arg Leu Tyr Phe Gly Glu Arg Asn Val Lys Gly Met Phe
290                 295                 300

Glu Val Leu Glu Pro Leu His Ala Met Met Glu Arg Gly Pro Gln Thr
305                 310                 315                 320

Leu Lys Glu Thr Ser Phe Asn Gln Ala Tyr Gly Arg Asp Leu Met Glu
            325                 330                 335

Ala Gln Glu Trp Cys Arg Lys Tyr Met Lys Ser Gly Asn Val Lys Asp
            340                 345                 350

Leu Thr Gln Ala Trp Asp Leu Tyr Tyr His Val Phe Arg Arg Ile Gly
        355                 360                 365

Ser Gly Ala Pro Glu Pro Lys Ser Pro Asp Lys Thr His Thr Cys Pro
370                 375                 380

Pro Cys Pro Ala Pro Pro Val Ala Gly Pro Ser Val Phe Leu Phe Pro
385                 390                 395                 400

Pro Lys Pro Lys Asp Thr Leu Met Ile Ala Arg Thr Pro Glu Val Thr
            405                 410                 415

Cys Val Val Val Asp Val Ser His Glu Asp Pro Glu Val Lys Phe Asn
            420                 425                 430

Trp Tyr Val Asp Gly Val Glu Val His Asn Ala Lys Thr Lys Pro Arg
        435                 440                 445

Glu Glu Gln Tyr Asn Ser Thr Tyr Arg Val Val Ser Val Leu Thr Val
450                 455                 460

Leu His Gln Asp Trp Leu Asn Gly Lys Glu Tyr Lys Cys Lys Val Ser
465                 470                 475                 480

Asn Lys Ala Leu Pro Ala Pro Ile Glu Lys Thr Ile Ser Lys Ala Lys
            485                 490                 495

Gly Gln Pro Arg Glu Pro Gln Val Tyr Thr Leu Pro Pro Ser Arg Asp
            500                 505                 510

Glu Leu Thr Lys Asn Gln Val Ser Leu Thr Cys Leu Val Lys Gly Phe
        515                 520                 525

Tyr Pro Ser Asp Ile Ala Val Glu Trp Glu Ser Asn Gly Gln Pro Glu
    530                 535                 540

Asn Asn Tyr Lys Thr Thr Pro Pro Val Leu Asp Ser Asp Gly Ser Phe
545                 550                 555                 560
```

Phe Leu Tyr Ser Lys Leu Thr Val Asp Lys Ser Arg Trp Gln Gln Gly
              565                 570                 575

Asn Val Phe Ser Cys Ser Val Met His Glu Ala Leu His Asn His Tyr
          580                 585                 590

Thr Gln Lys Ser Leu Ser Leu Ser Pro Gly Lys Lys Asp Ile Tyr Ile
          595                 600                 605

Trp Ala Pro Leu Ala Gly Thr Cys Gly Val Leu Leu Leu Ser Leu Val
          610                 615                 620

Ile Thr Leu Tyr Cys Arg Arg Gly Arg Lys Lys Leu Leu Tyr Ile Phe
625                 630                 635                 640

Lys Gln Pro Phe Met Arg Pro Val Gln Thr Thr Gln Glu Glu Asp Gly
              645                 650                 655

Cys Ser Cys Arg Phe Pro Glu Glu Glu Glu Gly Gly Cys Glu Leu Arg
              660                 665                 670

Val Lys Phe Ser Arg Ser Ala Asp Ala Pro Ala Tyr Gln Gln Gly Gln
              675                 680                 685

Asn Gln Leu Tyr Asn Glu Leu Asn Leu Gly Arg Arg Glu Glu Tyr Asp
          690                 695                 700

Val Leu Asp Lys Arg Arg Gly Arg Asp Pro Glu Met Gly Gly Lys Pro
705                 710                 715                 720

Arg Arg Lys Asn Pro Gln Glu Gly Leu Tyr Asn Glu Leu Gln Lys Asp
              725                 730                 735

Lys Met Ala Glu Ala Tyr Ser Glu Ile Gly Met Lys Gly Glu Arg Arg
              740                 745                 750

Arg Gly Lys Gly His Asp Gly Leu Tyr Gln Gly Leu Ser Thr Ala Thr
              755                 760                 765

Lys Asp Thr Tyr Asp Ala Leu His Met Gln Ala Leu Pro Pro Arg Glu
          770                 775                 780

<210> SEQ ID NO 81
<211> LENGTH: 664
<212> TYPE: PRT
<213> ORGANISM: artificial sequence
<220> FEATURE:
<223> OTHER INFORMATION: CD123-scCAR extra CID n?5

<400> SEQUENCE: 81

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
              20                  25                  30

Lys Lys Pro Gly Glu Thr Val Lys Ile Ser Cys Lys Ala Ser Gly Tyr
          35                  40                  45

Ile Phe Thr Asn Tyr Gly Met Asn Trp Val Lys Gln Ala Pro Gly Lys
      50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
              85                  90                  95

Ala Ser Thr Ala Tyr Leu His Ile Asn Asp Leu Lys Asn Glu Asp Thr
          100                 105                 110

Ala Thr Tyr Phe Cys Ala Arg Ser Gly Gly Tyr Asp Pro Met Asp Tyr
          115                 120                 125

Trp Gly Gln Gly Thr Ser Val Thr Val Ser Ser Gly Gly Gly Gly Ser
      130                 135                 140

```
Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
            165                 170                 175

Cys Arg Ala Ser Glu Ser Val Asp Asn Tyr Gly Asn Thr Phe Met His
                180                 185                 190

Trp Tyr Gln Gln Lys Pro Gly Gln Pro Pro Lys Leu Leu Ile Tyr Arg
            195                 200                 205

Ala Ser Asn Leu Glu Ser Gly Ile Pro Ala Arg Phe Ser Gly Ser Gly
            210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Arg Ser Asp Pro Gly Ser Gly
                260                 265                 270

Gly Val Gln Val Glu Thr Ile Ser Pro Gly Asp Gly Arg Thr Phe Pro
            275                 280                 285

Lys Arg Gly Gln Thr Cys Val Val His Tyr Thr Gly Met Leu Glu Asp
290                 295                 300

Gly Lys Lys Phe Asp Ser Ser Arg Asp Arg Asn Lys Pro Phe Lys Phe
305                 310                 315                 320

Met Leu Gly Lys Gln Glu Val Ile Arg Gly Trp Glu Glu Gly Val Ala
                325                 330                 335

Gln Met Ser Val Gly Gln Arg Ala Lys Leu Thr Ile Ser Pro Asp Tyr
            340                 345                 350

Ala Tyr Gly Ala Thr Gly His Pro Gly Ile Ile Pro Pro His Ala Thr
            355                 360                 365

Leu Val Phe Asp Val Glu Leu Leu Lys Leu Glu Gly Ser Gly Ala Pro
            370                 375                 380

Ala Pro Val Gly Leu Val Ala Arg Leu Ala Asp Glu Ser Gly His Val
385                 390                 395                 400

Val Leu Arg Trp Leu Pro Pro Pro Glu Thr Pro Met Thr Ser His Ile
                405                 410                 415

Arg Tyr Glu Val Asp Val Ser Ala Gly Asn Gly Ala Gly Ser Val Gln
            420                 425                 430

Arg Val Glu Ile Leu Glu Gly Arg Thr Glu Cys Val Leu Ser Asn Leu
            435                 440                 445

Arg Gly Arg Thr Arg Tyr Thr Phe Ala Val Arg Ala Arg Met Ala Glu
            450                 455                 460

Pro Ser Phe Gly Gly Phe Trp Ser Ala Trp Ser Glu Pro Val Ser Leu
465                 470                 475                 480

Leu Thr Pro Ser Asp Ile Tyr Ile Trp Ala Pro Leu Ala Gly Thr Cys
            485                 490                 495

Gly Val Leu Leu Leu Ser Leu Val Ile Thr Leu Tyr Cys Arg Arg Gly
            500                 505                 510

Arg Lys Lys Leu Leu Tyr Ile Phe Lys Gln Pro Phe Met Arg Pro Val
            515                 520                 525

Gln Thr Thr Gln Glu Glu Asp Gly Cys Ser Cys Arg Phe Pro Glu Glu
            530                 535                 540

Glu Glu Gly Gly Cys Glu Leu Arg Val Lys Phe Ser Arg Ser Ala Asp
545                 550                 555                 560

Ala Pro Ala Tyr Gln Gln Gly Gln Asn Gln Leu Tyr Asn Glu Leu Asn
```

```
                     565                 570                 575
Leu Gly Arg Arg Glu Glu Tyr Asp Val Leu Asp Lys Arg Arg Gly Arg
            580                 585                 590

Asp Pro Glu Met Gly Gly Lys Pro Arg Arg Lys Asn Pro Gln Glu Gly
        595                 600                 605

Leu Tyr Asn Glu Leu Gln Lys Asp Lys Met Ala Glu Ala Tyr Ser Glu
    610                 615                 620

Ile Gly Met Lys Gly Glu Arg Arg Arg Gly Lys Gly His Asp Gly Leu
625                 630                 635                 640

Tyr Gln Gly Leu Ser Thr Ala Thr Lys Asp Thr Tyr Asp Ala Leu His
                645                 650                 655

Met Gln Ala Leu Pro Pro Arg Glu
            660

<210> SEQ ID NO 82
<211> LENGTH: 652
<212> TYPE: PRT
<213> ORGANISM: artificial sequence
<220> FEATURE:
<223> OTHER INFORMATION: CD123-scCAR extra CID n?6

<400> SEQUENCE: 82

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Leu
            20                  25                  30

Lys Lys Pro Gly Glu Thr Val Lys Ile Ser Cys Lys Ala Ser Gly Tyr
        35                  40                  45

Ile Phe Thr Asn Tyr Gly Met Asn Trp Val Lys Gln Ala Pro Gly Lys
    50                  55                  60

Ser Phe Lys Trp Met Gly Trp Ile Asn Thr Tyr Thr Gly Glu Ser Thr
65                  70                  75                  80

Tyr Ser Ala Asp Phe Lys Gly Arg Phe Ala Phe Ser Leu Glu Thr Ser
                85                  90                  95

Ala Ser Thr Ala Tyr Leu His Ile Asn Asp Leu Lys Asn Glu Asp Thr
            100                 105                 110

Ala Thr Tyr Phe Cys Ala Arg Ser Gly Gly Tyr Asp Pro Met Asp Tyr
        115                 120                 125

Trp Gly Gln Gly Thr Ser Val Thr Val Ser Ser Gly Gly Gly Gly Ser
    130                 135                 140

Gly Gly Gly Gly Ser Gly Gly Gly Ser Asp Ile Val Leu Thr Gln
145                 150                 155                 160

Ser Pro Ala Ser Leu Ala Val Ser Leu Gly Gln Arg Ala Thr Ile Ser
                165                 170                 175

Cys Arg Ala Ser Glu Ser Val Asp Asn Tyr Gly Asn Thr Phe Met His
            180                 185                 190

Trp Tyr Gln Gln Lys Pro Gly Gln Pro Pro Lys Leu Leu Ile Tyr Arg
        195                 200                 205

Ala Ser Asn Leu Glu Ser Gly Ile Pro Ala Arg Phe Ser Gly Ser Gly
    210                 215                 220

Ser Arg Thr Asp Phe Thr Leu Thr Ile Asn Pro Val Glu Ala Asp Asp
225                 230                 235                 240

Val Ala Thr Tyr Tyr Cys Gln Gln Ser Asn Glu Asp Pro Pro Thr Phe
                245                 250                 255

Gly Ala Gly Thr Lys Leu Glu Leu Lys Arg Ser Asp Pro Gly Ser Gly
```

```
                260                 265                 270
Gly Arg Val Ala Ile Leu Trp His Glu Met Trp His Glu Gly Leu Glu
            275                 280                 285

Glu Ala Ser Arg Leu Tyr Phe Gly Glu Arg Asn Val Lys Gly Met Phe
        290                 295                 300

Glu Val Leu Glu Pro Leu His Ala Met Met Glu Arg Gly Pro Gln Thr
305                 310                 315                 320

Leu Lys Glu Thr Ser Phe Asn Gln Ala Tyr Gly Arg Asp Leu Met Glu
                325                 330                 335

Ala Gln Glu Trp Cys Arg Lys Tyr Met Lys Ser Gly Asn Val Lys Asp
            340                 345                 350

Leu Thr Gln Ala Trp Asp Leu Tyr Tyr His Val Phe Arg Arg Ile Gly
        355                 360                 365

Ser Gly Ala Pro Ala Pro Val Gly Leu Val Ala Arg Leu Ala Asp Glu
    370                 375                 380

Ser Gly His Val Val Leu Arg Trp Leu Pro Pro Glu Thr Pro Met
385                 390                 395                 400

Thr Ser His Ile Arg Tyr Glu Val Asp Val Ser Ala Gly Asn Gly Ala
                405                 410                 415

Gly Ser Val Gln Arg Val Glu Ile Leu Glu Gly Arg Thr Glu Cys Val
            420                 425                 430

Leu Ser Asn Leu Arg Gly Arg Thr Arg Tyr Thr Phe Ala Val Arg Ala
        435                 440                 445

Arg Met Ala Glu Pro Ser Phe Gly Gly Phe Trp Ser Ala Trp Ser Glu
    450                 455                 460

Pro Val Ser Leu Leu Thr Pro Ser Asp Ile Tyr Ile Trp Ala Pro Leu
465                 470                 475                 480

Ala Gly Thr Cys Gly Val Leu Leu Leu Ser Leu Val Ile Thr Leu Tyr
                485                 490                 495

Cys Arg Arg Gly Arg Lys Lys Leu Leu Tyr Ile Phe Lys Gln Pro Phe
            500                 505                 510

Met Arg Pro Val Gln Thr Thr Gln Glu Glu Asp Gly Cys Ser Cys Arg
        515                 520                 525

Phe Pro Glu Glu Glu Glu Gly Gly Cys Glu Leu Arg Val Lys Phe Ser
    530                 535                 540

Arg Ser Ala Asp Ala Pro Ala Tyr Gln Gln Gly Gln Asn Gln Leu Tyr
545                 550                 555                 560

Asn Glu Leu Asn Leu Gly Arg Arg Glu Glu Tyr Asp Val Leu Asp Lys
                565                 570                 575

Arg Arg Gly Arg Asp Pro Glu Met Gly Gly Lys Pro Arg Arg Lys Asn
            580                 585                 590

Pro Gln Glu Gly Leu Tyr Asn Glu Leu Gln Lys Asp Lys Met Ala Glu
        595                 600                 605

Ala Tyr Ser Glu Ile Gly Met Lys Gly Glu Arg Arg Arg Gly Lys Gly
    610                 615                 620

His Asp Gly Leu Tyr Gln Gly Leu Ser Thr Ala Thr Lys Asp Thr Tyr
625                 630                 635                 640

Asp Ala Leu His Met Gln Ala Leu Pro Pro Arg Glu
                645                 650

<210> SEQ ID NO 83
<211> LENGTH: 260
<212> TYPE: PRT
<213> ORGANISM: artificial sequence
```

<220> FEATURE:
<223> OTHER INFORMATION: IMP-intCID-n?1

<400> SEQUENCE: 83

Met Ala Leu Pro Val Thr Ala Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
        35                  40                  45

Arg Ser Gly Gly Val Gln Val Glu Thr Ile Ser Pro Gly Asp Gly Arg
    50                  55                  60

Thr Phe Pro Lys Arg Gly Gln Thr Cys Val Val His Tyr Thr Gly Met
65              70                  75                  80

Leu Glu Asp Gly Lys Lys Phe Asp Ser Ser Arg Asp Arg Asn Lys Pro
                85                  90                  95

Phe Lys Phe Met Leu Gly Lys Gln Glu Val Ile Arg Gly Trp Glu Glu
            100                 105                 110

Gly Val Ala Gln Met Ser Val Gly Gln Arg Ala Lys Leu Thr Ile Ser
        115                 120                 125

Pro Asp Tyr Ala Tyr Gly Ala Thr Gly His Pro Gly Ile Ile Pro Pro
    130                 135                 140

His Ala Thr Leu Val Phe Asp Val Glu Leu Leu Lys Leu Glu Gly Ser
145             150                 155                 160

Gly Ser Ser Ser Arg Ala Ala Arg Gly Thr Ile Gly Ala Arg Arg Thr
                165                 170                 175

Gly Gln Pro Leu Lys Glu Asp Pro Ser Ala Val Pro Val Phe Ser Val
            180                 185                 190

Asp Tyr Gly Glu Leu Asp Phe Gln Trp Arg Glu Lys Thr Pro Glu Pro
        195                 200                 205

Pro Val Pro Cys Val Pro Glu Gln Thr Glu Tyr Ala Thr Ile Val Phe
    210                 215                 220

Pro Ser Gly Met Gly Thr Ser Ser Pro Ala Arg Arg Gly Ser Ala Asp
225             230                 235                 240

Gly Pro Arg Ser Ala Gln Pro Leu Arg Pro Glu Asp Gly His Cys Ser
                245                 250                 255

Trp Pro Leu Glu
            260

<210> SEQ ID NO 84
<211> LENGTH: 248
<212> TYPE: PRT
<213> ORGANISM: artificial sequence
<220> FEATURE:
<223> OTHER INFORMATION: IMP-intCID-n?2

<400> SEQUENCE: 84

Met Ala Leu Pro Val Thr Ala Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
        35                  40                  45

Arg Ser Gly Gly Arg Val Ala Ile Leu Trp His Glu Met Trp His Glu
    50                  55                  60

Gly Leu Glu Glu Ala Ser Arg Leu Tyr Phe Gly Glu Arg Asn Val Lys

```
                 65                  70                  75                  80
Gly Met Phe Glu Val Leu Glu Pro Leu His Ala Met Met Glu Arg Gly
                 85                  90                  95

Pro Gln Thr Leu Lys Glu Thr Ser Phe Asn Gln Ala Tyr Gly Arg Asp
                100                 105                 110

Leu Met Glu Ala Gln Glu Trp Cys Arg Lys Tyr Met Lys Ser Gly Asn
                115                 120                 125

Val Lys Asp Leu Thr Gln Ala Trp Asp Leu Tyr Tyr His Val Phe Arg
130                 135                 140

Arg Ile Gly Ser Gly Ser Ser Arg Ala Ala Arg Gly Thr Ile Gly
145                 150                 155                 160

Ala Arg Arg Thr Gly Gln Pro Leu Lys Glu Asp Pro Ser Ala Val Pro
                165                 170                 175

Val Phe Ser Val Asp Tyr Gly Glu Leu Asp Phe Gln Trp Arg Glu Lys
                180                 185                 190

Thr Pro Glu Pro Pro Val Pro Cys Val Pro Glu Gln Thr Glu Tyr Ala
                195                 200                 205

Thr Ile Val Phe Pro Ser Gly Met Gly Thr Ser Ser Pro Ala Arg Arg
210                 215                 220

Gly Ser Ala Asp Gly Pro Arg Ser Ala Gln Pro Leu Arg Pro Glu Asp
225                 230                 235                 240

Gly His Cys Ser Trp Pro Leu Glu
                245
```

<210> SEQ ID NO 85
<211> LENGTH: 310
<212> TYPE: PRT
<213> ORGANISM: artificial sequence
<220> FEATURE:
<223> OTHER INFORMATION: IMP-intCID-n?3

<400> SEQUENCE: 85

```
Met Ala Leu Pro Val Thr Ala Leu Leu Leu Pro Leu Ala Leu Leu Leu
1               5                  10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Ala Leu Tyr Leu Leu Arg Arg Asp Gln Arg Leu Pro Pro Asp Ala
        50                  55                  60

His Lys Pro Pro Gly Gly Gly Ser Phe Arg Thr Pro Ile Gln Glu Glu
65                  70                  75                  80

Gln Ala Asp Ala His Ser Thr Leu Ala Lys Ile Gly Ser Gly Ser Gly
                85                  90                  95

Ser Gly Ser Ser Gly Gly Val Gln Val Glu Thr Ile Ser Pro Gly Asp
                100                 105                 110

Gly Arg Thr Phe Pro Lys Arg Gly Gln Thr Cys Val Val His Tyr Thr
                115                 120                 125

Gly Met Leu Glu Asp Gly Lys Lys Phe Asp Ser Ser Arg Asp Arg Asn
130                 135                 140

Lys Pro Phe Lys Phe Met Leu Gly Lys Gln Glu Val Ile Arg Gly Trp
145                 150                 155                 160

Glu Glu Gly Val Ala Gln Met Ser Val Gly Gln Arg Ala Lys Leu Thr
                165                 170                 175

Ile Ser Pro Asp Tyr Ala Tyr Gly Ala Thr Gly His Pro Gly Ile Ile
```

```
                    180                 185                 190
Pro Pro His Ala Thr Leu Val Phe Asp Val Glu Leu Leu Lys Leu Glu
            195                 200                 205

Gly Ser Gly Ser Gly Ser Arg Ala Ala Arg Gly Thr Ile Gly Ala Arg
        210                 215                 220

Arg Thr Gly Gln Pro Leu Lys Glu Asp Pro Ser Ala Val Pro Val Phe
225                 230                 235                 240

Ser Val Asp Tyr Gly Glu Leu Asp Phe Gln Trp Arg Glu Lys Thr Pro
                245                 250                 255

Glu Pro Pro Val Pro Cys Val Pro Glu Gln Thr Glu Tyr Ala Thr Ile
            260                 265                 270

Val Phe Pro Ser Gly Met Gly Thr Ser Ser Pro Ala Arg Arg Gly Ser
            275                 280                 285

Ala Asp Gly Pro Arg Ser Ala Gln Pro Leu Arg Pro Glu Asp Gly His
        290                 295                 300

Cys Ser Trp Pro Leu Glu
305                 310
```

<210> SEQ ID NO 86
<211> LENGTH: 288
<212> TYPE: PRT
<213> ORGANISM: artificial sequence
<220> FEATURE:
<223> OTHER INFORMATION: IMP-intCID-n?4

<400> SEQUENCE: 86

```
Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Pro Arg Arg Ser Pro Ala Gln Glu Asp Gly Lys Val Tyr Ile Asn
        50                  55                  60

Met Pro Gly Arg Gly Gly Ser Gly Ser Gly Ser Ser Gly Gly
65                  70                  75                  80

Val Gln Val Glu Thr Ile Ser Pro Gly Asp Gly Arg Thr Phe Pro Lys
                85                  90                  95

Arg Gly Gln Thr Cys Val Val His Tyr Thr Gly Met Leu Glu Asp Gly
            100                 105                 110

Lys Lys Phe Asp Ser Ser Arg Asp Arg Asn Lys Pro Phe Lys Phe Met
        115                 120                 125

Leu Gly Lys Gln Glu Val Ile Arg Gly Trp Glu Glu Gly Val Ala Gln
    130                 135                 140

Met Ser Val Gly Gln Arg Ala Lys Leu Thr Ile Ser Pro Asp Tyr Ala
145                 150                 155                 160

Tyr Gly Ala Thr Gly His Pro Gly Ile Ile Pro Pro His Ala Thr Leu
                165                 170                 175

Val Phe Asp Val Glu Leu Leu Lys Leu Glu Gly Ser Gly Ser Gly Ser
            180                 185                 190

Arg Ala Ala Arg Gly Thr Ile Gly Ala Arg Arg Thr Gly Gln Pro Leu
        195                 200                 205

Lys Glu Asp Pro Ser Ala Val Pro Val Phe Ser Val Asp Tyr Gly Glu
    210                 215                 220

Leu Asp Phe Gln Trp Arg Glu Lys Thr Pro Glu Pro Pro Val Pro Cys
```

```
                225                 230                 235                 240

Val Pro Glu Gln Thr Glu Tyr Ala Thr Ile Val Phe Pro Ser Gly Met
                245                 250                 255

Gly Thr Ser Ser Pro Ala Arg Arg Gly Ser Ala Asp Gly Pro Arg Ser
            260                 265                 270

Ala Gln Pro Leu Arg Pro Glu Asp Gly His Cys Ser Trp Pro Leu Glu
        275                 280                 285

<210> SEQ ID NO 87
<211> LENGTH: 328
<212> TYPE: PRT
<213> ORGANISM: artificial sequence
<220> FEATURE:
<223> OTHER INFORMATION: IMP-intCID-n?5

<400> SEQUENCE: 87

Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
        35                  40                  45

Arg Cys Val Lys Arg Arg Lys Pro Arg Gly Asp Val Val Lys Val Ile
    50                  55                  60

Val Ser Val Gln Arg Lys Arg Gln Glu Ala Glu Gly Glu Ala Thr Val
65                  70                  75                  80

Ile Glu Ala Leu Gln Ala Pro Pro Asp Val Thr Thr Val Ala Val Glu
                85                  90                  95

Glu Thr Ile Pro Ser Phe Thr Gly Arg Ser Pro Asn His Gly Ser Gly
            100                 105                 110

Ser Gly Ser Gly Ser Ser Gly Gly Val Gln Val Glu Thr Ile Ser Pro
        115                 120                 125

Gly Asp Gly Arg Thr Phe Pro Lys Arg Gly Gln Thr Cys Val Val His
    130                 135                 140

Tyr Thr Gly Met Leu Glu Asp Gly Lys Lys Phe Asp Ser Ser Arg Asp
145                 150                 155                 160

Arg Asn Lys Pro Phe Lys Phe Met Leu Gly Lys Gln Glu Val Ile Arg
                165                 170                 175

Gly Trp Glu Glu Gly Val Ala Gln Met Ser Val Gly Gln Arg Ala Lys
            180                 185                 190

Leu Thr Ile Ser Pro Asp Tyr Ala Tyr Gly Ala Thr Gly His Pro Gly
        195                 200                 205

Ile Ile Pro Pro His Ala Thr Leu Val Phe Asp Val Glu Leu Leu Lys
    210                 215                 220

Leu Glu Gly Ser Gly Ser Gly Ser Arg Ala Ala Arg Gly Thr Ile Gly
225                 230                 235                 240

Ala Arg Arg Thr Gly Gln Pro Leu Lys Glu Asp Pro Ser Ala Val Pro
                245                 250                 255

Val Phe Ser Val Asp Tyr Gly Glu Leu Asp Phe Gln Trp Arg Glu Lys
            260                 265                 270

Thr Pro Glu Pro Pro Val Pro Cys Val Pro Glu Gln Thr Glu Tyr Ala
        275                 280                 285

Thr Ile Val Phe Pro Ser Gly Met Gly Thr Ser Ser Pro Ala Arg Arg
    290                 295                 300

Gly Ser Ala Asp Gly Pro Arg Ser Ala Gln Pro Leu Arg Pro Glu Asp
```

Gly His Cys Ser Trp Pro Leu Glu
                325

<210> SEQ ID NO 88
<211> LENGTH: 298
<212> TYPE: PRT
<213> ORGANISM: artificial sequence
<220> FEATURE:
<223> OTHER INFORMATION: IMP-intCID-n?6

<400> SEQUENCE: 88

Met Ala Leu Pro Val Thr Ala Leu Leu Pro Leu Ala Leu Leu Leu
1               5                   10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Ala Leu Tyr Leu Leu Arg Arg Asp Gln Arg Leu Pro Pro Asp Ala
    50                  55                  60

His Lys Pro Pro Gly Gly Gly Ser Phe Arg Thr Pro Ile Gln Glu Glu
65                  70                  75                  80

Gln Ala Asp Ala His Ser Thr Leu Ala Lys Ile Gly Ser Gly Ser Gly
                85                  90                  95

Ser Gly Ser Ser Gly Gly Arg Val Ala Ile Leu Trp His Glu Met Trp
            100                 105                 110

His Glu Gly Leu Glu Glu Ala Ser Arg Leu Tyr Phe Gly Glu Arg Asn
        115                 120                 125

Val Lys Gly Met Phe Glu Val Leu Glu Pro Leu His Ala Met Met Glu
130                 135                 140

Arg Gly Pro Gln Thr Leu Lys Glu Thr Ser Phe Asn Gln Ala Tyr Gly
145                 150                 155                 160

Arg Asp Leu Met Glu Ala Gln Glu Trp Cys Arg Lys Tyr Met Lys Ser
                165                 170                 175

Gly Asn Val Lys Asp Leu Thr Gln Ala Trp Asp Leu Tyr Tyr His Val
            180                 185                 190

Phe Arg Arg Ile Gly Ser Gly Ser Gly Ser Arg Ala Ala Arg Gly Thr
        195                 200                 205

Ile Gly Ala Arg Arg Thr Gly Gln Pro Leu Lys Glu Asp Pro Ser Ala
    210                 215                 220

Val Pro Val Phe Ser Val Asp Tyr Gly Glu Leu Asp Phe Gln Trp Arg
225                 230                 235                 240

Glu Lys Thr Pro Glu Pro Pro Val Pro Cys Val Pro Glu Gln Thr Glu
                245                 250                 255

Tyr Ala Thr Ile Val Phe Pro Ser Gly Met Gly Thr Ser Ser Pro Ala
            260                 265                 270

Arg Arg Gly Ser Ala Asp Gly Pro Arg Ser Ala Gln Pro Leu Arg Pro
        275                 280                 285

Glu Asp Gly His Cys Ser Trp Pro Leu Glu
    290                 295

<210> SEQ ID NO 89
<211> LENGTH: 276
<212> TYPE: PRT
<213> ORGANISM: artificial sequence
<220> FEATURE:
<223> OTHER INFORMATION: IMP-intCID-n?7

<400> SEQUENCE: 89

```
Met Ala Leu Pro Val Thr Ala Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
            35                  40                  45

Arg Pro Arg Arg Ser Pro Ala Gln Glu Asp Gly Lys Val Tyr Ile Asn
        50                  55                  60

Met Pro Gly Arg Gly Ser Gly Ser Gly Ser Ser Gly Gly
65                  70                  75                  80

Arg Val Ala Ile Leu Trp His Glu Met Trp His Glu Gly Leu Glu Glu
                85                  90                  95

Ala Ser Arg Leu Tyr Phe Gly Glu Arg Asn Val Lys Gly Met Phe Glu
                100                 105                 110

Val Leu Glu Pro Leu His Ala Met Met Glu Arg Gly Pro Gln Thr Leu
            115                 120                 125

Lys Glu Thr Ser Phe Asn Gln Ala Tyr Gly Arg Asp Leu Met Glu Ala
        130                 135                 140

Gln Glu Trp Cys Arg Lys Tyr Met Lys Ser Gly Asn Val Lys Asp Leu
145                 150                 155                 160

Thr Gln Ala Trp Asp Leu Tyr Tyr His Val Phe Arg Arg Ile Gly Ser
                165                 170                 175

Gly Ser Gly Ser Arg Ala Ala Arg Gly Thr Ile Gly Ala Arg Arg Thr
            180                 185                 190

Gly Gln Pro Leu Lys Glu Asp Pro Ser Ala Val Pro Val Phe Ser Val
            195                 200                 205

Asp Tyr Gly Glu Leu Asp Phe Gln Trp Arg Glu Lys Thr Pro Glu Pro
        210                 215                 220

Pro Val Pro Cys Val Pro Glu Gln Thr Glu Tyr Ala Thr Ile Val Phe
225                 230                 235                 240

Pro Ser Gly Met Gly Thr Ser Ser Pro Ala Arg Arg Gly Ser Ala Asp
                245                 250                 255

Gly Pro Arg Ser Ala Gln Pro Leu Arg Pro Glu Asp Gly His Cys Ser
            260                 265                 270

Trp Pro Leu Glu
        275
```

<210> SEQ ID NO 90
<211> LENGTH: 316
<212> TYPE: PRT
<213> ORGANISM: artificial sequence
<220> FEATURE:
<223> OTHER INFORMATION: IMP-intCID-n?8

<400> SEQUENCE: 90

```
Met Ala Leu Pro Val Thr Ala Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
            35                  40                  45

Arg Cys Val Lys Arg Arg Lys Pro Arg Gly Asp Val Val Lys Val Ile
        50                  55                  60
```

Val Ser Val Gln Arg Lys Arg Gln Glu Ala Glu Gly Glu Ala Thr Val
65                  70                  75                  80

Ile Glu Ala Leu Gln Ala Pro Pro Asp Val Thr Thr Val Ala Val Glu
                85                  90                  95

Glu Thr Ile Pro Ser Phe Thr Gly Arg Ser Pro Asn His Gly Ser Gly
            100                 105                 110

Ser Gly Ser Gly Ser Ser Gly Gly Arg Val Ala Ile Leu Trp His Glu
            115                 120                 125

Met Trp His Glu Gly Leu Glu Glu Ala Ser Arg Leu Tyr Phe Gly Glu
            130                 135                 140

Arg Asn Val Lys Gly Met Phe Glu Val Leu Glu Pro Leu His Ala Met
145                 150                 155                 160

Met Glu Arg Gly Pro Gln Thr Leu Lys Glu Thr Ser Phe Asn Gln Ala
                165                 170                 175

Tyr Gly Arg Asp Leu Met Glu Ala Gln Glu Trp Cys Arg Lys Tyr Met
                180                 185                 190

Lys Ser Gly Asn Val Lys Asp Leu Thr Gln Ala Trp Asp Leu Tyr Tyr
            195                 200                 205

His Val Phe Arg Arg Ile Gly Ser Gly Ser Arg Ala Ala Arg
            210                 215                 220

Gly Thr Ile Gly Ala Arg Arg Thr Gly Gln Pro Leu Lys Glu Asp Pro
225                 230                 235                 240

Ser Ala Val Pro Val Phe Ser Val Asp Tyr Gly Glu Leu Asp Phe Gln
                245                 250                 255

Trp Arg Glu Lys Thr Pro Glu Pro Pro Val Pro Cys Val Pro Glu Gln
                260                 265                 270

Thr Glu Tyr Ala Thr Ile Val Phe Pro Ser Gly Met Gly Thr Ser Ser
                275                 280                 285

Pro Ala Arg Arg Gly Ser Ala Asp Gly Pro Arg Ser Ala Gln Pro Leu
            290                 295                 300

Arg Pro Glu Asp Gly His Cys Ser Trp Pro Leu Glu
305                 310                 315

<210> SEQ ID NO 91
<211> LENGTH: 260
<212> TYPE: PRT
<213> ORGANISM: artificial sequence
<220> FEATURE:
<223> OTHER INFORMATION: IMP-intCID-n?9

<400> SEQUENCE: 91

Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Ser Arg Ala Ala Arg Gly Thr Ile Gly Ala Arg Arg Thr Gly Gln
        50                  55                  60

Pro Leu Lys Glu Asp Pro Ser Ala Val Pro Val Phe Ser Val Asp Tyr
65                  70                  75                  80

Gly Glu Leu Asp Phe Gln Trp Arg Glu Lys Thr Pro Glu Pro Pro Val
                85                  90                  95

Pro Cys Val Pro Glu Gln Thr Glu Tyr Ala Thr Ile Val Phe Pro Ser
            100                 105                 110

```
Gly Met Gly Thr Ser Ser Pro Ala Arg Arg Gly Ser Ala Asp Gly Pro
            115                 120                 125

Arg Ser Ala Gln Pro Leu Arg Pro Glu Asp Gly His Cys Ser Trp Pro
    130                 135                 140

Leu Gly Ser Gly Ser Ser Ser Gly Gly Val Gln Val Glu Thr Ile Ser
145                 150                 155                 160

Pro Gly Asp Gly Arg Thr Phe Pro Lys Arg Gly Gln Thr Cys Val Val
                165                 170                 175

His Tyr Thr Gly Met Leu Glu Asp Gly Lys Lys Phe Asp Ser Ser Arg
            180                 185                 190

Asp Arg Asn Lys Pro Phe Lys Phe Met Leu Gly Lys Gln Glu Val Ile
        195                 200                 205

Arg Gly Trp Glu Glu Gly Val Ala Gln Met Ser Val Gly Gln Arg Ala
    210                 215                 220

Lys Leu Thr Ile Ser Pro Asp Tyr Ala Tyr Gly Ala Thr Gly His Pro
225                 230                 235                 240

Gly Ile Ile Pro Pro His Ala Thr Leu Val Phe Asp Val Glu Leu Leu
                245                 250                 255

Lys Leu Glu Glu
            260

<210> SEQ ID NO 92
<211> LENGTH: 248
<212> TYPE: PRT
<213> ORGANISM: artificial sequence
<220> FEATURE:
<223> OTHER INFORMATION: IMP-intCID-n?10

<400> SEQUENCE: 92

Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
        35                  40                  45

Arg Ser Arg Ala Ala Arg Gly Thr Ile Gly Ala Arg Arg Thr Gly Gln
    50                  55                  60

Pro Leu Lys Glu Asp Pro Ser Ala Val Pro Val Phe Ser Val Asp Tyr
65                  70                  75                  80

Gly Glu Leu Asp Phe Gln Trp Arg Glu Lys Thr Pro Glu Pro Pro Val
                85                  90                  95

Pro Cys Val Pro Glu Gln Thr Glu Tyr Ala Thr Ile Val Phe Pro Ser
            100                 105                 110

Gly Met Gly Thr Ser Ser Pro Ala Arg Arg Gly Ser Ala Asp Gly Pro
            115                 120                 125

Arg Ser Ala Gln Pro Leu Arg Pro Glu Asp Gly His Cys Ser Trp Pro
    130                 135                 140

Leu Gly Ser Gly Ser Ser Ser Gly Gly Arg Val Ala Ile Leu Trp His
145                 150                 155                 160

Glu Met Trp His Glu Gly Leu Glu Glu Ala Ser Arg Leu Tyr Phe Gly
                165                 170                 175

Glu Arg Asn Val Lys Gly Met Phe Glu Val Leu Glu Pro Leu His Ala
            180                 185                 190

Met Met Glu Arg Gly Pro Gln Thr Leu Lys Glu Thr Ser Phe Asn Gln
        195                 200                 205
```

```
Ala Tyr Gly Arg Asp Leu Met Glu Ala Gln Glu Trp Cys Arg Lys Tyr
            210                 215                 220

Met Lys Ser Gly Asn Val Lys Asp Leu Thr Gln Ala Trp Asp Leu Tyr
225                 230                 235                 240

Tyr His Val Phe Arg Arg Ile Glu
                245
```

<210> SEQ ID NO 93
<211> LENGTH: 308
<212> TYPE: PRT
<213> ORGANISM: artificial sequence
<220> FEATURE:
<223> OTHER INFORMATION: IMP-intCID-n?11

<400> SEQUENCE: 93

```
Met Ala Leu Pro Val Thr Ala Leu Leu Pro Leu Ala Leu Leu Leu
1               5                   10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Ala Leu Tyr Leu Leu Arg Arg Asp Gln Arg Leu Pro Pro Asp Ala
50                  55                  60

His Lys Pro Pro Gly Gly Gly Ser Phe Arg Thr Pro Ile Gln Glu Glu
65                  70                  75                  80

Gln Ala Asp Ala His Ser Thr Leu Ala Lys Ile Gly Ser Gly Ser Gly
                85                  90                  95

Ser Gly Ser Ser Arg Ala Ala Arg Gly Thr Ile Gly Ala Arg Arg Thr
            100                 105                 110

Gly Gln Pro Leu Lys Glu Asp Pro Ser Ala Val Pro Val Phe Ser Val
            115                 120                 125

Asp Tyr Gly Glu Leu Asp Phe Gln Trp Arg Glu Lys Thr Pro Glu Pro
130                 135                 140

Pro Val Pro Cys Val Pro Glu Gln Thr Glu Tyr Ala Thr Ile Val Phe
145                 150                 155                 160

Pro Ser Gly Met Gly Thr Ser Ser Pro Ala Arg Arg Gly Ser Ala Asp
                165                 170                 175

Gly Pro Arg Ser Ala Gln Pro Leu Arg Pro Glu Asp Gly His Cys Ser
            180                 185                 190

Trp Pro Leu Gly Ser Gly Ser Gly Val Gln Val Glu Thr Ile Ser
            195                 200                 205

Pro Gly Asp Gly Arg Thr Phe Pro Lys Arg Gly Gln Thr Cys Val Val
210                 215                 220

His Tyr Thr Gly Met Leu Glu Asp Gly Lys Lys Phe Asp Ser Ser Arg
225                 230                 235                 240

Asp Arg Asn Lys Pro Phe Lys Phe Met Leu Gly Lys Gln Glu Val Ile
                245                 250                 255

Arg Gly Trp Glu Glu Gly Val Ala Gln Met Ser Val Gly Gln Arg Ala
            260                 265                 270

Lys Leu Thr Ile Ser Pro Asp Tyr Ala Tyr Gly Ala Thr Gly His Pro
            275                 280                 285

Gly Ile Ile Pro Pro His Ala Thr Leu Val Phe Asp Val Glu Leu Leu
            290                 295                 300

Lys Leu Glu Glu
305
```

<210> SEQ ID NO 94
<211> LENGTH: 286
<212> TYPE: PRT
<213> ORGANISM: artificial sequence
<220> FEATURE:
<223> OTHER INFORMATION: IMP-intCID-n?12

<400> SEQUENCE: 94

```
Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
        35                  40                  45

Arg Pro Arg Arg Ser Pro Ala Gln Glu Asp Gly Lys Val Tyr Ile Asn
    50                  55                  60

Met Pro Gly Arg Gly Gly Ser Gly Ser Gly Ser Ser Arg Ala
65                  70                  75                  80

Ala Arg Gly Thr Ile Gly Ala Arg Arg Thr Gly Gln Pro Leu Lys Glu
                85                  90                  95

Asp Pro Ser Ala Val Pro Val Phe Ser Val Asp Tyr Gly Glu Leu Asp
            100                 105                 110

Phe Gln Trp Arg Glu Lys Thr Pro Glu Pro Pro Val Pro Cys Val Pro
        115                 120                 125

Glu Gln Thr Glu Tyr Ala Thr Ile Val Phe Pro Ser Gly Met Gly Thr
    130                 135                 140

Ser Ser Pro Ala Arg Arg Gly Ser Ala Asp Gly Pro Arg Ser Ala Gln
145                 150                 155                 160

Pro Leu Arg Pro Glu Asp Gly His Cys Ser Trp Pro Leu Gly Ser Gly
                165                 170                 175

Ser Gly Gly Val Gln Val Glu Thr Ile Ser Pro Gly Asp Gly Arg Thr
            180                 185                 190

Phe Pro Lys Arg Gly Gln Thr Cys Val Val His Tyr Thr Gly Met Leu
        195                 200                 205

Glu Asp Gly Lys Lys Phe Asp Ser Ser Arg Asp Arg Asn Lys Pro Phe
    210                 215                 220

Lys Phe Met Leu Gly Lys Gln Glu Val Ile Arg Gly Trp Glu Glu Gly
225                 230                 235                 240

Val Ala Gln Met Ser Val Gly Gln Arg Ala Lys Leu Thr Ile Ser Pro
                245                 250                 255

Asp Tyr Ala Tyr Gly Ala Thr Gly His Pro Gly Ile Ile Pro Pro His
            260                 265                 270

Ala Thr Leu Val Phe Asp Val Glu Leu Leu Lys Leu Glu Glu
        275                 280                 285
```

<210> SEQ ID NO 95
<211> LENGTH: 326
<212> TYPE: PRT
<213> ORGANISM: artificial sequence
<220> FEATURE:
<223> OTHER INFORMATION: IMP-intCID-n?13

<400> SEQUENCE: 95

```
Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30
```

Gly Thr Cys Gly Val Leu Leu Leu Ser Leu Val Ile Thr Leu Tyr Cys
            35                  40                  45

Arg Cys Val Lys Arg Lys Pro Arg Gly Asp Val Val Lys Val Ile
    50                  55                  60

Val Ser Val Gln Arg Lys Arg Gln Glu Ala Glu Gly Glu Ala Thr Val
65                  70                  75                  80

Ile Glu Ala Leu Gln Ala Pro Pro Asp Val Thr Thr Val Ala Val Glu
                85                  90                  95

Glu Thr Ile Pro Ser Phe Thr Gly Arg Ser Pro Asn His Gly Ser Gly
            100                 105                 110

Ser Gly Ser Gly Ser Ser Arg Ala Ala Arg Gly Thr Ile Gly Ala Arg
        115                 120                 125

Arg Thr Gly Gln Pro Leu Lys Glu Asp Pro Ser Ala Val Pro Val Phe
    130                 135                 140

Ser Val Asp Tyr Gly Glu Leu Asp Phe Gln Trp Arg Glu Lys Thr Pro
145                 150                 155                 160

Glu Pro Pro Val Pro Cys Val Pro Glu Gln Thr Glu Tyr Ala Thr Ile
                165                 170                 175

Val Phe Pro Ser Gly Met Gly Thr Ser Ser Pro Ala Arg Arg Gly Ser
            180                 185                 190

Ala Asp Gly Pro Arg Ser Ala Gln Pro Leu Arg Pro Glu Asp Gly His
        195                 200                 205

Cys Ser Trp Pro Leu Gly Ser Gly Ser Gly Gly Val Gln Val Glu Thr
    210                 215                 220

Ile Ser Pro Gly Asp Gly Arg Thr Phe Pro Lys Arg Gly Gln Thr Cys
225                 230                 235                 240

Val Val His Tyr Thr Gly Met Leu Glu Asp Gly Lys Lys Phe Asp Ser
                245                 250                 255

Ser Arg Asp Arg Asn Lys Pro Phe Lys Phe Met Leu Gly Lys Gln Glu
            260                 265                 270

Val Ile Arg Gly Trp Glu Glu Gly Val Ala Gln Met Ser Val Gly Gln
        275                 280                 285

Arg Ala Lys Leu Thr Ile Ser Pro Asp Tyr Ala Tyr Gly Ala Thr Gly
    290                 295                 300

His Pro Gly Ile Ile Pro Pro His Ala Thr Leu Val Phe Asp Val Glu
305                 310                 315                 320

Leu Leu Lys Leu Glu Glu
                325

<210> SEQ ID NO 96
<211> LENGTH: 296
<212> TYPE: PRT
<213> ORGANISM: artificial sequence
<220> FEATURE:
<223> OTHER INFORMATION: IMP-intCID-n?14

<400> SEQUENCE: 96

Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
            20                  25                  30

Gly Thr Cys Gly Val Leu Leu Leu Ser Leu Val Ile Thr Leu Tyr Cys
        35                  40                  45

Arg Ala Leu Tyr Leu Leu Arg Arg Asp Gln Arg Leu Pro Pro Asp Ala
    50                  55                  60

His Lys Pro Pro Gly Gly Gly Ser Phe Arg Thr Pro Ile Gln Glu Glu
65                  70                  75                  80

Gln Ala Asp Ala His Ser Thr Leu Ala Lys Ile Gly Ser Gly Ser Gly
                85                  90                  95

Ser Gly Ser Ser Arg Ala Ala Arg Gly Thr Ile Gly Ala Arg Arg Thr
            100                 105                 110

Gly Gln Pro Leu Lys Glu Asp Pro Ser Ala Val Pro Val Phe Ser Val
            115                 120                 125

Asp Tyr Gly Glu Leu Asp Phe Gln Trp Arg Glu Lys Thr Pro Glu Pro
        130                 135                 140

Pro Val Pro Cys Val Pro Glu Thr Glu Tyr Ala Thr Ile Val Phe
145                 150                 155                 160

Pro Ser Gly Met Gly Thr Ser Ser Pro Ala Arg Arg Gly Ser Ala Asp
                165                 170                 175

Gly Pro Arg Ser Ala Gln Pro Leu Arg Pro Glu Asp Gly His Cys Ser
            180                 185                 190

Trp Pro Leu Gly Ser Gly Ser Gly Arg Val Ala Ile Leu Trp His
        195                 200                 205

Glu Met Trp His Glu Gly Leu Glu Glu Ala Ser Arg Leu Tyr Phe Gly
210                 215                 220

Glu Arg Asn Val Lys Gly Met Phe Glu Val Leu Glu Pro Leu His Ala
225                 230                 235                 240

Met Met Glu Arg Gly Pro Gln Thr Leu Lys Glu Thr Ser Phe Asn Gln
                245                 250                 255

Ala Tyr Gly Arg Asp Leu Met Glu Ala Gln Glu Trp Cys Arg Lys Tyr
            260                 265                 270

Met Lys Ser Gly Asn Val Lys Asp Leu Thr Gln Ala Trp Asp Leu Tyr
        275                 280                 285

Tyr His Val Phe Arg Arg Ile Glu
    290                 295

<210> SEQ ID NO 97
<211> LENGTH: 274
<212> TYPE: PRT
<213> ORGANISM: artificial sequence
<220> FEATURE:
<223> OTHER INFORMATION: IMP-intCID-n?15

<400> SEQUENCE: 97

Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Pro Arg Arg Ser Pro Ala Gln Glu Asp Gly Lys Val Tyr Ile Asn
        50                  55                  60

Met Pro Gly Arg Gly Gly Ser Gly Ser Gly Ser Ser Arg Ala
65                  70                  75                  80

Ala Arg Gly Thr Ile Gly Ala Arg Arg Thr Gly Gln Pro Leu Lys Glu
                85                  90                  95

Asp Pro Ser Ala Val Pro Val Phe Ser Val Asp Tyr Gly Glu Leu Asp
            100                 105                 110

Phe Gln Trp Arg Glu Lys Thr Pro Glu Pro Pro Val Pro Cys Val Pro
        115                 120                 125

```
Glu Gln Thr Glu Tyr Ala Thr Ile Val Phe Pro Ser Gly Met Gly Thr
            130                 135                 140

Ser Ser Pro Ala Arg Arg Gly Ser Ala Asp Gly Pro Arg Ser Ala Gln
145                 150                 155                 160

Pro Leu Arg Pro Glu Asp Gly His Cys Ser Trp Pro Leu Gly Ser Gly
                165                 170                 175

Ser Gly Gly Arg Val Ala Ile Leu Trp His Glu Met Trp His Glu Gly
            180                 185                 190

Leu Glu Glu Ala Ser Arg Leu Tyr Phe Gly Glu Arg Asn Val Lys Gly
            195                 200                 205

Met Phe Glu Val Leu Glu Pro Leu His Ala Met Met Glu Arg Gly Pro
            210                 215                 220

Gln Thr Leu Lys Glu Thr Ser Phe Asn Gln Ala Tyr Gly Arg Asp Leu
225                 230                 235                 240

Met Glu Ala Gln Glu Trp Cys Arg Lys Tyr Met Lys Ser Gly Asn Val
                245                 250                 255

Lys Asp Leu Thr Gln Ala Trp Asp Leu Tyr Tyr His Val Phe Arg Arg
                260                 265                 270

Ile Glu

<210> SEQ ID NO 98
<211> LENGTH: 314
<212> TYPE: PRT
<213> ORGANISM: artificial sequence
<220> FEATURE:
<223> OTHER INFORMATION: IMP-intCID-n?16

<400> SEQUENCE: 98

Met Ala Leu Pro Val Thr Ala Leu Leu Leu Pro Leu Ala Leu Leu Leu
1               5                   10                  15

His Ala Ala Arg Pro Gly Ser Asp Ile Tyr Ile Trp Ala Pro Leu Ala
                20                  25                  30

Gly Thr Cys Gly Val Leu Leu Leu Ser Leu Val Ile Thr Leu Tyr Cys
            35                  40                  45

Arg Cys Val Lys Arg Arg Lys Pro Arg Gly Asp Val Val Lys Val Ile
50                  55                  60

Val Ser Val Gln Arg Lys Arg Gln Glu Ala Glu Gly Glu Ala Thr Val
65                  70                  75                  80

Ile Glu Ala Leu Gln Ala Pro Pro Asp Val Thr Thr Val Ala Val Glu
                85                  90                  95

Glu Thr Ile Pro Ser Phe Thr Gly Arg Ser Pro Asn His Gly Ser Gly
            100                 105                 110

Ser Gly Ser Gly Ser Ser Arg Ala Ala Arg Gly Thr Ile Gly Ala Arg
            115                 120                 125

Arg Thr Gly Gln Pro Leu Lys Glu Asp Pro Ser Ala Val Pro Val Phe
            130                 135                 140

Ser Val Asp Tyr Gly Glu Leu Asp Phe Gln Trp Arg Glu Lys Thr Pro
145                 150                 155                 160

Glu Pro Pro Val Pro Cys Val Pro Glu Gln Thr Glu Tyr Ala Thr Ile
                165                 170                 175

Val Phe Pro Ser Gly Met Gly Thr Ser Ser Pro Ala Arg Arg Gly Ser
            180                 185                 190

Ala Asp Gly Pro Arg Ser Ala Gln Pro Leu Arg Pro Glu Asp Gly His
            195                 200                 205
```

```
Cys Ser Trp Pro Leu Gly Ser Gly Gly Arg Val Ala Ile Leu
    210             215             220

Trp His Glu Met Trp His Glu Gly Leu Glu Glu Ala Ser Arg Leu Tyr
225             230             235             240

Phe Gly Glu Arg Asn Val Lys Gly Met Phe Glu Val Leu Glu Pro Leu
                245             250             255

His Ala Met Met Glu Arg Gly Pro Gln Thr Leu Lys Glu Thr Ser Phe
                260             265             270

Asn Gln Ala Tyr Gly Arg Asp Leu Met Glu Ala Gln Glu Trp Cys Arg
            275             280             285

Lys Tyr Met Lys Ser Gly Asn Val Lys Asp Leu Thr Gln Ala Trp Asp
290             295             300

Leu Tyr Tyr His Val Phe Arg Arg Ile Glu
305             310
```

<210> SEQ ID NO 99
<211> LENGTH: 481
<212> TYPE: PRT
<213> ORGANISM: artificial sequence
<220> FEATURE:
<223> OTHER INFORMATION: alpha-mcCAR-intCID-n?1

<400> SEQUENCE: 99

```
Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
                20                  25                  30

Gly Pro Glu Leu Lys Lys Pro Gly Glu Thr Val Lys Ile Ser Cys Lys
            35                  40                  45

Ala Ser Gly Tyr Ile Phe Thr Asn Tyr Gly Met Asn Trp Val Lys Gln
50                  55                  60

Ala Pro Gly Lys Ser Phe Lys Trp Met Gly Trp Ile Asn Thr Tyr Thr
65                  70                  75                  80

Gly Glu Ser Thr Tyr Ser Ala Asp Phe Lys Gly Arg Phe Ala Phe Ser
                85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
        115                 120                 125

Pro Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Asn Tyr Gly Asn
            180                 185                 190

Thr Phe Met His Trp Tyr Gln Gln Lys Pro Gly Gln Pro Pro Lys Leu
        195                 200                 205

Leu Ile Tyr Arg Ala Ser Asn Leu Glu Ser Gly Ile Pro Ala Arg Phe
    210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
                245                 250                 255
```

Pro Pro Thr Phe Gly Ala Gly Thr Lys Leu Glu Leu Lys Arg Ser Asp
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Phe Phe
305                 310                 315                 320

Ile Pro Leu Leu Val Ile Leu Phe Ala Val Asp Thr Gly Leu Phe
                325                 330                 335

Ile Ser Thr Gln Gln Gln Val Thr Phe Leu Leu Lys Ile Lys Arg Thr
                340                 345                 350

Arg Lys Gly Phe Arg Leu Leu Asn Pro His Pro Lys Pro Asn Pro Lys
                355                 360                 365

Asn Asn Arg Ser Gly Gly Val Gln Val Glu Thr Ile Ser Pro Gly Asp
            370                 375                 380

Gly Arg Thr Phe Pro Lys Arg Gly Gln Thr Cys Val Val His Tyr Thr
385                 390                 395                 400

Gly Met Leu Glu Asp Gly Lys Lys Phe Asp Ser Ser Arg Asp Arg Asn
                405                 410                 415

Lys Pro Phe Lys Phe Met Leu Gly Lys Gln Glu Val Ile Arg Gly Trp
                420                 425                 430

Glu Glu Gly Val Ala Gln Met Ser Val Gly Gln Arg Ala Lys Leu Thr
                435                 440                 445

Ile Ser Pro Asp Tyr Ala Tyr Gly Ala Thr Gly His Pro Gly Ile Ile
            450                 455                 460

Pro Pro His Ala Thr Leu Val Phe Asp Val Glu Leu Leu Lys Leu Glu
465                 470                 475                 480

Glu

<210> SEQ ID NO 100
<211> LENGTH: 469
<212> TYPE: PRT
<213> ORGANISM: artificial sequence
<220> FEATURE:
<223> OTHER INFORMATION: alpha-mcCAR-intCID-n?2

<400> SEQUENCE: 100

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
            20                  25                  30

Gly Pro Glu Leu Lys Lys Pro Gly Glu Thr Val Lys Ile Ser Cys Lys
        35                  40                  45

Ala Ser Gly Tyr Ile Phe Thr Asn Tyr Gly Met Asn Trp Val Lys Gln
    50                  55                  60

Ala Pro Gly Lys Ser Phe Lys Trp Met Gly Trp Ile Asn Thr Tyr Thr
65                  70                  75                  80

Gly Glu Ser Thr Tyr Ser Ala Asp Phe Lys Gly Arg Phe Ala Phe Ser
                85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
        115                 120                 125

Pro Met Asp Tyr Trp Gly Gln Gly Thr Ser Val Thr Val Ser Ser Gly

Gly Gly Gly Ser Gly Gly Gly Ser Gly Gly Gly Ser Asp Ile
            145                 150                 155             160

Val Leu Thr Gln Ser Pro Ala Ser Leu Ala Val Ser Leu Gly Gln Arg
                    165                 170                 175

Ala Thr Ile Ser Cys Arg Ala Ser Glu Ser Val Asp Asn Tyr Gly Asn
                180                 185                 190

Thr Phe Met His Trp Tyr Gln Gln Lys Pro Gly Gln Pro Pro Lys Leu
            195                 200                 205

Leu Ile Tyr Arg Ala Ser Asn Leu Glu Ser Gly Ile Pro Ala Arg Phe
        210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
                245                 250                 255

Pro Pro Thr Phe Gly Ala Gly Thr Lys Leu Glu Leu Lys Arg Ser Asp
                260                 265                 270

Pro Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Phe Phe
305                 310                 315                 320

Ile Pro Leu Leu Val Val Ile Leu Phe Ala Val Asp Thr Gly Leu Phe
                325                 330                 335

Ile Ser Thr Gln Gln Gln Val Thr Phe Leu Leu Lys Ile Lys Arg Thr
                340                 345                 350

Arg Lys Gly Phe Arg Leu Leu Asn Pro His Pro Lys Pro Asn Pro Lys
            355                 360                 365

Asn Asn Arg Ser Gly Gly Arg Val Ala Ile Leu Trp His Glu Met Trp
        370                 375                 380

His Glu Gly Leu Glu Glu Ala Ser Arg Leu Tyr Phe Gly Glu Arg Asn
385                 390                 395                 400

Val Lys Gly Met Phe Glu Val Leu Glu Pro Leu His Ala Met Met Glu
                405                 410                 415

Arg Gly Pro Gln Thr Leu Lys Glu Thr Ser Phe Asn Gln Ala Tyr Gly
                420                 425                 430

Arg Asp Leu Met Glu Ala Gln Glu Trp Cys Arg Lys Tyr Met Lys Ser
            435                 440                 445

Gly Asn Val Lys Asp Leu Thr Gln Ala Trp Asp Leu Tyr Tyr His Val
        450                 455                 460

Phe Arg Arg Ile Glu
465

<210> SEQ ID NO 101
<211> LENGTH: 531
<212> TYPE: PRT
<213> ORGANISM: artificial sequence
<220> FEATURE:
<223> OTHER INFORMATION: alpha-mcCAR-intCID-n?3

<400> SEQUENCE: 101

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser

-continued

```
                20                  25                  30
Gly Pro Glu Leu Lys Lys Pro Gly Glu Thr Val Lys Ile Ser Cys Lys
             35                  40                  45
Ala Ser Gly Tyr Ile Phe Thr Asn Tyr Gly Met Asn Trp Val Lys Gln
 50                  55                  60
Ala Pro Gly Lys Ser Phe Lys Trp Met Gly Trp Ile Asn Thr Tyr Thr
 65                  70                  75                  80
Gly Glu Ser Thr Tyr Ser Ala Asp Phe Lys Gly Arg Phe Ala Phe Ser
                     85                  90                  95
Leu Glu Thr Ser Ala Ser Thr Ala Tyr Leu His Ile Asn Asp Leu Lys
                100                 105                 110
Asn Glu Asp Thr Ala Thr Tyr Phe Cys Ala Arg Ser Gly Gly Tyr Asp
             115                 120                 125
Pro Met Asp Tyr Trp Gly Gln Gly Thr Ser Val Thr Val Ser Ser Gly
             130                 135                 140
Gly Gly Gly Ser Gly Gly Gly Ser Gly Gly Gly Ser Asp Ile
145                 150                 155                 160
Val Leu Thr Gln Ser Pro Ala Ser Leu Ala Val Ser Leu Gly Gln Arg
                165                 170                 175
Ala Thr Ile Ser Cys Arg Ala Ser Glu Ser Val Asp Asn Tyr Gly Asn
             180                 185                 190
Thr Phe Met His Trp Tyr Gln Gln Lys Pro Gly Gln Pro Pro Lys Leu
             195                 200                 205
Leu Ile Tyr Arg Ala Ser Asn Leu Glu Ser Gly Ile Pro Ala Arg Phe
         210                 215                 220
Ser Gly Ser Gly Ser Arg Thr Asp Phe Thr Leu Thr Ile Asn Pro Val
225                 230                 235                 240
Glu Ala Asp Asp Val Ala Thr Tyr Tyr Cys Gln Gln Ser Asn Glu Asp
                245                 250                 255
Pro Pro Thr Phe Gly Ala Gly Thr Lys Leu Glu Leu Lys Arg Ser Asp
             260                 265                 270
Pro Thr Thr Thr Pro Ala Pro Arg Pro Pro Thr Pro Ala Pro Thr Ile
             275                 280                 285
Ala Ser Gln Pro Leu Ser Leu Arg Pro Glu Ala Cys Arg Pro Ala Ala
 290                 295                 300
Gly Gly Ala Val His Thr Arg Gly Leu Asp Phe Ala Cys Asp Phe Phe
305                 310                 315                 320
Ile Pro Leu Leu Val Val Ile Leu Phe Ala Val Asp Thr Gly Leu Phe
                325                 330                 335
Ile Ser Thr Gln Gln Gln Val Thr Phe Leu Leu Lys Ile Lys Arg Thr
             340                 345                 350
Arg Lys Gly Phe Arg Leu Leu Asn Pro His Pro Lys Pro Asn Pro Lys
             355                 360                 365
Asn Asn Arg Ala Leu Tyr Leu Leu Arg Arg Asp Gln Arg Leu Pro Pro
 370                 375                 380
Asp Ala His Lys Pro Pro Gly Gly Gly Ser Phe Arg Thr Pro Ile Gln
385                 390                 395                 400
Glu Glu Gln Ala Asp Ala His Ser Thr Leu Ala Lys Ile Gly Ser Gly
                405                 410                 415
Ser Gly Ser Gly Ser Ser Gly Gly Val Gln Val Glu Thr Ile Ser Pro
             420                 425                 430
Gly Asp Gly Arg Thr Phe Pro Lys Arg Gly Gln Thr Cys Val Val His
             435                 440                 445
```

Tyr Thr Gly Met Leu Glu Asp Gly Lys Lys Phe Asp Ser Ser Arg Asp
            450                 455                 460

Arg Asn Lys Pro Phe Lys Phe Met Leu Gly Lys Gln Glu Val Ile Arg
465                 470                 475                 480

Gly Trp Glu Glu Gly Val Ala Gln Met Ser Val Gly Gln Arg Ala Lys
                485                 490                 495

Leu Thr Ile Ser Pro Asp Tyr Ala Tyr Gly Ala Thr Gly His Pro Gly
            500                 505                 510

Ile Ile Pro Pro His Ala Thr Leu Val Phe Asp Val Glu Leu Leu Lys
            515                 520                 525

Leu Glu Glu
        530

<210> SEQ ID NO 102
<211> LENGTH: 509
<212> TYPE: PRT
<213> ORGANISM: artificial sequence
<220> FEATURE:
<223> OTHER INFORMATION: alpha-mcCAR-intCID-n?4

<400> SEQUENCE: 102

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
            20                  25                  30

Gly Pro Glu Leu Lys Lys Pro Gly Glu Thr Val Lys Ile Ser Cys Lys
        35                  40                  45

Ala Ser Gly Tyr Ile Phe Thr Asn Tyr Gly Met Asn Trp Val Lys Gln
50                  55                  60

Ala Pro Gly Lys Ser Phe Lys Trp Met Gly Trp Ile Asn Thr Tyr Thr
65                  70                  75                  80

Gly Glu Ser Thr Tyr Ser Ala Asp Phe Lys Gly Arg Phe Ala Phe Ser
            85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
        115                 120                 125

Pro Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ser Leu Ala Val Ser Leu Gly Gln Arg
            165                 170                 175

Ala Thr Ile Ser Cys Arg Ala Ser Glu Ser Val Asp Asn Tyr Gly Asn
            180                 185                 190

Thr Phe Met His Trp Tyr Gln Gln Lys Pro Gly Gln Pro Pro Lys Leu
        195                 200                 205

Leu Ile Tyr Arg Ala Ser Asn Leu Glu Ser Gly Ile Pro Ala Arg Phe
    210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
            245                 250                 255

Pro Pro Thr Phe Gly Ala Gly Thr Lys Leu Glu Leu Lys Arg Ser Asp
            260                 265                 270

```
Pro Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Phe Phe
305                 310                 315                 320

Ile Pro Leu Leu Val Val Ile Leu Phe Ala Val Asp Thr Gly Leu Phe
                325                 330                 335

Ile Ser Thr Gln Gln Gln Val Thr Phe Leu Leu Lys Ile Lys Arg Thr
            340                 345                 350

Arg Lys Gly Phe Arg Leu Leu Asn Pro His Pro Lys Pro Asn Pro Lys
            355                 360                 365

Asn Asn Arg Pro Arg Arg Ser Pro Ala Gln Glu Asp Gly Lys Val Tyr
    370                 375                 380

Ile Asn Met Pro Gly Arg Gly Ser Gly Ser Gly Ser Gly Ser Ser
385                 390                 395                 400

Gly Gly Val Gln Val Glu Thr Ile Ser Pro Gly Asp Gly Arg Thr Phe
                405                 410                 415

Pro Lys Arg Gly Gln Thr Cys Val Val His Tyr Thr Gly Met Leu Glu
            420                 425                 430

Asp Gly Lys Lys Phe Asp Ser Ser Arg Asp Arg Asn Lys Pro Phe Lys
            435                 440                 445

Phe Met Leu Gly Lys Gln Glu Val Ile Arg Gly Trp Glu Glu Gly Val
    450                 455                 460

Ala Gln Met Ser Val Gly Gln Arg Ala Lys Leu Thr Ile Ser Pro Asp
465                 470                 475                 480

Tyr Ala Tyr Gly Ala Thr Gly His Pro Gly Ile Ile Pro Pro His Ala
                485                 490                 495

Thr Leu Val Phe Asp Val Glu Leu Leu Lys Leu Glu Glu
            500                 505

<210> SEQ ID NO 103
<211> LENGTH: 549
<212> TYPE: PRT
<213> ORGANISM: artificial sequence
<220> FEATURE:
<223> OTHER INFORMATION: alpha-mcCAR-intCID-n?5

<400> SEQUENCE: 103

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
                20                  25                  30

Gly Pro Glu Leu Lys Lys Pro Gly Glu Thr Val Lys Ile Ser Cys Lys
            35                  40                  45

Ala Ser Gly Tyr Ile Phe Thr Asn Tyr Gly Met Asn Trp Val Lys Gln
    50                  55                  60

Ala Pro Gly Lys Ser Phe Lys Trp Met Gly Trp Ile Asn Thr Tyr Thr
65                  70                  75                  80

Gly Glu Ser Thr Tyr Ser Ala Asp Phe Lys Gly Arg Phe Ala Phe Ser
                85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
            115                 120                 125
```

-continued

```
Pro Met Asp Tyr Trp Gly Gln Gly Thr Ser Val Thr Val Ser Ser Gly
    130                 135                 140
Gly Gly Gly Ser Gly Gly Gly Ser Gly Gly Gly Ser Asp Ile
145                 150                 155                 160
Val Leu Thr Gln Ser Pro Ala Ser Leu Ala Val Ser Leu Gly Gln Arg
                165                 170                 175
Ala Thr Ile Ser Cys Arg Ala Ser Glu Ser Val Asp Asn Tyr Gly Asn
            180                 185                 190
Thr Phe Met His Trp Tyr Gln Gln Lys Pro Gly Gln Pro Pro Lys Leu
        195                 200                 205
Leu Ile Tyr Arg Ala Ser Asn Leu Glu Ser Gly Ile Pro Ala Arg Phe
    210                 215                 220
Ser Gly Ser Gly Ser Arg Thr Asp Phe Thr Leu Thr Ile Asn Pro Val
225                 230                 235                 240
Glu Ala Asp Asp Val Ala Thr Tyr Tyr Cys Gln Gln Ser Asn Glu Asp
                245                 250                 255
Pro Pro Thr Phe Gly Ala Gly Thr Lys Leu Glu Leu Lys Arg Ser Asp
            260                 265                 270
Pro Thr Thr Thr Pro Ala Pro Arg Pro Pro Thr Pro Ala Pro Thr Ile
        275                 280                 285
Ala Ser Gln Pro Leu Ser Leu Arg Pro Glu Ala Cys Arg Pro Ala Ala
    290                 295                 300
Gly Gly Ala Val His Thr Arg Gly Leu Asp Phe Ala Cys Asp Phe Phe
305                 310                 315                 320
Ile Pro Leu Leu Val Ile Leu Phe Ala Val Asp Thr Gly Leu Phe
                325                 330                 335
Ile Ser Thr Gln Gln Gln Val Thr Phe Leu Leu Lys Ile Lys Arg Thr
            340                 345                 350
Arg Lys Gly Phe Arg Leu Leu Asn Pro His Pro Lys Pro Asn Pro Lys
        355                 360                 365
Asn Asn Arg Cys Val Lys Arg Arg Lys Pro Arg Gly Asp Val Val Lys
    370                 375                 380
Val Ile Val Ser Val Gln Arg Lys Arg Gln Glu Ala Glu Gly Glu Ala
385                 390                 395                 400
Thr Val Ile Glu Ala Leu Gln Ala Pro Pro Asp Val Thr Thr Val Ala
                405                 410                 415
Val Glu Glu Thr Ile Pro Ser Phe Thr Gly Arg Ser Pro Asn His Gly
            420                 425                 430
Ser Gly Ser Gly Ser Gly Ser Ser Gly Gly Val Gln Val Glu Thr Ile
        435                 440                 445
Ser Pro Gly Asp Gly Arg Thr Phe Pro Lys Arg Gly Gln Thr Cys Val
    450                 455                 460
Val His Tyr Thr Gly Met Leu Glu Asp Gly Lys Lys Phe Asp Ser Ser
465                 470                 475                 480
Arg Asp Arg Asn Lys Pro Phe Lys Phe Met Leu Gly Lys Gln Glu Val
                485                 490                 495
Ile Arg Gly Trp Glu Glu Gly Val Ala Gln Met Ser Val Gly Gln Arg
            500                 505                 510
Ala Lys Leu Thr Ile Ser Pro Asp Tyr Ala Tyr Gly Ala Thr Gly His
        515                 520                 525
Pro Gly Ile Ile Pro Pro His Ala Thr Leu Val Phe Asp Val Glu Leu
    530                 535                 540
```

Leu Lys Leu Glu Glu
545

<210> SEQ ID NO 104
<211> LENGTH: 519
<212> TYPE: PRT
<213> ORGANISM: artificial sequence
<220> FEATURE:
<223> OTHER INFORMATION: alpha-mcCAR-intCID-n?6

<400> SEQUENCE: 104

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
            20                  25                  30

Gly Pro Glu Leu Lys Lys Pro Gly Glu Thr Val Lys Ile Ser Cys Lys
        35                  40                  45

Ala Ser Gly Tyr Ile Phe Thr Asn Tyr Gly Met Asn Trp Val Lys Gln
    50                  55                  60

Ala Pro Gly Lys Ser Phe Lys Trp Met Gly Trp Ile Asn Thr Tyr Thr
65                  70                  75                  80

Gly Glu Ser Thr Tyr Ser Ala Asp Phe Lys Gly Arg Phe Ala Phe Ser
                85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
        115                 120                 125

Pro Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Asn Tyr Gly Asn
            180                 185                 190

Thr Phe Met His Trp Tyr Gln Gln Lys Pro Gly Gln Pro Pro Lys Leu
        195                 200                 205

Leu Ile Tyr Arg Ala Ser Asn Leu Glu Ser Gly Ile Pro Ala Arg Phe
    210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
                245                 250                 255

Pro Pro Thr Phe Gly Ala Gly Thr Lys Leu Glu Leu Lys Arg Ser Asp
            260                 265                 270

Pro Thr Thr Thr Pro Ala Pro Arg Pro Pro Thr Pro Ala Pro Thr Ile
        275                 280                 285

Ala Ser Gln Pro Leu Ser Leu Arg Pro Glu Ala Cys Arg Pro Ala Ala
    290                 295                 300

Gly Gly Ala Val His Thr Arg Gly Leu Asp Phe Ala Cys Asp Phe Phe
305                 310                 315                 320

Ile Pro Leu Leu Val Val Ile Leu Phe Ala Val Asp Thr Gly Leu Phe
                325                 330                 335

Ile Ser Thr Gln Gln Gln Val Thr Phe Leu Leu Lys Ile Lys Arg Thr
            340                 345                 350

```
Arg Lys Gly Phe Arg Leu Leu Asn Pro His Pro Lys Pro Asn Pro Lys
            355                 360                 365

Asn Asn Arg Ala Leu Tyr Leu Leu Arg Arg Asp Gln Arg Leu Pro Pro
    370                 375                 380

Asp Ala His Lys Pro Pro Gly Gly Ser Phe Arg Thr Pro Ile Gln
385                 390                 395                 400

Glu Glu Gln Ala Asp Ala His Ser Thr Leu Ala Lys Ile Gly Ser Gly
                405                 410                 415

Ser Gly Ser Gly Ser Gly Gly Arg Val Ala Ile Leu Trp His Glu
            420                 425                 430

Met Trp His Glu Gly Leu Glu Glu Ala Ser Arg Leu Tyr Phe Gly Glu
            435                 440                 445

Arg Asn Val Lys Gly Met Phe Glu Val Leu Glu Pro Leu His Ala Met
    450                 455                 460

Met Glu Arg Gly Pro Gln Thr Leu Lys Glu Thr Ser Phe Asn Gln Ala
465                 470                 475                 480

Tyr Gly Arg Asp Leu Met Glu Ala Gln Glu Trp Cys Arg Lys Tyr Met
                485                 490                 495

Lys Ser Gly Asn Val Lys Asp Leu Thr Gln Ala Trp Asp Leu Tyr Tyr
            500                 505                 510

His Val Phe Arg Arg Ile Glu
            515

<210> SEQ ID NO 105
<211> LENGTH: 497
<212> TYPE: PRT
<213> ORGANISM: artificial sequence
<220> FEATURE:
<223> OTHER INFORMATION: alpha-mcCAR-intCID-n?7

<400> SEQUENCE: 105

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
            20                  25                  30

Gly Pro Glu Leu Lys Lys Pro Gly Glu Thr Val Lys Ile Ser Cys Lys
        35                  40                  45

Ala Ser Gly Tyr Ile Phe Thr Asn Tyr Gly Met Asn Trp Val Lys Gln
    50                  55                  60

Ala Pro Gly Lys Ser Phe Lys Trp Met Gly Trp Ile Asn Thr Tyr Thr
65                  70                  75                  80

Gly Glu Ser Thr Tyr Ser Ala Asp Phe Lys Gly Arg Phe Ala Phe Ser
                85                  90                  95

Leu Glu Thr Ser Ala Ser Thr Ala Tyr Leu His Ile Asn Asp Leu Lys
            100                 105                 110

Asn Glu Asp Thr Ala Thr Tyr Phe Cys Ala Arg Ser Gly Gly Tyr Asp
        115                 120                 125

Pro Met Asp Tyr Trp Gly Gln Gly Thr Ser Val Thr Val Ser Ser Gly
    130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Asn Tyr Gly Asn
            180                 185                 190
```

```
Thr Phe Met His Trp Tyr Gln Gln Lys Pro Gly Gln Pro Pro Lys Leu
            195                 200                 205

Leu Ile Tyr Arg Ala Ser Asn Leu Glu Ser Gly Ile Pro Ala Arg Phe
        210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
                245                 250                 255

Pro Pro Thr Phe Gly Ala Gly Thr Lys Leu Glu Leu Lys Arg Ser Asp
                260                 265                 270

Pro Thr Thr Thr Pro Ala Pro Arg Pro Pro Thr Pro Ala Pro Thr Ile
            275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Phe Phe
305                 310                 315                 320

Ile Pro Leu Leu Val Val Ile Leu Phe Ala Val Asp Thr Gly Leu Phe
                325                 330                 335

Ile Ser Thr Gln Gln Gln Val Thr Phe Leu Leu Lys Ile Lys Arg Thr
                340                 345                 350

Arg Lys Gly Phe Arg Leu Leu Asn Pro His Pro Lys Pro Asn Pro Lys
            355                 360                 365

Asn Asn Arg Pro Arg Arg Ser Pro Ala Gln Glu Asp Gly Lys Val Tyr
        370                 375                 380

Ile Asn Met Pro Gly Arg Gly Ser Gly Ser Gly Ser Gly Ser Ser
385                 390                 395                 400

Gly Gly Arg Val Ala Ile Leu Trp His Glu Met Trp His Glu Gly Leu
                405                 410                 415

Glu Glu Ala Ser Arg Leu Tyr Phe Gly Glu Arg Asn Val Lys Gly Met
                420                 425                 430

Phe Glu Val Leu Glu Pro Leu His Ala Met Met Glu Arg Gly Pro Gln
            435                 440                 445

Thr Leu Lys Glu Thr Ser Phe Asn Gln Ala Tyr Gly Arg Asp Leu Met
        450                 455                 460

Glu Ala Gln Glu Trp Cys Arg Lys Tyr Met Lys Ser Gly Asn Val Lys
465                 470                 475                 480

Asp Leu Thr Gln Ala Trp Asp Leu Tyr Tyr His Val Phe Arg Arg Ile
                485                 490                 495

Glu

<210> SEQ ID NO 106
<211> LENGTH: 537
<212> TYPE: PRT
<213> ORGANISM: artificial sequence
<220> FEATURE:
<223> OTHER INFORMATION: alpha-mcCAR-intCID-n?8

<400> SEQUENCE: 106

Met Ala Pro Ala Met Glu Ser Pro Thr Leu Leu Cys Val Ala Leu Leu
1               5                   10                  15

Phe Phe Ala Pro Asp Gly Val Leu Ala Gln Ile Gln Leu Val Gln Ser
                20                  25                  30

Gly Pro Glu Leu Lys Lys Pro Gly Glu Thr Val Lys Ile Ser Cys Lys
            35                  40                  45

Ala Ser Gly Tyr Ile Phe Thr Asn Tyr Gly Met Asn Trp Val Lys Gln
```

```
                50                  55                  60
Ala Pro Gly Lys Ser Phe Lys Trp Met Gly Trp Ile Asn Thr Tyr Thr
 65                  70                  75                  80

Gly Glu Ser Thr Tyr Ser Ala Asp Phe Lys Gly Arg Phe Ala Phe Ser
                     85                  90                  95

Leu Glu Thr Ser Ala Ser Thr Ala Tyr Leu His Ile Asn Asp Leu Lys
                100                 105                 110

Asn Glu Asp Thr Ala Thr Tyr Phe Cys Ala Arg Ser Gly Gly Tyr Asp
                115                 120                 125

Pro Met Asp Tyr Trp Gly Gln Gly Thr Ser Val Thr Val Ser Ser Gly
        130                 135                 140

Gly Gly Gly Ser Gly Gly Gly Gly Ser Gly Gly Gly Gly Ser Asp Ile
145                 150                 155                 160

Val Leu Thr Gln Ser Pro Ala Ser Leu Ala Val Ser Leu Gly Gln Arg
                165                 170                 175

Ala Thr Ile Ser Cys Arg Ala Ser Glu Ser Val Asp Asn Tyr Gly Asn
                180                 185                 190

Thr Phe Met His Trp Tyr Gln Gln Lys Pro Gly Gln Pro Pro Lys Leu
        195                 200                 205

Leu Ile Tyr Arg Ala Ser Asn Leu Glu Ser Gly Ile Pro Ala Arg Phe
        210                 215                 220

Ser Gly Ser Gly Ser Arg Thr Asp Phe Thr Leu Thr Ile Asn Pro Val
225                 230                 235                 240

Glu Ala Asp Asp Val Ala Thr Tyr Tyr Cys Gln Gln Ser Asn Glu Asp
                245                 250                 255

Pro Pro Thr Phe Gly Ala Gly Thr Lys Leu Glu Leu Lys Arg Ser Asp
                260                 265                 270

Pro Thr Thr Thr Pro Ala Pro Arg Pro Thr Pro Ala Pro Thr Ile
        275                 280                 285

Ala Ser Gln Pro Leu Ser Leu Arg Pro Glu Ala Cys Arg Pro Ala Ala
        290                 295                 300

Gly Gly Ala Val His Thr Arg Gly Leu Asp Phe Ala Cys Asp Phe Phe
305                 310                 315                 320

Ile Pro Leu Leu Val Val Ile Leu Phe Ala Val Asp Thr Gly Leu Phe
                325                 330                 335

Ile Ser Thr Gln Gln Gln Val Thr Phe Leu Leu Lys Ile Lys Arg Thr
                340                 345                 350

Arg Lys Gly Phe Arg Leu Leu Asn Pro His Pro Lys Pro Asn Pro Lys
                355                 360                 365

Asn Asn Arg Cys Val Lys Arg Lys Pro Arg Gly Asp Val Val Lys
370                 375                 380

Val Ile Val Ser Val Gln Arg Lys Arg Gln Glu Ala Glu Gly Glu Ala
385                 390                 395                 400

Thr Val Ile Glu Ala Leu Gln Ala Pro Pro Asp Val Thr Thr Val Ala
                405                 410                 415

Val Glu Glu Thr Ile Pro Ser Phe Thr Gly Arg Ser Pro Asn His Gly
                420                 425                 430

Ser Gly Ser Gly Ser Gly Ser Gly Gly Arg Val Ala Ile Leu Trp
        435                 440                 445

His Glu Met Trp His Glu Gly Leu Glu Glu Ala Ser Arg Leu Tyr Phe
        450                 455                 460

Gly Glu Arg Asn Val Lys Gly Met Phe Glu Val Leu Glu Pro Leu His
465                 470                 475                 480
```

Ala Met Met Glu Arg Gly Pro Gln Thr Leu Lys Glu Thr Ser Phe Asn
                485                 490                 495

Gln Ala Tyr Gly Arg Asp Leu Met Glu Ala Gln Glu Trp Cys Arg Lys
                500                 505                 510

Tyr Met Lys Ser Gly Asn Val Lys Asp Leu Thr Gln Ala Trp Asp Leu
                515                 520                 525

Tyr Tyr His Val Phe Arg Arg Ile Glu
    530                 535

<210> SEQ ID NO 107
<211> LENGTH: 613
<212> TYPE: PRT
<213> ORGANISM: artificial sequence
<220> FEATURE:
<223> OTHER INFORMATION: CD123-scCAR-intraCID-n?1

<400> SEQUENCE: 107

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
                20                  25                  30

Val Gln Pro Gly Gly Ser Leu Ser Leu Ser Cys Ala Ala Ser Gly Phe
            35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
                100                 105                 110

Asp Ser Ala Thr Tyr Tyr Cys Ala Arg Asp Ala Ala Tyr Tyr Ser Tyr
            115                 120                 125

Tyr Ser Pro Glu Gly Ala Met Asp Tyr Trp Gly Gln Gly Thr Ser Val
    130                 135                 140

Thr Val Ser Ser Gly Gly Gly Gly Ser Gly Gly Gly Gly Ser Gly Gly
145                 150                 155                 160

Gly Gly Ser Met Ala Asp Tyr Lys Asp Ile Val Met Thr Gln Ser His
                165                 170                 175

Lys Phe Met Ser Thr Ser Val Gly Asp Arg Val Asn Ile Thr Cys Lys
                180                 185                 190

Ala Ser Gln Asn Val Asp Ser Ala Val Ala Trp Tyr Gln Gln Lys Pro
            195                 200                 205

Gly Gln Ser Pro Lys Ala Leu Ile Tyr Ser Ala Ser Tyr Arg Tyr Ser
    210                 215                 220

Gly Val Pro Asp Arg Phe Thr Gly Arg Gly Ser Gly Thr Asp Phe Thr
225                 230                 235                 240

Leu Thr Ile Ser Ser Val Gln Ala Glu Asp Leu Ala Val Tyr Tyr Cys
                245                 250                 255

Gln Gln Tyr Tyr Ser Thr Pro Trp Thr Phe Gly Gly Gly Thr Lys Leu
                260                 265                 270

Glu Ile Lys Arg Ser Asp Pro Thr Thr Thr Pro Ala Pro Arg Pro Pro
            275                 280                 285

Thr Pro Ala Pro Thr Ile Ala Ser Gln Pro Leu Ser Leu Arg Pro Glu
    290                 295                 300

```
Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
            325                 330                 335

Val Leu Leu Leu Ser Leu Val Ile Thr Leu Tyr Cys Arg Arg Gly Arg
            340                 345                 350

Lys Lys Leu Leu Tyr Ile Phe Lys Gln Pro Phe Met Arg Pro Val Gln
            355                 360                 365

Thr Thr Gln Glu Glu Asp Gly Cys Ser Cys Arg Phe Pro Glu Glu Glu
370                 375                 380

Glu Gly Gly Cys Glu Leu Arg Val Lys Phe Ser Arg Ser Ala Asp Ala
385                 390                 395                 400

Pro Ala Tyr Gln Gln Gly Gln Asn Gln Leu Tyr Asn Glu Leu Asn Leu
            405                 410                 415

Gly Arg Arg Glu Glu Tyr Asp Val Leu Asp Lys Arg Arg Gly Arg Asp
            420                 425                 430

Pro Glu Met Gly Gly Lys Pro Arg Arg Lys Asn Pro Gln Glu Gly Leu
            435                 440                 445

Tyr Asn Glu Leu Gln Lys Asp Lys Met Ala Glu Ala Tyr Ser Glu Ile
450                 455                 460

Gly Met Lys Gly Glu Arg Arg Arg Gly Lys Gly His Asp Gly Leu Tyr
465                 470                 475                 480

Gln Gly Leu Ser Thr Ala Thr Lys Asp Thr Tyr Asp Ala Leu His Met
            485                 490                 495

Gln Ala Leu Pro Pro Arg Ser Ser Gly Val Gln Val Glu Thr Ile
            500                 505                 510

Ser Pro Gly Asp Gly Arg Thr Phe Pro Lys Arg Gly Gln Thr Cys Val
            515                 520                 525

Val His Tyr Thr Gly Met Leu Glu Asp Gly Lys Lys Phe Asp Ser Ser
530                 535                 540

Arg Asp Arg Asn Lys Pro Phe Lys Phe Met Leu Gly Lys Gln Glu Val
545                 550                 555                 560

Ile Arg Gly Trp Glu Glu Gly Val Ala Gln Met Ser Val Gly Gln Arg
            565                 570                 575

Ala Lys Leu Thr Ile Ser Pro Asp Tyr Ala Tyr Gly Ala Thr Gly His
            580                 585                 590

Pro Gly Ile Ile Pro Pro His Ala Thr Leu Val Phe Asp Val Glu Leu
            595                 600                 605

Leu Lys Leu Glu Glu
    610

<210> SEQ ID NO 108
<211> LENGTH: 601
<212> TYPE: PRT
<213> ORGANISM: artificial sequence
<220> FEATURE:
<223> OTHER INFORMATION: CD123-scCAR-intraCID-n?2

<400> SEQUENCE: 108

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Ser Leu Ser Cys Ala Ala Ser Gly Phe
        35                  40                  45
```

-continued

Thr Phe Thr Asp Tyr Tyr Met Ser Trp Val Arg Gln Pro Pro Gly Lys
    50                      55                      60

Ala Leu Glu Trp Leu Ala Leu Ile Arg Ser Lys Ala Asp Gly Tyr Thr
65                      70                      75                      80

Thr Glu Tyr Ser Ala Ser Val Lys Gly Arg Phe Thr Leu Ser Arg Asp
                85                      90                      95

Asp Ser Gln Ser Ile Leu Tyr Leu Gln Met Asn Ala Leu Arg Pro Glu
                100                     105                     110

Asp Ser Ala Thr Tyr Tyr Cys Ala Arg Asp Ala Ala Tyr Tyr Ser Tyr
                115                     120                     125

Tyr Ser Pro Glu Gly Ala Met Asp Tyr Trp Gly Gln Gly Thr Ser Val
    130                     135                     140

Thr Val Ser Ser Gly Gly Gly Gly Ser Gly Gly Gly Gly Ser Gly Gly
145                     150                     155                     160

Gly Gly Ser Met Ala Asp Tyr Lys Asp Ile Val Met Thr Gln Ser His
            165                     170                     175

Lys Phe Met Ser Thr Ser Val Gly Asp Arg Val Asn Ile Thr Cys Lys
                180                     185                     190

Ala Ser Gln Asn Val Asp Ser Ala Val Ala Trp Tyr Gln Gln Lys Pro
                195                     200                     205

Gly Gln Ser Pro Lys Ala Leu Ile Tyr Ser Ala Ser Tyr Arg Tyr Ser
    210                     215                     220

Gly Val Pro Asp Arg Phe Thr Gly Arg Gly Ser Gly Thr Asp Phe Thr
225                     230                     235                     240

Leu Thr Ile Ser Ser Val Gln Ala Glu Asp Leu Ala Val Tyr Tyr Cys
                245                     250                     255

Gln Gln Tyr Tyr Ser Thr Pro Trp Thr Phe Gly Gly Gly Thr Lys Leu
                260                     265                     270

Glu Ile Lys Arg Ser Asp Pro Thr Thr Thr Pro Ala Pro Arg Pro Pro
    275                     280                     285

Thr Pro Ala Pro Thr Ile Ala Ser Gln Pro Leu Ser Leu Arg Pro Glu
    290                     295                     300

Ala Cys Arg Pro Ala Ala Gly Gly Ala Val His Thr Arg Gly Leu Asp
305                     310                     315                     320

Phe Ala Cys Asp Ile Tyr Ile Trp Ala Pro Leu Ala Gly Thr Cys Gly
                325                     330                     335

Val Leu Leu Leu Ser Leu Val Ile Thr Leu Tyr Cys Arg Arg Gly Arg
            340                     345                     350

Lys Lys Leu Leu Tyr Ile Phe Lys Gln Pro Phe Met Arg Pro Val Gln
            355                     360                     365

Thr Thr Gln Glu Glu Asp Gly Cys Ser Cys Arg Phe Pro Glu Glu Glu
    370                     375                     380

Glu Gly Gly Cys Glu Leu Arg Val Lys Phe Ser Arg Ser Ala Asp Ala
385                     390                     395                     400

Pro Ala Tyr Gln Gln Gly Gln Asn Gln Leu Tyr Asn Glu Leu Asn Leu
                405                     410                     415

Gly Arg Arg Glu Glu Tyr Asp Val Leu Asp Lys Arg Arg Gly Arg Asp
                420                     425                     430

Pro Glu Met Gly Gly Lys Pro Arg Arg Lys Asn Pro Gln Glu Gly Leu
            435                     440                     445

Tyr Asn Glu Leu Gln Lys Asp Lys Met Ala Glu Ala Tyr Ser Glu Ile
    450                     455                     460

```
Gly Met Lys Gly Glu Arg Arg Gly Lys Gly His Asp Gly Leu Tyr
465                 470                 475                 480

Gln Gly Leu Ser Thr Ala Thr Lys Asp Thr Tyr Asp Ala Leu His Met
            485                 490                 495

Gln Ala Leu Pro Pro Arg Ser Ser Gly Gly Arg Val Ala Ile Leu Trp
        500                 505                 510

His Glu Met Trp His Glu Gly Leu Glu Glu Ala Ser Arg Leu Tyr Phe
    515                 520                 525

Gly Glu Arg Asn Val Lys Gly Met Phe Glu Val Leu Glu Pro Leu His
530                 535                 540

Ala Met Met Glu Arg Gly Pro Gln Thr Leu Lys Glu Thr Ser Phe Asn
545                 550                 555                 560

Gln Ala Tyr Gly Arg Asp Leu Met Glu Ala Gln Glu Trp Cys Arg Lys
                565                 570                 575

Tyr Met Lys Ser Gly Asn Val Lys Asp Leu Thr Gln Ala Trp Asp Leu
            580                 585                 590

Tyr Tyr His Val Phe Arg Arg Ile Glu
            595                 600

<210> SEQ ID NO 109
<211> LENGTH: 624
<212> TYPE: PRT
<213> ORGANISM: artificial sequence
<220> FEATURE:
<223> OTHER INFORMATION: CD123-scCAR-intraCID-n?3

<400> SEQUENCE: 109

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Ser Leu Ser Cys Ala Ala Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
            85                  90                  95

Asp Ser Gln Ser Ile Leu Tyr Leu Gln Met Asn Ala Leu Arg Pro Glu
            100                 105                 110

Asp Ser Ala Thr Tyr Tyr Cys Ala Arg Asp Ala Ala Tyr Tyr Ser Tyr
            115                 120                 125

Tyr Ser Pro Glu Gly Ala Met Asp Tyr Trp Gly Gln Gly Thr Ser Val
130                 135                 140

Thr Val Ser Ser Gly Gly Gly Ser Gly Gly Gly Ser Gly Gly Ser Gly
145                 150                 155                 160

Gly Gly Ser Met Ala Asp Tyr Lys Asp Ile Val Met Thr Gln Ser His
                165                 170                 175

Lys Phe Met Ser Thr Ser Val Gly Asp Arg Val Asn Ile Thr Cys Lys
            180                 185                 190

Ala Ser Gln Asn Val Asp Ser Ala Val Ala Trp Tyr Gln Gln Lys Pro
            195                 200                 205

Gly Gln Ser Pro Lys Ala Leu Ile Tyr Ser Ala Ser Tyr Arg Tyr Ser
        210                 215                 220
```

Gly Val Pro Asp Arg Phe Thr Gly Arg Gly Ser Gly Thr Asp Phe Thr
225                 230                 235                 240

Leu Thr Ile Ser Ser Val Gln Ala Glu Asp Leu Ala Val Tyr Tyr Cys
            245                 250                 255

Gln Gln Tyr Tyr Ser Thr Pro Trp Thr Phe Gly Gly Gly Thr Lys Leu
        260                 265                 270

Glu Ile Lys Arg Ser Asp Pro Thr Thr Thr Pro Ala Pro Arg Pro Pro
    275                 280                 285

Thr Pro Ala Pro Thr Ile Ala Ser Gln Pro Leu Ser Leu Arg Pro Glu
290                 295                 300

Ala Cys Arg Pro Ala Ala Gly Gly Ala Val His Thr Arg Gly Leu Asp
305                 310                 315                 320

Phe Ala Cys Asp Ile Tyr Ile Trp Ala Pro Leu Ala Gly Thr Cys Gly
                325                 330                 335

Val Leu Leu Leu Ser Leu Val Ile Thr Leu Tyr Cys Arg Gly Arg Lys
            340                 345                 350

Lys Leu Leu Tyr Ile Phe Lys Gln Pro Phe Met Arg Pro Val Gln Thr
        355                 360                 365

Thr Gln Glu Glu Asp Gly Cys Ser Cys Arg Phe Pro Glu Glu Glu Glu
370                 375                 380

Gly Gly Cys Glu Leu Gly Ser Gly Ser Gly Ser Ser Gly Gly
385                 390                 395                 400

Val Gln Val Glu Thr Ile Ser Pro Gly Asp Gly Arg Thr Phe Pro Lys
                405                 410                 415

Arg Gly Gln Thr Cys Val Val His Tyr Thr Gly Met Leu Glu Asp Gly
            420                 425                 430

Lys Lys Phe Asp Ser Ser Arg Asp Arg Asn Lys Pro Phe Lys Phe Met
        435                 440                 445

Leu Gly Lys Gln Glu Val Ile Arg Gly Trp Glu Glu Gly Val Ala Gln
450                 455                 460

Met Ser Val Gly Gln Arg Ala Lys Leu Thr Ile Ser Pro Asp Tyr Ala
465                 470                 475                 480

Tyr Gly Ala Thr Gly His Pro Gly Ile Ile Pro Pro His Ala Thr Leu
                485                 490                 495

Val Phe Asp Val Glu Leu Leu Lys Leu Glu Gly Ser Gly Ser Gly Arg
            500                 505                 510

Val Lys Phe Ser Arg Ser Ala Asp Ala Pro Ala Tyr Gln Gln Gly Gln
        515                 520                 525

Asn Gln Leu Tyr Asn Glu Leu Asn Leu Gly Arg Arg Glu Glu Tyr Asp
530                 535                 540

Val Leu Asp Lys Arg Arg Gly Arg Asp Pro Glu Met Gly Gly Lys Pro
545                 550                 555                 560

Arg Arg Lys Asn Pro Gln Glu Gly Leu Tyr Asn Glu Leu Gln Lys Asp
                565                 570                 575

Lys Met Ala Glu Ala Tyr Ser Glu Ile Gly Met Lys Gly Glu Arg Arg
            580                 585                 590

Arg Gly Lys Gly His Asp Gly Leu Tyr Gln Gly Leu Ser Thr Ala Thr
        595                 600                 605

Lys Asp Thr Tyr Asp Ala Leu His Met Gln Ala Leu Pro Pro Arg Glu
610                 615                 620

<210> SEQ ID NO 110
<211> LENGTH: 612
<212> TYPE: PRT

<213> ORGANISM: artificial sequence
<220> FEATURE:
<223> OTHER INFORMATION: CD123-scCAR-intraCID-n?4

<400> SEQUENCE: 110

```
Met Ala Leu Pro Val Thr Ala Leu Leu Leu Pro Leu Ala Leu Leu Leu
1               5                   10                  15
His Ala Ala Arg Pro Glu Val Lys Leu Val Glu Ser Gly Gly Gly Leu
            20                  25                  30
Val Gln Pro Gly Gly Ser Leu Ser Leu Ser Cys Ala Ala Ser Gly Phe
        35                  40                  45
Thr Phe Thr Asp Tyr Tyr Met Ser Trp Val Arg Gln Pro Pro Gly Lys
    50                  55                  60
Ala Leu Glu Trp Leu Ala Leu Ile Arg Ser Lys Ala Asp Gly Tyr Thr
65                  70                  75                  80
Thr Glu Tyr Ser Ala Ser Val Lys Gly Arg Phe Thr Leu Ser Arg Asp
                85                  90                  95
Asp Ser Gln Ser Ile Leu Tyr Leu Gln Met Asn Ala Leu Arg Pro Glu
            100                 105                 110
Asp Ser Ala Thr Tyr Tyr Cys Ala Arg Asp Ala Ala Tyr Tyr Ser Tyr
        115                 120                 125
Tyr Ser Pro Glu Gly Ala Met Asp Tyr Trp Gly Gln Gly Thr Ser Val
    130                 135                 140
Thr Val Ser Ser Gly Gly Gly Gly Ser Gly Gly Gly Gly Ser Gly Gly
145                 150                 155                 160
Gly Gly Ser Met Ala Asp Tyr Lys Asp Ile Val Met Thr Gln Ser His
                165                 170                 175
Lys Phe Met Ser Thr Ser Val Gly Asp Arg Val Asn Ile Thr Cys Lys
            180                 185                 190
Ala Ser Gln Asn Val Asp Ser Ala Val Ala Trp Tyr Gln Gln Lys Pro
        195                 200                 205
Gly Gln Ser Pro Lys Ala Leu Ile Tyr Ser Ala Ser Tyr Arg Tyr Ser
    210                 215                 220
Gly Val Pro Asp Arg Phe Thr Gly Arg Gly Ser Gly Thr Asp Phe Thr
225                 230                 235                 240
Leu Thr Ile Ser Ser Val Gln Ala Glu Asp Leu Ala Val Tyr Tyr Cys
                245                 250                 255
Gln Gln Tyr Tyr Ser Thr Pro Trp Thr Phe Gly Gly Gly Thr Lys Leu
            260                 265                 270
Glu Ile Lys Arg Ser Asp Pro Thr Thr Thr Pro Ala Pro Arg Pro Pro
        275                 280                 285
Thr Pro Ala Pro Thr Ile Ala Ser Gln Pro Leu Ser Leu Arg Pro Glu
    290                 295                 300
Ala Cys Arg Pro Ala Ala Gly Gly Ala Val His Thr Arg Gly Leu Asp
305                 310                 315                 320
Phe Ala Cys Asp Ile Tyr Ile Trp Ala Pro Leu Ala Gly Thr Cys Gly
                325                 330                 335
Val Leu Leu Leu Ser Leu Val Ile Thr Leu Tyr Cys Arg Gly Arg Lys
            340                 345                 350
Lys Leu Leu Tyr Ile Phe Lys Gln Pro Phe Met Arg Pro Val Gln Thr
        355                 360                 365
Thr Gln Glu Glu Asp Gly Cys Ser Cys Arg Phe Pro Glu Glu Glu Glu
    370                 375                 380
Gly Gly Cys Glu Leu Gly Ser Gly Ser Gly Ser Ser Gly Gly
```

```
                385                 390                 395                 400
Arg Val Ala Ile Leu Trp His Glu Met Trp His Glu Gly Leu Glu Glu
                    405                 410                 415

Ala Ser Arg Leu Tyr Phe Gly Glu Arg Asn Val Lys Gly Met Phe Glu
                420                 425                 430

Val Leu Glu Pro Leu His Ala Met Met Glu Arg Gly Pro Gln Thr Leu
            435                 440                 445

Lys Glu Thr Ser Phe Asn Gln Ala Tyr Gly Arg Asp Leu Met Glu Ala
        450                 455                 460

Gln Glu Trp Cys Arg Lys Tyr Met Lys Ser Gly Asn Val Lys Asp Leu
465                 470                 475                 480

Thr Gln Ala Trp Asp Leu Tyr Tyr His Val Phe Arg Arg Ile Gly Ser
                485                 490                 495

Gly Ser Gly Arg Val Lys Phe Ser Arg Ser Ala Asp Ala Pro Ala Tyr
                500                 505                 510

Gln Gln Gly Gln Asn Gln Leu Tyr Asn Glu Leu Asn Leu Gly Arg Arg
            515                 520                 525

Glu Glu Tyr Asp Val Leu Asp Lys Arg Arg Gly Arg Asp Pro Glu Met
        530                 535                 540

Gly Gly Lys Pro Arg Arg Lys Asn Pro Gln Glu Gly Leu Tyr Asn Glu
545                 550                 555                 560

Leu Gln Lys Asp Lys Met Ala Glu Ala Tyr Ser Glu Ile Gly Met Lys
                565                 570                 575

Gly Glu Arg Arg Arg Gly Lys Gly His Asp Gly Leu Tyr Gln Gly Leu
                580                 585                 590

Ser Thr Ala Thr Lys Asp Thr Tyr Asp Ala Leu His Met Gln Ala Leu
            595                 600                 605

Pro Pro Arg Glu
        610

<210> SEQ ID NO 111
<211> LENGTH: 617
<212> TYPE: PRT
<213> ORGANISM: artificial sequence
<220> FEATURE:
<223> OTHER INFORMATION: CD123-scCAR-intraCID-n?5

<400> SEQUENCE: 111

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
                20                  25                  30

Val Gln Pro Gly Gly Ser Leu Ser Leu Ser Cys Ala Ala Ser Gly Phe
            35                  40                  45

Thr Phe Thr Asp Tyr Tyr Met Ser Trp Val Arg Gln Pro Pro Gly Lys
        50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
            100                 105                 110

Asp Ser Ala Thr Tyr Tyr Cys Ala Arg Asp Ala Ala Tyr Tyr Ser Tyr
        115                 120                 125

Tyr Ser Pro Glu Gly Ala Met Asp Tyr Trp Gly Gln Gly Thr Ser Val
```

```
                130             135             140
Thr Val Ser Ser Gly Gly Gly Ser Gly Gly Gly Ser Gly Gly
145             150             155             160
Gly Gly Ser Met Ala Asp Tyr Lys Asp Ile Val Met Thr Gln Ser His
                165             170             175
Lys Phe Met Ser Thr Ser Val Gly Asp Arg Val Asn Ile Thr Cys Lys
                180             185             190
Ala Ser Gln Asn Val Asp Ser Ala Val Ala Trp Tyr Gln Gln Lys Pro
                195             200             205
Gly Gln Ser Pro Lys Ala Leu Ile Tyr Ser Ala Ser Tyr Arg Tyr Ser
210             215             220
Gly Val Pro Asp Arg Phe Thr Gly Arg Gly Ser Gly Thr Asp Phe Thr
225             230             235             240
Leu Thr Ile Ser Ser Val Gln Ala Glu Asp Leu Ala Val Tyr Tyr Cys
                245             250             255
Gln Gln Tyr Tyr Ser Thr Pro Trp Thr Phe Gly Gly Gly Thr Lys Leu
                260             265             270
Glu Ile Lys Arg Ser Asp Pro Thr Thr Thr Pro Ala Pro Arg Pro Pro
                275             280             285
Thr Pro Ala Pro Thr Ile Ala Ser Gln Pro Leu Ser Leu Arg Pro Glu
290             295             300
Ala Cys Arg Pro Ala Ala Gly Gly Ala Val His Thr Arg Gly Leu Asp
305             310             315             320
Phe Ala Cys Asp Ile Tyr Ile Trp Ala Pro Leu Ala Gly Thr Cys Gly
                325             330             335
Val Leu Leu Leu Ser Leu Val Ile Thr Leu Tyr Cys Arg Ser Gly Gly
                340             345             350
Val Gln Val Glu Thr Ile Ser Pro Gly Asp Gly Arg Thr Phe Pro Lys
                355             360             365
Arg Gly Gln Thr Cys Val Val His Tyr Thr Gly Met Leu Glu Asp Gly
370             375             380
Lys Lys Phe Asp Ser Ser Arg Asp Arg Asn Lys Pro Phe Lys Phe Met
385             390             395             400
Leu Gly Lys Gln Glu Val Ile Arg Gly Trp Glu Glu Gly Val Ala Gln
                405             410             415
Met Ser Val Gly Gln Arg Ala Lys Leu Thr Ile Ser Pro Asp Tyr Ala
                420             425             430
Tyr Gly Ala Thr Gly His Pro Gly Ile Ile Pro Pro His Ala Thr Leu
                435             440             445
Val Phe Asp Val Glu Leu Leu Lys Leu Glu Gly Ser Gly Ser Ser Arg
450             455             460
Gly Arg Lys Lys Leu Leu Tyr Ile Phe Lys Gln Pro Phe Met Arg Pro
465             470             475             480
Val Gln Thr Thr Gln Glu Glu Asp Gly Cys Ser Cys Arg Phe Pro Glu
                485             490             495
Glu Glu Glu Gly Gly Cys Glu Leu Arg Val Lys Phe Ser Arg Ser Ala
                500             505             510
Asp Ala Pro Ala Tyr Gln Gln Gly Gln Asn Gln Leu Tyr Asn Glu Leu
                515             520             525
Asn Leu Gly Arg Arg Glu Glu Tyr Asp Val Leu Asp Lys Arg Arg Gly
530             535             540
Arg Asp Pro Glu Met Gly Gly Lys Pro Arg Arg Lys Asn Pro Gln Glu
545             550             555             560
```

-continued

```
Gly Leu Tyr Asn Glu Leu Gln Lys Asp Lys Met Ala Glu Ala Tyr Ser
                565                 570                 575

Glu Ile Gly Met Lys Gly Glu Arg Arg Arg Gly Lys Gly His Asp Gly
            580                 585                 590

Leu Tyr Gln Gly Leu Ser Thr Ala Thr Lys Asp Thr Tyr Asp Ala Leu
        595                 600                 605

His Met Gln Ala Leu Pro Pro Arg Glu
    610                 615

<210> SEQ ID NO 112
<211> LENGTH: 605
<212> TYPE: PRT
<213> ORGANISM: artificial sequence
<220> FEATURE:
<223> OTHER INFORMATION: CD123-scCAR-intraCID-n°6

<400> SEQUENCE: 112

Met Ala Leu Pro Val Thr Ala Leu Leu Leu Pro Leu Ala Leu Leu Leu
1               5                   10                  15

His Ala Ala Arg Pro Glu Val Lys Leu Val Glu Ser Gly Gly Gly Leu
            20                  25                  30

Val Gln Pro Gly Gly Ser Leu Ser Leu Ser Cys Ala Ala Ser Gly Phe
        35                  40                  45

Thr Phe Thr Asp Tyr Tyr Met Ser Trp Val Arg Gln Pro Pro Gly Lys
    50                  55                  60

Ala Leu Glu Trp Leu Ala Leu Ile Arg Ser Lys Ala Asp Gly Tyr Thr
65                  70                  75                  80

Thr Glu Tyr Ser Ala Ser Val Lys Gly Arg Phe Thr Leu Ser Arg Asp
                85                  90                  95

Asp Ser Gln Ser Ile Leu Tyr Leu Gln Met Asn Ala Leu Arg Pro Glu
            100                 105                 110

Asp Ser Ala Thr Tyr Tyr Cys Ala Arg Asp Ala Ala Tyr Tyr Ser Tyr
        115                 120                 125

Tyr Ser Pro Glu Gly Ala Met Asp Tyr Trp Gly Gln Gly Thr Ser Val
    130                 135                 140

Thr Val Ser Ser Gly Gly Gly Gly Ser Gly Gly Gly Gly Ser Gly Gly
145                 150                 155                 160

Gly Gly Ser Met Ala Asp Tyr Lys Asp Ile Val Met Thr Gln Ser His
                165                 170                 175

Lys Phe Met Ser Thr Ser Val Gly Asp Arg Val Asn Ile Thr Cys Lys
            180                 185                 190

Ala Ser Gln Asn Val Asp Ser Ala Val Ala Trp Tyr Gln Gln Lys Pro
        195                 200                 205

Gly Gln Ser Pro Lys Ala Leu Ile Tyr Ser Ala Ser Tyr Arg Tyr Ser
    210                 215                 220

Gly Val Pro Asp Arg Phe Thr Gly Arg Gly Ser Gly Thr Asp Phe Thr
225                 230                 235                 240

Leu Thr Ile Ser Ser Val Gln Ala Glu Asp Leu Ala Val Tyr Tyr Cys
                245                 250                 255

Gln Gln Tyr Tyr Ser Thr Pro Trp Thr Phe Gly Gly Gly Thr Lys Leu
            260                 265                 270

Glu Ile Lys Arg Ser Asp Pro Thr Thr Thr Pro Ala Pro Arg Pro Pro
        275                 280                 285

Thr Pro Ala Pro Thr Ile Ala Ser Gln Pro Leu Ser Leu Arg Pro Glu
    290                 295                 300
```

-continued

```
Ala Cys Arg Pro Ala Ala Gly Gly Ala Val His Thr Arg Gly Leu Asp
305                 310                 315                 320
Phe Ala Cys Asp Ile Tyr Ile Trp Ala Pro Leu Ala Gly Thr Cys Gly
                325                 330                 335
Val Leu Leu Leu Ser Leu Val Ile Thr Leu Tyr Cys Arg Ser Gly Gly
            340                 345                 350
Arg Val Ala Ile Leu Trp His Glu Met Trp His Glu Gly Leu Glu Glu
        355                 360                 365
Ala Ser Arg Leu Tyr Phe Gly Glu Arg Asn Val Lys Gly Met Phe Glu
    370                 375                 380
Val Leu Glu Pro Leu His Ala Met Met Glu Arg Gly Pro Gln Thr Leu
385                 390                 395                 400
Lys Glu Thr Ser Phe Asn Gln Ala Tyr Gly Arg Asp Leu Met Glu Ala
                405                 410                 415
Gln Glu Trp Cys Arg Lys Tyr Met Lys Ser Gly Asn Val Lys Asp Leu
            420                 425                 430
Thr Gln Ala Trp Asp Leu Tyr Tyr His Val Phe Arg Arg Ile Gly Ser
        435                 440                 445
Gly Ser Ser Arg Gly Arg Lys Lys Leu Leu Tyr Ile Phe Lys Gln Pro
    450                 455                 460
Phe Met Arg Pro Val Gln Thr Thr Gln Glu Glu Asp Gly Cys Ser Cys
465                 470                 475                 480
Arg Phe Pro Glu Glu Glu Glu Gly Gly Cys Glu Leu Arg Val Lys Phe
                485                 490                 495
Ser Arg Ser Ala Asp Ala Pro Ala Tyr Gln Gln Gly Gln Asn Gln Leu
            500                 505                 510
Tyr Asn Glu Leu Asn Leu Gly Arg Arg Glu Glu Tyr Asp Val Leu Asp
        515                 520                 525
Lys Arg Arg Gly Arg Asp Pro Glu Met Gly Gly Lys Pro Arg Arg Lys
    530                 535                 540
Asn Pro Gln Glu Gly Leu Tyr Asn Glu Leu Gln Lys Asp Lys Met Ala
545                 550                 555                 560
Glu Ala Tyr Ser Glu Ile Gly Met Lys Gly Glu Arg Arg Arg Gly Lys
                565                 570                 575
Gly His Asp Gly Leu Tyr Gln Gly Leu Ser Thr Ala Thr Lys Asp Thr
            580                 585                 590
Tyr Asp Ala Leu His Met Gln Ala Leu Pro Pro Arg Glu
        595                 600                 605
```